US012139528B2

(12) United States Patent
Bigal et al.

(10) Patent No.: US 12,139,528 B2
(45) Date of Patent: Nov. 12, 2024

(54) TREATING REFRACTORY MIGRAINE

(71) Applicant: Teva Pharmaceuticals International GmbH, Jona (CH)

(72) Inventors: Marcelo Bigal, Doylestown, PA (US); Ernesto Aycardi, Andover, MA (US)

(73) Assignee: Teva Pharmaceuticals International GmbH, Jona (CH)

( * ) Notice: Subject to any disclaimer, the term of this patent is extended or adjusted under 35 U.S.C. 154(b) by 0 days.

(21) Appl. No.: 18/111,172

(22) Filed: Feb. 17, 2023

(65) Prior Publication Data

US 2023/0242631 A1  Aug. 3, 2023

Related U.S. Application Data

(63) Continuation of application No. 17/308,580, filed on May 5, 2021, which is a continuation of application No. 17/076,759, filed on Oct. 21, 2020, now Pat. No. 11,028,160, which is a continuation of application No. 16/508,574, filed on Jul. 11, 2019, now abandoned, which is a continuation of application No. 15/712,444, filed on Sep. 22, 2017, now Pat. No. 10,392,434.

(60) Provisional application No. 62/558,557, filed on Sep. 14, 2017, provisional application No. 62/399,180, filed on Sep. 23, 2016.

(51) Int. Cl.
*C07K 16/18* (2006.01)
*A61K 9/00* (2006.01)
*A61K 39/395* (2006.01)
*A61K 45/06* (2006.01)
*A61P 25/06* (2006.01)
*A61K 39/00* (2006.01)

(52) U.S. Cl.
CPC ............ *C07K 16/18* (2013.01); *A61K 9/0019* (2013.01); *A61K 39/3955* (2013.01); *A61K 45/06* (2013.01); *A61P 25/06* (2018.01); *A61K 2039/505* (2013.01); *A61K 2039/54* (2013.01); *A61K 2039/545* (2013.01); *C07K 2317/21* (2013.01); *C07K 2317/24* (2013.01); *C07K 2317/33* (2013.01); *C07K 2317/34* (2013.01); *C07K 2317/55* (2013.01); *C07K 2317/56* (2013.01); *C07K 2317/565* (2013.01); *C07K 2317/76* (2013.01); *C07K 2317/92* (2013.01); *C07K 2317/94* (2013.01)

(58) Field of Classification Search
CPC ............... C07K 16/18; C07K 2317/21; C07K 2317/92; C07K 2317/24; C07K 2317/33; C07K 2317/34; C07K 2317/55; C07K 2317/56; C07K 2317/565; C07K 2317/76; C07K 2317/94; A61K 39/3955; A61K 9/0019; A61K 45/06; A61K 2039/505; A61K 2039/54; A61K 2039/545; A61P 25/06

See application file for complete search history.

(56) References Cited

U.S. PATENT DOCUMENTS

| | | |
|---|---|---|
| 4,816,567 A | 3/1989 | Cabilly et al. |
| 5,116,964 A | 5/1992 | Capon et al. |
| 5,500,362 A | 3/1996 | Robinson et al. |
| 5,545,806 A | 8/1996 | Longberg et al. |
| 5,545,807 A | 8/1996 | Surani et al. |
| 5,569,825 A | 10/1996 | Longberg et al. |
| 5,625,126 A | 4/1997 | Longberg et al. |
| 5,633,425 A | 5/1997 | Longberg et al. |
| 5,661,016 A | 8/1997 | Longberg et al. |
| 5,750,373 A | 5/1998 | Garrard et al. |
| 5,821,337 A | 10/1998 | Carter et al. |
| 5,851,556 A | 12/1998 | Breton et al. |
| 5,932,215 A | 8/1999 | De Lacharriere et al. |
| 5,935,586 A | 8/1999 | De Lacharriere et al. |
| 5,938,586 A | 8/1999 | De Lacharriere et al. |
| 6,168,809 B1 | 1/2001 | De Lacharriere et al. |
| 6,180,370 B1 | 1/2001 | Queen et al. |
| 6,313,097 B1 | 11/2001 | Eberlein et al. |
| 6,344,438 B1 | 2/2002 | De Lacharriere et al. |
| 6,344,449 B1 | 2/2002 | Rudolf et al. |
| 6,509,014 B1 | 1/2003 | De Lacharriere et al. |
| 6,521,609 B1 | 2/2003 | Doods et al. |
| 6,552,043 B1 | 4/2003 | Patchett et al. |
| 6,586,458 B1 | 7/2003 | Plachetka |
| 6,737,056 B1 | 5/2004 | Presta |
| 6,767,056 B2 | 5/2004 | Presta |
| 6,861,441 B1 | 3/2005 | Clayton et al. |
| 7,109,214 B2 | 9/2006 | Zimmer et al. |
| 7,384,930 B2 | 6/2008 | Chaturvedula et al. |

(Continued)

FOREIGN PATENT DOCUMENTS

| | | |
|---|---|---|
| CA | 2563687 | 11/2005 |
| CL | 2013003336 | 6/2014 |

(Continued)

OTHER PUBLICATIONS

U.S. Appl. No. 13/621,981, filed Sep. 18, 2012, Poulsen et al.
U.S. Appl. No. 13/623,206, filed Sep. 20, 2012, Poulsen et al.
U.S. Appl. No. 13/835,394, filed Mar. 25, 2013, Zeller et al.
U.S. Appl. No. 14/612,117, filed Feb. 2, 2015, Zeller et al.
U.S. Appl. No. 14/855,959, filed Sep. 16, 2015, Pios et al.

(Continued)

*Primary Examiner* — Olga N Chernyshev
(74) *Attorney, Agent, or Firm* — Fish & Richardson P.C.

(57) ABSTRACT

Disclosed herein are methods of treating or reducing incidence of migraine and/or at least one secondary symptom associated with refractory migraine in a subject having refractory migraine comprising administering to the subject a monoclonal antibody that modulates the CGRP pathway. Compositions for use in the disclosed methods are also provided. Antagonist antibody G1 and antibodies derived from G1 directed to CGRP are also described.

19 Claims, 8 Drawing Sheets

Specification includes a Sequence Listing.

(56) References Cited

U.S. PATENT DOCUMENTS

| | | |
|---|---|---|
| 7,479,488 B2 | 1/2009 | Mueller et al. |
| 7,772,224 B2 | 8/2010 | Paone et al. |
| 8,007,794 B2 | 8/2011 | Zeller et al. |
| 8,168,592 B2 | 5/2012 | Gegg, Jr. et al. |
| 8,293,239 B2 | 10/2012 | Poulsen et al. |
| 8,298,536 B2 | 10/2012 | Poulsen et al. |
| 8,586,045 B2 | 11/2013 | Zeller et al. |
| 8,597,649 B2 | 12/2013 | Zeller et al. |
| 8,623,366 B2 | 1/2014 | Pios et al. |
| 8,669,368 B2 | 3/2014 | Leahy et al. |
| 8,734,802 B1 | 5/2014 | Zeller et al. |
| 9,115,194 B2 | 8/2015 | Zeller et al. |
| 9,266,951 B2 | 2/2016 | Zeller et al. |
| 9,328,167 B2 | 5/2016 | Poulsen et al. |
| 9,328,168 B2 | 5/2016 | Zeller et al. |
| 9,340,614 B2 | 5/2016 | Zeller et al. |
| 9,346,881 B2 | 5/2016 | Zeller et al. |
| 9,365,648 B1 | 6/2016 | Zeller et al. |
| 9,505,838 B2 | 11/2016 | Allan et al. |
| 9,884,907 B2 | 2/2018 | Zeller et al. |
| 9,884,908 B2 | 2/2018 | Zeller et al. |
| 9,890,210 B2 | 2/2018 | Zeller et al. |
| 9,890,211 B2 | 2/2018 | Zeller et al. |
| 9,896,502 B2 | 2/2018 | Bigal et al. |
| 10,329,343 B2 | 6/2019 | Zeller et al. |
| 10,519,224 B2 | 12/2019 | Bigal et al. |
| 11,028,160 B2 | 6/2021 | Bigal et al. |
| 11,028,161 B2 | 6/2021 | Bigal et al. |
| 11,555,064 B2 | 1/2023 | Bigal et al. |
| 2002/0137892 A1 | 9/2002 | Foord et al. |
| 2002/0162125 A1 | 10/2002 | Salmon et al. |
| 2002/0164707 A1 | 11/2002 | Adamou et al. |
| 2003/0069231 A1 | 4/2003 | Rudolf et al. |
| 2003/0194404 A1 | 10/2003 | Greenfeder et al. |
| 2004/0110170 A1 | 6/2004 | Pisegna et al. |
| 2005/0222206 A1 | 10/2005 | Cohen et al. |
| 2005/0234054 A1 | 10/2005 | Mueller et al. |
| 2006/0183700 A1 | 8/2006 | Vater et al. |
| 2009/0220489 A1 | 9/2009 | Zeller et al. |
| 2010/0172895 A1 | 7/2010 | Boone et al. |
| 2011/0054150 A1 | 3/2011 | Poulsen et al. |
| 2011/0257371 A1 | 10/2011 | Poulsen et al. |
| 2011/0305711 A1 | 10/2011 | Poulsen et al. |
| 2012/0009192 A1 | 1/2012 | Zeller et al. |
| 2012/0225075 A1 | 9/2012 | Pios et al. |
| 2012/0294797 A1 | 11/2012 | Kovacevich et al. |
| 2012/0294802 A1 | 11/2012 | Russo et al. |
| 2012/0294822 A1 | 11/2012 | Russo et al. |
| 2013/0216535 A1 | 8/2013 | Zeller et al. |
| 2013/0295087 A1 | 11/2013 | Poulsen et al. |
| 2013/0295088 A1 | 11/2013 | Poulsen et al. |
| 2014/0147438 A1 | 5/2014 | Zeller et al. |
| 2014/0308290 A1 | 10/2014 | Pios et al. |
| 2014/0314767 A1 | 10/2014 | Pios et al. |
| 2015/0050267 A1 | 2/2015 | Zeller et al. |
| 2015/0216535 A1 | 8/2015 | Herbowy et al. |
| 2015/0259415 A1 | 9/2015 | Allan et al. |
| 2015/0266948 A1 | 9/2015 | Bigal et al. |
| 2015/0291690 A1 | 10/2015 | Zeller et al. |
| 2015/0302690 A1 | 10/2015 | Poulsen et al. |
| 2015/0307607 A1 | 11/2015 | Bigal et al. |
| 2015/0322142 A1 | 12/2015 | Zeller et al. |
| 2015/0361171 A1 | 12/2015 | Zeller et al. |
| 2015/0361172 A1 | 12/2015 | Zeller et al. |
| 2015/0361173 A1 | 12/2015 | Zeller et al. |
| 2015/0376286 A1 | 12/2015 | Boone et al. |
| 2016/0168244 A1 | 2/2016 | Zeller et al. |
| 2016/0311913 A1 | 10/2016 | Sun et al. |
| 2017/0073403 A1 | 3/2017 | Allan et al. |
| 2017/0073412 A1 | 3/2017 | Pios et al. |
| 2017/0081395 A1 | 3/2017 | Zeller et al. |
| 2017/0088612 A1 | 3/2017 | Bigal et al. |
| 2018/0111984 A1 | 4/2018 | Bigal et al. |
| 2018/0127490 A1 | 5/2018 | Bigal et al. |
| 2019/0092841 A1 | 3/2019 | Zeller et al. |
| 2020/0102377 A1 | 4/2020 | Bigal et al. |
| 2020/0148761 A1 | 5/2020 | Bigal |
| 2020/0247878 A1 | 8/2020 | Zeller et al. |
| 2020/0331991 A1 | 10/2020 | Bigal et al. |
| 2020/0377581 A1 | 12/2020 | Bigal et al. |
| 2022/0048986 A1 | 2/2022 | Bigal |
| 2022/0056114 A1 | 2/2022 | Zeller et al. |
| 2022/0098287 A1 | 3/2022 | Bigal et al. |
| 2023/0235032 A1 | 7/2023 | Bigal et al. |
| 2024/0158481 A1 | 5/2024 | Zeller et al. |

FOREIGN PATENT DOCUMENTS

| | | |
|---|---|---|
| CL | 2017002686 | 10/2017 |
| CL | 2017001379 | 12/2017 |
| CN | 1282241 | 1/2001 |
| CN | 1308676 | 5/2001 |
| CN | 1671711 | 9/2005 |
| CN | 1723039 | 1/2006 |
| CN | 101309704 | 11/2008 |
| CN | 102740884 | 10/2012 |
| CN | 103143016 | 6/2013 |
| CN | 103421114 | 12/2013 |
| CN | 103748111 | 4/2014 |
| EP | 0212432 | 3/1987 |
| EP | 1031350 | 8/2000 |
| EP | 1556020 | 7/2005 |
| EP | 1770091 | 4/2007 |
| EP | 2380592 | 10/2011 |
| EP | 2579894 | 4/2013 |
| EP | 2709662 | 3/2014 |
| EP | 2709663 | 3/2014 |
| EP | 2710039 | 3/2014 |
| JP | H07-196700 | 8/1995 |
| JP | H08-268874 | 10/1996 |
| JP | 2001-526217 | 12/2001 |
| JP | 2007-523870 | 8/2007 |
| JP | 2008-538209 | 10/2008 |
| JP | 2009-515942 | 4/2009 |
| JP | 2011-46710 | 3/2011 |
| JP | 2011-513387 | 4/2011 |
| JP | 5123197 | 1/2013 |
| JP | 2015-506174 | 3/2015 |
| JP | 2015-509981 | 4/2015 |
| RU | 2329062 | 7/2008 |
| WO | WO 1991/000737 | 1/1991 |
| WO | WO 1994/021665 | 9/1994 |
| WO | WO 1995/05468 | 2/1995 |
| WO | WO 1996/004928 | 2/1996 |
| WO | WO 1996/33735 | 10/1996 |
| WO | WO 1997/009046 | 3/1997 |
| WO | WO 1997/041223 | 11/1997 |
| WO | WO 1998/003534 | 1/1998 |
| WO | WO 1998/008630 | 3/1998 |
| WO | WO 1998/009630 | 3/1998 |
| WO | WO 1998/011128 | 3/1998 |
| WO | WO 1998/056779 | 12/1998 |
| WO | WO 99/32103 | 7/1999 |
| WO | WO 1999/058572 | 11/1999 |
| WO | WO 2000/018764 | 4/2000 |
| WO | WO 2001/027160 | 4/2001 |
| WO | WO 2003/027252 | 4/2003 |
| WO | WO 2003/093472 | 11/2003 |
| WO | WO 2003/104236 | 12/2003 |
| WO | WO 2004/003019 | 1/2004 |
| WO | WO 2004/014351 | 2/2004 |
| WO | WO 2004/050683 | 6/2004 |
| WO | WO 2004/082602 | 9/2004 |
| WO | WO 2004/082605 | 9/2004 |
| WO | WO 2004/082678 | 9/2004 |
| WO | WO 2004/083187 | 9/2004 |
| WO | WO 2004/087649 | 10/2004 |
| WO | WO 2004/091514 | 10/2004 |
| WO | WO 2004/092166 | 10/2004 |
| WO | WO 2004/092168 | 10/2004 |
| WO | WO 2004/097421 | 11/2004 |
| WO | WO 2005/009962 | 2/2005 |
| WO | WO 2005/041757 | 5/2005 |
| WO | WO 2005/100360 | 10/2005 |

(56) References Cited

FOREIGN PATENT DOCUMENTS

| | | |
|---|---|---|
| WO | WO 2006/077212 | 7/2006 |
| WO | WO 2006/100009 | 9/2006 |
| WO | WO 2007/025212 | 3/2007 |
| WO | WO 2007/025286 | 3/2007 |
| WO | WO 2007/035906 | 3/2007 |
| WO | WO 2007/048026 | 4/2007 |
| WO | WO 2007/054809 | 5/2007 |
| WO | WO 2007/061676 | 5/2007 |
| WO | WO 2007/076336 | 7/2007 |
| WO | WO 2008/011190 | 1/2008 |
| WO | WO 2008/097824 | 8/2008 |
| WO | WO 2009/055350 | 4/2009 |
| WO | WO 2009/109908 | 9/2009 |
| WO | WO 2009/109911 | 9/2009 |
| WO | WO 2010/006168 | 1/2010 |
| WO | WO 2010/075238 | 7/2010 |
| WO | WO 2011/024113 | 3/2011 |
| WO | WO 2011/156324 | 12/2011 |
| WO | WO 2012/161956 | 11/2012 |
| WO | WO 2012/162243 | 11/2012 |
| WO | WO 2012/162253 | 11/2012 |
| WO | WO 2012/162257 | 11/2012 |
| WO | WO 2013/028635 | 2/2013 |
| WO | WO 2014/145650 | 9/2014 |
| WO | WO 2014/146074 | 9/2014 |
| WO | WO 2015/003122 | 1/2015 |
| WO | WO 2015/143409 | 9/2015 |
| WO | WO 2016/044224 | 3/2016 |
| WO | WO 2016/171742 | 10/2016 |
| WO | WO 2016/205037 | 12/2016 |
| WO | WO 2020/041468 | 2/2020 |

OTHER PUBLICATIONS

U.S. Appl. No. 15/879,900, filed Jan. 25, 2018, Bigal et al.
U.S. Appl. No. 60/753,044, filed Dec. 22, 2005, Benschop et al.
"A study of LY2951742 in Participants with Episodic Cluster Headache," Clinical Trials.gov, last verified Mar. 2016, 6 pages.
"Amgen Reports Aimovig™(Erenumab) Met All Primary And Secondary Endpoints In Unique Phase 3b Study In Episodic Migraine Patients Who Have Failed Multiple Prior Preventive Treatments," Amgen 2016 [online] URL: <http://investors.amgen.com/phoenix.zhtml?c=61656&p-irol-newsArticle&ID-2327769>, 10 pages.
"Declaration of Marcelo Bigal, M.D., Ph.D.," European Patent No. EP1957106 B1, EP Application No. 06809207, dated Feb. 3, 2015, 41 pages.
"Emerging Concepts in GPCR Research and Their Implications for Drug Discovery," Wiley Handbook of Current and Emerging Drug Therapies vol. 1-4: 369-386, 2007, 18 pages.
"Emgality (galcanezumab-gnlm) Prescribing Information," Sep. 2018, 29 pages.
"Guidance for Industry—Estimating the Maximum Safe Starting Dose in Initial Clinical Trials for Therapeutics in Adult Healthy Volunteers," U.S. Department of Health and Human Services, Food and Drug Administration, Center for Drug Evaluation and Research (CDER), Jul. 2005, 30 pages.
"Guidance for Industry Migraine: Developing Drugs for Acute Treatment," U.S. Department of Health and Human Servies Food and Drug Administration, Oct. 2014, 13 pages.
"Highlights of the American Academy of Neurology 2016 Annual Meeting," Fourth Edition, Highlights from Monday, Apr. 18, 2016, 4 pages.
"List of Monoclonal Antibodies Approved by the EMA and FDA for Therapeutic Use (status 2017)," on the Animal Cell Technology Industrial Platform (2017), 1 pages.
"Physician's Desk Reference," PDR, 58 Edition, 2004, 39 pages.
"Physician's Desk Reference," PDR, 59 Edition, 2005, 28 pages.
"Thermo Scientific Pierce Antibody Production and Purification Technical Handbook," Version 2, Thermo Scientific, 2016, 41 pages.

"Medication Overuse Headache," American Migraine Foundation, retrieved from URL <https://americanmigrainefoundation.org/resource-library/medication -overuse-headache-2/>, retrieved on May 28, 2019, 25 pages.
AAN (American Academy of Neurology), "New Drugs Offer Hope for Migraine Prevention," AAN 66th Annual Meeting Abstract, Apr. 22, 2014, 1 pages.
Abbott et al., "Structure and function of the blood-brain barrier," Neurobiology of Disease 37, 13-25, Jan. 2010, 13 pages.
Abbott, "Astrocyte-endothelial interactions and blood-brain barrier permeability", Journal of Anatomy 200(6):629-638, Jun. 2002, 10 pages.
Abbott, "Chapter 15: Comparative Physiology of the Blood-Brain Barrier", Physiology and Pharmacology of the Blood-Brain Barrier, pp. 371-396, 1992, 26 pages.
Abbott, "Evidence for bulk flow of brain interstitial fluid: significance for physiology and pathology", Neurochemistry International 45(4):545-552, Sep. 2004, 8 pages.
Abstracts of the XII Congress of the International Headache Society, IHC 2005, Oct. 9-12, 2005, Cephalalgia 25:923, Oct. 9-12, 2005, 3 pages.
ACHE' [online], "Migraine Attack: The Four Phases / ACHE," available on or before Aug. 1, 2014, retrieved on Oct. 13, 2015, retrieved from URL < http://www.achenet.org/resources/migraine attack the four phases>, 4 pages.
Adam et al., "Severity of mucosal inflammation as a predictor for alterations of visceral sensory function in a rat model," Pain 123(1-2): 179-86, Jul. 2006, 8 pages.
Adams et al., "Monoclonal antibody therapy of cancer", Nature Biotechnology 23(9):1147-1157, Sep. 2005, 11 pages.
Adelman et al., "Comparison of rizatriptan and other triptans on stringent measures of efficacy," Neurology vol. 57, 1377-83, Oct. 2001, 8 pages.
Adwanikar et al., "Spinal CGRP1 receptors contribute to supraspinally organized pain behavior and pain-related sensitization of amygdala neurons," Pain 132(1-2):53-66, Nov. 2007, 14 pages.
Afridi et al., "Glyceryl trinitrate triggers premonitory symptoms in migraineurs", Pain 110:675-680, Aug. 2004, 6 pages.
Afridi et al., "Verapamil and lymphomatoid papulosis in chronic cluster headache", Journal of Neurology 251:473-475, Apr. 2004, 3 pages.
Aggarwal, "Signalling pathways of the TNF superfamily: a double-edged sword," Natural Review of Immunol., vol. 3, 745-756, Sep. 2003, 12 pages.
Ahn and Basbaum, "Where do triptans act in the treatment of migraine?" Pain 115: 1- 4, May 2005, 4 pages.
Ahn and Goadsby, "Animal Models of Headache," The Headaches 213-219 2006, 2013, 7 pages.
Aiyar et al., "A cDNA encoding the calcitonin gene-related peptide type 1 receptor," the Journal of Biological Chemisty, vol. 271, No. 19, May 1996, 6 pages.
Aiyar et al., "Pharmacology of SB-273779, a nonpeptide calcitonin gene-related peptide 1 receptor antagonist," J Pharmacolog Exp Therap 296(3):768-775, 2001, 8 pages.
Akerman and Goadsby, "Topiramate inhibits cortical spreading depression in rat and cat: impact in migraine aura", Neuroreport 16:1383-1387, Aug. 2005, 5 pages.
Akerman et al., "Oxygen inhibits neuronal activation in the trigeminocervical complex after stimulation of trigeminal autonomic reflex but not during direct dural activation of trigeminal afferents," Headache 49; 1131-1143, Sep. 2009, 13 pages.
Akerman et al., "The effect of adrenergic compounds on neurogenic dural vasodilation", European Journal of Pharmacology 424(1):53-58, Aug. 2001, 6 pages.
Akerman et al., "The effect of adrenergic compounds on neurogenic vasodilation of dural meningeal vessels," Cephalalgia 20: 281-283, Jul. 2000, 2 pages.
Akerman et al., "The effect of anti-migraine compounds on nitric oxide induced dilation of dural meningeal vessels", European Journal of Pharmacology 452:223-228, Oct. 2002, 6 pages.
Akerman et al., "Topiramate inhibits trigeminovascular activation: an intravital microscopy study", British Journal of Pharmacology 146:7-14, Sep. 2005, 8 pages.

(56) References Cited

OTHER PUBLICATIONS

Alberts et al., "Molecular Biology of the Cell," pg G-34, 4th Edition, Garland Science, Taylor & Francis Group, New York, 2002, 5 pages.
Alemam et al., "Calcitonin Gene-Related Peptide as a Biomarker in Migraine," Journal of Neurology Research, 7(6): 103-107, Jan. 2017, 5 pages.
Alexander et al., "Calcitonin, amylin, CGRP and adrenomedullin," British Journal of Pharmacology, 158(Suppl. 1), Nov. 2009, 2 pages.
Al-Lazikani et al., "Standard conformations for the canonical structures of immunoglobulins," J Mol Biol 273(4):927-948, Nov. 7, 1997, 22 pages.
Allen et al., "Calcitonin Gene-Related Peptide and Reperfusion Injury," Journal of Orthopaedic Research, vol. 15, No. 2, Mar. 1997, 6 pages.
Allt et al., "Is the pial microvessel a good model for blood-brain barrier studies?" Brain Research Reviews, vol. 24:67-76, Jun. 1997, 10 pages.
Almagro and Strohl, "Antibody engineering: humanization, affinity maturation, and selection technique," Therapeutic Monoclonal Antibodies Chapter 13, pp. 311-334, 2009, 24 pages.
Al-Quliti et al., "New advances in prevention of migraine: Review of current practice and recent advances," Neurosciences, Jul. 2016, 21(3):207-214.
Amara et al., "Expression in brain of a messenger RNA encoding a novel neuropeptide homologous to calcitonin gene-related peptide," Science 229(4718):1094-1097, Sep. 13, 1985, 4 pages.
Ambalavanar et al., "Deep tissue inflammation upregulates neuropeptides and evokes nociceptive behaviors which are modulated by a neuropeptide antagonist," Pain 120(1-2):53-68, Jan. 2006, 16 pages.
American Headache Society, "Initial Results for LY2951742, A New Investigational Medicine for Migraine Prevention," 2014. Available at URL: <http://www.americanheadachesociety.org/initial_results_for_ly2951742 a new_investigational_medicine_for_migraine_prevention>. Accessed May 15, 2014, 2 pages.
American Headache Society, "The American Headache Society Position Statement On Integrating New Migraine Treatments Into Clinical Practice," Headache, Jan. 2019, 18 pages.
Amgen, "Amgen Presents First-Of-Its-Kind Data At AAN Annual Meeting Reinforcing Robust And Consistent Efficacy Of Aimovig™(erenumab) For Migraine Patients With Multiple Treatment Failures" Thousand Oaks, CA, PRNewswire, Apr. 17, 2018, Available online: <http://investors.amgen.com/phoenix.zhtml?c-61656&p-irol-newsArticle Print&ID-2343028>, 10 pages.
An, "Therapeutic Monoclonal Antibodies From Bench to Clinic," Wiley Chapter 31, pp. 711-762, 2009, 55 pages.
Andreou et al., "Animal models of headache: from bedside to bench and back to bedside," Expert Reviews Neurother. 10(3) 389-411, Mar. 2010, 23 pages.
Andreou et al., "Prospective real-world analysis of OnabotulinumtoxinA in chronic migraine post-National Institute for Health and Care Excellence UK technology appraisal," Eur J Neurol., Aug. 2018, 25(8):19 pages.
Andrew et al., "Monoclonal antibodies distinguishing alpha and beta forms of calcitonin gene-related peptide," J Immunol Methods 134(1):87-94, Nov. 6, 1990, 8 pages.
Annequin et al., "Last-Minute Poster Presentations", Cephalalgia 25:1189-1205, Dec. 2005, 7 pages.
Antonaci et al., "Recent advances in migraine therapy," Springer Plus 2016, No. 5, 637, May 2016, 14 pages.
Arfors et al., "Microvascular transport of macromolecules in normal and inflammatory conditions", Acta Physiol Scand Suppl., 463:93-103, 1979, 11 pages.
Armour et al., "Pharmacological characterization of receptor-activity-modifying proteins (RAMPs) and the human calcitonin receptor", J Pharmacol Toxicol 42: 217-224, Dec. 1999, 8 pages.
Armour et al., "Recombinant human IgG molecules lacking Fcγ receptor I binding and monocyte triggering activities," Eur J Immunol 29(8):2613-2624, Aug. 1999, 12 pages.
Arndt et al., "CGRP Antagonism—A Valid New Concept for the Treatment of Migraine Pain," Neuropeptides vol. 38, No. 2-3, Apr./Jun. 2004, 6 pages.
Arulmani et al., "Calcitonin gene-related peptide and its role in migraine pathophysiology," Eur J Pharmacol 500(1-3):315-330, Oct. 1, 2004, 16 pages.
Arulmani et al., "Effects of the Calcitonin Gene-Related Peptide (CGRP) Receptor Antagonist BIBN2096BS on a-CGRP-Induced Regional Haemodynamic Changes in Anaesthetized Rats," Pharmacology & Toxicology, vol. 94, 2004, 7 pages.
Arulmani et al., "Lack of effect of the adenosine A1 receptor agonist, GR79236, on capsaicininduced CGRP release in anaesthetized pigs," Cephalalgia 25(11):1082-1090, Nov. 2005, 9 pages.
Arulmozhi et al., "Migraine: current concepts and emerging therapies," Vascul Pharmacol 43(3):176-187, Sep. 2005, 12 pages.
Asahina et al., "Specific induction of cAMP in Langerhans cells by calcitonin gene-related peptide: Relevance to functional effects," Proceed Nat Acad Sci USA 92(18):8323-8327, Aug. 1995, 5 pages.
Asghar et al., "Calcitonin Gene-Related Peptide Modulates Heat Nociception in the Human Brain—An fMRI Study in healthy volunteers", Plos One 11(3):e0150334, Mar. 18, 2016, 20 pages.
Asghar et al., "Dilation by CGRP of middle meningeal artery and reversal by sumatriptan in normal volunteers," Neurology 75(17):1520-1526, Oct. 26, 2010, 7 pages.
Asghar et al., "Effect of CGRP and sumatriptan on the BOLD response in visual cortex," Journal of Headache Pain 13(2): 159-166, Mar. 2012, 8 pages.
Ashina et al., "A phase 3, randomized, double-blind, placebo-controlled study to evaluate the efficacy and safety of erenumab in migraine prevention: Primary results of the ARISE trial," European Journal of Neurology, Jul. 2017, 24(Suppl 1):470.
Ashina et al., "Calcitonin gene-related peptide levels during nitric oxide-induced headache in patients with chronic tension-type headache," Eur J Neurol 8(2):173-178, Mar. 2001, 6 pages.
Ashina et al., "Efficacy and safety of erenumab (AMG334) in chronic migraine patients with prior preventive treatment failure: A subgroup analysis of a randomized, double-blind, placebo-controlled study," Cephalalgia, Jul. 2018, 38(10):1-11.
Ashina et al., "Efficacy and safety of erenumab (AMG334) in chronic migraine patients with prior preventive treatment failure: A subgroup analysis of a randomized, double-blind, placebo-controlled study," Cephalalgia, Jul. 2018, 38(10):1611-1621.
Ashina et al., "Efficacy of erenumab (AMG 334) in chronic migraine patients with prior prophylactic treatment failure: Subgroup analysis of the phase 2, randomised, double-blind, placebo-controlled study," European Journal of Neurology, 2017, 24(Suppl 1):470-471.
Ashina et al., "Efficacy of erenumab (AMG 334) in chronic migraine patients with prior prophylactic treatment failure: Subgroup analysis of the phase 2, randomised, double-blind, placebo-controlled study," Journal of Headache and Pain, Nov. 2017, 18(Suppl 1):24.
Ashina et al., "Erenumab (AMG 334) in episodic migraine," Neurology, Sep. 2017, 89(12):8 pages.
Ashina et al., "Evidence for increased plasma levels of calcitonin gene-related peptide in migraine outside of attacks," Pain 86(1-2): 133-138, May 2000, 6 pages.
Ashina et al., "Long-term efficacy of erenumab in patients with chronic migraine who failed prior prophylactic treatment," Headache, Sep. 2018, 58(8):1296-1297.
Ashina et al., "Maintenance of clinical response to erenumab (AMG334) in episodic migraine: Complete one year results from an ongoing open-label extension study," Cephalalgia, Sep. 2016, 36(Suppl 1):13.
Ashina et al., "Patient-reported outcomes from the ARISE trial: A phase 3, randomized, double-blind study of erenumab in subjects with episodic migraine," Headache, Jun. 2017, 57(Suppl 3):192.
Ashina et al., "Plasma levels of calcitonin gene-related peptide in chronic tension- type headache," Neurology 55(9):1335-1340, Nov. 2000, 6 pages.
Ashina, "Calcitonin Gene-Related Peptide in Tension-Type Headache," The Scientific World 2:1527-1531, Jun. 2002, 6 pages.
Ashina, "Vascular changes have a primary role in migraine," Cephalalgia 32(5):428-430, Apr. 2012, 3 pages.

(56) References Cited

OTHER PUBLICATIONS

Ashkenazi et al., "Botulinum toxin and other new approached to migraine therapy," Annual Review of Medicine, vol. 55, Feb. 2004, 14 pages.
Ashkenazi et al., "Headache management for the pain specialist," Regional Anesthesia and Pain Medicine, vol. 29, No. 5, Sep.-Oct. 2004, 14 pages.
Ashkenazi et al., "The evolving management of migraine," Current Opinion in Neurology, Jun. 2003, 5 pages.
ATCC website search for PTA-6866 deposit, Jan. 22, 2010, 1 page.
ATCC website search for PTA-6866 deposit, Oct. 22, 2010, 1 page.
ATCC website search for PTA-6867 deposit, Jan. 22, 2010, 1 page.
ATCC website search for PTA-6867 deposit, Oct. 22, 2010, 1 pages.
Aubrée-Lecat et al., "Influence of Barrier-Crossing Limitations on the Amount of Macromolecular Drug Taken up by its Target", Journal of Pharmacokinetics and Biopharmaceutics 21 1 75-98, Feb. 1993, 24 pages.
Augustin et al., "Differentiation of endothelial cells: Analysis of the constitutive and activated endothelial cell phenotypes," BioEssays vol. 16(12), Dec. 1994, 6 pages.
Avastin (bevacizumab), "Prescribing Information," Feb. 2004, 27 pages.
Avastin® (bevacizumab) EMA, "Scientific Discussion," EMEA 2005, 61 pages.
Ayata et al., "Suppression of cortical spreading depression in migraine prophylaxis", Annals of Neurology 59(4):652-661, Apr. 2006, 10 pages.
Aycardi et al., "Efficacy and safety of 2 dose regimens of subcutaneous administration of fremanezumab (TEV-48125) versus placebo for the preventive treatment of episodic migraine," Journal of Headache and Pain, Nov. 2017, 18(Suppl 1):77.
Aycardi et al., "Fremanezumab (formerly TEV-48125) decreases migraine symptoms such as nausea, vomiting, photophobia and phonophobia and reduces the need for acute medications in the first week of treatment in the HFEM study," Headache, Jun. 2017, 57(Suppl 3):184-185.
Aycardi et al., "Fremanezumab (formerly TEV-48125) reduces headache pain within the first week of beginning treatment in the phase 2 episodic migraine study," Headache, Jun. 2017, 57(Suppl 3):129-130.
Aziz, "Visceral hypersensitivity: fact or fiction," Gastroenterology 131(2):661-664, Aug. 2006, 4 pages.
Bahra et al., "Oral zolmitriptan is effective in the acute treatment of cluster headache," presented in part at the annual meeting of the American Academy of Neurology, Apr. 17-24, 1999, Neurology 54:1832-1839, May 2000, 8 pages.
Baker et al., "Rational design of a monoclonal antibody (mAb) inhibiting calcitonin gene related peptide (CGRP), ALD403, intended for the prevention of migraine," Neurology, Apr. 2017, 88(16 Suppl): 6 pages.
Balint and Larrick, "Antibody engineering by parsimonious mutagenesis," Gene 137(1):109-118, Dec. 1993, 10 pages.
Ballabh et al., "The Blood-brain barrier: an overview—structure regulation and clinical implications," Neurobiology of Disease, vol. 16(1), 1-13, Jun. 2004, 13 pages.
Bard et al., "Peripherally administered antibodies against amyloid beta-peptide enter the central nervous system and reduce pathology in a mouse model of Alzheimer disease," Nat Med 6(8):916-919, Aug. 2000, 4 pages.
Bell, "Calcitonin Gene-Related Peptide Receptor Antagonists: New Therapeutic Agents for Migraine," J Med Chem 57(19):7838-7858, Jun. 24, 2014, 21 pages.
Benemei et al., "CGRP receptors in the control of pain and inflammation," Current Opinion in Pharmacology, 9:9-14, Feb. 2009, 6 pages.
Bennett et al., "Alleviation of mechanical and thermal allodynia by CGRP(8-37) in a rodent model of chronic central pain," Pain 86(1-2):163-175, May 2000, 13 pages.

Benromano et al., "Mild closed head injury promotes a selective trigeminal hypernociception: Implications for the acute emergence of post-traumatic headache," Eur J Pain 19(5):612-628, Aug. 29, 2014, 8 pages.
Benschop et al., "Development of a novel antibody to calcitonin gene-related peptide for the treatment of osteoarthritis-related pain," Osteoarthritis Cartilage 22(4):578-585, Apr. 2014, 8 pages.
Bergerot et al., "Animal models of migraine: looking at the component parts of a complex disorder", European Journal of Neuroscience 24(6):1517-1534, Sep. 2006, 18 pages.
Bernardis et al., "Human Domain Antibodies Against Virulence Traits of Candida Albicans Inhibit Fungus Adherence to Vaginal Epithelium and Protect Against Experimental Vaginal Candidiasis," J. Infectious Diseases vol. 195, 2007, 149-157.
Bernstein et al., "Sensitization of the Trigeminovascular Pathway: Perspective and Implications to Migraine Pathophysiology," Journal Clinical Neurology, 8:89-99, Jun. 2012, 11 pages.
Bexxar (131 I-tositumomab), "Prescribing Information," Corixa Corporation and GlaxoSmithKline, Jun. 2003, 49 pages.
Bhaskar et al., "Recent progress in migraine pathophysiology: role of cortical spreading depression and magnetic resonance imaging", European Journal of Neuroscience 38(11):3540-3551, Dec. 2013, 12 pages.
Bigal et al., "A multicenter, randomized, double-blind, double-dummy, placebo-controlled, parallel group, multi dose study comparing subcutaneous TEV-48125 to placebo for the preventive treatment of high frequency episodic migraine," Headache, Nov. 2015, 55(Suppl 5):251-252.
Bigal et al., "Calcitonin gene-related peptide (CGRP) and migraine current understanding and state of development", Headache: The Journal of Head and Face Pain 53(8):1230-1244, Sep. 2013, 15 pages.
Bigal et al., "Cardiovascular and hemodynamic parameters in women following prolonged CGRP inhibition using LBR-101, a monoclonal antibody against CGRP," Cephalalgia 34(12):968-976, Oct. 2014, 9 pages.
Bigal et al., "Emerging drugs for migraine prophylaxis and treatment," MedGenMed 8(2): 31, May 4, 2006, 12 pages.
Bigal et al., "Migraine in the Triptan Era: Lessons From Epidemiology, Pathophysiology, and Clinical Science", Headache 49:S21-S33, Feb. 2009, 13 pages.
Bigal et al., "Migraine in the Triptan Era: Progresses achieved, lessons learned and future developments," Arquivos de Neuro-Psiquiatria 67(2-B):559-569, Jun. 2009, 11 pages.
Bigal et al., "Monoclonal Antibodies for Migraine: Preventing Calcitonin Gene- Related Peptide Activity ," CNS Drugs, 28(5): 389-399, Mar. 2014, 11 pages.
Bigal et al., "New Migraine preventive options: an update with pathophysiological considerations," Rev Hosp Clin Fae Med Sao Paulo 57(6):293-298, Nov.-Dec. 2002, 6 pages.
Bigal et al., "Safety and tolerability of LBR-101, a humanized monoclonal antibody that blocks the binding of CGRP to its receptor: Results of the Phase 1 program," Cephalalgia 34(7):483-492, Dec. 23, 2013, 10 pages.
Bigal et al., "Safety, tolerability and efficacy of TEV-48125 for preventive treatment of chronic migraine: a multicentre randomised, double-blind, placebo-controlled, phase 2b study," Neurology Articles Lancel Neurol, Sep. 30, 2015, 1091-1100, 10 pages.
Bigal et al., "TEV-48125 for the preventive treatment of chronic migraine," Neurology 87(1):41-48, Jul. 5, 2016, 8 pages.
Bigal et al., "TEV-48125 for the preventive treatment of chronic migraine-efficacy at early time points," Headache, Nov. 2015, 55(Suppl 5):265.
Bigal et al., "Therapeutic antibodies against CGRP or its receptor," Brit J Clin Pharmacol 79(6):886-895, Jun. 22, 2015, 10 pages.
Bigal, "Experimental Agent Boosts Hope for Monoclonal Antibody Treatment of Migraine," Neurology Reviews 22(5):5, 6, May 2014, 3 pages.
Bigal, "Safety, tolerability, and efficacy of TEV-48125 for preventive treatment of high-frequency episodic migraine: a multicentre, randomised, double-blind, placebo- controlled, phase 2b study," neurology articles Lancet Neurology, Sep. 30, 2015, 1081-1090, 10 pages.

(56) References Cited

OTHER PUBLICATIONS

Bird et al., "Single-chain antigen-binding proteins," Science 242(4877):423-426, Oct. 21, 1988, 5 pages.
Bjarnadottir, "Comprehensive repertoire and phylogenetic analysis of the G protein- coupled receptors in human and mouse", Genomics 88(3):263-273, Sep. 2006, 11 pages.
Boel et al., "Functional human monoclonal antibodies of all isotypes constructed from phage display library-derived single-chain Fv antibody fragments," Journal of Immunology Methods, vol. 236(1-2), May 2000, 14 pages.
Boerner et al., "Production of antigen-specific human monoclonal antibodies from in vitro-primed human splenocytes," J Immunol 147(1):86-95, Jul. 1, 1991, 10 pages.
Bolay et al., "Intrinsic brain activity triggers trigeminal meningeal afferents in a migraine model, " Nature medicine 8(2): 136, Feb. 2002, 7 pages.
Boross et al., "IgA EGFR antibodies mediate tumor killing in vivo," EMBO Molecular Medicine, vol. 5, Aug. 2013, 14 pages.
Botox Package Insert, "BLA STN 103000/5215—FDA Approved Labeling Text," Oct. 2010, 25 pages.
Bousser and Welch, "Relation between migraine and stroke," Lancet Neurology, vol. 4, Sep. 2005, 10 pages.
Bowen et al., "Tumor necrosis factor-alpha stimulation of calcitonin gene-related peptide expression and secretion from rat trigeminal ganglion neurons," J Neurochem 96(1):65-77, Jan. 2006, 13 pages.
Bower et al., "Mapping the calcitonin receptor in human brain stem," American Journal of Physiol. Integr Comp. Physiol, vol. 310(9), May 2016, 6 pages.
Boyce and Hill, "Substance P (NK1) Receptor Antagonists—Analgesics or Not?" Handbook of Experimental Pharmacology Stress, Immunology and Behaviour, 2004, 23 pages.
Brain and Edvinsson, "Chapter 16: Calcitonin Gene-Related Peptide and Other Peptides," The Headaches, Third Edition, pp. 159-164, 2006, 8 pages.
Brain and Grant, "Vascular actions of calcitonin gene-related peptide and adrenomedullin," Physiol Rev 84(3):903-934, Jul. 2004, 32 pages.
Brain et al., "CGRP receptors: a headache to study, but will antagonists prove therapeutic in migraine?", Trends in Pharmaceutical Sciences 23(2): 51-53, Feb. 2002, 3 pages.
Brain et al., "Calcitonin Gene-Related Peptide is a Potent Vasodilator," Nature vol. 313: 54-56, Jan. 1985, 3 pages.
Brain, "Calcitonin gene-related peptide (CGRP) antagonists: blockers of neuronal transmission in migraine," Brit J Pharmacol 142(7):1053-1054, Aug. 2004, 2 pages.
Brandes et al., "Chronic migraine treatment with erenumab: Responder rates," Headache, Jun. 2017, 57(Suppl 3):197-198.
Brandes et al., "Topiramate for Migraine Prevention," J Am Med Assoc 291(8):965-973, Feb. 25, 2004, 9 pages.
Bree and Levy, "Development of CGRP-dependent pain and headache related behaviours in a rat model of concussion: Implications for mechanisms of post-traumatic headache," Cephalalgia, Dec. 7, 2016, 13 pages.
Breeze et al., "Solution structure of human calcitonin gene-related peptide by 1H NMR and distance geometry with retrained molecular dynamics," BioChemistry, vol. 30(2): 575-82, Jan. 1991, 8 pages.
Brekke and Sandlie, "Therapeutic Antibodies for Human Diseases at the Dawn of the Twenty-First Century," Nature Reviews, Drug Discovery, vol. 2, Jan. 2003, 11 pages.
British National Formulary, "British National Formulary, 52nd Edition," pp. 234-239, BMJ Publishing Group with RPS Publishing, Sep. 2006, 8 pages.
Brody et al., "Aptamers as therapeutic and diagnostic agents," Reviews in Molecular Biotechnology 74(1):5-13, Mar. 2000, 9 pages.
Brorson et al., "Mutational analysis of avidity and fine specificity of anti-levan antibodies," J Immunol 163(12):6694-6701, Dec. 15, 1999, 9 pages.
Brown and Morice, "Clinical Pharmacology of Vasodilator Peptides", Journal of Cardiovascular Pharmacology 10 Suppl 12:S82-87, Feb. 1987, 6 pages.
Bruera et al., "Cancer pain," JAMA 290(18):2476-2479, Nov. 12, 2003, 4 pages.
Brüggemann et al., "Comparison of the Effector Functions of Human Immunoglobulins Using a Matched Set of Chimeric Antibodies," Journal of Exp. Med. 166: 1351-1361, Nov. 1987, 11 pages.
Brummell et al., "Probing the combining site of an anti-carbohydrate antibody by saturation-mutagenesis: role of the heavy-chain CDR3 residues," Biochemistry, 32(4):1180-1187, Feb. 2, 1993, 2 pages.
Brunstock, "Autonomic Neuromuscular Junctions: Current Developments and Futrue Directions, " Journal of Anat. Vol. 146, pp. 1-30, 1986, 30 pages.
Buckley et al., "The partial inhibition of inflammatory responses induced by capsaicin using the Fab fragment of a selective calcitonin gene-related peptide antiserum in rabbit skin, " Neuroscience 48(4):963-968, Jun. 1992, 6 pages.
Buntinx et al., "Development of anti-migraine therapeutics using the capsaicin-induced dermal blood flow model," Brit J Clin Pharmacol 80(5):992-1000, Oct. 6, 2015, 9 pages.
Burks et al., "In vitro scanning saturation mutagenesis of an antibody binding pocket," Proc Natl Acad Sci USA 94(2):412-417, Jan. 21, 1997, 6 pages.
Burstein and Jakubowski, "Analgesic Triptan Action in an Animal Model of Intracranial Pain: A Race against the Development of Central Sensitization," Ann Neurol 55(1):27-36, Jan. 2004, 8 pages.
Burstein et al., "Defeating Migraine Paine with Triptans: A Race against the Development of Cutaneous Allodynia," Ann Neurol 55(1):19-26, Jan. 2004, 8 pages.
Buse et al., "Patient-reported outcomes from the STRIVE trial: A phase 3, randomized, double-blind study of erenumab in subjects with episodic migraine," Headache, Jun. 2017, 57(Suppl 3):198-199
Buse et al., "Psychiatric comorbidities of episodic and chronic migraine," J Neurl 260:1960-1969, Nov. 2013, 11 pages.
Buse et al., "Reducing the impact of migraine on functioning: Results from the STRIVE trial, a phase 3, randomised, double-blind, placebocontrolled study of erenumab in patients with episodic migraine," Journal of Headache and Pain, Nov. 2017, 18(Suppl 1):69-70.
Buzzi and Moskowitz, "The Pathophysiology of Migraine: Year 2005," Journal of Headache Pain, vol. 6, pp. 105-111, Jun. 2005, 7 pages.
Buzzi et al., "The antimigraine drug, sumatriptan (GR43175), selectively blocks neurogenic plasma extravasation from blood vessels in dura mater," British Journal of Pharmacology, 99(1):202-206, Jan. 1990, 5 pages.
Bylund and Toews, "Radioligand Binding Methods: Practical Guide and Tips," Invited Review, American J. Physiological, 265: L421-L429, Nov. 1993, 9 pages.
Byrne, "Chapter 6: Neuromuscular and Synaptic Transmission," in Essential Medical Physiology, 3rd Edition, Elsevier Academic Press, Amsterdam, 2003, 28 pages.
Cady and Dodick, "Diagnosis and Treatment of Migraine," Mayo Clinical Proceedings, vol. 77, Mar. 2002, 7 pages.
Caekebeke et al., "The antimigraine drug sumatriptan increases blood flow velocity in large cerebral arteries during migraine attacks," Neurology, vol. 42, 1522-26, Aug. 1992, 6 pages.
Camporeale et al., "A phase 3, long-term, open-label safety study of Galcanezumab in patients with migraine, " BMC Neurol., Nov. 2018, 18(1):188, 1-12.
Capel et al., "Heterogeneity of human IgG Fc receptors," Immunomethods 4(1):25-34, Feb. 1994, 10 pages.
Caraceni et al., "Pain measurement tools and methods in clinical research in palliative care: recommendations of an Expert Working Group of the European Association of Palliative Care," J Pain Symptom Manage 23(3):239-255, Mar. 2002, 17 pages.
Cardarelli et al., "Binding to CD20 by Anti-B1 antibody or F(ab')(2) is Sufficient for Induction of Apoptosis in B-Cell Lines," Cancer Immunol. Immunother. 51: 15-24, Mar. 2002, 10 pages.

(56) References Cited

OTHER PUBLICATIONS

Carter et al., "Humanization of an Anti-p185HER2 Antibody for Human Cancer Therapy," Proceedings of the National Academy of Sciences of the United States of America, vol. 89, May 1992, 5 pages.
Carter, "Potent antibody therapeutics by design," Nature Reviews Immunology 6(5):343-57, May 2006, 20 pages.
Carter, "Improving the Efficacy of Antibody-Based Cancer Therapies," Nature Reviews Cancer, vol. 1, Nov. 2001, 12 pages.
Casset et al., "A peptide mimetic of an anti-CD4 monoclonal antibody by rational design," Biochem Biophys Res Commun 307(1):198-205, Jul. 18, 2003, 8 pages.
Catty, "Antibodies vol. 1: A practical approach," Chapter 1-4, Practical Approach Series, 1988, 90 pages.
Catty, "Antibodies vol. II: A Practical Approach," Chapter 4: ELISA and related enzyme immunoassays, 1989, 60 pages.
Center for Drug Evaluation and Research, "Application No. 761089Orig1s000, Product Quality Review(s)," Aug. 16, 2018, Ajovy, 74 pages.
Cervero et al., "Visceral pain," Lancet 353(9170):2145-2148, Jun. 19, 1999, 4 pages.
Chai et al., "The role of calcitonin gene-related peptide (CGRP) in ischemic preconditioning in isolated rat hearts," Eur. J. Pharmacol. 531: pp. 246-253, 2006.
Chan et al., "Glutamate receptor antagonists in the management of migraine, " Drugs vol. 72(11): 1165-76, Jul. 2014, 12 pages.
Chan et al., "Therapeutic antibodies for autoimmunity and inflammation," Nature Reviews: Immunology 10(5):301-316, May 2010, 16 pages.
Chapman, "PEGylated antibodies and antibody fragments for improved therapy: a review," Advanced Drug Deliv. Rev., vol. 54(4): 531-545, Jun. 2002, 15 pages.
Chapman, "Therapeutic antibody fragments with prolonged in vivo half-lives," Nature America, Nature BioTechnology, vol. 17, Aug. 1999, 4 pages.
Charles et al., "Memantine for prevention of migraine: a retrospective study of 60 cases," J. Headache Pain, 2007, 8(4):248-250.
Charles, "Migraine is not primarily a vascular disorder," Cephalalgia 32(5):431-432, Apr. 20, 2012, 2 pages.
Charles, "Vasodilation out of the picture as a cause of migraine headache", Lancet Neurol 12(5):419-420, May 2013, 2 pages.
Chen et al., "Generation and analysis of random point mutations in an antibody CDR2 sequence: many mutated antibodies lose their ability to bind antigen," J Exp Med 176(3):855-866, Sep. 1992, 12 pages.
Chen et al., "Selection and analysis of an optimized anti-VEGF antibody: crystal structure of an affinity-matured Fab in complex with antigen," J Mol Biol 293(4):865-881, Nov. 5, 1999, 17 pages.
Chen et al., "Use of Constitutive G Protein-Coupled Receptor Activity for Drug Discovery," Molecular Pharmacology 57(1):125-134, Jan. 2000, 10 pages.
Chen, "Enhancement and destruction of antibody function by somatic mutation: unequal occurrence is controlled by V gene combinatorial associations", EMBO Journal 14(12):2784-2794, Jun. 1995, 11 pages.
Chester and Hawkins, "Clinical Issues in Antibody Design," Trends Biotechnol. vol. 13: 294-300, Aug. 1995, 7 pages.
Chiba et al., "Calcitonin gene-related peptide receptor antagonist human CGRP-(8- 37)," American Journal of Physiology: Endocrine and Metabolism, vol. 256:E331- 35, Feb. 1989, 7 pages.
Chothia et al., "Conformations of immunoglobulin hypervariable regions," Nature 342(6252):877-883, Dec. 21-28, 1989, 7 pages.
Cittadini et al., "Effectiveness of intranasal zolmitriptan in acute cluster headache. A randomized, placebo-controlled, double-blind crossover study", Archives of Neurology 63:1537-1542, Nov. 2006, 6 pages.
Clinical Trial NCT02025556, "A Multicenter Assessment of LBR-101 in High Frequency Episodic Migraine," Mar. 20, 2014, retrieved from URL <https://clinicaltrials.gov/ct2/history/NCT02025556?V_6=View#StudyPageTop>, 5 pages.
Clinical Trial NCT03308968, "An Efficacy and Safety Study of Fremanezumab in Adults With Migraine (FOCUS)," Oct. 13, 2017, retrieved on Mar. 22, 2021, retrieved from URL <https://www.clinicaltrials.gov/ct2/show/NCT03308968>, 10 pages.
Clinicaltrials.gov [online], "A Study Evaluating the Effectiveness of AMG 334 Injection in Preventing Migraines in Adults Having Failed Other Therapies (LIBERTY), " Mar. 30, 2017, retrieved on Oct. 16, 2020, retrieved from URL <https://www.clinicaltrials.gov/ct2/show/record/NCT03096834?view=record>, 7 pages.
Clinicaltrials.gov [online], "A Study of Galcanezumab (LY2951742) in Adults With Treatment-Resistant Migraine (CONQUER)," Jun. 18, 2018, retrieved on Oct. 16, 2020, retrieved from URL <https://clinicaltrials.gov/ct2/show/NCT03559257>, 12 pages.
Clinicaltrials.gov [online], "A Study to Evaluate the Efficacy and Safety of Erenumab (AMG 334) in Chronic Migraine Prevention," Feb. 19, 2014, retrieved from URL <https://clinicaltrials.gov/ct2/show/NCT02066415>, 10 pages.
Clinicaltrials.gov [online], "Evaluation of Efficacy & Safety of Galcanezumab in the Prevention of Episodic Migraine- the EVOLVE-2 Study (EVOLVE-2)," Nov. 2015, retrieved on Oct. 19, 2020, retrieved from URL <https://clinicaltrials.gov/ct2/show/NCT02614196?cond=galcanezumab&phase=2&draw=3&rank=11>, 10 pages.
Clinicaltrials.gov [online], "Evaluation of Galcanezumab in the Prevention of Episodic Migraine—the EVOLVE-1 Study (EVOLVE-1)," Nov. 25, 2015, retrieved on Oct. 19, 2020, retrieved from URL <https://clinicaltrials.gov/ct2/show/NCT02614183?cond-galcanezumab&phase=2&draw=2&rank-8>, 10 pages.
Clinicaltrials.gov [online], "I5Q-MC-CGAH (a) Clinical Protocol: A Phase 3, Randomized, Double-Blind, Placebo-Controlled Study of LY2951742 in Patients with Episodic Migraine—the EVOLVE-2 Study," Jan. 2016, retrieved on Oct. 19, 2020, retrieved from URL <https://clinicaltrials.gov/ProvidedDocs/96/NCT02614196/Prot_000.pdf>, 77 pages.
Clinicaltrials.gov [online], "Protocol I5Q-MC-CGAG: A Phase 3, Randomized, Double-Blind, Placebo-Controlled Study of LY2951742 in Patients with Episodic Migraine—the EVOLVE-1 Study," Sep. 2015, retrieved on Oct. 19, 2020, retrieved from URL <https://clinicaltrials.gov/ProvidedDocs/83/NCT02614183/Prot_000.pdf>, 65 pages.
Clinicaltrials.gov [online], "Protocol 15Q-MC-CGAW: A Randomized, Double-Blind, Placebo-Controlled Study of Galcanezumab in Adults with Treatment-Resistant Migraine—the CONQUER Study," Mar. 2018, retrieved on Oct. 16, 2020, retrieved from URL <https://clinicaltrials.gov/ProvidedDocs/57/NCT03559257/Prot_000.pdf>, 72 pages.
Clinicaltrials.gov [online], "Study to Evaluate the Efficacy and Safety of Erenumab (AMG 334) Compared to Placebo in Migraine Prevention (ARISE)," Jun. 29, 2015, retrieved on Oct. 16, 2020, 9 pages.
Clinicaltrialsregister.eu [online], "Clinical trials for eudract No. 2016-002211-18," Oct. 2016, retrieved on Oct. 16, 2020, retrieved from URL <https://clinicaltrials.gov/ct2/show/NCT03559257>, 1 page.
Clynes et al., "Fc receptors are required in passive and active immunity to melanoma," Proc Natl Acad Sci USA 95(2):652-656, Jan. 20, 1998, 5 pages.
Cohen et al., "Fremanezumab as Add-On Treatment for Patients Treated With Other Migraine Preventative Medicines", Headache 1375-1384, Oct. 2017, 10 pages.
Cole et al., "The EBV-hybridoma technique and its application to human lung cancer," Monoclonal Antibodies and Cancer Therapy 27:77-96, 1985, 20 pages.
Cole et al., "Human IgG2 Variants of Chimeric Anti-CD3 are Nonmitogenic to T cells," J. Immunol. 159: 3613-3621, 1997, 10 pages.
Colman, "Effects of amino acid sequence changes on antibody-antigen interactions," Res Immunol 145(1):33-36, Jan. 1994, 4 pages.
Conner et al., "Characterization of CGRP Receptor Binding", Current Protocols in Pharmacology 24:1-30, Sep. 2004, 11 pages.
Conner et al., "Interaction of calcitonin-gene-related peptide with its receptors," Biochem Soc Trans 30(4):451-455, Aug. 2002, 5 pages.

(56) References Cited

OTHER PUBLICATIONS

Connor et al., "GR205171 Clinical Study Group: Clinical evaluation of a novel, potent, CNS penetrating NK receptor antagonist in the acute treatment of migraine," Cephalalgia 18, 1998, 1 page.
Connor et al., "Interaction of calcitonin-gene-related peptide with its receptors," Biochemical Scoeity Transactions, vol. 30, Part 4, Aug. 2002, 5 pages.
Correia, "Stability of IgG isotypes in serum," mAbs 2(3):221-232, May/Jun. 2010, 12 pages.
Covell et al., "Pharmacokinetics of monoclonal immunoglobulin G1, F(ab')2, and Fab' in mice," Cancer Res 46(8):3969-3978, Aug. 1986, 10 pages.
Cruickshank et al., "ß-Adrenoreceptor-Blocking Agents and the Blood-Brain Barrier," Clinical Science, pp. 453s-455s, vol. 59, Dec. 1980, 3 pages.
Cumberbatch et al., "Differential effects of the 5HT 1B/1D receptor agonist naratriptan on trigeminal versus spinal nociceptive responses," Cephalalgia 18:659-663, Dec. 1998, 5 pages.
Cumberbatch et al., "Dural vasodilation causes a sensitization of rat caudal trigeminal neurones in vivo that is blocked by a 5-HT$_{1B/1D}$ agonist," British Journal of Pharmacology 126:1478-1486, 1999, 9 pages.
Cumberbatch et al., "Reversal of behavioral and electrophysiological correlates of experimental peripheral neuropathy by the NK1 receptor antagonist GR205171 in rats," Neuropharmacology 37:1535-1543, Dec. 1998, 9 pages.
Cumberbatch et al., "Rizatriptan has central antinociceptive effects against durally evoked responses", European Journal of Pharmacology 328:37-40, Jun. 1997, 4 pages.
Cumberbatch et al., "The effects of 5-HT1A, 5-HT1B and 5-HT1D receptor agonists on trigeminal nociceptive neurotransmission in anaesthetized rats", European Journal of Pharmacology 362(1):43-46, Nov. 1998, 4 pages.
Cutrer et al., "Priorities for triptan treatment attributes and the implications for selecting an oral triptan for acute migraine: a study of US primary care physicians (the TRIPSTAR Project)", Clinical Therapeutics 26:1533-1545, Sep. 2004, 13 pages.
D.H.E. 45 and Migranal (dihydroergotamine mesylate, USP), "Prescribing Information," Novartis, N5-929 S-032 S-033, Jul. 31, 2002, 37 pages.
D'Amico et al., "When should "chronic migraine" be considered "refractory" to pharmacological prophylaxis?" Neurol Sci Suppl. 1:S55-S58, 2008, 4 pages.
Dahlof et al., "Within-patient consistency of response of rizatriptan for treating migraine," Neurology vol. 55, 1511-1516, Nov. 2000, 7 pages.
Daiutolo et al., "Cortical Injury Modulates the Pain Pathway Partially through Inducible Nnitric Oxide Synthase," Department of Neurosurgery Faculty Papers, Paper 65, Jul. 1, 2014, retrieved from the Internet: URL<http://jdc.jefferson.edu/cgi/viewcontent.cgi?article=1065&context=neurosurgeryfp>, 1 page.
Dalmau et al., "Autoantibodies to synaptic receptors and neuronal cell surface proteins in autoimmune diseases of the central nervous system", Physiological Reviews 97(2):839-887, Mar. 2017, 49 pages.
D'Amico and Tepper, "Prophylaxis of migraine: general principles and patient acceptance", Neuropsychiatric Disease and Treatment 4(6):1155-1167, Dec. 2008, 14 pages.
Davies and Riechmann, "Affinity improvement of single antibody VH domains: residues in all three hypervariable regions affect antigen binding," Immunotechnology 2(3):169-179, Sep. 1996, 11 pages.
Davis et al., "Fundamentals of Neurologic Disease," pp. 204-207, Demos Medical Publishing Inc., 2005, 6 pages.
Davis et al., "The Tortuous Road to an Ideal CGRP function blocker for the treatment of migraine", Current Topics in Medicinal Chemistry 8(16):1468-1479, Nov. 2008, 12 pages.
Davletov et al., "Beyond BOTOX: advantages and lilnitations of individual botulinum neurotoxins," Trends Neurosci 28(8):446-452, Aug. 2005, 7 pages.

De Felice et al., "Opiate-induced persistent pronociceptive trigeminal neural adaptations: potential relevance to opiate-induced medication overuse headache," Cephalalgia 29(12):1277-1284, May 2009, 9 pages.
De Haas et al., "Fc gamma receptors of phagocytes," J Lab Clin Med 126(4):330-341, Oct. 1995, 12 pages.
De Pascalis et al., "Grafting of "abbreviated" complementarity-determining regions containing specificity-determining residues essential for ligand contact to engineer a less immunogenic humanized monoclonal antibody," J Immunol 169(6):3076-3084, Sep. 15, 2002, 9 pages.
De Prado et al., "CGRP receptor antagonists: a new frontier of anti-migraine medications," Drug Discovery Today: Therapeutic Strategies, Nervous System Disorders, vol. 3, No. 4, Winter 2006, 5 pages.
De Vries et al., "Genetic biomarkers of migraine," Headache, Jul.-Aug. 2006, 10 pages.
Dechant et al., "Chimeric IgA antibodies against HLA class II effectively trigger lymphoma cell killing," Blood vol. 100, No. 13, Dec. 2002, 7 pages.
Dechant et al., "IgA antibodies for cancer therapy," Critical Review in Oncology/Hematology vol. 39, Jul.-Aug. 2001, 9 pages.
Deckert-Schluter et al., "Crucial role of TNF receptor type-1 (p55), but not of TNF receptor type-2 (p75) in murine toxoplasmosis," Journal of Immunology, vol. 160:3427-3436, Jul. 1990, 11 pages.
Declaration Dr. Jes Olesen No. 2, dated Feb. 7, 2016, 15 pages.
Declaration Dr. Marcelo Bigal and Dr. Bigal's Cirruculum Vitae, dated Mar. 2, 2015, 41 pages.
Declaration of Dr. Jes Olesen No. 3 regarding EP1957106, dated Jun. 12, 2017, 20 pages.
Declaration of Dr. Jes Olesen regarding EP1957106, dated Jul. 11, 2014, 58 pages.
Declaration of Dr. Leonard Presta No. 2, regarding EP1957106, dated Jun. 12, 2017, 10 pages.
Declaration of Dr. Leonard Presta regarding EP1957106, dated Jul. 11, 2014, 53 pages.
Declaration of Dr. Robert Benschop regarding EP1957106, dated Jul. 16, 2014, 13 pages.
Declaration of Dr. Stephen D. Silberstein (with Annex A), dated Oct. 23, 2017, 153 pages.
Delafoy et al., "Interactive involvement of brain derived neurotrophic factor, nerve growth factor, and calcitonin gene related peptide in colonic hypersensitivity in the rat," Gut 55(7):940-945, Jul. 2006, 6 pages.
Deleu, "Guidelines for the prevention of migraine," Saudi Med J 20(7):495-500, Jul. 1999.
Delves et al., "Chapter 3: Antibodies," in Roitt's Essential Immunology, Blackwell Publishing, 2006, 24 pages.
Denekas et al., "Inhibition of stimulated meningeal blood flow by a calcitonin gene- related peptide binding mirror-image RNA oligonucleotide," Brit J Pharmacol 148(4):536-543, Jun. 2006, 8 pages.
Dennis et al., "hCGRP8-37: a calcitonin gene-related peptide antagonist revealed calcitonin gene-related peptide receptor heterogeneity in brain and periphery," Journal of Pharmacology Exp. Ther. vol. 254(1), Jul. 1990, 6 pages.
Dennis et al., "Strutcture-Activity Profile of Calcitonin Gene-Related Peptide in Peripheral and Brain Tissues. Evidence for Receptor Multiplicity," The Journal of Pharmacology and Experimental Therapeutics 251(2):718-725, 1989, 8 pages.
Detke et al., "A phase 3 placebo-controlled study of galcanezumab in patients with chronic migraine: Results from the 3-month double-blind treatment phase of the REGAIN study," Journal of Headache and Pain, Nov. 2017, 18(Suppl 1):137-138.
Detke et al., "Galcanezumab in chronic migraine: The randomized, double-blind, placebo-controlled REGAIN study," Neurology, Dec. 2018, 91(24): e2211-e2221.
Di Angelantonio et al., "A Novel Class of Peptides with Facilitating Action on Neuronal Nicotinic Receptors of Rat Chromaffin Cells in Vitro: Functional and Molecular Dynamic Studies," Molecular Pharmacology 61(1):43-54, 2002, 12 pages.
Diamond et al., "Intranasal Civamide for the Acute Treatment of Migraine Headaches," Cephalalgia (2000) 20: 596-602.

(56) References Cited

OTHER PUBLICATIONS

Diener et al., "Chronic migraine treatment with erenumab: Responder rates," Journal of Headache and Pain, Nov. 2017, 18(Suppl 1):26.
Diener et al., "Efficacy of erenumab for the treatment of patients with chronic migraine in presence of medication overuse," European Journal of Neurology, Jul. 2017, 24(Suppl 1):472.
Diener et al., "New therapeutic approaches for the prevention and treatment of migraine", Lancet Neurology, vol. 14:1010-1022, Oct. 2015, 14 pages.
Diener et al., "RPR100893, a Substance-P antagonist, is not effective in the treatment of migraine attacks," Cephalalgia, vol. 23, Apr. 2003, 3 pages.
Djavadi-Ohaniance et al., "Chapter 4: Measuring Antibody Affinity in Solution," in Antibody Engineering: A Practical Approach 77-117, 1st ed. 1996, 42 pages.
Dockray et al., "Immunoneutralization studies with calcitonin gene-related peptide," Ann N Y Acad Sci 657:258-267, Jun. 30, 1992, 10 pages.
Dodick and Silberstein, "Central sensitization theory of migraine: clinical implications," Headache, Nov. 2006, 10 pages.
Dodick et al., "A phase 3, randomized, double-blind, placebo-controlled study to evaluate the efficacy and safety of erenumab in migraine prevention: Primary results of the ARISE trial, " Headache, Jun. 2017, 57(Suppl 3):191-192.
Dodick et al., "ARISE: A Phase 3 randomized trial of erenumab for episodic migraine", Cephalalgia, Jan. 2018, 12 pages.
Dodick et al., "Botulinum neurotoxin for the treatment of migraine and other primary headache disorders," Clinics in Dermatology, Apr. 2004, 6 pages.
Dodick et al., "Cardiovascular tolerability and safety of triptans: a review of clinical data," Headache, May 2004, 11 pages.
Dodick et al., "CGRP monoclonal antibody LY2951742 for the prevention of migraine: A phase 2, randomized, double-blind, placebo-controlled study," Headache, Sep. 2014, 54(8):1430.
Dodick et al., "CGRP monoclonal antibody LY2951742 for the prevention of migraine: A Phase 2, Randomized, double-blind, placebo-controlled study," Neurology, Jul. 2014, 83(2):e39-e40.
Dodick et al., "Cluster Headache," Cephalalgia, Nov. 2000, 17 pages.
Dodick et al., "Consensus Statement: Cardiovascular Safety Profile of Triptans (5- HT1B/1D Agonists) in the Acute Treatment of Migraine," Headache 44(5):414-425, May 2004, 12 pages.
Dodick et al., "Effect of fremanezumab compared with placebo for prevention of episodic migraine a randomized clinical trial," Journal of the American Medical Association, May 2018, 319(19):1999-2008.
Dodick et al., "Is there a preferred triptan?" Headache, Jan. 2002, 7 pages.
Dodick et al., "OnabotulinumtoxinA for Treatment of Chronic Migraine: Pooled Results From the Double-Blind, Randomized, Placebo-Controlled Phases of the PREEMPT Clinical Program," Headache 50(6):921-936, Jun. 2010, 16 pages.
Dodick et al., "Predictors of migraine headache recurrence: a pooled analysis from the eletriptan database," Headache, vol. 48(2), 184-193, Feb. 2008, 10 pages.
Dodick et al., "Prioritizing treatment attributes and their impact on selecting an oral triptan: results from the TRIPSTAR project," Current Pain and Headache Reports 8:435-442, Dec. 2004, 8 pages.
Dodick et al., "Randomized, double-blind, placebo-controlled Trial of ALD403, an anti-CGRP peptide antibody in the prevention of chronic migraine," Neurology, Apr. 2017, 88: 16(Suppl 1): 7 pages.
Dodick et al., "Safety and efficacy of ALD403, an antibody to calcitonin gene-related peptide, for the prevention of frequent episodic migraine: a randomised, double-blind, placebo-controlled, exploratory phase 2 trial," Lancet Neurol 13(11):1100-1107, Nov. 2014, 8 pages.
Dodick et al., "Safety and efficacy of LY2951742, a monoclonal antibody to calcitonin gene-related peptide, for the prevention of migraine: a phase 2, randomised, double-blind, placebo-controlled study," Lancet Neurol 13(9):885-892, Sep. 2014, 8 pages.
Dodick et al., "Sustained response outcomes from a phase 2a, randomized, double-blind, placebo-controlled study of LY2951742, a monoclonal antibody to calcitonin gene-related peptide, for the prevention of migraine: A post-hoc analysis," Cephalalgia, May 2015, 35:6(Suppl 1):52.
Dodick et al., "Sustained response outcomes from a phase iia, randomized, double-blind, placebo-controlled study of ly2951742, a monoclonal antibody to calcitonin gene-related peptide for the prevention of migraine: A post-hoc analysis," Postgraduate Medicine, 2016, 128(Suppl 2):23-24.
Dodick et al., Authors' reply re Site of effect of LY2951742 for migraine prophylaxis. Www.thelancet.com/neueology. vol. 14, 32-33, Jan. 2015, 3 pages.
Doenicke et al., "Possible benefit of GR43175, a novel 5-HT1-like receptor agonist, for the acute treatment of severe migraine," Lancet vol. 331 No. 8598, Jun. 11, 1988, 3 pages.
Dolgin, "Antibody drugs set to revive flagging migraine target," Nat Rev Drug Discov 12(4):249-250, Apr. 2013, 2 pages.
Dolgin, "Migraine drug race turns its final corner FDA decisions in sight", Nature biotechnolgy 36:207-8, Mar. 2018, 2 pages.
Donnet et al., "Migraine Burden and Costs: A Nationwide Population-based Controlled Cohort Study Using the French EGB Database," American Headache Society 60th Scientific Meeting, Jun. 2018, 127-128.
Doods et al., "Pharmacological profile of BIBN4096BS, the first selective small molecule CGRP antagonist," Brit J Pharmacol 129(3):420-423, Feb. 2000, 4 pages.
Doods, "Development of CGRP antagonists for the treatment of migraine," Current Opinion in Investigation Drugs, Sep. 2001, 8 pages.
Doods, "The Potential of CGRP Receptor Antagonists for the Treatment of Pain: Focus on Migraine," Neuropeptides, 7th Joint Meeting of the European Neuropeptide Club and the Summer Neuropeptide Conference, Jun. 21-24, 2010, 30 pages.
Dressler et al., "Botulinum toxin: mechanisms of action," Eur Neurol 53(1):3-9, 2005, 6 pages.
Drossman et al., "Functional Bowel Disorders, A multicenter comparison of health status and development of illness severity index," Digestive Diseases and Sciences 40(5): 986-995, May 1995.
Dubel et al., "Chapter 1: Therapeutic Antibodies—from Past to Future," Handbook of Therapeutic Antibodies, Second edition Chapter 1:1-14, 2014, 14 pages.
Dufner et al., "Harnessing phage and ribosome display for antibody optimisation," Trends Biotechnol 24(11):523-529, Nov. 2006, 7 pages.
Durham and Russo, "Regulation of Calcitonin Gene-Related Peptide Secretion by a Serotonergic Antimigraine Drug," Journal of Neuroscience, vol. 19, pp. 3423-3429, May 1, 1999, 7 pages.
Durham and Vause, "Calcitonin gene-related peptide (CGRP) receptor antagonists in the treatment of migraine", CNS Drugs 24(7):539-548, Jul. 2010, 12 pages.
Durham et al., "CGRP-receptor antagonists—a fresh approach to migraine therapy?" N Eng J Med 350(11):1073-1075, Mar. 11, 2004, 3 pages.
Durham, "Calcitonin Gene-Related Peptide (CGRP) and Migraine," Emerging Neural Theories of Migraine Pathogenesis, Headache 46(1): S3-S8, Jun. 2006, 6 pages.
Durham, "CGRP receptor antagonists: A new choice for acute treatment of migraine?" Current Opinion in Investigational Drugs 5(7):731-735, Jul. 2004, 5 pages.
Durham, "Diverse Physiological Roles of Calcitonin Gene-Related Peptide in Migraine Pathology: Modulation of Neuronal-Glial-Immune Cells to Promote Peripheral and Central Sensitization," Current Pain and Headache Reports 20(8):48, Aug. 2016, 9 pages.
Durham, "Inhibition of Calcitonin Gene-Related Peptide Function: A Promising Strategy for Treating Migraine," Headache 38(8):1269-1275, Sep. 2008, 7 pages.
Duvernoy and Risold, "The circumventricular organs: An atlas of comparative anatomy and vascularization," Brain Research Reviews vol. 56(1), Nov. 2007, 29 pages.
Ebersberger et al., "Release of Substance P, Calcitonin Gene-Related Peptide and Prostaglandin E2 from Rat Dura Mater Enchephali

(56) References Cited

OTHER PUBLICATIONS

Following Electrical and Chemical Stimulation in Vitro," Neuroscience, vol. 89(3):901-907, Mar. 1999, 7 pages.

Edvinsson and Goadsby, "Neuropeptides in migraine and cluster headache," Cephalalgia vol. 14, 1994, 8 pages.

Edvinsson and Hargreaves, "Chapter 31: CGRP Involvement in Migraines," in The Headaches, Third Edition, pp. 289-299, 2006, 13 pages.

Edvinsson and Tfelt-Hansen, "The blood-brain barrier in migraine treatment," Cephalalgia 28(12):1245-1258, Dec. 2008, 14 pages.

Edvinsson and Uddman, "Neurobiology in primary headaches," Brain Res Rev 48(3):438-456, Jun. 2005, 19 pages.

Edvinsson et al. "Characterisation of the effects of a non-peptide CGRP receptor antagonist in SK-N-MC cells and isolated human cerebral arteries," European Journal of Pharmacology 415:39-44, 2001, 6 pages.

Edvinsson et al., "Amylin localisation effects on cerebral arteries and on local cerebral blood flow in the cat," Scientific World Journal, vol. 1: 168-180, May 2001, 14 pages.

Edvinsson et al., "Calcitonin Gene-Related Peptide (CGRP) in Cerebrovascular Disease," Scientific World Journal, vol. 2, May 30, 2002, 7 pages.

Edvinsson et al., "Effect of the CGRP receptor antagonist BIBN4096BS in human cerebral., coronary and omental arteries and in SK-N-MC cells," Eur J Pharmacol 434(1-2):49-53, Jan. 2, 2002, 5 pages.

Edvinsson et al., "Inhibitory effect of BIBN4096BS, CGRP8-37, a CGRPantibody and an RNA-Spiegelmer on CGRP induced vasodilatation in the perfused and non-perfused rat middle cerebral artery," Brit J Pharmacol 150(5):633-640, Mar. 2007, 8 pages.

Edvinsson et al., "Innervation of the human middle meningeal artery immunohistochemistry, ultrastructure, and role of endotherlium for vasomotility," Peptides vol. 19(7), 1998, 13 pages.

Edvinsson et al., "Measurement of vasoactive neuropeptides in biological materials: Problems and pitfalls from 30 years of experience and novel future approaches," Cephalalgia 30(6):761-766, Jun. 2010, 7 pages.

Edvinsson, "Blockade of CGRP receptors in the intracranial vasculature: a new target in the treatment of headache," Cephalalgia 24:611-622, 2004, 12 pages.

Edvinsson, "CGRP blockers in migraine therapy: where do they act?" Brit J Pharmacol 155(7):967-969, Dec. 2008, 3 pages.

Edvinsson, "CGRP receptor antagonists and antibodies against CGRP and its receptor in migraine treatment," Brit J Clin Pharmacol 80(2):193-199, Aug. 2015, 7 pages.

Edvinsson, "Clinical Data on the CGRP Antagonist BIBN4096BS for Treatment of Migraine Attacks," CNS Drug Reviews 11(1):69-76, Mar. 2005, 8 pages.

Edvinsson, "New therapeutic target in primary headaches—blocking the CGRP receptor," Expert Opinion Ther Targets 7(3):377-383, Jun. 2003, 7 pages.

Edvinsson, "Novel migraine therapy with calcitonin gene-regulated peptide receptor antagonists", Expert Opinion on Therapeutic Targets 11(9):1179-1188, Sep. 2007, 11 pages.

Edvinsson, "The journey to establish CGRP as a migraine target: a retrospective view," Headache 55(9):1249-1255, Oct. 2015, 7 pages.

Edvinsson, "The Trigeminovascular Pathway: Role of CGRP and CGRP Receptors in Migraine", American Headache Society 57:47-55, May 2017, 9 pages.

Eek et al., "Patient-reported preferences for oral versus intravenous administration for the treatment of cancer: a review of the literature," Patient Preference and Adherence 10:1609-1621, Aug. 2016, 13 pages.

Eftekhari et al., "Localization of Cgrp, Cgrp receptor, PACAP and glutamate in trigeminal ganglion. Relation to the blood-brain barrier", Brain Research 1600:93-109, Mar. 2015, 5 pages.

Ekbom et al., "Treatment of Acute Cluster Headache with Sumatriptan," New England Journal of Medicine, vol. 325(5), Aug. 1, 1991, 5 pages.

Ekstein et al., "Postictal headache," Epilepsy and Behavior, Jun. 2010, 5 pages.

El Vidge, "Anti-CGRP antibodies for migraine turn industry heads," Nat Biotechnol 32(8): 707, Aug. 2014, 1 page.

Elgert, "Immunology: Understanding the Immune System," 1st Edition, 58-78, Wiley-Liss Inc, 1996, 24 pages.

Elliott et al., "Nociceptive Neuropeptide Increases and Periorbital Allodynia in a Model of Traumatic Brain Injury, " Headache 52(6):96-984, Jun. 2012, 28 pages.

Elshourbagy et al., "Molecular cloning and characterization of the porcine calcitonin gene-related peptide receptor," Endocrinology 139(4):1678-1683, Apr. 1998, 6 pages.

Ema.europa.eu [online], "Emgality: EPAR—Product Information," Feb. 14, 2019, retrieved on Oct. 19, 2020, retrieved from URL <https://www.ema.europa.eu/en/documents/product-information/emgality-epar-product-information_en.pdf>, 59 pages.

Emilien and Maloteaux, "Current Therapeutic Uses and Potential of ß- Adrenoreceptor Agonists and Antagonists," European Journal of Clinical Pharmacology, vol. 53, pp. 389-404, Feb. 1998, 16 pages.

Enever et al., "Engineering High Affinity Superantigens by Phage Display," J. Mol Biol. (2005) 347: 107-120.

Enger et al., "Dynamics of ionic shifts in cortical spreading depression", Cerebral Cortex 25(11):4469-4476, Nov. 2015, 8 pages.

EP Opposition: Interlocutory Decision in Opposition Proceedings against European Patent No. 1957106, dated Feb. 1, 2017, 47 pages.

Escott and Brain, "Effect of a calcitonin gene-related peptide antagonist ($CGRP_{8-37}$) on skin vasodilatation and oedema induced by stimulation of the rat saphenous nerve," Brit J Pharmacol 110(2):772-776, Oct. 1993, 5 pages.

Escott et al., "Trigeminal ganglion stimulation increases facial skin blood flow in the rat: a major role for calcitonin gene-related peptide," Brain Res 669(1):93-99, Jan. 9, 1995, 7 pages.

European Medicines Agency, "Scientific conclusions and ground for variation of the terms of the marketing authorisations of suspension for the marketing authorisations, as application, taking into considerings the approved indicated for each product," available on or before Jan. 18, 2012, 7 pages.

European Notice of Opposition in European Patent No. 1957106, dated Jul. 11, 2014, 56 pages.

European Notice of Opposition in European Patent No. 1957106, dated Jul. 16, 2014, 51 pages.

European Office Action in Application No. 10754584, dated Dec. 16, 2013, 6 pages.

European Search Report and Opinion in European Application No. 16154418.4, dated May 10, 2016, 8 pages.

European Search Report in Application No. 11166787.9, dated May 8, 2012, 7 pages.

Evers and Mylecharane, "Chapter 58: Nonsteroidal Anti-Inflammatory and Miscellaneous Drugs in Migraine Prophylaxis," in the Headaches 553-566, 3rd Edition, 2006, 24 pages.

Evers et al., "EFNS guideline on the drug treatment of migraine—report of an EFNS task force," European Journal of Neurology 13:560-572, Jun. 2006, 13 pages.

Evidence of Publication Date of Edvinsson, CNS Drug Reviews 11(1):69-76, 2005, 1 page.

Extended European Search Report in Application No. 15765287.6, dated Aug. 8, 2017, 8 pages.

Extended European Search Report in Application No. 16154411.9, dated Jul. 18, 2016, 8 pages.

Extended European Search Report in Application No. 17152503.3, dated May 3, 2017, 13 pages.

Fanciullacci et al., "Increase in plasma calcitonin gene-related peptide from the extracerebral circulation during nitroglycerin-induced cluster headache attack," Pain 60(2):119-123, Feb. 1995, 5 pages.

Faraci et al., "Vascular responses of dura mater," American Journal of Physiology, Jul. 1989, 5 pages.

Fekrazad et al., "Interictal levels of calcitonin gene related peptide in gingival crevicular fluid of chronic migraine patients," Neurological Sciences Apr. 13, 2018, 8 pages.

Felson et al., "The American College of Rheumatology preliminary core set of disease activity measures for rheumatoid arthritis clinical trials. The Committee on Outcome Measures in Rheumatoid Arthritis Clinical Trials," Arthritis Rheum 36(6):729-740, Jun. 1993, 12 pages.

(56) References Cited

OTHER PUBLICATIONS

Feniuk et al., "The selective carotid arterial vasoconstrictor action of GR43175 in anaesthetized dogs, " British Journal of Pharmacology 96(1):83-90, Jan. 1989, 8 pages.

Ferrara et al., "Recombinant renewable polyclonal antibodies," mAbs, Jan. 2015, 7(1):32-41.

Ferrara et al., "Discovery and Development of Bevacizumab, an Anti-VEGF Antibody for Treating Cancer," Nature Review Drug Discovery, vol. 3: 391-400, May 2004, 10 pages.

Ferrari et al., "5-HT1 receptors in migraine pathophysiology and treatment," European Journal of Neurology vol. 2(1):5-21, Mar. 1995, 17 pages.

Ferrari et al., "Acute treatment of migraine attacks," Current Opinion in Neurology, 8(3):237-4, Jun. 1995, 6 pages.

Ferrari et al., "Cerebral blood flow during migraine attacks without aura and effect of sumatriptan," Arch Neurol vol. 135-139, Feb. 1995, 5 pages.

Ferrari et al., "Chapter 28: Migraine as a cerebral ionopathy with impaired central sensory processing, " molecular neurology pp. 439-461, 2007, 28 pages.

Ferrari et al., Clinical and experimental effects of sumatriptan in humans. Trends in Pharmacol Sci 14:129-133, Apr. 1993, 5 pages.

Ferrari et al., "Clinical effects and mechanism of action of sumatriptan in migraine," Clinical Neurology and Neurosurgery, 94(suppl):S73-S77, 1992, 5 pages.

Ferrari et al., "Combinatie van een triptaan met een NSAID bij migraine," Ned Tijdsch Geneeskd, 151, 36, Sep. 2007, 2 pages.

Ferrari et al., "Efficacy of ICS 205-930, a novel 5-Hydroxytryptamine3 (5HT3) receptor antagonist, in the prevention of migraine attacks. A complex answer to a simple question," Pain vol. 45:283-291, Jun. 1991, 9 pages.

Ferrari et al., "Fremanezumab versus placebo for migraine prevention in patients with documented failure to up to four migraine preventive medication classes (FOCUS): a randomised, double-blind, placebo-controlled, phase 3b trial," The Lancet, Sep. 2019, 394(10203):1030-1040.

Ferrari et al., "From molecules to migraine patient," proceedings of the 2nd International Congress of the European Headache Federation in Liege, Jun. 1994, Cephalalgia Oct. 1995, 43 pages.

Ferrari et al., "Methionine-Enkephalin in migraine and tension headache. Differences between classic migraine, common migraine and tension headache, and changes during attacks," presented in part at the 6th International Migraine Symposium, Oct. 1986, Headache 30:160-164, 1990, 5 pages.

Ferrari et al., "Migraine pathophysiology lessons from mouse models and human genetics," Lancet Neurology, vol. 14, Jan. 2015, 16 pages.

Ferrari et al., "Monoamine oxidase, phenosulphotransferase and serotonin metabolism in common and classic migraine and tension headache," Cephalalgia 7,suppl.6:144-146, 1987, 3 pages.

Ferrari et al., "Neuro-excitatory plasma aminoacids are elevated in migraine," Neurology 40:1582-1586, Oct. 1990, 5 pages.

Ferrari et al., "Oral sumatriptan: effect of a second dose, incidence and treatment of headache recurrences," Cephalalgia 14:330-338, Oct. 1994, 9 pages.

Ferrari et al., "Oral triptans (serotonin 50HT 1B/1D agonists) in acute migraine treatment: a meta-analysis of 53 trials," The Lancet 358(9294):1668-175, Nov. 2001, 8 pages.

Ferrari et al., "Plasma aminoacids in common and classic migraine and tension headache," Cephalalgia vol. 7, suppl.6:246-247, 1987, 2 pages.

Ferrari et al., "Release of platelet Met-enkephalin, but not serotonin, in migraine. A platelet-response unique to migraine patients?" Journal of the Neurological Sciences, vol. 93:51-60, Oct. 1989, 10 pages.

Ferrari et al., "Sumatriptan in the treatment of migraine," Neurology 1993;43(suppl 3):S43-47, Jun. 1993, 6 pages.

Ferrari et al., "The genetics of migraine: implication for treatment approaches," J Neural Transm Suppl. (63):111-27, 2002, 18 pages.

Ferrari et al., "The use of multiattribute decision models in evaluating triptan treatment options in migraine," J Neurology 252:1026-1032, Sep. 2005, 7 pages.

Ferrari et al., "Triptan medications to treat acute migraine," Lancet vol. 359: 1152- 53, Mar. 30, 2002, 1 page.

Ferrari et al., "Triptans (serotonin, 5-HT 1B/1D agonists) in migraine: detailed results and methods of a meta-analysis of 53 trials," Cephalalgia 22(8):633-658, Oct. 2002, 26 pages.

Ferrari, "Should we advise patients to treat migraine attacks early: methodologic issues," European Neurology, vol. 53, suppl 1, May 3, 2005, 5 pages.

Ferrari, "311C90: Increasing the options for therapy with effective acute antimigraine 5HT1B/1D receptor agonists," Neurology, Mar. 1997, 4 pages.

Ferrari, "Current perspectives on effective migraine treatments: are small clinical differences important for patients?" Drugs of Today (Barc) vol. 39 Suppl D:37-41, 2003, 4 pages.

Ferrari, "From genetics to prophylaxis," Cephalalgia 17(suppl 17):2-5, Jun. 1997, 4 pages.

Ferrari, "How to assess and compare drugs in the management of migraine: success rates in terms of response and recurrence," Cephalalgia, 19 Suppl 23:2-8, Mar. 1999, 7 pages.

Ferrari, "Migraine," Lancet, vol. 351, Apr. 4, 1998, 9 pages.

Ferrari, "Rizatriptan: a new milestone in migraine treatment. Introduction," Cephalalgia 20 Suppl 1:1, Nov. 2000, 19 pages.

Ferrari, "Should we advise patients to treat migraine attacks early?" Cephalalgia, Nov. 2004, 3 pages.

Ferrari, "The clinical effectiveness of 311C90 in the acute treatment of migraine," Eur Neurol 36(suppl 2):4-7, 1996, 4 pages.

Ferrari, "Treatment of migraine attacks with sumatriptan: The Subcutaneous Sumatriptan International Study Group," the New England Journal of Medicine, vol. 325:316-321, Aug. 1, 1991, 6 pages.

Ferro et al., "A comparison of the contractile effects of 5-hydroxytryptamine, sumatriptan and MK-462 on human coronary artery in vitro," British Journal of Pharmacology 40(3):245-251, Sep. 1995, 7 pages.

Fewou et al., "The pre-synaptic motor nerve terminal as a site for antibody-mediated neurotoxicity in autoimmune neuropathies and synaptopathies," Journal of Anatomy 224(1):36-4, Jan. 2014, 9 pages.

Fischer et al., "The Nonpeptide Calcitonin Gene-Related Peptide Receptor Antagonist BIBN4096BS Lowers the Activity of Neurons with Meningeal Input in the Rat Spinal Trigeminal Nucleus," J Neurosci 25(25):5877-5883, Jun. 22, 2005, 7 pages.

Flower, "Modelling G-protein-coupled receptors for drug design," Biochimica et Biophysica Acta 1422: 207-234, Nov. 1999, 28 pages.

Foord and Craig, "Isolation and characterisation of a human calcitonin-gene-related-peptide receptor," European Journal of Biochemistry 170 1-2 373-9, Dec. 1987, 7 pages.

Foord et al., "New methods for researching accessory proteins," Journal of Molecular Neuroscience, vol. 26, Issue 2-3, Jun. 2005, 12 pages.

Foote et al., "Antibody Framework Residues Affecting the Conformation of the Hypervariable Loops," Journal of Molecular Biology, vol. 224, Mar. 1992, 13 pages.

Ford et al., "Measures of functioning using MSQ v2.1 in patients with a history of episodic migraine and treated with galcanezumab or placebo injections in a phase 2 clinical trial," Headache, Jun. 2017, 57(Suppl 3):182.

Ford et al., "Measures of functioning using MSQ v2.1 in patients with a history of episodic migraine and treated with galcanezumab or placebo injections in a Phase 2 clinical trial, " Neurology, Apr. 2017, 88:16(Suppl 1): 6 pages.

Forster and Dockray, "The role of calcitonin gene-related peptide in gastric mucosal protection in the rat," Exp Physiol 76(4):623-626, Jul. 1991, 4 pages.

Foulkes et al., "Differential vasodilator profile of calcitonin gene-related peptide in porcine large and small diameter coronary artery rings," European Journal of Pharmacology, 201, 143-149, Aug. 1991, 7 pages.

(56) References Cited

OTHER PUBLICATIONS

Francis et al., "The irritable bowel severity scoring system: a simple method of monitoring irritable bowel syndrome and its progress," Aliment Pharmacol Ther 11(2):395-402, Apr. 1997, 8 pages.
Friedman et al., "Fremanezumab: a disease-specific option for the preventive treatment of migraine, including difficult-to-treat migraine," Emerging Topics in Life Sciences, Sep. 2020, 4(2): 12 pages.
Friend et al., "Phase I Study of an Engineered Aglycosylated Humanized CD3 Antibody in Renal Transplant Rejection," Transplantation vol. 68, No. 11, Dec. 15, 1999, 6 pages.
Fries et al., "The dimensions of health outcomes: the health assessment questionnaire, disability and pain scales," J Rheumatol 9(5):789-793, Sep.-Oct. 1982, 6 pages.
Frobert et al. "A sensitive sandwich enzyme immunoassay for calcitonin gene-related peptide (CGRP): characterization and application," Peptides 20(2):275-284, Feb. 1999, 10 pages.
Gallai et al., "Vasoactive peptide levels in the plasma of young migraine patients with and without aura assessed both interictally and ictally," Cephalalgia 15(5):384-390, Oct. 15, 1995, 7 pages.
Gardiner et al., "Antagonistic effect of Human α-CGRP [8-37] on the in vivo regional haemodynamic actions of human α-CGRP," Biochemical and Biophysical Research Communications 171(3):938-943, Sep. 28, 1990, 6 pages.
Gardiner et al., "Haemodynamic effects of human α-calcitonin gene-related peptide following administration of endothelin-1 or NG-nitro-L-arginine methyl ester in conscious rats," British Journal of Pharmacology 103(1):1256-662, May 1991, 7 pages.
Gardiner et al., "Regional haemodynamic effects of calcitonin gene-related peptide," American Journal of Physiology-Regulatory, Integrative and Comparative Physiology 256(2):R332-R338, Feb. 1989, 7 pages.
Gardiner et al., "Regional haemodynamic effects of human α- and β-calcitonin gene-related peptide in conscious Wistar rats," British Journal of Pharmacology 98(4):1225-132, Dec. 1989, 8 pages.
Garg and Balthasar, "Investigation of the Influence of FcRn on the distribution of IgG to the brain," The AAPS Journal, vol. II, No. 3 553-557, Sep. 2009, 5 pages.
Garlick and Renkin, "Transport of large molecules from plasma to interstitial fluid and lymph in dogs," American Journal of Physiology vol. 219, No. 6, Dec. 1970, 11 pages.
Gavilondo and Larrick, "Antibody Engineering at the Millennium," BioTechniques 29: 128-145, Jul. 2000, 15 pages.
Gay et al., "Interleukin-6 genetic ablation protects from trinitrobenzene sulfonic acid-induced colitis in mice," NeuroImmunoModulation 13(2):114-121, 2006, 8 pages.
GE Healthcare, "Biacore Sensor Surface Handbook," BR-1005-71 Edition AB, 2005, 100 pages.
Geerligs et al., "The influence of different adjuvants on the immune response to a synthetic peptide comprising amino acid residues 9-21 of herpes simplex virus type 1 glycoprotein D.," Journal of Immunological Methods, vol. 124, 95-102, Nov. 1989, 8 pages.
Geppetti et al., "CGRP and migraine: neurogenic inflammation revisited," J Headache Pain 6(2):61-70, Apr. 2005, 10 pages.
Ghatta et al., "Calcitonin gene related peptide: Understanding its role," Indian Journal of Pharmacology, vol. 36, Issue 5, Oct. 2004, 7 pages.
Giamberadino and Marrtelletti, "Emerging drugs for migraine treatment," Expert Opininon 20(1):137-147, 2015, 11 pages.
Giffin et al., "Effect of the adenosine A 1 receptor agonist GR79236 on trigeminal nociception with blink reflex recordings in healthy human subjects," Cephalalgia 23(4):287-292, May 2003, 6 pages.
Gijsman et al., "Dihydoergotamine nasal spray," Neurology 45:397-98, Feb. 1995, 2 pages.
Gijsman et al., "Double-blind, placebo-controlled, dose-finding study of rizatriptan (MK-462) in the acute treatment of migraine," Cephalalgia 17:647-51, Oct. 1997, 9 pages.
Gijsman et al., "Pharmacokinetic and pharmacodynamic profile of oral and intravenous meta-chlorophenylpiperazine in healthy volunteers," J Clin Psychopharmacol 1998;18:289-95, Aug. 1998, 14 pages.
Goadsby and Boes, "Chronic daily headache," J Neurol Neurosurg Psychiatry 72(Suppl II):ii2-ii5, Jun. 2002, 4 pages.
Goadsby and Boes, "New daily persistent headache," Journal of Neurology Neurosurgery Psychiatry 72(Suppl II): ii6-ii9, Jun. 2002, 4 pages.
Goadsby and Edvinsson, "Human in vivo Evidence for Trigeminovascular Activation in Cluster Headache:—Neuropeptide Changes and Effects of Acute Attacks Therapies," Brain vol. 117: 427-434, 1994, 8 pages.
Goadsby and Edvinsson, "The Trigeminovascular System and Migraine: Studies Characterizing Cerebrovascular and Neuropeptide Changes Seen in Humans and Cats," Annals of Neurology, 33(1): 48-56, Jan. 1993, 9 pages.
Goadsby and Hargreaves, "Refractory Migraine and Chronic Migraine: Pathophysiological Mechanisms", Headache 48:799-804, 2008, 8 pages.
Goadsby and Kernick, "Chapter 4: The migraine attack," in Headache: A Practical Manual (Oxford Care Manuals) 2009, 18 pages.
Goadsby and Ramadan, "Potential New Drugs for Acute and Prophylactic Treatment of Migraines," The Headaches, 3rd Edition, Chapter 60, 569-576, 2006, 8 pages.
Goadsby et al., "A controlled trial of erenumab for episodic migraine," New England Journal of Medicine, Nov. 2017, 377(22):2123-2132.
Goadsby et al., "Chapter 6: Treatment of headache and prophylaxis," in The Effective of Management written by Andrew Dowson, Aesculapius Medical Press, 1999, 16 pages.
Goadsby et al., "Chapter 61: Migraine," in Diseases of the Nervous System: Clinical Neuroscience and Therapeutic Principles, Third Edition, vol. I, 2002, 9 pages.
Goadsby et al., "Effect of erenumab on patient-reported outcomes in patients with episodic migraine with 2-4 prior preventive treatment failures: Results from the liberty study," Cephalalgia, Sep. 2018, 38(1S):60-62.
Goadsby et al., "EHMTI-0178. CGRP monoclonal antibody LY2951742 for the prevention of migraine: A phase 2, randomized, double-blind, placebo-controlled study," Journal of Headache and Pain, Sep. 2014, 15(Suppl 1): 1 page.
Goadsby et al., "Extracranial vasodilatation mediated by vasoactive intestinal polypeptide (VIP), " Brain Research 329(1-2):285-288, Mar. 1985, 4 pages.
Goadsby et al., "Mechanisms and Management of Headache," CME Neurology—I, Journal of Royal College of Physicians of London, vol. 33, No. 3, pp. 228-234, May-Jun. 1999, 7 pages.
Goadsby et al., "Migraine—Current Understanding and Treatment," N Eng J Med 346(4):257-270, Jan. 24, 2002, 14 pages.
Goadsby et al., "Onset of efficacy of LY2951742 in migraine prevention: Data from a phase IIa, randomized, double-blind, placebo-controlled study of a monoclonal antibody to calcitonin gene-related peptide (a post-hoc analysis), " Postgraduate Medicine, 2016, 128(Suppl 2):83-84.
Goadsby et al., "Phase 3, randomized, double-blind, placebo-controlled study to evaluate the efficacy and safety of erenumab (AMG 334) in migraine prevention: Primary results of the STRIVE Trial," European Journal of Neurology, Jul. 2017, 24(Suppl 1):117.
Goadsby et al., "Phase 3, randomized, double-blind, placebo-controlled study to evaluate the efficacy and safety of erenumab (AMG 334) in migraine prevention: Primary results of the STRIVE trial, " Headache, Jun. 2017, 57(Suppl 3):128-129.
Goadsby et al., "Randomized, double-blind, placebo-controlled trial of ALD403, an anti-CGRP peptide antibody in the prevention of frequent episodic migraine," Headache, Sep. 2014, 54(8):1420.
Goadsby et al., "Randomized, double-blind, placebo-controlled trial of ALD403, an anti-CGRP peptide antibody in the prevention of frequent episodic migraine," Neurology, Jul. 2014, 83(2):e40.
Goadsby et al., "Towards a definition of intractable headache for use in clinical practice and trials," Cephalalgia, vol. 26: 1168-1170, Sep. 2006, 3 pages.
Goadsby et al., "Treatment of a Migraine," New England Journal of Medicine, vol. 347, No. 10, Sep. 5, 2002, 3 pages.
Goadsby et al., "TRIPSTAR: Prioritizing triptan treatment attributes in migraine management," Acta Neurologica Scandinavica 110:137-143, Sep. 2004, 7 pages.

(56) References Cited

OTHER PUBLICATIONS

Goadsby et al., "Vasoactive peptide release in the extracerebral circulation of humans during migraine headache," Ann Neurol 28(2): 183-187, Aug. 1990, 5 pages.
Goadsby, "Advances in the understanding of headache," British Medical Bulletin 73-74:83-92, Jan. 2005, 10 pages.
Goadsby, "Calcitonin Gene-Related Peptide Antagonists as Treatments of Migraine and Other Primary Headaches," Drugs 65(18):2557-2567, Dec. 2005, 11 pages.
Goadsby, "Can we Develop Neurally Acting Drugs for the Treatment of Migraine?" Nat Rev Drug Discov 4:741-750, Sep. 2005, 10 pages.
Goadsby, "Chapter 55: Primary neurovascular headache," in Textbook of Pain Wall and Melzack Neurovascular Headache, pp. 851-874, 2006, 24 pages.
Goadsby, "Cortical Spreading Depression—Better Understanding and More Questions," Journal of Neurophysiol. Vol. 97, Apr. 4, 2007, 1 page.
Goadsby, "Efficacy and safety of erenumab in episodic migraine patients with 2-4 prior preventive treatment failures: Results from the phase 3b LIBERTY study," Headache, Jun. 2018, 58(Suppl 2):77.
Goadsby, "Efficacy and safety of topiramate for the treatment of chronic migraine: a randomized, double-blind placebo-controlled trial", Headache 47(2):170-180, Feb. 2007, 11 pages.
Goadsby, "Eletriptan in acute migraine: a double-blind, placebo-controlled comparison to sumatriptan," Neurology 54:156-163, Jan. 2000, 8 pages.
Goadsby, "Incredible progress for an era of better migraine care," Nat Rev Neurol 11(11):621-622, Nov. 2015, 2 pages.
Goadsby, "Migraine Pathophysiology," Headache vol. 45(Suppl. 1), Apr. 2005, 11 pages.
Goadsby, "Migraine, Aura, and Cortical Spreading Depression: Why are we still talking about it?" Annals of Neurology 49(1):4-6, Jan. 2001, 3 pages.
Goadsby, "Migraine: emerging treatment options for preventive and acute attack therapy," Expert Opinion on emerging drugs 11(3):419-427, Sep. 2006, 9 pages.
Goadsby, "New directions in migraine research," Journal of Clinical Neuroscience 9:116, Jul. 2002, 6 pages.
Goadsby, "New targets in the acute treatment of headache," Curr Opin Neurol 18(3):283-288, Jun. 2005, 6 pages.
Goadsby, "Pathophysiology of cluster headache: a trigeminal autonomic cephalgia," Lancet Neurology 1:251-257, 2002, 7 pages.
Goadsby, "Pathophysiology of Migraine", Neurol Clin 27:335-360, May 2009, 6 pages.
Goadsby, "Post-triptan Era for the Treatment of Acute Migraine," Current Pain and Headache Reports 8(5):393-398, Oct. 2004, 6 pages.
Goadsby, "Recent advances in the diagnosis and management of migraine," BMJ 332:25-29, Jan. 7, 2006, 5 pages.
Goadsby, "Recent advances in understanding migraine mechanisms, molecules and therapeutics," Trends in Molecular Medicine 13(1):39-44, Jan. 2007, 6 pages.
Goadsby, "The vascular theory of migraine—a great story wrecked by the facts," Brain: A Journal of Neurology, 132:6-7, Jan. 2009, 2 pages.
Goadsby, "Therapeutic Prospects for Migraine: Can Paradise Be Regained?" Ann Neurol 74:423-434, Sep. 2013, 12 pages.
Goadsby, "Trigeminal autonomic cephalalgias (TACs)", Acta Neurologica Belgica 101:10-19, Mar. 2001, 10 pages.
Goadsby, Silberstein, Dodick, "Chronic Daily Headache for Clinicians," Chapters 1-6, 11, 18, Jul. 2005, 112 pages.
Goldberg and Silberstein, "Targeting CGRP: A New Era for Migraine Treatment," CNS Drugs 29: 443-452, Jun. 2015, 10 pages.
Goldstein et al., "Considerations for animal models of blast-related traumatic brain injury and chronic traumatic encephalopathy," Alzheimer's Res & Ther 6:64, Sep. 5, 2014, 10 pages.
Goldstein et al., "Ineffectiveness of neurokinin-1 antagonist in acute migraine: a crossover study," Cephalagia, Nov. 1997, 11 pages.
Goldstein et al., "Lanepitant, an NK-1 antagonist, in migraine prevention," Cephalalgia vol. 21, Mar. 2001, 5 pages.
Goldstein et al., "Selective seratonin 1F (5-HT1F) receptor agonist LY334370 for acute migraine a randomised controlled trial," Lancet vol. 358, Oct. 13, 2001, 5 pages.
Goldstein et al., "Biological Efficacy of a Chimeric Antibody to the Epidermal Growth Factor Receptor in a Human Tumor Xenograft Model," Clinical Cancer Research, vol. 1: 1311-1318, Nov. 1995, 9 pages.
Goyal and Hirano, "The enteric nervous system," Mechanism of Disease, Review Article, The New England Journal of Medicine 334(17):1106-1115, Apr. 25, 1996, 10 pages.
Graham et al., "Mechanism of migraine headache and action of ergotamine tartrate," Arch NeurPhsych, vol. 39 Issue 4, Apr. 1938, 27 pages.
Green et al., U.S. Appl. No. 60/753,004, filed Dec. 22, 2005, 18 pages.
Grennan and Jayson, "Rheumatoid arthritis," Textbook of Pain pp. 397-407, 1994, 15 pages.
Gupta et al., "Antibodies against G-protein coupled receptors: novel uses in screening and drug development," Comb Chem High Throughput Screen 11(6): 463-467, Jul. 2008, 9 pages.
Gupta et al., "Improvement of the closed cranial window model in rats by intracarotid infusion of signalling molecules implicated in migraine," Cephalalgia 30(1):27-36, Apr. 28, 2009, 10 pages.
Gupta et al., "Intravital microscopy on a closed cranial window in mice: a model to study trigeminovascular mechanisms involved in migraine," Cephalalgia 26:1294-12303, Nov. 2006, 10 pages.
Guyer et al., "Immunoglobulin binding by mouse intestinal epithelial cell receptors," J Immunol 117(2):587-593, Aug. 1976, 8 pages.
Haan et al., "Lisinopril heeft geen relevant preventief effect bij migraine," Ned Tijdsch Geneeskd, vol. 15, 755, 2001, 3 pages.
Haar et al., "Crystal Structure of the Ectodomain Complex of the CGRP Receptor, a Class-B GPCR, Reveals the Site of Drug Antagonism," Structure 18: 1083-1093, Sep. 8, 2010, 11 pages.
Hakala et al., "Modelling constrained calcitonin gene-related peptide analogues," Protein Eng 9(2):143-148, Feb. 1996, 6 pages.
Halker et al., "Sustained migraine and headache day improvement with fremanezumab (TEV-48125)," Headache, Jun. 2017, 57(Suppl 3):185-186.
Hamann and Berger, "Chapter 12: Mylotarg—The First Antibody-Targeted Chemotherapy Agent," in: PagéM. (eds) Tumor Targeting in Cancer Therapy. Cancer Drug Discovery and Development. Humana Press, Totowa, NJ. 2002, 16 pages.
Hareendran et al., "Reducing impaired days: Results from the STRIVE trial, a phase 3, randomised, double-blind study of erenumab for episodic migraine," Journal of Headache and Pain, Nov. 2017, 18(Suppl 1):70.
Hargreaves and Shepheard, "Pathophysiology of Migraine—New Insights," Can. J. Neurol. Sci 26(3): S12-S19, Nov. 1999, 8 pages.
Hargreaves, "New Migraine and Pain Research," American Headache Society 47(Suppl 1):S26-S43, Apr. 2007, 18 pages.
Hargreaves, "Triptans to calcitonin gene-related peptide modulators- small molecules to antibodies—the evolution of a new migraine drug class," Biogen, Neurobiological Basis of Migraine, pp. 157-174, Jun. 19, 2017, 18 pages.
Hargreaves, Chapter 9: Triptans to Calcitonin Gene-Related Peptide Modulators—Small molecules to Antibodies—the Evolution of a New Migraine Drug Class, Neurological Basis of Migraine 157-174 (1st ed. 2017).
Harlow, "Using Antibodies: A Laboratory Manual," Chapters 1, 2, 11, Cold Spring Harbor Laboratory Press, 1999, 64 pages.
Hasbak et al., "Investigration of GCRP Receptors and Peptide Pharmacology in Human Coronary Arteries: Characterization with a Nonpeptide Antagonist," the Journal of Pharmacology and Experimental Therapeutics, vol. 304: 326-33, Jan. 2003, 9 pages.
Haut, "Predicting Seizures: Are We There Yet?" Epilepsy Currents, Current Literature in Clinical Science, 2013, 3 pages.
Hay et al., "A comparison of the actions of BIBN4096BS and $CGRP_{8-37}$ on CGRP and adrenomedullin receptors expressed on SK-N-MC, L6, col. 29 and Rat 2 cells," Brit J Pharmacol 137(1):80-86, Sep. 2002, 7 pages.

(56) References Cited

OTHER PUBLICATIONS

Hay et al., "CGRP modulation by RAMPS," Pharmacology and Therapeutics 109:173-197, 2006, 25 pages.
Hay et al., "Determinants of 1-Piperidinecarboxamide, N-[2-[[5-Amino-1-[[4-(4- pyridinyl)-1-piperazinyl]carbonyl]pentyl]amino]-1-[(3,5-dibromo-4- hydroxyphenyl)methyl]-2-oxoethyl]-4-(1,4-dihydro-2-oxo-3(2H)-quinazolinyl) (BIBN4096BS) Affinity for Calcitonin Gene-Related Peptide and Amylin Receptors-The Role of Receptor Activity Modifying Protein 1," Mol Pharmacol 70(6): 1984-1991, Dec. 2006, 8 pages.
Hay et al., "International Union of Pharmacology. LXIX. Status of the Calcitonin Gene-Related Peptide Subtype 2 Receptor," Pharmacological Reviews 60(2):143-145, 2008, 3 pages.
Hay et al., "Pharmacological Discrimination of Calcitonin Receptor: Receptor Activity-Modifying Protein Complexes," Mol Pharmacol 67(5):1655-1665, May 2005, 11 pages.
Haydon and Carmignoto, "Astrocyte Control of Synaptic Transmission and Neurovascular Coupling," Physiological Reviews 86(3):1009-1031, Jul. 2006, 23 pages.
Haywood et al., "Vasculature of the normal and arthritic synovial joint," Histology and Histopathology, Cellular Molecular Biology, vol. 16: 277-284, Jan. 2001, 8 pages.
Healy et al., "Pharmacokinetics and Biodistribution of Novel Aptamer Compositions," Pharm. Res. 2004, vol. 21, pp. 2234-2246, 13 pages.
Hepp et al., "Systematic Review of Migraine Prophylaxis Adherence and Persistence", Journal of Managed Care Pharmacy 20(1):22-33, Jan. 2004, 12 pages.
Herceptin® (trastuzumab) Prescribing Information, Genentech Inc, Sep. 1998, 2 pages.
Hershey et al., "Investigation of the species selectivity of a nonpeptide CGRP receptor antagonist using a novel pharmacodynamic assay," Regulatory Peptides 127(1):71-77, Apr. 2005, 7 pages.
Herzenberg et al., "Chapter 12: Antibody-Antigen Binding: Structure-Function Relationships Viewed at Atomic Scale Resolution," in Weir's Handbook of Experimental Immunology—vol. I: Immunochemistry and Molecular Immunology, 2007, 49 pages.
Herzenberg et al., "Weir's Handbook of Experimental Immunology—vol. IV: The Integrated Immune System," 1997, 121 pages.
Hilairet et al., "Protein-protein Interaction and not Glycosylation Determines the Binding Selectivity of Heterodimers between the Calcitonin Receptor-like Receptor and the Receptor Activity-modifying Proteins," Journal of Biological Chemistry, Aug. 2001, 8 pages.
Hill and Oliver, "Neuropeptide and Kinin Antagonists," HEP 177: 181-216, 2006, 36 pages.
Hill, "Chapter 12—Predicting Dose and Selective Efficacy in Clinical Studies from Preclinical Experiments: Practical Pharmacodynamics, " in Pharmacology for Chemists: Drug Discovery in Context, 2018, 22 pages.
Hill, "New Targets for Analgesic Drugs," Chapter 36, proceedings of the 10th World Congress on Pain, Progress in Pain Research and Management 24: 419-436, 2003, 18 pages.
Hill, "$NK_1$ (substance P) receptor antagonists—why are they not analgesic in humans?," TiPS 21:244-246, Jul. 2000, 3 pages.
Hinton et al., "An Engineered human IgG1 Antibody with Longer Serum Half-Life," The Journal of Immunology, Jan. 2006, 11 pages.
Ho et al., "CGRP and its receptors provide new insights into migraine pathophysiology," Nat Rev Neurol 6:573-582, Oct. 2010, 10 pages.
Ho et al., "Efficacy and tolerability of MK-0974 (telcagepant), a new oral antagonist of calcitonin gene-related receptor, compared with zolmitriptan for acute migraine: a randomised, placebo-controlled, parallel-treatment trial," Lancet vol. 372: 2115-2123, Dec. 2008, 9 pages.
Ho et al., "Randomized Controlled Trial of an Oral CGRP Receptor Antagonist, MK-0974, in Acute Treatment of Migraine," Neurology (2008) 70: 1304-1312.

Hoare, 'Mechanisms of peptide and nonpeptide ligand binding to Class B G-protein-coupled receptors, Drug Discovery Today 10(6):417-427, Mar. 2005, 11 pages.
Hoelig et al., "A novel CGRP-neutralizing Spiegelmer attenauates neurogenic plasma protein extravasation," British Journal of Pharmacology 172:3086-3098, 2015, 13 pages.
Hoff et al., "A breathtaking headache," Journal of Neurology and Neurosurgery Psychiatry, vol. 75: 506-509, Apr. 2004, 6 pages.
Hogue et al., "Pathophysiology and first-line treatment of osteoarthritis," Ann Pharmacother 36(4):679-686, Apr. 2002, 8 pages.
Hollenstein et al., "Insights into the structure of class B GPCRs," Cell Press, Trends in Pharmacological Sciences, vol. 35(1):12-22, Jan. 2014, 11 pages.
Holm et al., "Functional mapping and single chain construction of the anti-cytokeratin 8 monoclonal antibody TS1," Mol Immunol 44(6):1075-1084, Feb. 2007, 10 pages.
Holman et al., "Human alpha- and beta-CGRP and rat alpha-CGRP are coronary vasodilators in the rat," Peptides 7(2):231-235, Mar.-Apr. 1986, 5 pages.
Holt et al., "Anti-serum albumin domain antibodies for extending the half-lives of short lived drugs," Protein Engineering, Design and Selection, vol. 21(5): 283-288, May 2008, 6 pages.
Holt et al., "Domain antibodies: proteins for therapy," Trends Biotechnol 21(11):484-490, Nov. 2003, 7 pages.
Holton III et al., "Biodistribution of Monoclonal IgG1, F(ab')2, and Fab' in Mice After Intravenous Injection, Comparison between Anti-B Cell (Anti-LyBS.2) and Irrelevant (MPOC-21) Antibodies," J. Immunol., 139(9): pp. 3041-3049, 1987.
Hong et al., "Pharmacological coupling and functional role for CGRP receptors in the vasodilation of rat pial arterioles," Am J Phsyiol 270(1):H317-H323, Jan. 1, 1996, 6 pages.
Hong et al., "Pharmacological evidence that calcitonin gene-related peptide is implicated in cerebral autoregulation," Am J Physiology-Heart Circ Physiol 266(1):H11-H16, 1994, 6 pages.
Honore et al., "Murine models of inflammatory, neuropathic and cancer pain each generates a unique set of neurochemical changes in the spinal cord and sensory neurons," Neuroscience 98(3):585-598, 2000, 14 pages.
Hoogenboom and Winter, "By-passing immunisation. Human antibodies from synthetic repertoires of germline VH gene segments rearranged in vitro," J Mol Biol 227(2):381-388, Sep. 20, 1992, 8 pages.
Hopkins, "The druggable genome," Nature Reviews: Drug Discovery, Nature Publishing Group, vol. 1, Sep. 2002, 4 pages.
Hostetler et al., "In Vivo Quantification of Calcitonin Gene-Related Peptide Receptor Occupancy by Telcagepant in Rhesus Monkey and Human Brain Using the Positron Emission Tomography Tracer [11C]MK-4232," J Pharmacol Experim Therapeut 347(2):478-486, Nov. 1, 2013, 9 pages.
Hotta, "Chapter 1: Neurogenic control of parenchymal arterioles in the cerebral cortex," Progress in Brain Research 225:3-39, Apr. 2016, 37 pages.
Hruby, "Designing Peptide Receptor Agonists and Antagonists," Nat Rev Drug Discov 1:835-858, Nov. 2002, 14 pages.
Hu et al., "A new view of Starling's hypothesis at the microstructural level," Microvascular Research Vo. 58:281-304, Nov. 1999, 24 pages.
Hubbard et al., "Identification of the epitopes of calcitonin gene-related peptide (CGRP) for two anti-CGRP monoclonal antibodies by 2D NMR," Protein Science 6: 1945-1952, Sep. 1997, 8 pages.
Huls et al., "Antitumor Immune Effector Mechanisms Recruited by Phage Display-derived Fully Human IgG1 and IgA1 Monoclonal Antibodies," Cancer Research vol. 59, Nov. 15, 1999, 8 pages.
Humphrey et al., "Chapter 32: Consistency of pain relief over multiple migraine attacks following treatment with rizatriptan & Chapter 40: Clinical efficacy and tolerability of the triptans—discussion summary," in The Triptans—Novel Drugs for Migraine, Oxford University Press, 2001, 12 pages.
Humphrey et al., "Preclinical Studies on the Anti-Migraine Drug, Sumatriptan," Eur. Neurol., vol. 31, No. 5, pp. 282-290, 1991, 9 pages.
Humphrey et al., "Serotonin and Migraine," Annals N.Y. Acad. Science, vol. 600, Issue 1, pp. 587-600, Oct. 1990, 14 pages.

(56) References Cited

OTHER PUBLICATIONS

Humphrey et al., "GR43175, a selective agonist for the 5-HT1-like receptor in dog isolated saphenous vein," Br. J. Pharmacol. 94, 1123-1132, Aug. 1988, 10 pages.
Hurley, "CGRP Drug Improves Wellness on Headache-Free Days, Study Finds," Neurology Today, p. 31, Jul. 7, 2016, 1 page.
Huston et al., "Protein engineering of antibody binding sites: recovery of specific activity in an anti-digoxin single-chain Fv analogue produced in *Escherichia coli*," Proc Natl Acad Sci USA 85(16):5879-5883, Aug. 1988, 5 pages.
Hutchings et al., "Opportunities for therapeutic antibodies directed at G-protein coupled receptors," Nature Reviews: Drug Discovery 16(9):787-810, Sep. 2017, 24 pages.
Hutchings, "Theraputic antibodies directed at G protein-coupled receptors," mAbs 2(6):594-606, Nov./Dec. 2010, 14 pages.
Idusogie et al., "Mapping of the C1q binding site on rituxan, a chimeric antibody with a human IgG1 Fc," J Immunol 15;164(8):4178-84, Apr. 15, 2000.
Ignatovich et al., "The Creation of Diversity in the Human Immunoglobulin Vλ Repertoire," J. Mol Biol. (1997) 268:69-77.
IHC 2019 Programme Book, International Headache Society 2019 Conference, Dublin, Ireland, Sep. 5-8, 2019, 1 page.
Image of the CGRP signaling pathway, in U.S. Appl. No. 14/711,705 on Apr. 8, 2016, 2 pages, from physrev.physiology.org/content/physrev/94/4/1099/F2.large.jpg.
International Classification of Diseases and Related Health Problems: Version for 2005 (ICD), 10 pages.
International Classification of Diseases and Related Health Problems: Version for 2006 (ICD), 10 pages.
International Preliminary Report on Patentability in Application No. PCT/IB2006/003181, dated May 14, 2008, 9 pages.
International Search Report and Written Opinion in Application No. PCT/IB2006/003181, dated May 9, 2007, 14 pages.
International Search Report and Written Opinion in Application No. PCT/IB2009/050849, dated Jul. 31, 2009, 6 pages.
International Search Report and Written Opinion in Application No. PCT/IB2009/050852, dated Jul. 29, 2009, 12 pages.
International Search Report and Written Opinion in Application No. PCT/IB2010/053787, dated Nov. 11, 2010, 12 pages.
International Search Report and Written Opinion in Application No. PCT/IB2016/055720, dated Dec. 23, 2016, 14 pages.
International Search Report and Written Opinion in Application No. PCT/IB2017/055777, dated Jan. 11, 2018, 15 pages.
International Search Report and Written Opinion in Application No. PCT/US2015/021887, dated Jul. 8, 2015, 12 pages.
International Search Report and Written Opinion issued in International Application No. PCT/IB2017/055776 on Dec. 22, 2017, 17 pages.
International Search Report and Written Opinion issued in International Application No. PCT/US2018/020536 on Jun. 18, 2018, 19 pages.
International Search Report and Written Opinion issued in International Application No. PCT/US2018/020537 on Jun. 7, 2018, 17 pages.
Iovino et al., "Safety, Tolerability and Pharmacokinetics of BIBN 4096 BS, the First Selective Small Molecule Calcitonin Gene-Related Peptide Receptor Antagonist, Following Single Intravenous Administration in Healthy Volunteers," Cephalalgia, 24: 645-656, Aug. 2004, 12 pages.
Irani et al., "Molecular properties of human IgG subclasses and their implications for designing therapeutic monoclonal antibodies against infectious diseases," Molecular Immunology, 67: 171-182, Oct. 2015, 12 pages.
Irie et al., "Phase I pilot clinical trial for human IgM monoclonal antibody to ganglioside GM3 in patients with metastatic melanoma," Cancer Immunol. Immunother vol. 53, Feb. 2004, 8 pages.
Irimia et al., "Refractory migraine in a headache clinic population," BMC Neurol 11:94, 2011, 6 pages.
Iyengar et al., "Evaluation of efficacy and safety of LY2951742 in randomized, double-blind, placebo-controlled, singledose and dose-ranging studies in patients with migraine," Neuropsychopharmacology, Dec. 2016, 41(Suppl 1):S381-S382.
Iyengar et al., "The role of calcitonin gene-related peptide in peripheral and central pain mechanisms including migraine, " PAIN 158(4):543-559, Apr. 2017, 17 pages.
Janeway and Travers, "Immunobiology: The Immune System in Health and Disease, Second Edition," Chapter 2, 3 and 12, Current Biology Ltd./Garland Publishing Inc., 1996, 134 pages.
Janeway and Travers, Immunobiology: The Immune System in Health and Disease, Garland Publishing. p. G-2, 1994, 3 pages.
Janeway et al., "Immunobiology, 5th Edition: The Immune Systems in Health and Disease," pp. 123-154, Garland Publishing, Taylor and Francis Group, 2001, 35 pages.
Janeway et al., "Immunobiology, 5th Edition: The Immune Systems in Health and Disease," pp. 341-380, Garland Publishing, Taylor and Francis Group, 2001, 44 pages.
Janeway et al., "Immunobiology, 5th Edition: The Immune Systems in Health and Disease," pp. 626-627, Garland Publishing, Taylor and Francis Group, 2001, 5 pages.
Janeway et al., "Immunobiology, 5th Edition: The Immune Systems in Health and Disease," pp. 93-122 Garland Publishing, Taylor and Francis Group, 2001, 34 pages.
Jang et al., "The structural basis for DNA binding by an anti-DNA autoantibody," Mol Immunol 35(18):1207-1217, Dec. 1998, 11 pages.
Jansen-Olesen, "Animal Migraine Models for Drug Development: Status and Future Perspectives," CNS Drugs 27(12):1049-1068, Dec. 2013, 20 pages.
Jefferis, "Antibody terapeutics: isotype and glycoform selection," Expert Opinion Biol Ther, vol. 7, No. 9, 1401-1413, Sep. 2007, 13 pages.
Jefferis, "Glycosylation of recombinant antibody therapeutics," Biotechnology Progress, American Institute of Chemical Engineers 21(1):11-16, Jan. 1, 2005, 6 pages.
Jefferis, "The antibody paradigm: present and future development as a scaffold for biopharmaceutical drugs", Biotechnology and Genetic Engineering Reviews 26:1-42, Jul. 2009, 43 pages.
Jhee, "Pharmacokinetics and pharmacodynamics of the triptan antimigraine agents: a comparative review," Drug Disposition, Pharmacokinet, vol. 40, Issue 3, Feb. 2001, 17 pages.
Jin et al. "LY2951742, A Monoclonal Antibody Against CGRP, Failed to Reduce Signs and Symptoms of Knee Osteoarthritis," Abstracts/Osteoarthritis and Cartilage 24, S50, Apr. 2016, 1 page.
Johnston et al., "Short-term Prognosis After Emergency Department Diagnosis of TIA," JAMA 284(22): pp. 2901-2906, 2000.
Johnstone et al., "The Effect of Temperature on the Binding Kinetics and Equilibrium Constants of Monoclonal Antibodies to Cell Surface Antigens," Molecular Immunology, vol. 27, No. 4, Apr. 1990, 7 pages.
Jones et al., "Replacing the Complementarity-Determining Regions in a Human Antibody with Those from a Mouse," Nature vol. 321, May 29, 1986, 4 pages.
Jones et al., "The INNs and outs of antibody nonproprietary names," www.tandfonline.com, pp. 1-9, Mabs 8(1), Jan. 2016, 9 pages.
Juhasz et al., "NO-induced migraine attack: strong increase in plasma calcitonin gene-related peptide (CGRP) concentration and negative correlation with platelet serotonin release, " Pain 106(3):461-470, Dec. 2003, 10 pages.
Juhl et al., "Effect of two novel CGRP-binding compounds in a closed cranial window rat model," Europ J Pharmacol 657(1-2):117-124, Jul. 12, 2007, 8 pages.
Julia and Bueno, "Tachykininergic mediation of viscerosensitive responses to acute inflammation in rats: role of CGRP," Am J Physiol 272(1 Pt 1):G141-G146, Jan. 1997, 6 pages.
Kajekar et al., "Effect of a 5-HT1 receptor agonist, CP-122,288, on oedema formation induced by stimulation of the rat saphenous nerve," British Journal of Pharmacology 115(1):1-2, May 1995, 2 pages.
Kallner et al., "Calcitonin Gene-Related Peptide in Myocardial Ischaemia and Reperfusion in the Pig," Cardiovascular Research (1998) 38: 493-499.

(56) References Cited

OTHER PUBLICATIONS

Kane et al., "A mouse model of human repetitive mild traumatic brain injury," J Neurosci Meth 203(1):41-49, Jan. 15, 2012, 24 pages.
Kapoor et al., "Effects of BIBN4096BS on Cardiac Output Distribution and on CGRP-Induced Carotid Haemodynamic Responses in the Pig," European J. Pharmacology (2003) 475: 69-77.
Kar et al., "Increased calcitonin gene-related peptide (CGRP), substance P, and EYKephalin immunoreactivities in dorsal spinal cord and loss of CGRP-immunoreactive motoneurons in arthritic rats depend on intact peripheral nerve supply," J Mol Neurosci 3(1):7-18, 1991, 12 pages.
Katz et al., "Measurement of pain," Surg Clin North Am 79(2):231-252, Apr. 1999, 12 pages.
Kaube et al., "Inhibition by sumatriptan of central trigeminal neurons only after blood-brain barrier disruption," British Journal of Pharmacology 109 788-792, Jul. 1993, 5 pages.
Kawamura et al., "Antinociceptive effect of intrathecally administered antiserum against calcitonin gene-related peptide on thermal and mechanical noxious stimuli in experimental hyperalgesic rats," Brain Res 497(1):199-203, Sep. 11, 1989, 5 pages.
Keller et al., "Lack of Efficacy of the Substance P (Neurokinin1 Receptor) Antagonist Aprepitant in the Treatment of Major Depressive Disorder," Biological Psychiatry 59(3):216-223, Feb. 2005, 8 pages.
Kelley, "Thermodynamics of Protein-Protein Interaction Studied by Using BIAcore and Single-Site Mutagenesis," Methods: A companion to methods in Enzymology, vol. 6, Issue 2, 111-120, Jun. 1994, 10 pages.
Kenakin and Onaran, "The ligand paradox between affinity and efficacy: can you be there and not make a difference?" TRENDS in Pharmaceutical Sciences 23(6): 275-280, Jun. 2002, 6 pages.
Kenakin, "Drug Efficacy at G Protein-Coupled Receptors," Annu Rev Pharmacol Toxicol 42: 349-379, 2002, 33 pages.
Kenakin, "Efficacy of G-protein-coupled receptors," Nature Reviews, Drug Discovery, vol. 1, Macmillan Magazines, Feb. 2002, 8 pages.
Kenakin, "G-Protein Coupled Receptors as Allosteric Machines," Receptors and Channels 10: 51-60, 2004, 10 pages.
Kenakin, "New concepts in pharmacological efficacy of 7TM receptors: IUPHAR review 2," British Journal of Pharmacology, vol. 168(3), Feb. 2013, 22 pages.
Kenakin, "Principles: Receptor Theory in Pharmacology," TRENDS in Pharmacological Sciences 25(4) 186-224, Apr. 2004, 7 pages.
Kenney et al., "Influence of adjuvants on the quantity, affinity, isotype and epitope specificity of murine antibodies," Journal of Immunological Methods, 121, 157-166, Jul. 1989, 10 pages.
Kernick et al., "Cluster headache in primary care: unmissable, underdiagnosed and undertreated," British Journal of General Practice, 56(528):486-487, Jul. 2006, 2 pages.
Kettleborough et al., "Humanization of a Mouse Monoclonal Antibody by CDR-Grafting: The Importance of Framework Residues on Loop Conformation," Protein Engineering, vol. 4, No. 7, Oct. 1991, 11 pages.
Khan et al., "CGRP, a target for preventive therapy in migraine and cluster headache: Systematic review of clinical data," Cephalalgia, pp. 1-16, Jan. 2017, 16 pages.
Khazaeli et al., "Human Immune Response to Monoclonal Antibodies," Journal of Immunotherapy, 15: 42-52, Jan. 1994, 11 pages.
Kim et al., "Antibody Engineering for the Development of Therapeutic Antibodies," Molecules and Cells, vol. 20, No. 1, Aug. 2005, 13 pages.
Kipriyanov and Le Gall, "Generation and Production of Engineered Antibodies," Molecular Biotechnology, vol. 26, Jan. 2004, 22 pages.
Kipriyanov, "Generation of antibody molecules through antibody engineering," Methods Mol Biol 207:3-25, 2003, 23 pages.
Knauf et al., "Relationship of effective molecular size to systemic clearence in rats of recombinant interleukin-2 chemical modified with water-soluable polymers," The Journal of Biological Chemistry, vol. 263, No. 29, Issue of Oct. 15, 1988, 7 pages.
Knight et al., "4991W93 inhibits release of calcitonin gene-related peptide in the cat but only at doses with 5HT1B/1D receptor agonist activity," Neuropharmacology 40:520-525, Mar. 2001, 6 pages.
Knight et al., "Pharmacodynamic Enhancement of the Anti-Platelet Antibody Fab Abciximab by Site-Specific Pegylation," Platelets 15(7), Nov. 2004, 11 pages.
Knudsen et al., "Chapter 5: Morphology, Physiology and Pathophysiology of the brain barrier," in Basic Mechanisms of Migraine, 1988, 12 pages.
Kobayashi et al., "Tryptophan H33 plays an important role in pyrimidine (6-4) pyrimidone photoproduct binding by a high-affinity antibody," Protein Eng 12(10):879-884, Oct. 1999, 6 pages.
Kobeissy, "Chapter 13: Characterization and Management of Headache after Mild Traumatic Brain Injury," Brain Neurotrauma: Molecular, Neuropsychological, and Rehabilitation Aspects. Boca Raton (FL):CRC Press/Taylor & Francis, 2015, 13 pages.
Kohler and Milstein, "Continuous cultures of fused cells secreting antibody of predefined specificity," Nature 256(5517):495-497, Aug. 7, 1975, 3 pages.
Kraljevic et al., "Accelerating drug discovery," European Molecular Biology Organization (EMBO) reports, 5(9): 837-842, Sep. 2004, 6 pages.
Kretschmer et al., "Antibody Isotypes for Tumor Immunotherapy," (2017) Transfus Med Hemother, 44(5): 320-326, Sep. 2017, 7 pages.
Krogsgaard-Larsen et al., "Textbook of Drug Design and Discovery," p. 7-8, Taylor and Francis, 2002, 4 pages.
Kruit et al., "Brain stem and cerebellar hyperintense lesions in migraine," Stroke 37:1109-1112, Feb. 2006, 4 pages.
Kruit et al., "Iron accumulation in deep brain nuclei in migraine: a population-based magnetic resonance imaging study," Cephalalgia 29:351-359, Mar. 2009, 14 pages.
Kruit et al., "Migraine as a Risk Factor for Subclinical Brain Lesions," JAMA vol. 291: 427-434, Jan. 28, 2004, 8 pages.
Kruit et al., "Migraine as a risk factor for white matter lesions, silent infarctions, and ischemic stroke: the evidence for a link," Headache Currents, vol. 2, No. 3:62-71, Jun. 2005, 9 pages.
Kruit et al., "MRI findings in migraine," Revue Neurologique 161,6/7:661-666, 2005, 5 pages.
Kruuse et al., "Plasma levels of CAMP, cGMP and CGRP in sildenafil-induced headache," Cephalalgia 24(7):547-553, Jul. 2004, 7 pages.
Kumar et al., "Molecular cloning and expression of the Fabs of human autoantibodies in *Escherichia coli*. Determination of the heavy or light chain contribution to the anti-DNA/-cardiolipin activity of the Fab," J Biol Chem 275(45):35129-35136, Nov. 10, 2000, 8 pages.
Kuraishi et al., "Antinociception induced in rats by intrathecal administration of antiserum against calcitonin gene-related peptide," Neurosci Lett 92(3):325-329, Oct. 17, 1988, 5 pages.
Kurosawa et al., "Increase of meningeal blood flow after electrical stimulation of rat dura mater encephali: mediation by calcitonin gene-related peptide," British Journal of Pharmacology 114:1397-1402, Apr. 1995, 6 pages.
Kurth et al., "Migraine and Risk of Cardiovascular Disease in Women," JAMA vol. 296(3), Jul. 19, 2006, 10 pages.
Kussie, "A single engineered amino acid substitution changes antibody fine specificity", J Immunol 152(1):146-152, Jan. 1994, 7 pages.
Lambru et al., "A prospective real-world analysis of erenumab in refractory chronic migraine," The Journal of Headache and Pain, Jun. 2020, 21(61):10 pages.
Lanteri-Minet et al., "Patient-reported outcomes in chronic migraine patients with prior prophylactic treatment failure receiving placebo or erenumab: Subgroup analysis of a pivotal randomised study," Cephalalgia, 2018, 38(1 Suppl):49-50.
Lassen et al., "CGRP may play a causative role in migraine," Cephalalgia 22(1):54-61, Feb. 2002, 8 pages.
Lassen et al., "Comorbidity," Poster Presentations, Cephalagia 23:581-762, 2003, 1 page.

(56) References Cited

OTHER PUBLICATIONS

Lassen et al., "Involvement of calcitonin gene-related peptide in migraine: regional cerebral blood flow and blood flow velocity in migraine patients," J Headache Pain 9(3):151-157, Jun. 2008, 7 pages.
Lassen et al., "Nitric oxide synthase inhibition in migraine," Lancet, vol. 349, Feb. 1997, 2 pages.
Laukkanen et al., "Hevein-specific recombinant IgE from human single-chain antibody phage display libraries," Journal of Immunological Methods, vol. 278:271-281, Jul. 2003, 11 pages.
Launer et al., "The prevalence and characteristics of migraine in a population-based cohort, the GEM study, " Neurology vol. 53: 537-542, Aug. 1999, 17 pages.
Lauritzen, "Pathophysiology of the migraine aura: The spreading depression theory," Oxford University Press, Feb. 1994, 12 pages.
Leavy, "Therapeutic antibodies: past, present and future," Nature Reviews: Immunology 10(5):297, May 2010, 1 pages.
Léger et al., "Humanization of a Mouse Antibody against Human Alpha-4 Integrin: A Potential Therapeutic for the Treatment of Multiple Sclerosis," Human Antibodies vol. 8: 3-16, Mar. 1, 1997, 14 pages.
Lenz et al., "Prevention of episodic migraine with AMG 334, a human anti-calcitonin gene-related peptide receptor monoclonal antibody: Phase 2 study results and 52-week analysis of openlabel extension," Neurology, Apr. 2016, 86:16(Suppl 1): 7 pages.
Lenz et al., "Results of a randomized, double-blind, placebocontrolled, phase 2 study to evaluate the efficacy and safety of AMG 334 for the prevention of episodic migraine," Cephalalgia, May 2015, 35:6(Suppl 1):5.
Lenzer et al., "FDA advisers warn: COX2 inhibitors increase risk of heart attack and stroke," BMJ, vol. 330, Feb. 26, 2005, 1 page.
Letter from Patentee's representative dated Feb. 12, 2013, 4 pages.
Levine and Taiwo, "Inflammatory pain," Textbook of Pain, pp. 45-56, 1994, 17 pages.
Levy et al., "Calcitonin Gene-Related Peptide Does Not Excite or Sensitize Meningeal Nociceptors: Implications for the Pathophysiology of Migraine," Annal Neurol 58(5):698-705, Nov. 2005, 8 pages.
Levy et al., "Disruption of communication between peripheral and central trigeminovascular neurons mediates the antimigraine action of 5HT1B/1D receptor agonists," PNAS 101(12):4274-4279, Mar. 23, 2004, 6 pages.
Levy et al., "Octreotide is not effective in the acute treatment of migraine," Cephalalgia 25:48-55, Jan. 2005, 8 pages.
Levy et al., "Current understanding of megingeal and cerebral vascular function underlying migraine headache," Cephalalgia, pp. 1-17, Jan. 2018, 17 pages.
Li and Schwartz, "The TNFa transgenic mouse model of inflammatory arthritis," Springer Seminars in Immunopathology, Aug. 2003, 15 pages.
Li et al., "Calcitonin gene-related peptide stimulation of nitric oxide synthesis and release from trigeminal ganglion glial cells," Brain Res 1196:22-32, Feb. 27, 2008.
Li et al., "Valproate ameliorates nitroglycerin-induced migraine in trigeminal nucleus caudalis in rats through inhibition of NF-KB," Journal of Headache and Pain, Springer Verlag italia, Milan, IT, vol. 17, No. 1, May 6, 2016, 9 pages.
Lin et al., "Preclinical pharmacokinetics, interspecies scaling and tissue distribution of a humanized monoclonal antibody against vascular endothelial growth factor," Journal of Pharmacology and Experimental Therapeutics, 288:371-378, Jan. 1999, 8 pages.
Lipinski et al., "Experimental and computational approaches to estimate solubility and permeability in drug discovery and development settings," Advanced Drug Delivery Reviews, vol. 23: 3-25, Jan. 1997, 24 pages.
Lipton and Stewart, "Acute migraine therapy: do doctors understand what patients with migraine want from therapy," Headache vol. 39, Suppl. 2: S20-S26, Aug. 1999, 7 pages.
Lipton et al., "75% responder rates provide improvement in HIT6 scores from week 4 through 12 following a single infusion of ALD403, or placebo," Neurology, Apr. 2017, 88(16 Suppl):7 pages.
Lipton et al., "Classification of primary headaches," Journal of Neurology, vol. 63, Views and Reviews, Aug. 2004, 9 pages.
Lipton et al., "Double-blind clinical trials of oral triptans versus other classes of acute migraine medication," Cephalalgia 24:321-332, May 2004, 12 pages.
Lipton et al., "Eager for better migraine therapies", Neurology 83:954-955, Sep. 9, 2014, 3 pages.
Lipton et al., "How treatment priorities influence triptan preferences in clinical practice: perspectives of migraine sufferers, neurologists, and primary care physicians," Current Medical Research and Opinion 21:413-424, Mar. 2005, 12 pages.
Lipton et al., "Migraine practice patterns among neurologists," Neurology, Jun. 2004, 7 pages.
Lipton et al., "Migraine prevalence, disease burden, and the need for preventive therapy", Neurology. 68(5):343-9, Jan. 30, 2007, 8 pages.
Lipton et al., "Migraine. Identifying and removing barriers to care," Neurology vol. 44, Suppl. 4, S63-S68, Jun. 1994, 6 pages.
Lipton et al., "Moving Forward - Essential Questions for the Next 10 Years," Headache 49: S43-S46, Feb. 2009, 4 pages.
Lipton et al., "Patient-reported outcomes in patients with chronic migraine receiving placebo or erenumab (AMG 334) in a phase 2, randomised, double-blind study," Journal of Headache and Pain, Nov. 2017, 18(Suppl 1):70-71.
Lipton et al., "Patient-reported outcomes in patients with chronic migraine receiving placebo or erenumab (AMG 334) in a phase 2, randomized, double-blind study," Headache, Jun. 2017, 57(Suppl 3):198.
Lipton et al., "Responders to ALD403 (eptinezumab) show significant reduction in headache impact at weeks 4 through 12 following a single infusion in chronic migraine, " Headache, Jun. 2017, 57(Suppl 3):176-177.
Lipton et al., "The impact of fremanezumab on migraine-specific health-related quality of life and overall health status in chronic migraine," Journal of Headache and Pain, Nov. 2017, 18(Suppl 1):46.
Lipton et al., "The impact of fremanezumab on migraine-specific health-related quality of life in episodic migraine," Journal of Headache and Pain, Nov. 2017, 18(Suppl 1):73-74.
Lipton et al., "The impact of fremanezumab on migraine-specific health-related quality of life in episodic migraine," Neurology, Apr. 2018, 90(15 Suppl. 1): 6 pages.
Lipton et al., "The positive impact of fremanezumab on work productivity and activity impairment in patients with chronic migraine," Journal of Headache and Pain, Nov. 2017, 18(Suppl 1):74-75.
Lipton et al., "The role of headache-related disability in migraine management," Neurology 56(Supp 1):S35-S42, 2001, 8 pages.
Lipton et al., "Treatment preferences and the selection of acute migraine medications: results from a population-based survey," Journal of Headache Pain, vol. 5, Issue 2, Aug. 2004, 8 pages.
Lipton et al., "Why headache treatment fails?" Neurology 60:1064-1070, Apr. 2003, 7 pages.
Lipton, "CGRP antagonists in the acute treatment of migraine", The Lancet Neurology 3:332, Jun. 2004, 1 page.
Little et al., "Of mice and men: hybridoma and recombinant antibodies, " Immunol Today 21(8):364-370, Aug. 2000, 7 pages.
Lodish et al., "Molecular Cell Biology," 5th Edition, W.H. Freeman and Company, pp. 537-539, 2004, 4 pages.
Longmore et al., "5-HT1D receptor agonists and human coronary artery reactivity in vitro" crossover comparisons of 5-HT and sumatriptan with rizatriptan and L-741,519, Br J Clin Pharmacol 42:431-441, 1996, 11 pages.
Longmore et al., "Comparison of the vasoconstrictor effects of the selective 5-HT1D-receptor agonist L-775,606 with the mixed 5-HT1B/1D-receptor agonist sumatriptan and 5-HT in human isolated coronary artery," J Clin Pharmacol 49:126-131, 2000, 6 pages.
Longmore et al., "Effects of two truncated forms of human calcitonin-gene related peptide: implications for receptor classification," European Journal of Pharmacology 265:53-59, Nov. 1994, 7 pages.
Longstreth et al., "Functional bowel disorders," Gastroenterology 130(5):1480-1491, Apr. 2006, 15 pages.

(56) References Cited

OTHER PUBLICATIONS

Louis et al., "Antibodies to calcitonin-gene related peptide reduce inflammation induced by topical mustard oil but not that due to carrageenin in the rat," Neurosci Lett 102(2-3):257-260, Jul. 31, 1989, 4 pages.
Louis et al., "The role of substance P and calcitonin gene-related peptide in neurogenic plasma extravasation and vasodilatation in the rat," Neuroscience 32(3):581-586, 1989, 6 pages.
Lu et al., "Evidence for calcitonin gene-related peptide-mediated ischemic preconditioning in the rat heart," Regulatory Peptides, 82: pp. 53-57, 1999.
Lu et al., "Mice Lacking α-Calcitonin Gene-Related Peptide Exhibit Normal Cardiovascular Regulation and Neuromuscular Development," Molecular & Cellular Neuroscience (1999) 14: 99-120.
Lucas, "Posttraumatic Headache: Clinical Characterization and Management," Curr Pain Headache Rep 19:48, Aug. 18, 2015, 9 pages.
Luykx et al., "Are migraineurs at increased risk of adverse drug responses ?: A meta-analytic comparison of topiramate-related adverse drug reactions in epilepsy and migraine," Clinical Pharmacology & Therapeutics, vol. 85, No. 3, Mar. 2009, 6 pages.
Ma et al., "Colocalization of CGRP with 5-HT 1B/1D receptors and substance P in trigeminal ganglion neurons in rats," European Journal of Neuroscience 13:2099- 2104, Jun. 2001, 6 pages.
Maassen VanDenBrink et al., "5-HT1B-receptor polymorphism and clinical response to sumatriptan," Headache, vol. 38:288-91, Apr. 1998, 4 pages.
Maassen VanDenBrink et al., "Augmented contraction of the human isolated coronary artery by sumatriptan: a possile role for endogenous thromboxane," British Journal of Pharmacology, vol. 119:855-62, Nov. 1996, 8 pages.
Maassen VanDenBrink et al., "Calcitonin gene-related peptide (receptor) antibodies: an exciting avenue for migraine treatment," Genome Medicine 10(10), Feb. 2018, 3 pages.
Maassen VanDenBrink et al., "Wiping out CGRP: Potential Cardiovascular Risks," Trends in Pharmacological Sciences 37(9):779-788, Sep. 2016, 10 pages.
MabCampath® (alemtuzumab), "Scientific Discussion," EMEA 2005, 22 pages.
MacCallum et al., "Antibody-antigen interactions: contact analysis and binding site topography," J Mol Biol 262(5): 732-745, Oct. 11, 1996, 14 pages.
MacEwan, "TNF receptor subtype signaling differences and cellular consequences," Cell Signal vol. 14, 477-492, Jun. 2002, 16 pages.
MacGregor et al., "Guidelines for All Healthcare Professionals in the Diagnosis and Management of Migraine," British Association for the Study of Headaches (BASH), Sep. 2010, 53 pages.
Macolino et al., "Mechanical alloydnia induced by traumatic brain injury is inependent of restraint stress, " J Neurosci Meth 226:139-146, Apr. 15, 2014, 8 pages.
Maini and Feldmann, "How Does Infliximab Work in Rheumatoid Arthritis?" Arthritis Research, vol. 4, Suppl. 2, Mar. 27, 2002, 7 pages.
Malhothra, "Understanding migraine: Potential role of neurogenic inflammation," Ann Ind Acad Neurol. vol. 19 (2), Apr.-Jun. 2016, 12 pages.
Malik et al., "Research Submission—Acute migraine treatment: patterns of use and satisfaction in clinical population," Headache, May 2006, 8 pages.
Mallee et al., "Receptor activity-modifying protein 1 determines the species selectivity of non-peptide CGRP receptor antagonists," J Biol Chem 277(16): 14294-14298, Apr. 19, 2002, 8 pages.
Manack et al., "The Evolution of Chronic Migraine: Classification and Nomenclature", Headache 49:1206-1213, Sep. 2009, 8 pages.
Manack et al., "Chronic Migraine: Epidemiology and Disease Burden," Curr Pain Headache Rep 15:70-78, Feb. 2011, 9 pages.
Mankarious et al., "The half-lives of IgG subclasses and specific antibodies in patients with primary immunodeficiency who are receiving intravenously administered immunoglobulin," J Lab of Clinical Medicine, vol. 112, No. 5, Nov. 1988, 634-640, 7 pages.
Marks et al., "By-passing immunization. Human antibodies from V-gene libraries displayed on phage," J Mol Biol 222(3):581-597, Dec. 5, 1991, 17 pages.
Marks et al., "By-passing immunization: building high affinity human antibodies by chain shuffling," Biotechnol 10(7):779-783, Jul. 1992, 17 pages.
Marquez de Prado and Russo, "CGRP receptor antagonists: A new frontier of anti-migraine medications," Drug Discov Today Ther Strateg 3(4):593-597, 2006, 8 pages.
Marshall et al., "Human and rat alpha-CGRP but not calcitonin cause mesenteric vasodilatation in rats, " Eur J Pharmacol 123(2):217-222, Apr. 16, 1986, 6 pages.
Martinelletti et al., "The Global Campaign (GC) to reduce the burden of headache worldwide: The international team for specialist education (ITSE)," Journal of Headache Pain, vol. 6(4), Jul. 20, 2005, 3 pages.
Mason et al., "Induction of Migraine-Like Photophobic Behaviour in Mice by Both Peripheral and Central CGRP Mechanisms", The Journal of Neuroscience 37(1):204-216, Jan. 4, 2017, 13 pages.
Mason et al., "Vascular Contributions to Migraine: Time to Revisit?" Front Cell Neurosci, vol. 12, Article 233, Aug. 2018, 10 pages.
Mason et al., "Release of the Predicted Calcitonin Gene-Related Peptide from Cultured Rat Trigeminal Ganglion Cells," Nature vol. 308: 653-655, Apr. 1984, 3 pages.
Matharu and Goadsby, "Trigeminal autonomic cephalalgias," J Neurol Neurosurf Psychiatry 72)Suppl II):ii19-ii26, 2002, 8 pages.
Matharu et al., "Verapamil-induced gingival enlargement in cluster headache," Journal of Neurology, Neruosurgery, and Psychiatry 76:124-127, Jan. 2005, 4 pages.
May et al., "EFNS guidelines on the treatment of cluster headache and other trigeminalautonomic cephalalgias," European Journal of Neurology 13:1066-1077, Oct. 2006, 12 pages.
May et al., "PET and MRA findings in cluster headache and MRA in experimental pain," Neurology 55:1328-1335, Nov. 2000, 8 pages.
May et al., "Retinal plasma extravasation in animals but not in humans: implications for the pathophysiology of migraine," Brain, 121(7): pp. 1231-1237, 1998.
May, "Cluster headache: pathogenesis, diagnosis, and management," Lancet 366:843-855, 2005, 13 pages.
Maynard and Georgiou, "Antibody Engineering," Annu. Rev. Biomed. Eng. 2: 339-376, 2000, 38 pages.
McAllister et al., "Efficacy of Fremanezumab in Migraine Patients Who Have Failed at Least One Prior Migraine Preventive Medication," Poster P1.011 Presented at American Academy of Neurology 71st Annual Meeting, Philadelphia, Pennsylvania, May 4-10, 2019, 1 page.
McAllister et al., "Efficacy of fremanezumab in migraine patients who have failed at least one prior migraine preventive medication," The Journal of Headache and Pain, 2018, 19(Suppl 1):38.
McAllister, "Monoclonal Antibodies and Migraine: What the Neurologists Need to Know," Pratical Neurology, May 2017, 5 pages.
McCafferty et al., "Phage antibodies: filamentous phage displaying antibody variable domains, " Nature 348(6301):552-554, Dec. 6, 1990, 3 pages.
McCarthy et al., "Osteoarthritis," Textbook of Pain, pp. 387-395, 1994, 15 pages.
McCulloch et al., "Calcitonin gene-related peptide: Functional role in cerebrovascular regulation," Proc Natl Acad Sci USA 83:5731-5735, Aug. 1986, 5 pages.
McLatchie et al., "RAMPs regulate the transport and ligand specificity of the calcitoninreceptor-like receptor," Nature 393(6683):333-339, May 28, 1998, 7 pages.
Medhurst et al., "A rat model of bone cancer pain," Pain 96(1-2):129-140, Mar. 2002, 12 pages.
Meenan et al., "The arthritis impact measurement scales. Further investigations of a health status measure," Arthritis Rheum 25(9):1048-1053, Sep. 1982, 6 pages.
Melo-Carrillo et al., "Fremanezumab: a humanized monoclonal anti-CGRP antibody-inhibits thinly myelinated but not unmyelinated (C) meningeal nociceptors", Journal of Neuroscience 37(30):7149-7163, Jul. 2017, 32 pages.

(56) References Cited

OTHER PUBLICATIONS

Melo-Carrillo et al., "Selective Inhibition of Trigeminovascular Neurons by Fremanezumab: A Humanized Monoclonal Anti-CGRP Antibody," The Journal of Neuroscience: The Official Anti-CGRP Antibody, Journal of Neuroscience: The Official Journal of the Society for Neuroscience, vol. 37, No. 30, Jul. 26, 2017, 15 pages.
Mense, "Pathophysiology of low back pain and the transition to the chronic state - experimental data and new concepts," Schmerz 15(6):413-417, Dec. 2001, Article in German, 5 pages.
Merck manual., Pain, 17th Ed. p. 1367, #167. (in Japanese with Engish translation), 1999, 5 pages.
Merskey et al., "Classification of Chronic Pain, Descriptions of Chronic Pain Syndromes and Definitions of Pain Terms," IASP Task Force on Taxonomy 1994. 2nd Edition. 238 pages.
Messlinger et al., "Abstracts of the XII Congress of the International Headache Society/ IHC 2005," Cephalalgia, Believe in Headache Relief, IHC 2005 Kyoto, Oct. 2005, 193 pages.
Messlinger et al., "Inhibition of neurogenic blood flow increases in the rat cranial dura mater by a CGRP-binding Spiegelmer," Cephalalgia 25:923, Oct. 2005, 3 pages.
Messlinger et al., "Poster—Inhibition of neurogenic blood flow increases in the rat cranial dua mater by a CGRP-binding Spiegelmer," Cephalalgia 25:923, Oct. 2005, 1 page.
Michelson et al., "Lack of efficacy of L-759274, a novel neurokinin 1 (substance P) receptor antagonist, for the treatment of generalized anxiety disorder," International Journal of Neuropsychopharmacology 16(1):1-11, Feb. 2013, 11 pages.
Miller et al., "A controlled trial of Natalizumab for Relapsing Multiple Sclerosis," New England Journal of Medicine, vol. 348, 2003, 15-23, 9 pages.
Miller et al., "Evaluation of treatment-emergent anti-drugantibodies following administration of LY2951742, a calcitonin gene related peptide antibody, to migraine patients, " Headache (2016) 56 SUPPL. 1 (68-69). Date of Publication: Jun. 2016.
Mironov et al., "Cystolic Prion Protein in Neurons," Journal of Neurosci. vol. 23, No. 18, 2003, 7183-7193, 11 pages.
Mitsikostas et al., "New players in the preventive treatment of migraine," BMC Medicine, vol. 13, No. 1, Nov. 10, 2015, 7 pages.
Miyamoto et al., "Heparin-Binding EGF-Like Growth Factor Is a Promising Target for Ovarian Cancer Therapy," Cancer Research (2004) 64: 5720-5727.
Moore and Salvatore, "Targeting a family B GPCR/RAMP receptor complex: CGRP receptor antagonists and migraine," Brit J Pharmacol 166(1):66-78, Apr. 10, 2012, 13 pages.
Morara et al., "Calcitonin Gene-Related Peptide Receptor Expression in the Neurons and Glia of Developing Rat Cerebellum: An Autoradiographic and Immunohistochemical Analysis," Neuroscience 100(2):381-391, 2000, 11 pages.
Morell et al., "Metabolic properties of IgG subclasses in man," J Clin Invest 49(4):673-680, Apr. 1970, 8 pages.
Moreno et al., "Efficacy of the non-peptide antagonist BIBN4096BS in blocking CGRP-induced dilations in human and bovine cerebral arteries," Neuropharmacology 42(4):568-576, Mar. 2002, 9 pages.
Morrison et al., "Chimeric human antibody molecules: Mouse antigen-binding domains with human constant region domains," Proceedings of the National Academy of Science, USA, vol. 81(21), Nov. 1984, 6851-6855, 5 pages.
Moskowitz, "Interpreting vessel diameter changes in vascular headaches," Cephalalgia, Feb. 1992, 5-7, 3 pages.
Moskowitz, "Neurogenic versus vascular mechanisms of sumatriptan and ergot alkaloids in migraine", Trends in Pharmacological Sciences 13(8):307-311, Aug. 1992, 5 pages.
Mulderry et al., "Differential expression of alpha-CGRP and beta-CGRP by primary sensory neurons and enteric autonomic neurons of the rat," Neuroscience 25(1):195-205, Apr. 1988, 11 pages.
Mulleners et al., "Safety and efficacy of galcanezumab in patients for whom previous migraine preventive medication from two to four categories had failed (CONQUER): a multicentre, randomised, double-blind, placebo-controlled, phase 3b trial, " Lancet Neurol, Oct. 2020, 19:814-825.

Mullins et al., "Characterization of a calcitonin gene-related peptide (CGRP) receptor on mouse bone marrow cells," Regul Pept 49(1):65-72, Nov. 19, 1993 (Abstract only), 1 page.
Nakamura-Craig and Gill, "Effect of neurokinin A, substance P and calcitonin gene related peptide in peripheral hyperalgesia in the rat paw," Neurosci Lett 124(1):49-51, Mar. 11, 1991, 3 pages.
National Cancer Institute, "Efficacy," retrieved on Jun. 27, 2019, retrieved from URL <https://www.cancer.gov/publications/dictionaries/cancer-terms/def/efficacy>, 1 page.
Negro et al., "A two years open-label prospective study of OnabotulinumtoxinA 195 U in medication overuse headache: a real-world experience," Journal of Headache and Pain, 2016, 17(1):1-9.
Nestorov, "Clinical pharmacokinetics of tumor necrosis factor antagonists," The Journal of Rheumatology 74:13-18, Mar. 2005, 7 pages.
nice.org.uk [online], "Erenumab for preventing migraine [ID1188]," National Institute for Health and Care Excellence, Jan. 2019, retrieved Oct. 16, 2020, retrieved from URL <https://www.nice.org.uk/guidance/gid-ta10302/documents/committee-papers-2>, 361 pages.
nice.org.uk [online], "Galcanezumab for preventing migraine: Lead team presentation," Oct. 15, 2020, retrieved Nov. 10, 2020, retrieved from URL <https://www.nice.org.uk/guidance/gid-ta10454/documents/1>, 26 pages.
nice.org.uk [online], "National Institute for Health and Care Excellence, Final appraisal document, Galcanezumab for preventing migraine," Oct. 15, 2020, retrieved Nov. 10, 2020, retrieved from URL <https://www.nice.org.uk/guidance/gid-ta10454/documents/final-appraisal-determination-document>, 22 pages.
nice.org.uk [online], "Single Technology Appraisal, Galcanezumab for preventing migraine [ID1372], Committee Papers," Oct. 15, 2020, retrieved Nov. 10, 2020, retrieved from URL <https://www.nice.org.uk/guidance/gid-ta10454/documents/committee-papers>, 578 pages.
Nilsson et al., "Placebo response rates in cluster headache trials, a review," Cephalalgia 23:504-510, Sep. 2003, 7 pages.
Noble et al., "Fremanezumab increases the maximum No. of consecutive headache free days for patients with high frequency episodic migraine," Headache, Jun. 2017, 57(Suppl 3):185.
Noble et al., "Fremanezumab increases the maximum number of consecutive headache free days for patients with high frequency episodic migraine," Journal of Headache and Pain, Nov. 2017, 18(Suppl 1):39.
Noble et al., "Treatment-induced improvement in migraine classification in the fremanezumab HFEM Study," Journal of Headache and Pain, Nov. 2017, 18(Suppl 1):71.
Norman et al., "A placebo-controlled, in-clinic study to explore the preliminary safety and efficacy of intravenous L-758,298 (a prodrug of the NK1 receptor antagonist L-754,030) in the acute treatment of migraine," Cephalalgia 18, Poster Presentations, 1998, 1 page.
Notice from the European Patent Office dated Oct. 2, 2015, concerning the staying of proceedings due to referral G 1/15, 2 pages.
Notice of Opposition to European Patent No. EP3045182 B1, European Application No. 16154418.4 on Dec. 7, 2018, 43 pages.
Nyholt et al., "A high-density association screen of 155 ion transport genes for involvement with common migraine," Human Molecular Genetics, 17: 3318-3331, Nov. 2008, 14 pages.
Oakes et al., "Efficacy and safety of LY2951742 in a randomized, double-blind, placebo-controlled, dose-ranging study in patients with migraine," Headache, Jun. 2016, 56(Suppl 1):68.
Oakes et al., "Efficacy and safety of LY2951742 in a randomized, double-blind, placebo-controlled, dose-ranging study in patients with migraine," Postgraduate Medicine, 2016, 128(Suppl 2):103-104.
Oakes et al., "Safety and tolerability of galcanezumab in a phase 2 migraine prevention study," Headache, Jun. 2017, 57(Suppl 3):190-191.
O'Connell et al., "On the role of the C-terminus of α-calcitonin-gene-related peptide (αCGRP) The Structure of des-phenylalaninamide$^{37}$-αCGRP and it's interaction with the CGRP receptor," Biochem J 291:205-210, 1993, 6 pages.
Odink et al., "F229: Plasma aminoacids in common and classic migraine and tension headache," Neurochemistry Int., 13,suppl. 1:155-56, 1988, 1 pages.

(56) References Cited

OTHER PUBLICATIONS

Olesen (and the First Headache Classification Subcommittee Members), "The International Classification of Headache Disorders: 2rd Edition," Blackwell Publishing, 2004, 150 pages.
Olesen and Ashina, "Emerging migraine treatments and drug targets," Trends Pharmacol Sci 32(6):352-359, Jun. 2011, 8 pages.
Olesen and Goadsby, "The Headaches: Third Edition," Chapters 2, 9, 10, 16, 22, 28, 30, 31, 33, 47, 48, 49, 50-60, 2005, 259 pages.
Olesen and Hargreaves, "CGRP Involvement in Migraines," The Headaches, Lippincott Williams & Wilkins, Chapter 31, pp. 289-299, Oct. 1, 2005, 13 pages.
Olesen et al., "Brief Report—New appendix criteria open for a broader concept of chronic migraine," Cephalalgia 26: 742-746, Jun. 2006, 5 pages.
Olesen et al., "Calcitonin gene-related peptide receptor antagonist BIBN 4096 BS for the acute treatment of migraine," N Eng J Med 350(11):1104-1110, Mar. 11, 2004, 7 pages.
Olesen et al., "Origin of pain in migraine: evidence for peripheral sensitisation," Lancet Neruol 8(7):679-690, Jul. 2009, 12 pages.
Olesen et al., "The International Classification of Headache Disorders, 3rd edition (beta version)," Headache Classification Committee of the International Headache Society, Cephalalgia, Jul. 2013, 180 pages.
Olesen et al., "The Peptidergic Innervation of the Human Superficial Temporal Artery: Immunohistochemistry, Ultrastructure and Vasomotility," Peptides, vol. 16, No. 2, pp. 275-287, 1995, 13 pages.
Olesen et al., "Timing and Topography of Cerebral Blood Flow, Aura, and the Headache during Migraine Attacks," Ann Neurol. Vol. 28, No. 6, Dec. 1990, 791-798, 8 pages.
Olesen et al., "S26 CGRP Antagonism as a New Therapeutic Principle in Acute Migraine," Neuropeptides 38: 110-131, No. 2-3, Apr./Jun. 2004, 6 pages.
Olesen, "CGRP in migraine," Cephalalgia, letter to the editor, 2011, 31(5):638, 1 page.
Olesen, "Chapter 11: Chronic migraine," in Classification and Diagnosis of Headache Disorders, Oxford University Press 2005, 8 pages.
Olesen, "In-depth characterization of CGRP receptors in human intracranial arteries," European Journal of Pharmacology, vol. 481, Nov. 2003, 207-216, 10 pages.
Olesen, "The treatment of acute migraine," Rev Neurol (Paris) 161(6-7):679-680, Jul. 2005, 2 pages.
Oliver et al., "Immunohistochemical Localization of Calcitonin Receptor-Like Receptor and Receptor Activity-Modifying Proteins in the Human Cerebral Vasculature," Journal of Cerebral Blood Flow & Metabolism 22: 620-629, May 2002, 10 pages.
Oliver et al., "Distribution of novel CGRP1 receptor and adrenomedullin receptor mRNAs in the rat central nervous system," Molecular Brain Research 57: 149-154, Jun. 1998, 6 pages.
Oliver et al., "Regional and cellular localization of calcitonin gene-related peptide-receptor component protin mRNA in the guinea-pig central nervous system," Molecular Brain Research 66: 201-210, Mar. 1999, 6 pages.
Ophoff et al., "P/Q-type Ca2+ channel defects in migraine, ataxia and epilepsy," Trends in Pharmacological Sciences vol. 19:121-127, Apr. 1998, 7 pages.
Ophoff et al., "The impact of pharmacogenetics for migraine," European Journal of Pharmacology, vol. 413:1-10, Feb. 2001, 10 pages.
Opposition of Dec. 4, 2018 in European Patent No. EP3045182 B1, European Application No. 16154418.4 on Dec. 4, 2018, 19 pages.
Oshinsky et al., "Episodic dural stimulation in awake rats: a model for recurrent headache," Headache 47(7):1026-1036, Jul.-Aug. 2007, 17 pages.
Overington et al., "How many drug targets are there?" Nature Reviews: Drug Discovery 5(12):993-996, Dec. 2006, 4 pages.
Overy and Tansey, "Migraine: Diagnosis, Treatment and Understanding c.1960-2010," vol. 49, Queen Mary University of London, 2013, 149 pages.

Pacharinsak et al., "Animal models of cancer pain," Comp Med 58(3):220-233, Jun. 2008, 14 pages.
Paemeleire et al., "Efficacy of erenumab in subjects with episodic migraine with prior preventive treatment failure(s)," Journal of Headache and Pain, Nov. 2017, 18(Suppl 1):135-136.
Papadopoulos et al., "Binding and neutralization of vascular endothelial growth factor (VEGF) and related ligands by VEGF Trap, ranibizumab and bevacizumab," Angiogenesis 15(2):171-185, Jun. 2012, 15 pages.
Parameswaran et al., "Activation of multiple mitogen-activation protein kinases by recombinant calcitonin gene-related peptide receptor," European Journal of Pharmacology, vol. 389(2-3): 125-30, Feb. 2000, 6 pages.
Pardridge, "CNS Drug Design Based on Principles of Blood-Brain Barrier Transport," Journal of Neurochemistry, vol. 70 No 5, 1781-1792, May 1998, 12 pages.
Pardridge, "The Blood-Brain Barrier: Bottleneck in Brain Drug Development," NeuroRx: The Journal of American Society for Experimental NeuroTherapeutics, vol. 2, 3-14, Jan. 2005, 12 pages.
Park et al., "Alteration of cancer pain-related signals by radiation: proteomic analysis in an animal model with cancer bone invasion," Int J Radiation Oncol Biol Phys 61(5):1523-1534, Apr. 2005, 12 pages.
Parsons et al., "Tonabersat (SB-220453) a novel benzopyran with anticonvulsant properties attenuates trigeminal nerve-induced neurovascular reflexes," British Journal of Pharmacology 132:1549-1557, Apr. 2001, 9 pages.
Pascual et al., "Analysis of injection site reactions across four placebo controlled trials of erenumab for migraine prevention," Journal of Headache and Pain, Nov. 2017, 18(Suppl 1):40.
Pascual et al., "Effect of erenumab on patient-reported outcomes in episodic migraine patients with prior prophylactic treatment failure: Results from a post hoc analysis of the strive study," Cephalalgia, Sep. 2018, 38 (1S):47-48.
Pascual et al., "Effect of erenumab on patient-reported outcomes in episodic migraine patients with prior prophylactic treatment failure: Results from a post-hoc analysis of the STRIVE study, " Headache, Jun. 2018, 58(Suppl. 2):179-180.
Paulus et al., "Analysis of improvement in individual rheumatoid arthritis patients treated with disease-modifying antirheumatic drugs, based on the findings in patients treated with placebo. The Cooperative Systematic Studies of Rheumatic Diseases Group," Arthritis Rheum 33(4):477-484, Apr. 1990, 8 pages.
Paus and Winter, "Mapping epitopes and antigenicity by site-directed masking", PNAS 103 (24):9172-9177, Jun. 13, 2006, 6 pages.
PCT International Preliminary Report on Patentability in International Appln. No. PCT/IB2017/055776, mailed Apr. 4, 2019, 9 pages.
PCT International Preliminary Report on Patentability in International Appln. No. PCT/IB2017/055777, mailed Apr. 4, 2019, 8 pages.
Pellesi et al., "Spotlight on Anti-CGRP Monoclonal Antibodies in Migraine: The Clinical Evidence to Date," Clinical Pharmacology in Drug Development 6(6):534-547, Nov. 2017, 14 pages.
Pendergrast et al., "Nucleic Acid Aptamers for Target Validation and Therapeutic Applications," J. Biomolecular Techniques (2005) 16: 224-234.
Peroutka, "Neurogenic Inflammation and Migraine: Implications for Therapeutics," Mol Interv 5(5):304-311, Oct. 2005, 8 pages.
Peskar et al., "A monoclonal antibody to calcitonin gene-related peptide abolishes capsaicin-induced gastroprotection," Eur J Pharmacol 250(1):201-203, Nov. 30, 1993, 3 pages.
Peterlin et al., "Posttaumatic Stress Disorder in Migraine," Headache, Research Submission, Apr. 2009, 541-551, 11 pages.
Petersen et al., "BIBN4096BS Antagonizes Human α-calcitonin Gene Related Peptide-induced Headache and Extracerebral Artery Dilatation," Clin Pharmacol Ther 77(3):202-213, Mar. 7, 2005, 12 pages.
Petersen et al., "Effect of hypotension and carbon dioxide changes in an improved genuine closed cranial window rat model," Cephalalgia 25(1):23-29, Jan. 2005, 7 pages.

(56) References Cited

OTHER PUBLICATIONS

Petersen et al., "Inhibitory effect of BIBN4096BS on cephalic vasodilatation induced by CGRP or transcranial electrical stimulation in the rat, " Brit J Pharmacol 143(6):697-704, Nov. 2004, 8 pages.

Petersen et al., "Presence and function of the calcitonin gene-related peptide receptor on rat pial arteries investigated in vitro and in vivo," Cephalalgia 25(6):424-432, Jun. 2005, 9 pages.

Petersen et al., "The CGRP-antagonist, BIBN4096BS does not affect cerebral or systemic haemodynamics in healthy volunteers," Cephalalgia 25(2):139-147, Feb. 2005, 9 pages.

Petersen et al., "The effect of the nonpeptide CGRP-antagonist, BIBN4096BS on human-alpha CGRP induced headache and hemodynamics in healthy volunteers," Cephalagia 23:725, 2003, 1 page.

Petitti et al., "Incidence of Stroke and Myocardial Infarction in Women of Reproductive Age," Stroke (1997) 28: 280-283.

Pietrobon and Striessnig, "Neurobiology of Migraine," Nature Reviews Neuroscience, 2003, 4:386-398.

Pietrobon et al., "Pathophysiology of migraine," Annual Review of Physiology 75:365-391, 2013, 30 pages.

Pietrobon, "Migraine: New Molecular Mechanisms," The Neuroscientist 11(4):373-386, Aug. 2005, 14 pages.

Pilgrim, "Methodology of Clinical Trials of Sumatriptan in Migraine and Cluster Headache, " European Neurology 31(5):295-299, 1991, 5 pages.

Plessas et al., "Migraine-like episodic pain behavior in a dog: can dogs suffer from migraines?" J Vet Intern Med 27(5):1034-1040, Sep.-Oct. 2013, 7 pages.

Plourde et al., "Calcitonin gene-related peptide in viscerosensitive response to colorectal distension in rats," Am J Physiol 273(1 Pt 1):G191-G196, Jul. 1997, 7 pages.

Poduslo et al., "Macromolecular permeability across the blood-nerve and blood-brain barriers," PNAS, vol. 91:5705-5709, Jun. 1994, 5 pages.

Pollack, "F.D.A. Approves a Multiple Sclerosis Drug," New York Times, Nov. 24, 2004, 4 pages.

Pollack, "Pfizer to Buy Rinat, a Biotechnology Drug Maker," The New York Times, Apr. 7, 2006, 2 pages.

Pottier et al., "Rethinking the INN system for therapeutic antibodies," Mabs 9(1) 5-11, Jan. 2017, 7 pages.

Poyner et al., "CGRP receptors: beyond the CGRP(1)-CGRP(2) subdivision," Trends in Pharmacological Sciences, vol. 22, No. 5, May 2001, 1 page.

Poyner et al., "International Union of Pharmacology. XXXII. The Mammalian Calcitonin Gene-Related Peptides, Adrenomedullin, Amylin, and Calcitonin Receptors," Pharmacological Reviews 54(2):233-246, Jun. 2002, 14 pages.

Poyner et al., "Structural determinants for binding to CGRP receptors expressed by human SK-N-MC and col. 29 cells: studies with chimeric and other peptides," Brit J Pharmacol 124(8):1659-1666, Aug. 1998, 8 pages.

Poyner et al., "The CGRP Family: Calcitonin Gene-Related Peptide (CGRP), Amylin and Adrenomedullin," Molecular Biology Intelligence Unit 10, Chapters 1-7, and 15-16, 2000, 88 pages.

Poyner, "Calcitonin Gene-Related Peptide: Multiple actions, multiple receptors," Pharmacology & Therapeutics 56(1):23-51, Feb. 1992, 29 pages.

PR Newswire, "Labrys Biologics Secures $31 Million Series A Financing from Venture Capital Firms; Acquires Phase 2 Ready Antibody for Chronic Migraine from Pfizer," Jan. 3, 2013, retrieved on Jun. 28, 2019, retrieved from URL <https://www.prnewswire.com/news-releases/labrys-biologics-secures-31-million- series-a-financing-from-venture-capital-firms-acquiresphase-2-ready-antibody-for-chronic-migraine-from-pfizer-185522772.html>, 3 pages.

Presta, "Selection, Design, and Engineering of Therapeutic Antibodies," Journal of Allergy and Clinical Immunology, vol. 116, Issue 4, 731-736, Oct. 2005, 6 pages.

Prewett et al., "The biologic effects of C225, a chimeric monoclonal antibody to the EGFR, on human prostate carcinoma," J Immunother Emphasis Tumor Immunol 19(6):419-427, Nov. 1996, 9 pages.

Pringsheim, "Canadian Headache Society guideline for migraine prophylaxis," Canadian J Neruol Sci 36:S1-S2, Mar. 2012, 2 pages.

Projan et al., "Small Molecules for Small Minds? The Case for Biologic Pharmaceuticals," Expert Opinion Biol. Ther. 4:1345-1350, Aug. 2004, 7 pages.

Puledda et al., "An update on migraine current understanding and future directions," Journal of Neurology, vol. 264(9), Sep. 2017, 9 pages.

Purves et al., "Neuroscience: Third Edition," pp. 763-773, Sinauer Associates, Inc., 2004, 14 pages.

Qiao and Grider, "Up-regulation of calcitonin gene-related peptide and receptor tyroside kinase TrkB in rat bladder afferent neurons following TNBS," Experimental Neurology, vol. 204, Apr. 2004, 667-679, 13 pages.

Queen et al., "A Humanized Antibody that Binds to the Interleukin 2 Receptor," Proceedings of the National Academy of Sciences of the United States of America, vol. 86: 10029-10033, Dec. 1989, 5 pages.

Raddant and Russo, "Calcitonin gene-related peptide in migraine: intersection of peripheral inflammation and central modulation," published in final edited form in Expert Rev. Mol. Med., Nov. 2011, 13:e36, author manuscript published in Expert Rev. Mol. Med., Author Manuscript; available in PMC Jun. 26, 2012, 22 pages.

Raddant et al., "Calcitonin gene-related peptide in migraine: intersection of peripheral inflammation and central modulation", Expert Reviews in Molecular Medicine 13, Nov. 2011, 22 pages.

Rader et al., "Chemically Programmed Monoclonal Antibodies for Cancer Therapy: Adaptor Immunotherapy Based on a Covalent Antibody Catalyst," Proc. Natl. Acad. Science. USA, vol. 100, No. 9, pp. 5396-5400, Apr. 29, 2003, 5 pages.

Ramadan and Buchanan, "New and future migraine therapy," Pharmacology and Therapeutics, 112(1): 199-212, Oct. 2006, 14 pages.

Rang, "Pharmacology: 5th Edition," Chapters 2, 3, 9, 13, 31, Elsevier Science Limited, 2003, 76 pages.

Rapoport and Bigal, "Migraine Preventive Therapy: Current and Emerging Treatment Options," Neurol. Sci. (2005) 26: S111-S120.

Rapoport et al., "Naratriptan in the Preventive Treatment of Refractory Chronic Migraine: A Review of 27 Cases," Headache (2003) 43: 482-489.

Rapoport et al., "Which Triptan for Which Patient?," Neurol. Sci. (2006) 27: S123- S129.

Rapp et al., "Botulinum Toxin Type A Inhibits Cacitonin Gene-Related Peptide Release from Isolated Rat Bladder," Journal of Urology, American Urological Association, vol. 175, No. 1138-1142, Mar. 2006, 5 pages.

Ravetch et al., "Fc receptors," Annu Rev Immunol 9:457-492, 1991, 36 pages.

Ray and Wolff, "Experimental Studies of Headache," Archives of Surgery, vol. 41, No. 4, Oct. 1940, 813-856, 44 pages.

Recober and Goadsby, "Calcitonin gene-related peptide (CGRP): a molecular link between obesity and migraine?", Drug News Perspect 23(2):112-117, Mar. 2010, 9 pages.

Reff et al., "Depletion of B Cells in vivo by a Chimeric Mouse Human Monoclonal Antibody to CD20," Blood vol. 83, No. 2, 435-445, Jan. 15, 1994, 12 pages.

Regev et al., "Hepatic safety of galcanezumab in patients with migraine: Results of three Phase 2 doubleblind placebocontrolled trials," Neurology, Apr. 2017, 88:16(Suppl 1): 6 pages.

Reichert et al., "Monoclonal Antibody Successes in the Clinic," Nature Biotechnology 23(9): 1073-1078, Sep. 2005, 6 pages.

Reinshagen et al., "Calcitonin gene-related peptide mediates the protective effect of sensory nerves in a model of colonic injury," J Pharmacol Exp Ther 286(2):657-661, Aug. 1998, 5 pages.

Remicade (infliximab), "Prescribing Information," 5007 & 5090 Combined (clean copy): FDA Revisions on Dec. 13, 2004, 32 pages.

Reuter et al., "Early onset of efficacy with erenumab in a phase 2 clinical trial of subjects with chronic migraine," European Journal of Neurology, Jul. 2017, 24(Suppl 1):387.

(56) References Cited

OTHER PUBLICATIONS

Reuter et al., "Efficacy and safety of erenumab in episodic migraine patients with 2-4 prior preventive treatment failures: Results from the phase 3b liberty study," Cephalalgia, 2018, 38 (1S):60.
Reuter et al., "Efficacy and safety of erenumab in episodic migraine patients with 2-4 prior preventive treatment failures: results from the phase 3b LIBERTY study," Neurology, Jun. 2018, 90(24):e2186-e2187.
Reuter et al., "Efficacy and tolerability of erenumab in patients with episodic migraine in whom two-to-four previous preventive treatments were unsuccessful: a randomised, double-blind, placebo-controlled, phase 3b study," The Lancet, Nov. 2018, 392(10161):2280-2287.
Reuter et al., "Efficacy of erenumab (AMG 334) in patients with chronic migraine in North America and Europe: Subgroup analysis of a phase 2, randomised, double- blind, placebo-controlled study," European Journal of Neurology, Jul. 2017, 24(Suppl 1):548.
Reuter et al., "Efficacy of erenumab in patients with episodic migraine who have failed 2-4 prior preventive treatments: Results from prespecified subgroup analyses of the LIBERTY study," Cephalalgia, 2018, 38(1S):88-89.
Reuter et al., "Experimental models of migraine," Funct Neurol 15(S3):9-18, 2000, 10 pages.
Reuter et al., "Phase 3, randomised, double-blind, placebo-controlled study to evaluate the efficacy and safety of erenumab (AMG 334) in migraine prevention: Primary results of the STRIVE trial," Journal of Headache and Pain, Nov. 2017, 18(Suppl 1):136.
Reuter et al., "Use of acute headache and migraine medications in patients with episodic migrainein the STRIVE Phase 3 trial of erenumab for migraine prevention," Journal of Headache and Pain, Nov. 2017, 18(Suppl 1):68-69.
Reuter, "Anti-CGRP antibodies: a new approach to migraine prevention," The Lancet 13(9):857-859, Sep. 2014, 3 pages.
Reuter, "Galcanezumab CONQUERs migraine prevention," The Lancet, Oct. 2020, 19:798-799.
Revoltella, R., et al. "Comparison of conventional immunoassays (RIA, ELISA) with surface plasmon resonance for pesticide detection and monitoring," Biotherapy 11: 135-45 (1998).
Riechers II et al., "Post-traumatic headaches," Handbook of Clinical Neurology 128:567-578, Dec. 2014, 12 pages.
Rist et al., "CGRP 27-37 analogues with high affinity to the CGRP1 receptor show antagonistic properties in a rat blood flow assay," Regul. Pept. Vol. 79: 153-58, Feb. 1999, 8 pages.
Rist et al., "From Micromolar to Nanomolar Affinity: A Systematic Approach to Identify the Binding Site of CGRP at the Human Calcitonin Gene-Related Peptide 1 Receptor," J. Med. Chem. 41: 117-123, Jan. 1998, 7 pages.
Ritter et al., "A Textbook of Clinical Pharmacology: 4th Edition," Chapters 16, 22, 24, Oxford University Press, 1999, 25 pages.
RituxanTM (rituximab) Prescribing Information, Nov. 1997, 2 pages.
Rizzoli, "Synaptic Vesicle Pools," Nature Reviews: Neuroscience, vol. 6, Jan. 2005, 57-69, 13 pages.
Roon et al., "Bovine isolated middle cerebral artery contractions to antimigraine drugs," Naunyn-Schmiedeberg's Arch Pharmacol vol. 360:591-596, Nov. 1999, 6 pages.
Roon et al., "No Acute Antimigraine Efficacy of CP-122,288, a Highly Potent Inhibitor of Neurogenic Inflammation: Results of Two Randomized, Double-Blind, Placebo-Controlled Clinical Trials," Ann Neurol 47(2):238-241, Feb. 2000, 4 pages.
Roon et al., "Pharmacokinetic profile of alniditan nasal spray during and outside migraine attacks," Br J Clin Pharmacol vol. 47:285-290, Mar. 1999, 6 pages.
Rovero et al., "CGRP Antagonist Activity of Short C-Terminal Fragments of Human aCGRP, CGRP(23-37) and CGRP(19-37)," Peptides 13(5):1025-1027, Sep.-Oct. 1992, 3 pages.
Rozen, "Cluster headache: diagnosis and treatment," Curr Pain Headache Rep 9:135- 140, 2005, 6 pages.

Rudikoff et al., "Single amino acid substitution altering antigen-binding specificity," Proc Natl Acad Sci USA 79(6):1979-1983, Mar. 1982, 5 pages.
Ruscheweyh et al., "Therapie der chronischen Migräne mit Botulinumneurotoxin A: Expertenempfehlung der Deutschen Migräne- und Kopfschmerzgesellschaft [Treatment of chronic migraine with botulinum neurotoxin A: Expert recommendations of the German Migraine and Headache Society]," Der Nervenarzt, Jun. 2018, 25 pages (with English abstract).
Russell et al., "Calcitonin Gene-related paptide: physiology and pathophysiology," Physiolog Rev 94(4):1099-1142, Oct. 1, 2014, 44 pages.
Russo, "Calcitonin gene-related peptide (CGRP): a new target for migraine," Annu Rev Pharmacol Toxicol 55:533-552, 2015, 23 pages.
Sacco et al., "European headache federation consensus on the definition of resistant and refractory migraine," The Journal of Headache and Pain, Jun. 2020, 21(76):12 pages.
Saleh et al., "Phase I trial of the chimeric anti-GD2 monoclonal antibody ch14.18 in patients with malignant melanoma," Hum Antibodies Hybridomas 3(1):19-24, Jan. 1992, 6 pages.
Salman et al., "An Improved Protocol for Coupling Synthetic Peptides to Carrier Proteins for Antibody Production Using DMF to Solubilize Peptides," Journal of Biomolecular Techniques 18:173-176, Jul. 2007, 4 pages.
Sanchez del Rio et al., "How to pick optimal acute treatment for migraine headache," Current Pain and Headache Reports, vol. 5, Apr. 2001, 9 pages.
Sandborn and Yednock, "Novel Approaches to Treating Inflammatory Bowel Disease: Targeting Alpha-4 Integrin," The American Journal of Gastroenterology, vol. 98, No. 11, Nov. 2003, 11 pages.
Sandor, "Nervous control of the cerebrovascular system: doubt and facts," Neurochemistry International 35:237-259, 1999, 23 pages.
Santora et al., "Characterization of Noncovalent Complexes of Recombinant Human Monoclonal Antibody and Antigen Using Cation Exchange, Size Exclusion Chromatography, and BIAcore," Analytical Biochemistry, 299: 119-129, Dec. 2001, 11 pages.
Saper et al., "DHE in the Pharmacotheraphy of Migraine Potential for a Larger Role," Headache, vol. 46(Suppl. 4), Nov. 2006, S212-S220, 9 pages.
Saper et al., "Intranasal Civamide for the Treatment of Episodic Cluster Headaches," Arch Neurol. (2002) 59: 990-994.
Saxena et al., "5HT1-like receptor agonists and the pathophysiology of migraine," Trends Pharmacol Sci vol. 10,5:200-204, May 1989, 5 pages.
Saxena et al., "Effects of tertatolol, a ß-adrenoceptor antagonist with agonist affinity at 5-HT1A receptors, in an animal model of migraine: comparison with propanolol and pindolol," European Journal of Pharmacology, 220, Sep. 1992, 8 pages.
Schabacker et al., "Exploring the Feasibility of an Anti-Idiotypic Cocaine Vaccine: Analysis of the Specificity of Anticocaine Antibodies (AB1) Capable of Inducing Ab2B Anti-Idiotypic Antibodies," Immunology, vol. 100, pp. 48-56, 2000, 9 pages.
Schaible et al., "Mechanisms of pain in arthritis," Ann N Y Acad Sci 966:343-354, Jun. 2002, 16 pages.
Scher et al., "Cardiovascular risk factors and migraine. The GEM population-based study," Neurology 64:614-620, Feb. (2 of 2) 2005, 7 pages.
Schmitz et al., "Frontal lobe structure and executive function in migraine patients," Neuroscience Letters, 1;440(2):92-6, Aug. 2008, 5 pages.
Schoenen et al., "Neurophysical features of the migrainous brain," Features of the Migrainous Brain, Neurol Sci, vol. 27, S77-S81, May 2006, 5 pages.
Schoenen et al., "No effect of eletriptan administration during the aura phase of migraine," European Journal of Neurology, vol. 11, 671-677, Oct. 2004, 7 pages.
Schoenen et al., "When should triptans be taken during a migraine attack?" Leading Article, CNS Drugs, vol. 15(8), Aug. 2001, 5 pages.
Schoonman et al., "Chapter 1: The prevalence of premonitory symptoms in migraine: a questionnaire study in 461 patients," Cephalalgia 26:1209-1213, 2006, 8 pages.

(56) References Cited

OTHER PUBLICATIONS

Schoonman et al., "Chapter 3: Normobaric hypoxia and nitroglycerin as trigger factors for migraine," Cephalalgia, vol. 26(7):816-9, Jul. 2006, 8 pages.
Schoonman et al., "Gabapentin in Migraine Prophylaxis: Is it Effective and Well Tolerated?" Headache, vol. 42, Issue 3, Mar. 2002, 1 page.
Schoonman et al., "Is stress a trigger factor for migraine?" Psychoneuroendocrinology 32(5):532-538, Jun. 2007, 7 pages.
Schoonman et al., "Magnetic resonance angiography of the human middle meningeal artery: implications for migraine," Journal of Magnetic Resonance Imagining, 24:918-921, Oct. 2006, 4 pages.
Schoonman et al., "Migraine headache is not associated with cerebral or meningeal vasodilatation - a 3T magnetic resonance angiography study," Brain 131:2192-2200, Aug. 2008, 9 pages.
Schou et al., "Calcitonin gene-related peptide and pain: a systematic review," The Journal of Headache and Pain, 18:34, Dec. 2017, 17 pages.
Schueren et al., "Reproductivility of the capsaicin-induced dermal blood flow response as assessed by laser Doppler perfusion imaging," Br J Clin Pharmacol 64(5):580-590, 2007, 11 pages.
Schulman et al., "Defining Refractory Migraine and Refractory Chronic Migraine: Proposed Criteria From the Refractory Headache Special Interest Section of the American Headache Society", Headache 48:778-782, 2008, 6 pages.
Schuster and Rapoport, "Calcitonin Gene-Related Peptide-Targeted Therapies for Migraine and Cluster Headache: A Review", Clinical Neuropharmacology, vol. 40:169-174, Jul.-Aug. 2017, 6 pages.
Schytz et al., "PACAP38 induces migraine-like attacks in patients with migraine without aura, " Brain, vol. 132 (part 1): 16-25, Jan. 2009, 10 pages.
Scimemi and Beato, "Determining the Neurotransmitter Concentration Profile at Active Synapses", Molecular Neurobiology 40(3): 289-306, Oct. 2009, 18 pages.
Scott et al., "Sumatriptan and cerebral perfusion in healthy volunteers," British Journal of Clinical Pharmacology 33(4):401-404, Apr. 1992, 4 pages.
seekingalpha.com' [online], "Teva Pharmaceutical Industries (TEVA) Q3 2017 Results—Earnings Call Transcript," available on or before Nov. 2, 2017, retrieved on Dec. 11, 2018, retrieved from URL: <https://seekingalpha.com/article/4119613-teva-pharmaceutical-industries-teva-q3-2017-results-earnings-call-transcript#question-answer-session>, 3 pages.
Seifert et al., "Chapter 7: (Patho)physiological and Therapeutic Relevance of Constitutive Activity and Inverse Agonism at G Protein-Coupled Receptors" in G-Protein-Coupled Receptors as Drug Targets: Analysis of Activation and Constitutive Activity, vol. 24, 2006, 11 pages.
Seon et al., "Isolation, Structure, Synthesis, and Activity of a New Member of the Calcitonin Gene-related Peptide Family from Frog Skin and Molecular Cloining of Its Precursor," The Journal of Biological Chemistry 275(8):5934-5940, 2000, 8 pages.
Seong et al., "Radiation-induced alteration of pain-related signals in an animal model with bone invasion from cancer," Ann N Y Acad Sci 1030:179-186, Dec. 2004, 8 pages.
Shahien, "Intravenous sodium valproate aborts migraine headaches rapidly," Acta Neurol Scand, 2011, 123(4):257-265 (abstract only).
Shapiro and Goadsby, "The long drought the dearth public funding for headache research," Cephalalgia, vol. 27, Sep. 2007, 991-994, 4 pages.
Shaw et al., "The effect of monoclonal antibodies to calcitonin gene-related peptide (CGRP) on CGRP-induced vasodilatation in pig coronary artery rings," Brit J Pharmacol 106:196-198, 1992, 3 pages.
Shawket et al., "Prolonged effect of CGRP in Raynaud's patients: a double-blind randomised comparison with prostacyclin," Br J Clin Pharmac 32:209-213, 1991, 5 pages.
Shawket et al., "Selective Suprasensitivity to Calcitonin-Gene-Related Peptide in the Hands in Raynaud's Phenomenon, " The Lancet 1354-1385, Dec. 9, 1989, 4 pages.

Sheets et al., "Efficient construction of a large nonimmune phage antibody library: the production of high-affinity human single-chain antibodies to protein antigens," Proc Natl Acad Sci USA 95(11):6157-6162, May 26, 1998, 7 pages.
Sheftell et al., "Naratriptan in the Preventive Treatment of Refractory Transformed Migraine: A Prospective Pilot Study," Headache (2005) 45: 1400-1406.
Shen et al., "Effects of Inhibition of α-CGRP Receptors on Cardiac and Peripheral Vascular Dynamics in Conscious Dogs with Chronic Heart Failure," J. Cardiovasc. Pharmacol. (2003) 42(5): 656-661.
Shepheard et al., "Possible antimigraine mechanisms of action of the 5HTIF receptor agonist LY334370," Cephalalgia 19:851-858, Dec. 1999, 8 pages.
Shepherd and Dean, "Monoclonal Antibodies: A Practical Approach," Chapters 1, 2, 12, 13, 20, 21, Oxford University Press, Jul. 13, 2000, 151 pages.
Shevel, "The Extracranial Vascular Theory of Migraine—A Great Story Confirmed by the Facts," Headache vol. 51, Mar. 2011, 409-417, 9 pages.
Shields and Goadsby, "Seritonin receptors modulate trigeminovascular responses in ventroposteromedial nucleus of thalamus: a migraine target?" Neurobiology of Disease 23:491-501, Sep. 2006, 11 pages.
Shields et al., "Inhibition of Allergic Reactions with Antibodies to IgE," International Archives for Allergy and Immunology, 107: 308-312, May-Jun. 1995, 5 pages.
Sigma-Aldrich, "Biochemicals & Reagents for Life Science Research," pp. 350-352, 2004, 7 pages.
Silberstein et al., "Advances in the understanding of the pathophysiology headache," Neurology, vol. 42(suppl.2): 6-10, Mar. 1992, 5 pages.
Silberstein et al., "Botulinum toxin type A for the prophylactic treatment of chronic daily headache: a randomized, double-blind, placebo-controlled trial," Mayo Clinic Proceedings, Sep. 2005, 1126-1137, 12 pages.
Silberstein et al., "Chapter 5: Pathophysiology of Headache, Chapter 6: Genetics of Headache, Chapter 9: Migraine - Diagnosis and Treatment & Chapter 12: Cluster Headache—Diagnosis, Management and Treatment," in Wolff's Headache and other head pain: Seventh Edition, Oxford Press 2001, 180 pages.
Silberstein et al., "CNS effects of sumatriptan and rizatriptan," Cephalalgia, Jan. 2004, 2 pages.
Silberstein et al., "Efficacy and Safety of Topiramate for the Treatment of Chronic Migraine: A Randomized, Double-Blind, Placebo-Controlled Trial," Headache 170-180, Feb. 2007, 11 pages.
Silberstein et al., "Evidence-based guideline update: Pharmacologic treatment for episodic migraine prevention in adults," Am Acad Neurol 78:1337-1345, Apr. 24, 2012, 12 pages.
Silberstein et al., "Fremanezumab for the Preventive Treatment of Chronic Migraine", The New England Journal of Medicine 377(22):2113-2122, Nov. 2017, 10 pages.
Silberstein et al., "From migraine mechanisms to innovative therapeutic drugs," Neurology, vol. 64 (Suppl 2), May 2005, 3 pages.
Silberstein et al., "Impact of fremanezumab on response rates, migraine days, and acute medication use in patients with chronic migraine who have failed at least one prior migraine preventive medication," The Journal of Headache and Pain, 2018, 19(Suppl 1):37-38.
Silberstein et al., "Migraine: preventive treatment," Cephalalgia, vol. 22, Sep. 2002, 22 pages.
Silberstein et al., "Preventive treatment of migraine," Neurology, 60(Suppl 2):S38-S44, 2003, 7 pages.
Silberstein et al., "Removing barriers to appropriate migraine treatment: formulary limitations and triptan package size, " Headache, Oct. 2005, 5 pages.
Silberstein et al., "Section 2: Primary Headache Disorders, Chapter 6: Migraine: diagnosis and treatment," in Headache in Primary Care, Isis Medical Media, 1999, 32 pages.
Silberstein et al., "The International Classification of Headache Disorders, 2nd Edition (ICHD-II)-Revision of Criteria for 8.2 Medication-Overuse Headache," Cephalalgia (2005) 25: 460-465.
Silberstein, "Cardiovascular risk factors associated with migraine," Lancet Neurol, Jul. 2005, 2 pages.

(56) References Cited

OTHER PUBLICATIONS

Silberstein, "Chronic migraine: diagnosis and management strategy," Reviews in Neuological Diseases, vol. 1, No. 3, Summer 2004, 6 pages.
Silberstein, "Current Preventive Therapy: Preventive treatment mechanism," Headache Currents, vol. 3, No. 5, Sep./Oct. 2006, 8 pages.
Silberstein, "Emerging target-based paradigms to prevent and treat migraine," Clin Pharmacol Ther 93(1):78-85, Jan. 2013, 8 pages.
Silberstein, "Migraine pathophysiology and its clinical implications," Cephalalgia, 24 Suppl. 2, Feb. 2004, 6 pages.
Silberstein, "Migraine prevention medication reduces resource utilization," Research Submissions: Headache, Mar. 2003, 8 pages.
Silberstein, "Migraine," Lancet, vol. 363, Jan. 2004, 381-391, 11 pages.
Silberstein, "Migraine: preventive treatment," Current Medical Research and Opinion, vol. 17, Suppl. 1, S87-93, 2001, 7 pages.
Silberstein, "Preventive treatment of headaches," Current Opinion in Neurology, Jun. 2005, 4 pages.
Silberstein, "Preventive treatment of migraine," Review in Neurological Diseases, vol. 2, No. 4, Fall 2005, 9 pages.
Silberstein, "Preventive treatment of migraine," Trends in Pharmacological Sciences, vol. 27, No. 8, Aug. 2006, 6 pages.
Silberstein, "Review of botulinum toxin type A and its clinical applications in migraine headache," Expert Opinion Phermacother, vol. 2 (10), Oct. 2001, 6 pages.
Silberstein, "The International Classification of Headache Disorders, 2nd Edition (ICHD-II)—revision of criteria for 8.2 Medication-overuse headache," Cephalalgia, Jun. 2005, 6 pages.
Silberstein, "Topiramate in migraine prevention," Headache, Apr. 2005, S57-S65, 9 pages.
Silberstein, "A new Frontier for headache," Frontiers in Neurology, vol. 1, Article 135, p. 1, Oct. 20, 2010, 1 pages.
Silberstein, "Migraine," Discovery Medicine, Jul. 12, 2009, pp. 1.
Silberstein, "Preventive Migraine Treatment," Continuum, 21(4):973-989, Aug. 2015, 17 pages.
Simulect® (basiliximab), "Prescribing Information," Novartis Pharmaceuticals Corporation, May 1998, 7 pages.
Sixt et al., "Calcitonin gene-related peptide receptor antagonist olcegepant acts in the spinal trigeminal nucleus," Brain 132:3134-3141, Nov. 2009, 8 pages.
Skljarevski et al., "Effect of Different Doses of Galcanezumab vs Placebo for Episodic Migraine Prevention A Randomized Clinical Trial", JAMA Neurology 75(2):187-193, Dec. 2017, 7 pages.
Skljarevski et al., "Efficacy and safety of LY2951742 in a randomized, double-blind, placebocontrolled, dose-ranging study in patients with migraine," Cephalalgia, Sep. 2016, 36(Suppl 1):42.
Skljarevski et al., "Efficacy of LY2951742 in subgroups of patients with migraine of different frequency," Cephalalgia, Sep. 2016, 36(Suppl 1):42-43.
Skljarevski et al., "Efficacy of LY2951742 in subgroups of patients with migraine of different frequency," Headache, Jun. 2016, 56(Suppl 1):67.
Skljarevski et al., "Efficacy of LY2951742 in subgroups of patients with migraine of different frequency," Postgraduate Medicine, 2016, 128(Suppl 2):104.
Skljarevski et al., "Phase 3 studies (EVOLVE-1 and EVOLVE-2) of galcanezumab in episodic migraine: Results of 6-month treatment phase," Journal of Headache and Pain, Nov. 2017, 18(Suppl 1): 144.
Skljarevski et al., "Efficacy and Safety of Galcanezumab for the Prevention of Episodic Migraine: Results of the EVOLVE-2 Phase 3 Randomized Controlled Clinical Trial," Cephalalgia, 2018, 38(8):1-13.
Smith et al., "ALD403 (eptinezumab) elicits meaningful reductions in migraine activity 24 hours after a single intravenous administration," Headache, Jun. 2017, 57(Suppl 3): 179-180.
Smith et al., "An immunocytochemical investigation of human trigeminal nucleus caudalis: CGRP, substance P and 5-HTID-receptor immunoreactivities are expressed by trigeminal sensory fibres," Cephalalagia 22:242-432, Jul. 2002, 10 pages.
Smith et al., "Proof of concept clinical trial of ALD403, an anti-calcitonin gene-related peptide (CGRP) antibody in the prevention of migraine-6 month data," Cephalalgia, May 2015, 35:6(Suppl 1):4-5.
Smith et al., "Randomized, double-blind, placebo-controlled trial of ALD403 (eptinezumab), an anti-CGRP monoclonal antibody for the prevention of chronic migraine," Headache, Jun. 2017, 57(Suppl 3):130.
Smith et al., "Randomized, double-blind, placebocontrolled trial of ALD403, an antiCGRP peptide antibody in the prevention of chronic migraine," Cephalalgia, Sep. 2016, 36 (Suppl 1):43.
Smith et al., "Reversal of advanced digoxin intoxication with Fab fragments of digoxin-specific antibodies," N Eng J Med 294(15): 797-800, Apr. 8, 1976, 4 pages.
Smith-Gill et al., "Contributions of immunoglobulin heavy and light chains to antibody specificity for lysozyme and two haptens," J Immunol 139(12):4135-4144, Dec. 15, 1987, 10 pages.
Song et al., "Light chain of natural antibody plays a dominant role in protein antigen binding," Biochem Biophys Res Commun 268(2):390-394, Feb. 16, 2000, 5 pages.
Sparey, "Embracing partnerships: the Merck philosophy", Biopartnering Magazine, Spring 2006, 3 pages.
Spillner, "Recombiant IgE antibody engineering to target EGFR," Cancer Immunology Immunother. vol. 61(9), Sep. 2012, 9 pages.
Sprenger and Goadsby, "Migraine pathogenesis and state of pharmacological treatment options, " BMC Med 7(71), 5 pages, Nov. 16, 2009, 5 pages.
Stam, "Migraine: new treatment options from molecular biology," Expert Rev Neurotherapeutrics, 5(5), Sep. 2005, 9 pages.
St-Amour et al., "Brain bioavailability of human intravenous immunoglobulin and its transport through the murine blood-brain barrier," Journal of Cerebral Blood Flow and Metabolism, 33(12):1983-92, Dec. 2013, 10 pages.
Stauffer et al., "Evaluation of Galcanezumab for the Prevention of Episodic Migraine: The EVOLVE-1 Randomized Clinical Trial," JAMA Neurol., May 2018, 75(9):1080-1088.
Steiner et al., "BASH Guidelines for Diagnosis and Management of Migraine, Tension-Type Headache, Cluster Headache and Medication-Overuse Headache: third edition," 2010, 53 pages.
Steiner et al., "BASH Management Guidelines: Guidelines for all Doctors in the Diagnosis and Management of Migraine and Tension-Type Headache (2nd edition)," BASH Management Guidelines, Mar. 2000, 31 pages.
Steiner et al., "The prevalence and disability burden of adult migraine in England and their relationships to age, gender and ethnicity," Cephalalgia, vol. 23, Sep. 2003, 519-527, 9 pages.
Sternini, "Enteric and Visceral Afferent CGRP Neurons, Targets of Innercation and Differential Expression Patterns," Annals New York Academy of Sciences 170-185, 1992, 17 pages.
Stjernsward et al., "The World Health Organization Cancer Pain and Palliative Care Program. Past, present, and future," J Pain Symptom Manage 12(2):65-72, Aug. 1996, 8 pages.
Storer et al., "Calcitonin gene-related peptide (CGRP) modulates nociceptive trigeminovascular transmission in the cat," Brit J Pharmacol 142(7): 1171-1181, Aug. 2004, 11 pages.
Strecker et al., "Nitric Oxide Releases Calcitonin-Gene-Related Peptide from Rat Dura mater Encephali Promoting Increases in Meningeal Blood Flow," Journal of Vascular Research 39:489-496, Nov.-Dec. 2002, 8 pages.
Strorer and Goadsby, "Topiramate inhibits trigeminovascular neurons in the cat," Cephalalgia 24:1049-1056, Dec. 2004, 8 pages.
Struthers et al., "Human calcitonin gene related peptide: a potent endogenous vasodilator in man," Clinical Science 70:389-393, 1986, 5 pages.
Subramanian, "Antibodies vol. 2—Novel Technologies and Therapeutic Use," Springer Science+Business Media New York, Jan. 2004, 239 pages.
Sun et al., "Randomised, double-blind, phase-2 study and 52-Week interim results of an openlabel extension to evaluate AMG334 for the prevention of episodic migraine," European Journal of Neurology, Jun. 2016, 23(Suppl 2):81.
Sun et al., "Results of the open-label extension of a phase 2, randomized, double-blind, placebo-controlled, study to evaluate the

(56) References Cited

OTHER PUBLICATIONS efficacy and safety of AMG 334 for the prevention of episodic migraine," Headache, Nov. 2015, 55(Suppl 5):256-257.
Sun et al., "Safety and efficacy of AMG 334 for prevention of episodic migraine: A randomised, double-blind, placebo-controlled, phase 2 trial," The Lancet Neurology, Apr. 2016, 15(4):9 pages.
Supowit et al., "Calcitonin Gene-Related Peptide Protects Against Hypertension- Induced Heart and Kidney Damage," Hypertension, vol. 45:109-14, Jan. 2005, 8 pages.
Swillens, "Interpretation of Binding Curves Obtained with High Receptor Concentrations: Practical Aid for Computer Analysis," Molecular Pharmacology 47:1197-1203, 1995, 7 pages.
Synagis® (palivizumab) EMA Scientific Discussion, 2004, 19 pages.
Szabat et al., "Production and characterization of monoclonal antibody against human calcitonin gene-related peptide (CGRP) and its immunohistochemical application to salivary glands," Histochemical Journal 26:317-326, 1994, 10 pages.
Tajti et al., "Migraine and neuropeptides," Neuropeptides 52:19-30, Aug. 2015, 12 pages.
Takhshid et al., "Characterization and effects on cAMP accumulation of adrenomedullin and calcitonin gene-related peptide (CGRP) receptors in dissociated rat spinal cord cell culture," Brit J Pharmacol 148(4):459-468, Jun. 2006, 10 pages.
Tamura et al., "Structural correlates of an anti carcinoma antibody: identification of specificity-determining residues (SD Rs) and development of a minimally immunogenic antibody variant by retention ofSDRs only," J Immunol 164(3):1432-1441, Feb. 1, 2000, 11 pages.
Tan et al., "Calcitonin gene-related peptide as an endogenous vasodilator: immunoblockade studies in vivo with an anti-calcitonin gene-related peptide monoclonal antibody and it's Fab' fragment," Clinical Science 89(6):565-573, Dec. 1, 1995, 9 pages.
Tan et al., "Demonstration of the neurotransmitter role of calcitonin gene-related peptides (CGRP) by immunoblockade with anti-CGRP monoclonal antibodies, " Brit J Pharmacol 111(3):703-710, Mar. 1994, 8 pages.
Tan, "Application of Monoclonal Antibodies to the Investigation of the Role of Calcitonin Gene-Related Peptide as a Vasodilatory Neurotransmitter," Dissertation Submitted to the University of Cambridge (1994), 275 pages.
Tao and Morrison, "Studies of Aglycosylated Chimeric Mouse-Human Ig :. Role of Carbohydrate in the Structure and Effector Functions Mediated by the Human IgG Constant Region," Journal of Immunology, 143: 2595-2601, No. 8, Oct. 15, 1989, 8 pages.
Tassorelli et al., "Optimizing the long-term management of chronic migraine with onabotulinumtoxinA in real life," Expert Review of Neurotherapeutics, Feb. 2018, 18(2):11 pages.
Tepper et al., "A phase 2 randomized, double-blind, placebo-controlled study to evaluate the efficacy and safety of erenumab (AMG 334) in chronic migraine prevention," Headache, Jun. 2017, 57(Suppl 3):130.
Tepper et al., "Botulinum neurotoxin type A in the preventive treatment of refractory headache: a review of 100 consecutive cases," Headache 44(8):794-800, Sep. 2004, 8 pages.
Tepper et al., "Early onset of efficacy in a phase 2 clinical trial of erenumab in patients with chronic migraine," Headache, Jun. 2017, 57(Suppl 3):193.
Tepper et al., "Efficacy of erenumab for the treatment of patients with chronic migraine in presence of medication overuse, " Headache, Jun. 2017, 57(Suppl 3): 197.
Tepper et al., "Evaluating the efficacy and safety of Erenumab (AMG 334) in chronic migraine prevention in a phase 2 randomized, double-blind, placebo-controlled study," Neurology, Apr. 2017, 88(16)(Suppl 1): 7 pages.
Tepper et al., "Mechanisms of Action of the 5-HT 1B/1D Receptor Agonists," Neurological Review, Arch. Neurol. Vol. 59, pp. 1084-1088, Jul. 2002, 5 pages.
Tepper et al., "Patient reported outcomes in patients with chronic migraine receiving placebo or erenumab (AMG 334) in a phase 2, randomized, double blind study," Neurology, Apr. 2017, 88(16 Suppl): 7 pages.
Tepper et al., "Patient-reported outcomes in chronic migraine patients receiving placebo or erenumab (AMG 334) in a phase 2, randomized, double-blind study," Cephalalgia, Sep. 2016, 36(Suppl 1):45-46.
Tepper et al., "Phase 2, randomized, double-blind, placebo-controlled study to evaluate the efficacy and safety of erenumab (AMG 334) in chronic migraine prevention," Cephalalgia, Sep. 2016, 36(Suppl 1):44-45.
Tepper et al., "Safety and efficacy of erenumab for preventive treatment of chronic migraine: a randomised, double-blind, placebo-controlled phase 2 trial," The Lancet Neurology, Jun. 2017, 16(6):425-434.
Tepper et al., "Erenumab in Chronic Migraine with Medication Overuse," Neurology (2019) 92(20): e2309-e2320.
Terwindt et al., "Hemiplegic and basilar-type migraine: current and future treatment," Headache Currents No. 4:97-99, Jul.-Aug. 2006, 4 pages.
Terwindt et al., "Migraine en cardiovasculaireisico," Ned Tijdsch Geneeskd 151(37) 2029-2031, 2007, 3 pages.
Terwindt et al., "The impact of migraine on quality of life in the general population. The GEM study," Neurology vol. 55:624-629, Sep. 2000, 6 pages.
Teva Pharmaceutical Industries, "Teva announces U.S. Approval of AJOVY (fremanezumab-vfrm) injection, the first and only anti-CGRP treatment with both quarterly and monthly dosing for the prevention of migraine in Adults," Teva Pharmaceutical Industries Ltd., available on or before Sep. 14, 2018, 8 pages.
Teva Press Release, "Teva to Aquire Labrys Biologies, Inc .: Novel Migraine Prophylaxis Treatment Adds Significant New Dimension to Teva's growing Pain Care Franchise," RSS Content, 2014, 4 pages.
Textbook of Pain Levine et al., Textbook of Pain pp. 45-56, 1994, 17 pages.
Textbook of Pain McCarthy et al., Textbook of Pain pp. 387-395, 1994, 15 pages.
Tfelt-Hansen and Olesen, "Possible site of action of CGRP antagonists in migraine," Cephalalgia 31(6):748-750, Apr. 2011, 3 pages.
Tfelt-Hansen et al., "Calcitonin gene-related peptide in blood is it increased in the external jugular vein during migraine and cluster headache: A review," Journal of Headache Pain, vol. 10, Jun. 2009, 7 pages.
Tfelt-Hansen et al., "Ergotamine in the acute treatment of migraine-a review and European consensus," Brain 123:9-18, Jan. 2000, 10 pages.
Tfelt-Hansen et al., "Guidelines for controlled trials of drugs in migraine: second edition," Cephalalgia vol. 20:765-786, Nov. 2000, 22 pages.
Tfelt-Hansen et al., "Guidelines for controlled trials of drugs in migraine: Third edition. A guide for investigators," Cephalalgia, 2012, 32(1):6-38, 33 pages.
Tfelt-Hansen, "Site of effect of LY2951742 for migraine prophylaxis," Lancet Neurol 14(1):31-32, Jan. 2015, 2 pages.
Tfelt-Hansen, "Site of effect of LY2951742 for migraine prophylaxis," The Lancet, 14:31-32, Jan. 2015, (includes Authors' reply), 2 pages.
Tomlinson, "Next-Generation Protein Drugs," Nature Biotechnology (2004) 22(5):521-522.
Troltzsch et al., "The calcitonin gene-related peptide (CGRP) receptor antagonist BIBN4096BS reduces neurogenic increases in dural blood flow," European Journal of Pharmacology 562:103-110, 2007, 8 pages.
Tsai et al., "Cerebral arterial innervation by nerve fibers containing Cgrp: I. Distribution and Origin of CGRP Perivascular Innervation in the Rat," The Journal of Comparative Neurology, vol. 271: 435-444, May 1988, 10 pages.
Tso et al., "Anti-CGRP Monoclonal Antibodies: the Next Era of Migraine Prevention?" Curr Treat Options Neurol, Aug. 2017, 19(27):1-11, 11 pages.

(56) References Cited

OTHER PUBLICATIONS

Tsurushita et al., "Design of Humanized Antibodies: From anti-Tac to Zenapax," Methods 36: 69-83, May 2005, 15 pages.

Tucker, "New Data on CGRP Monoclonal Antibodies for Migraine Prevention," Jul. 23, 2015, Retrieved from the Internet: URL <http://www.medscape.com/viewarticle/846893_print>, retrieved on Dec. 13, 2016, 3 pages.

Tuma, "Phase I Antibody Risks: Trial Safety Explained," Journal of Natural Cancer Inst. Vol. 98(14): 956-98, Jul. 19, 2006, 3 pages.

Tvedskov et al., "CGRP receptor antagonist olcegepant (BIBN4096BS) does not prevent glyceryl trinitrate-induced migraine," Cephalalgia 30(11):1346-1353, Nov. 2010, 8 pages.

Tvedskov et al., "No Increase of Calcitonin Gene-Related Peptide in Jugular Blood during Migraine", Annals of Neurobilogy, vol. 58, No. 4, Oct. 2005, 8 pages.

Tvedskov et al., "The prophylactic effect of valproate on glyceryltrinitrate induced migraine," Cephalalgia 24(7):576-585, Jul. 2004, 10 pages.

Tysabri (natalizumab), "Prescribing Information," Biogen Idec Inc., Nov. 2004, 11 pages.

Tysabri® Letter from the Food and Drug Administration, Nov. 2004, 7 pages.

Tzabazis et al., "Antihyperalgesic effect of a recombinant herpes virus encoding antisense for calcitonin gene-related peptide," Anesthesiology 106(6):1196-1203, Jun. 2007, 8 pages.

U.S. Department of Health and Human Services, "Health, United States, 2005 with Chartbook and Trends in the Health of Americans," Centers for Disease Control and Prevention, 2005, 550 pages.

U.S. Securities and Exchange Commission, "Pfizer Delivers Strong Second-Quarter 2006 Results, Driven By Performance Of Major In-Line And New Products," Exhibit 99, Jul. 20, 2006, retireved on Jun. 14, 2019, retrieved from URL <https://www.sec.gov/Archives/edgar/data/78003/000127528706003681/pi6456ex99.txt>, 17 pages.

Uddman et al., "Calcitonin gene-related peptide (CGRP) pervascular distribution and vasodilatory effects," Regulatory Peptides, vol. 15, Aug. 1986, 23 pages.

Uddman et al., "Innvervation of the feline cerebral vasculature by nerve fibers containing CGRP," Neuroscience Letters, vol. 62, Nov. 1985, 6 pages.

Underwood, "Will antibodies finally put an end to migraines?", www.sciencemag.org, Jan. 2016, 13 pages.

Urban et al., "Functional Selectivity and Classical Concepts of Quantitative pharmacology," The Journal of Pharmacology and Experimental Therapeutics 320(1):1-13, Jan. 2007, 13 pages.

Vajdos et al., "Comprehensive functional maps of the antigen-binding site of an anti-ErbB2 antibody obtained with shotgun scanning mutagenesis, " J Mol Biol 320(2):415-428, Jul. 5, 2002, 14 pages.

Van der Kamp et al., "Interictal cortical hyperexcitability in migraine patients demonstrated with transcranial magnetic stimulation," Journal of the Neurological Sciences, vol. 139:106-110, Jul. 1996, 5 pages.

Van der Schueren, "Reproducibility of the capsaicin-induced dermal blood flow response as assessed by laser Doppler perfusion imaging," British Journal of Clinical Pharmacology 64:580-590, Nov. 2007, 11 pages.

Van Dijk et al., "Human antibodies as next generation therapeutics," Current Opinion in Chemical Biology, vol. 5: 368-374, Aug. 2001, 7 pages.

Van Dijk et al., "No confirmation of visual evoked potential diagnostic test for migraine," Lancet vol. 337 i:517-518, Mar. 2, 1991, 2 pages.

Van Dijk et al., "Visual evoked potentials and background EEG activity in migraine," Headache 31:392-395, Jun. 1991, 4 pages.

Van Regenmortal et al., "Improving the Quality of BIACORE-Based Affinity Measurements," Dev. Biol. (Basel), 112: 141-151, 2003, 11 pages.

Van Valen et al., "Calcitonin Gene-Related Peptide (CGRP) Receptors are Linked to Cyclic Adenosine Monophosphate Production in SK-N-MC Human Neuroblastoma Cells," Neuroscience Letters 119: 195-198, Nov. 1990, 4 pages.

Van Vliet et al., "Cardiovascular autonomic function tests in cluster headache," Cephalalgia 26:329-331, Mar. 2006, 3 pages.

Van Vliet et al., "Evaluating the IHS criteria for cluster headache - a comparison between patients meeting all criteria and patients failing one criterion," Cephalalgia 26: 241-245, Mar. 2006, 5 pages.

Van Vliet et al., "Features involved in the diagnostic delay of cluster headache," J Neurol Neurosurg Psychiatry vol. 74(8):1123-1125, Aug. 2003, 3 pages.

Van Vliet et al., "Intranasal sumatriptan in cluster headache," Neurology 60 :- 633, Feb. (2 of 2) 2003, 5 pages.

Van Wijngaarden et al., "Inhibitors of Ocular Neovascularization: Promises and Potential Problems," JAMA, American Medical Association 293(12):1509-1513, Mar. 2005, 5 pages.

Vander Pluym et al., "Effect of monoclonal calcitonin gene-related peptide antibody (TEV-48125) on wellness during headache free days," Headache, Jun. 2016, 56(Suppl 1):7.

Vater and Klussmann, "Toward third-generation aptamers: Spieglemers and their therapeutic prospects," Curr Opin Drug Discov & Devel 6(2):253-261, Mar. 2003, 9 pages.

Vater et al., "Short bioactive Spiegelmers to migraine-associated calcitonin gene- related peptide rapidly identified by a novel approach: tailored-SELEX," Nucleic Acids Res 31(21):e130, Nov. 1, 2003, 7 pages.

Vaughan et al., "Human antibodies by design," Nat. Biotechnol., vol. 16, issue 6, pp. 535-539, 1998.

Vaughan et al., "Human antibodies with sub-nanomolar affinities isolated from a large non-immunized phage display library," Nat Biotechnol 14(3):309-314, Mar. 1996, 6 pages.

Vecsei et al., "CGRP antagonists and antibodies for the treatment of migraine," Expert opinion on investigational drugs 24(1):31-41, Jan. 2, 2015, 12 pages.

Verhoeff et al., "Dopamine D2-receptor imaging with 123I-Iodobenzamide SPECT in migraine patients abusing ergotamine: does ergotamine cross blood brain barrier?" Cephalalgia 13:325-329, Oct. 1993, 5 pages.

Verkman, "Drug discovery in academia," Am J Physiol Cell Physiol 286:C465-C47, Mar. 2004, 10 pages.

Vermeersch et al., "Translational Pharmacodynamics of Calcitonin Gene-Related Peptide Monoclonal Antibody LY2951742 in a Capsaicin-Induced Dermal Blood Flow Model", J Pharmacol Exp Ther 354:350-357, Sep. 2015, 8 pages.

Vincent et al., "Molecular targets for autoimmune and genetic disorders of neuromuscular transmission," Eur J Biochem 267(23):6717-6728, Dec. 2000, 12 pages.

Visser et al., "311C90, A new central and peripherally acting 5-HT1D receptor agonist in the acute oral treatment of migraine: a double blind, placebo-controlled, dose-range finding study," presented in part at the 10th Migraine Trust, Sep. 5- 8, 1994, Neurology, Feb. 1996, 5 pages.

Visser et al., "Clinical trials and therapeutics, Pharmacokinetic and pharmacodynamic profiles of sumatriptan in migraine patients with headache recurrence or no response," Clinical Pharmacology and Therapeutics, vol. 60, No. 4, Oct. 1996, 9 pages.

Visser et al., "Subcutaneous Sumatriptan International Study Group. Treatment of migraine attacks with migraine attacks with subcutaneous sumatriptan: first placebo- controlled study," Cephalalgia 12:308-314, Oct. 1992, 6 pages.

Visser et al., "Sumatriptan in clinical practice: a 2-year review of 453 migraine patients," Neurology 47:46-51, Jul. 1996, 7 pages.

Visser et al., "Sumatriptan non-responders: a survey in 366 migraine patients," Headache vol. 36:471-475, Sep. 1996, 5 pages.

Vollbracht et al., "The pipeline in headache therapy," CNS Drugs 27(9):717-729, Sep. 2013, 13 pages.

Vugmeyster et al., "Pharmacokinetics and toxicology of therapeutic proteins: Advances and challenges", World J Biolog Chem 3(4):73-92, Apr. 26, 2012, 20 pages.

Wacnik et al., "Tumor-induced mechanical hyperalgesia involves CGRP receptors and altered innervation and vascularization of DsRed2 fluorescent hindpaw tumors," Pain 115(1-2):95-106, May 2005, 6 pages.

Waeber et al., "Migraine as an inflammatory disorder", Neurology 64(10 Suppl 2):S9-15, May 2005, 7 pages.

(56) References Cited

OTHER PUBLICATIONS

Walker and Hay, "CGRP in the trigeminovascular system: a role for CGRP, adrenomedullin and amylin receptors?" British Journal of Pharmacology 170(7): 1293-1307, Dec. 2013, 15 pages.
Walter and Bigal, "TEV-48125: a Review of a Monoclonal CGRP antibody in Development for the Preventative Treatment of Migraine," Curr Pain Headache Rep 19:6, Mar. 2015, 6 pages.
Walter et al., "Evaluation of cardiovascular parameters in cynomolgus monkeys following IV administration of LBR-101, a monoclonal antibody against calcitonin gene-related peptide," MAbs 6(4):871-878, Jul.-Aug. 2014, 9 pages.
Wang and Yu, "Postictal headache in epileptic patients," Molecular & Cellular Epilepsy vol. 1, e197, 2014, 5 pages.
Wang et al., "Monoclonal antibody pharmacokinetics and pharmacodynamics", Clinical Pharmacology and Therapeutics, 84(5), 548-558, Nov. 2008, 11 pages.
Wang et al., "IgG engineering to modulate antibody effector functions," Protein Cell 9(1):63-73, Jan. 2018, 11 pages.
Ward et al., "Binding activities of a repertoire of single immunoglobulin variable domains secreted from *Escherichia coli*," Nature 341(6242):544-546, Oct. 12, 1989, 3 pages.
Weiner et al., "Monoclonal antibodies: versatile platforms for cancer immunotherapy", Nature Reviews: Immunology 10(5):317-327, May 2010, 11 pages.
Weir et al., "Formatting antibody fragments to mediate specific therapeutic functions," Biochemical society transations vol. 30, part 4, Aug. 2002, 512-516, 5 pages.
Welch, "MRI of the occipital cortex, red nucleus, and substantia nigra during visual aura of migraine," Neuology, vol. 51:1465-1469, Nov. 1998, 5 pages.
Werry and Aman, "Practitioner's Guide to Psychoactive Drugs for Children and Adolescents, 2nd Edition," Plenum Publishing Corporation, pp. 42-50, 1999, 11 pages.
Werther et al., "Humanization of an Anti-lymphocyte Function—Associated Antigen (LFA)-1 Monoclonal Antibody and Reengineering of the Humanized Antibody for Binding to Rhesus LFA-1," J. Immunol. 157: 4986-4995, Dec. 1996, 10 pages.
West et al., "Frequency of Patent Foramen Ovale and Migraine in Patients With Cryptogenic Stroke," Stroke, 49: pp. 1123-1128, 2018.
Wicher et al., "Immunogenicity of Three Recombinant Treponema pallidum Antigens Examined in Guinea Pigs," Int. Arch. Allergy Appl. Immunol. 89 128-135, 1989, 8 pages.
Wick et al., "Transient receptor potential vanilloid 1, calcitonin gene-related peptide, and substance P mediate nociception in acute pancreatitis," Am J Physiol Gastrointest Liver Physiol 290(5):G959-G969, May 2006, 11 pages.
Wiendels and Ferrari, "Treating migraine attacks asap: concept and methodological issues," Progress in Neurotherapeutics and Neuropsychopharmacology, vol. 1 p. 53- 61, Jan. 2006, 9 pages.
Wiendels et al., "Chapter 2: Chronic frequent headache in the general population - prevalence and associated factors & Chapter 3: Chronic frequent headaches in the general population - comorbidity and quality of life," Cephalalgia vol. 26:1434-1442, 2006, 161 pages.
Wiig et al., "Interstitial Fluid and Lymph Formation and transport," Physiological Review, vol. 92, Jul. 2012, 1005-1060, 56 pages.
Wild et al., "Determination of the Human Cytochrome P450 Isoforms Involved in the Metabolism of Zolmitriptan," Xenobiotica, vol. 29, pp. 847-857, Aug. 1999, 12 pages.
Williamson et al., "Intravital microscope studies on the effects of neurokinin agonists and calcitonin gene-related peptide on dural vessel diameter in the anaesthetized rat," Cephalalgia 17(4):518-524, Jun. 1997, 14 pages.
Williamson et al., "Role of opioid receptors in neurogenic dural vasodilation and sensitization of trigeminal neurons in anaesthetized rats," British Journal of Pharmacology 133 807-814, Jul. 2001, 8 pages.
Williamson et al., "Sumatriptan inhibits neurogenic vasodilation of dural blood vessels in the anaesthetized rat -- intravital microscope studies," Cephalalgia 17(4):525-531, Jun. 1997, 12 pages.
Williamson et al., "The Novel Anti-Migraine Agent Rizatriptan Inhibits Neurogenic Dural Vasodilation and Extravasation," European Journal of Pharmacology, vol. 328, pp. 61-64, Jun. 1997, 4 pages.
Wimalawansa et al., "Isolation, Purification, and Characterization of Calcitonin Gene-Related Peptide Receptor," Peptides 14:691-699, 1993, 9 pages.
Wimalawansa, "Cacitonin Gene-Related Peptide and Its Receptors: Molecular Genetics, Physiology, Pathophysiology, and Therapeutic Potentials," Endocrine Reviews 17(5):533-585, Oct. 1996, 53 pages.
Winkler et al., "Changing the antigen binding specificity by single point mutations of an anti-p24 (HIV-1) antibody," J Immunol 165(8):4505-4514, Oct. 15, 2000, 11 pages.
Winner et al., "Impact of Fremanezumab on Response Rates, Acute Medication Use, and Disability in Patients With Episodic Migraine Who Have Failed at Least One Prior Migraine Preventive Medication," Neurology, May 2019, 92(15 Suppl.): 3 pages.
Winner et al., "Impact of fremanezumab on response rates, acute medication use, and disability in patients with episodic migraine who have failed at least one prior migraine preventive medication," The Journal of Headache and Pain, 2018, 19(Suppl 1):37.
Winner et al., "The impact of fremanezumab on headache-related disability in patients with chronic migraine using the headache impact test (HIT-6)," Headache, Jun. 2018, 58(Suppl. 2):84-85.
Winner et al., "The impact of fremanezumab on headache-related disability in patients with chronic migraine using the headache impact test (HIT-6)," Neurology, Apr. 2018, 90 (15 Suppl. 1):6 pages.
Winner et al., "The impact of fremanezumab on headache-related disability in patients with chronic migraine using the Headache Impact Test," Journal of Headache and Pain, Nov. 2017, 18(Suppl 1):43.
Winner et al., "The impact of fremanezumab on headache-related disability in patients with chronicmigraine using the Headache Impact Test (HIT-6)," Neurological Sciences, Jun. 2019, 40 (Suppl 2):S236-S237.
Winner et al., "The impact of fremanezumab on headache-related disability in patients with episodic migraine using the migraine disability assessment," Journal of Headache and Pain, Nov. 2017, 18(Suppl 1):74.
Winner et al., "The impact of fremanezumab on headache-related disability in patients with episodic migraine using the Migraine Disability Assessment," Neurological Sciences, Jun. 2019, 40 (Suppl 2):S237.
Wisskrichen et al., "Bioactive B-bend structures for the antagonist hα CGRP $_{8-37}$ at the CGRP$_1$ receptor of the rat pulmonary artery," British Journal of Pharmacology 129:1049-+1055, 2000, 7 pages.
Witte, "The madness of migraine," Scientific American Mind 39-43, Dec. 2006-Jan. 2007, 6 pages.
Wong et al., "A Randomized, Placebo Controlled, Double-Blind, Study to Evaluate the Pharmacokinetics Safety and Tolerability of LBR-101 When Administered Intravenously," Cephalgia 33(11), Aug. 2013, 1 page.
Wong et al., "Monoclonal antibody to rat alpha-CGRP: production, characterization, and in vivo immunoneutralization activity," Hybridoma 12(1):93-106, Feb. 1993, 14 pages.
Wong et al., "Preparation of a monoclonal antibody to rat alpha-CGRP for in vivo immunoneutralization of peptides," Ann N Y Acad Sci 657:525-527, Jun. 30, 1992, 3 pages.
Woods et al., "Bilateral spreading cerebral hypoperfusion during spontaneous migraine and headache," the New England Journal of Medicine, Brief Report, vol. 331, No. 25, Dec. 1994, 1689-1692, 4 pages.
World Health Organization (WHO), "General policies for monoclonal antibodies," INN Working Document 09.251 Revised, Dec. 2009, 4 pages.
World Health Organization (WHO), "WHO Drug Information, " WHO Drug Information vol. 30, No. 2, 2016, 187 pages.

(56) References Cited

OTHER PUBLICATIONS

World Health Organization, "The use of stems in the selection of international nonproprietary names (INN) for pharmaceutical substances," Programme on International Nonproprietary Names (INN), 2006, 170 pages.
Wright and Morrison, "Effect of Glycosylation on Antibody Function: Implications for Genetic Engineering," Trends Biotechnology 15: 26-32, Jan. 1997, 7 pages.
Wu et al., "Development and potential of non-peptide antagonists for calcitonin-gene-related peptide (CGRP) receptors: evidence for CGRP receptor heterogeneity," Biochem Soc Trans 30(4):468-473, Aug. 2002, 6 pages.
Wu et al., "Humanization of a murine monoclonal antibody by simultaneous optimization of framework and CDR residues," J Mol Biol 294(1):151-162, Nov. 19, 1999, 12 pages.
Wu et al., "Effects of Calcitonin Gene-Related Peptide and BIBN4096BS on Myocardial Ischemia in Anesthetized Rats," Acta Pharmacol. Sin. (2001) 22(7): 588-594.
Wu et al., "Stepwise in vitro Affinity Maturation of Vitaxin, an alphavbeta3-Specific Humanized mAb," Proc. Natl. Acad. Sci. USA 95: 6037-42, May 1998, 6 pages.
Wu et al., "Ultra-Potent Antibodies Against Respiratory Syncytial Virus: Effects of Binding Kinetics and Binding Valence on Viral Neutralization," J. Mol. Biol. 350: 126-144, Jul. 2005, 19 pages.
Wyon et al., "Urinary Excretion of Calcitonin Gene-related Peptide in Males with Hot Flushes after Castration for Carcinoma of the Prostate," Scand J Urol Nephrol 35:92-96, May 2001, 5 pages.
Xu et al., "Essential role of the TNF-TNFR2 cognate interation in mouse dendritic cell-natural killer cell crosstalk," Blood, vol. 109, No. 8, Apr. 2007, 3333-3341, 10 pages.
Xu, "Study on the Mechanism of SP and CGRP in the Chronic Pain and Knee Joint," Master Thesis. Guangxi Medical University. May 2005. (In Chinese with Engish abstract), 57 pages.
Yang et al., "CDR Walking Mutagenesis for the Affinity Maturation of a Potent Human Anti-HIV-1 Antibody into the Picomolar Range," J. Mol. Biol. 254: 392-403, Dec. 1995, 12 pages.
Yeomans et al., U.S. Appl. No. 60/711,950, filed Aug. 26, 2005, 47 pages.
Yeung et al., "Early onset of action with fremanezumab versus placebo for the preventive treatment of chronic migraine," Journal of Headache and Pain, Nov. 2017, 18(Suppl 1):47-48.
Young et al., "Transcranial Doppler: technique and application to headache," Headache, Mar. 1992, 7 pages.
Zanetti and Capra, "The Antibodies vol. 1," Chapters 2, 3, 4, 5, 6, Harwood Academic Publishers, 1995, 137 pages.
Zeller et al., "CGRP function-blocking antibodies inhibit neurogenic vasodilatation without affecting heart rate or arterial blood pressure in the rat," Brit J Pharmacol 155(7):1093-1103, Dec. 2008, 11 pages.
ZevalinTM (ibritumomab tiuxetan) Prescribing Information, Dec. 21, 2001, 38 pages.
Zhang et al. "Activation of meningeal nociceptors by cortical spreading depression: implications for migraine with aura." Journal of Neuroscience 30(26):8807-8814, Jun. 2010, 16 pages.
Zhang et al., "Activation of central trigeminovascular neurons by cortical spreading depression", Annals of neurology 69(5):855-865, May 2011, 16 pages.
Zhang et al., "Efficacy of Galcanezumab in Patients Who Failed to Respond to Preventives Previously: Results from EVOLVE-1, EVOLVE-2 and REGAIN Studies," Headache, Jun. 2018, 58(Suppl. 2):165-166.
Zhang et al., "Rheumatoid factor specificity of a VH3-encoded antibody is dependent on the heavy chain CDR3 region and is independent of protein A binding," J Immunol 161(5):2284-2289, Sep. 1, 1998, 7 pages.
Zhang et al., "Sensitization of calcitonin gene-related peptide receptors by receptor activity-modifying protein-1 in the trigeminal ganglion," J Neurosci 27(10):2693-2703, Mar. 7, 2007, 11 pages.
Zhang, "Therapeutic Protein Protein-Drug Interactions: An FDA Perspective," Office of Clinical Pharmacology Office of Translational Sciences CDER, FDA Jun. 4, 2012, 28 pages.
Zittel et al., "Role of spinal afferents and calcitonin gene-related peptide in the postoperative gastric ileus in anesthetized rats," Ann Surg 219(1):79-87, Jan. 1994, 9 pages.
Zomig (zolmitriptan) tablets and Zomig-ZMT (zolmitriptan) Orally Disintegrating Tablets, "Prescribing Information," AstraZeneca 2000, last revised: Feb. 12, 2001, 28 pages.
Zwetsloot et al., "Blood flow velocities in the vertebrobasilar system during migraine attacks—a transcranial Doppler study," Cephalalgia vol. 12:29-32, Feb. 1992, 4 pages.
Zwetsloot et al., "Blood Flow velocity changes in migraine attacks—a transcranial doppler study," Cephalalgia vol. 11:103-107, May 1991, 5 pages.
Zwetsloot et al., "Lack of asymmetry of middle cerebral artery blood flow velocity in unilateral migraine," Stroke, vol. 24, No. 9, Sep. 1993, 4 pages.
Zwetsloot et al., "Vascular reactivity during migraine attacks: a transcranial Doppler study," Headache, Oct. 1991, 3 pages.
*Eli Lilly and Company v Teva Pharmaceuticals International GMBH*, "Declaration of Dr. Alain P. Vasserot, Ph.D.," Case No. IPR2018-01711, U.S. Pat. No. 9,884,907, Sep. 27, 2018, 78 pages.
*Eli Lilly and Company v Teva Pharmaceuticals International GMBH*, "Declaration of Dr. Andrew Charles," Case No., IPR2018-01711, U.S. Pat. No. 9,884,907, Oct. 1, 2018, 114 pages.
*Eli Lilly and Company v Teva Pharmaceuticals International GMBH*, "Petitioner's Exhibit List as of Oct. 1, 2018," Case No., IPR2018-01711, U.S. Pat. No. 9,884,907, Oct. 1, 2018, 20 pages.
*Eli Lilly and Company v Teva Pharmaceuticals International GMBD*, "Declaration of Alain P. Vasserot," Case No. IPR2018-01710, U.S. Pat. No. 8,586,045 on Sep. 9, 2018, 86 pages.
*Eli Lilly and Company v Teva Pharmaceuticals International GMBH*, "Declaration of Alain P. Vasserot," Case No. IPR2018-01423, U.S. Pat. No. 9,266,951, Aug. 2018, 80 pages.
*Eli Lilly and Company v Teva Pharmaceuticals International GMBH*, "Declaration of Alain P. Vasserot," Case No. IPR2018-01424, U.S. Pat. No. 9,346,881, Aug. 2018, 85 pages.
*Eli Lilly and Company v Teva Pharmaceuticals International GMBH*, "Declaration of Alain P. Vasserot," Case No. IPR2018-01425, U.S. Pat. No. 9,890,210, Aug. 2018, 75 pages.
*Eli Lilly and Company v Teva Pharmaceuticals International GMBH*, "Declaration of Alain P. Vasserot," Case No. IPR2018-01426, U.S. Pat. No. 9,890,211, Aug. 2018, 93 pages.
*Eli Lilly and Company v Teva Pharmaceuticals International GMBH*, "Declaration of Alain P. Vasserot," Case No. IPR2018-01427, U.S. Pat. No. 8,597,649, Aug. 2018, 88 pages.
*Eli Lilly and Company v Teva Pharmaceuticals International GMBH*, "Declaration of Andrew Charles, M.D.," Case No. IPR2018-01422, U.S. Pat. No. 9,340,614, Aug. 7, 2018, 93 pages.
*Eli Lilly and Company v Teva Pharmaceuticals International GMBH*, "Declaration of Andrew Charles, M.D.," Case No. IPR2018-01424, U.S. Pat. No. 9,346,881, Aug. 7, 2018, 99 pages.
*Eli Lilly and Company v Teva Pharmaceuticals International GMBH*, "Declaration of Andrew Charles, M.D.," Case No. IPR2018-01426, U.S. Pat. No. 9,890,211, Aug. 8, 2018, 100 pages.
*Eli Lilly and Company v Teva Pharmaceuticals International GMBH*, "Declaration of Andrew Charles, M.D.," Case No. IPR2018-01427, U.S. Pat. No. 8,597,649, Aug. 8, 2018, 94 pages.
*Eli Lilly and Company v Teva Pharmaceuticals International GMBH*, "Declaration of Andrew Charles, M.D.," IPR2018-01423, U.S. Pat. No. 9,266,951, Aug. 7, 2018, 98 pages.
*Eli Lilly and Company v Teva Pharmaceuticals International GMBH*, "Declaration of Andrew Charles, M.D.," IPR2018-01425, U.S. Pat. No. 9,890,210, Aug. 8, 2018, 93 pages.
*Eli Lilly and Company v Teva Pharmaceuticals International GMBH*, "Declaration of Andrew Charles, M.D.," IPR2018-01710, U.S. Pat. No. 8,586,045 on Sep. 27, 2018, 113 pages.
*Eli Lilly and Company v Teva Pharmaceuticals International GMBH*, "Petition for Inter Parte Review," Case No. IPR2018-01711, U.S. Pat. No. 9,884,907, filed Oct. 1, 2018, 74 pages.

(56) References Cited

OTHER PUBLICATIONS

*Eli Lilly and Company* v *Teva Pharmaceuticals International GMBH*, "Petition for Inter Partes Review," Case No. IPR2018-01422, U.S. Pat. No. 9,340,614, dated Aug. 8, 2018, 71 pages.
*Eli Lilly and Company* v *Teva Pharmaceuticals International GMBH*, "Petition for Inter Partes Review," Case No. IPR2018-01423, U.S. Pat. No. 9,266,951, dated Aug. 8, 2018, 76 pages.
*Eli Lilly and Company* v *Teva Pharmaceuticals International GMBH*, "Petition for Inter Partes Review," Case No. IPR2018-01424, U.S. Pat. No. 9,346,881, dated Aug. 8, 2018, 78 pages.
*Eli Lilly and Company* v *Teva Pharmaceuticals International GMBH*, "Petition for Inter Partes Review," Case No. IPR2018-01425, U.S. Pat. No. 9,890,210, dated Aug. 8, 2018, 67 pages.
*Eli Lilly and Company* v *Teva Pharmaceuticals International GMBH*, "Petition for Inter Partes Review," Case No. IPR2018-01426, U.S. Pat. No. 9,890,211, dated Aug. 8, 2018, 77 pages.
*Eli Lilly and Company* v *Teva Pharmaceuticals International GMBH*, "Petition for Inter Partes Review," Case No. IPR2018-01427, U.S. Pat. No. 8,597,649, dated Aug. 8, 2018, 76 pages.
*Eli Lilly and Company* v *Teva Pharmaceuticals International GMBH*, "Petition for Inter Partes Review," Case No. IPR2018-01710, U.S. Pat. No. 8,586,045 on Sep. 28, 2018, 79 pages.
*Eli Lilly and Company* v *Teva Pharmaceuticals International GMBH*, "Petitioner's Exhibit List as of Sep. 28, 2018," Case No. IPR2018-01710, U.S. Pat. No. 8,586,045 on Sep. 28, 2018, 21 pages.
*Eli Lilly and Company* v *Teva Pharmaceuticals International GMBH*, "Judgement, Final Written Decision, Determining All Challenged Claims Unpatentable," IPR2018-01422 (U.S. Pat. No. 9,340,614 B2), IPR2018-01423 (U.S. Pat. No. 9,266,951 B2), IPR2018-01425 (U.S. Pat. No. 9,890,210 B2), Feb. 18, 2020, 168 pages.
*Eli Lilly and Company* v *Teva Pharmaceuticals International GMBH*, "Judgement, Final Written Decision, Determining All Challenged Claims Unpatentable," IPR2018-01424 (U.S. Pat. No. 9,346,881 B2), IPR2018-01426 (U.S. Pat. No. 9,890,211 B2), IPR2018-01427 (U.S. Pat. No. 8,597,649 B2), Feb. 18, 2020, 174 pages.
*Eli Lilly and Company* v *Teva Pharmaceuticals International GMBH*, "Judgement, Final Written Decision, Determining No. Challenged Claims Unpatentable," IPR2018-01710 (U.S. Pat. No. 8,586,045 B2), IPR2018-01711 (U.S. Pat. No. 9,884,907 B2), IPR2018-01712 (U.S. Pat. No. 9,884,908 B2), Mar. 31, 2020, 166 pages.
*Eli Lilly and Company* v *Teva Pharmaceuticals International GMBH*, "Petitioner's Exhibit List as of Aug. 8, 2018," Case No. IPR2018-01422, U.S. Pat. No. 9,340,614, dated Aug. 8, 2018, 20 pages.
*Eli Lilly and Company* v *Teva Pharmaceuticals International GMBH*, "Petitioner's Exhibit List as of Aug. 8, 2018," Case No. IPR2018-01423, U.S. Pat. No. 9,266,951, dated Aug. 8, 2018, 18 pages.
*Eli Lilly and Company* v *Teva Pharmaceuticals International GMBH*, "Petitioner's Exhibit List as of Aug. 8, 2018," Case No. IPR2018-01424, U.S. Pat. No. 9,346,881, dated Aug. 8, 2018, 19 pages.
*Eli Lilly and Company* v *Teva Pharmaceuticals International GMBH*, "Petitioner's Exhibit List as of Aug. 8, 2018," Case No. IPR2018-01425, U.S. Pat. No. 9,890,210, dated Aug. 8, 2018, 20 pages.
*Eli Lilly and Company* v *Teva Pharmaceuticals International GMBH*, "Petitioner's Exhibit List as of Aug. 8, 2018," Case No. IPR2018-01426, U.S. Pat. No. 9,890,211, dated Aug. 8, 2018. 21 pages.
*Eli Lilly and Company* v *Teva Pharmaceuticals International GMBH*, "Petitioner's Exhibit List as of Aug. 8, 2018," Case No. IPR2018-01427, U.S. Pat. No. 8,597,649, dated Aug. 8, 2018, 19 pages.
*Eli Lilly and Company* v *Teva Pharmaceuticals International GMBH.*, "Declaration of Alain P. Vasserot," Case No. IPR2018-01422, U.S. Pat. No. 9,340,614, Aug. 2018, 78 pages.
*Eli Lilly and Company* v *Teva Pharmaceuticals International GMBH*, "Declaration of Dr. Alain P. Vasserot," Case No. IPR2018-01712, U.S. Pat. No. 9,884,908, Sep. 27, 2018, 93 pages.
*Eli Lilly and Company* v *Teva Pharmaceuticals International GMBH*, "Declaration of Dr. Andrew Charles," Case No. IPR2018-01712, U.S. Pat. No. 9,884,908, Oct. 1, 2018, 119 pages.
*Eli Lilly and Company* v *Teva Pharmaceuticals International GMBH*, "Petition for Inter Partes Review," Case No., IPR2018- 01712, U.S. Pat. No. 9,884,908, Oct. 1, 2018, 79 pages.

*Eli Lilly and Company* v *Teva Pharmaceuticals International GMBH*, "Petitioner's Exhibit List of Oct. 1, 2018," Case No., IPR2018-01712, U.S. Pat. No. 9,884,908, Oct. 1, 2018, 21 pages.
*Eli Lilly and Company* v *Teva Pharmaceuticals International GMBH*, "Petitioner's Updated Exhibit List as of Jul. 17, 2023," Case No. IPR2022-00738, U.S. Pat. No. 11,028,160, filed Jul. 17, 2023, 24 pages.
*Eli Lilly and Company* v *Teva Pharmaceuticals International GMBH*, "Patent Owner's Updated Exhibit List," Case No. IPR2022-00738, U.S. Pat. No. 11,028,160, filed Jul. 17, 2023, 14 pages.
*Eli Lilly and Company* v *Teva Pharmaceuticals International GMBH*, "Petitioner's Updated Exhibit List as of Jul. 17, 2023," Case No. IPR2022-00739, U.S. Pat. No. 11,028,161, filed Jul. 17, 2023, 24 pages.
*Eli Lilly and Company* v *Teva Pharmaceuticals International GMBH*, "Patent Owner's Updated Exhibit List," Case No. IPR2022-00739, U.S. Pat. No. 11,028,161, filed Jul. 17, 2023, 14 pages.
*Eli Lilly and Company* v *Teva Pharmaceuticals International GMBH*, "Petitioner's Updated Exhibit List as of Jul. 17, 2023," Case No. IPR2022-00796, U.S. Pat. No. 10,392,434, filed Jul. 17, 2023, 23 pages.
*Eli Lilly and Company* v *Teva Pharmaceuticals International GMBH*, "Patent Owner's Updated Exhibit List as of Jul. 17, 2023," Case No. IPR2022-00796, U.S. Pat. No. 10,392,434, filed Jul. 17, 2023, 12 pages.
Bigal et al., "Target Doses and Titration Schedules for Migraine Preventive Medications," Headache, Jan. 2006, 46:160-164.
Boudreau et al., "Prophylactic onabotulinumtoxinA in patients with chronic migraine and comorbid depression: An open-label, multicenter, pilot study of efficacy, safety and effect on headache-related disability, depression, and anxiety," International Journal of General Medicine, Feb. 2015, 9:79-86.
Corrected Declaration of Dr. Deborah Hay, *Eli Lilly and Company*, Petitioner, v. *Teva Pharmaceuticals International GmBH*, Patent Owner, Case No. IPR2022-00738, U.S. Pat. No. 11,028,160, May 16, 2023, 64 pages.
Corrected Declaration of Dr. Deborah Hay, *Eli Lilly and Company*, Petitioner, v. *Teva Pharmaceuticals International GmBH*, Patent Owner, Case No. IPR2022-00739, U.S. Pat. No. 11,028,161, May 16, 2023, 64 pages
Corrected Declaration of Dr. Deborah Hay, *Eli Lilly and Company*, Petitioner, v. *Teva Pharmaceuticals International GmBH*, Patent Owner, Case No. IPR2022-00796, U.S. Pat. No. 10,392,434, May 16, 2023, 64 pages.
Declaration of Dr. Deborah Hay, *Eli Lilly and Company*, Petitioner, v. *Teva Pharmaceuticals International GmBH*, Patent Owner, Case No. IPR2022-00738, U.S. Pat. No. 11,028,160, May 10, 2023, 64 pages.
Declaration of Dr. Deborah Hay, *Eli Lilly and Company*, Petitioner, v. *Teva Pharmaceuticals International GmBH*, Patent Owner, Case No. IPR2022-00739, U.S. Pat. No. 11,028,161, May 10, 2023, 64 pages.
Declaration of Dr. Deborah Hay, *Eli Lilly and Company*, Petitioner, v. *Teva Pharmaceuticals International GmBH*, Patent Owner, Case No. IPR2022-00796, U.S. Pat. No. 10,392,434, May 10, 2023, 64 pages.
Declaration of Lauren Gluckman, *Eli Lilly and Company*, Petitioner, v. *Teva Pharmaceuticals International GmBH*, Patent Owner, Case No. IPR2022-00738, U.S. Pat. No. 11,028,160, May 25, 2023, 13 pages.
Declaration of Lauren Gluckman, *Eli Lilly and Company*, Petitioner, v. *Teva Pharmaceuticals International GmBH*, Patent Owner, Case No. IPR2022-00739, U.S. Pat. No. 11,028,161, May 25, 2023, 13 pages.
Declaration of Lauren Gluckman, *Eli Lilly and Company*, Petitioner, v. *Teva Pharmaceuticals International GmBH*, Patent Owner, Case No. IPR2022-00796, U.S. Pat. No. 10,392,434, May 25, 2023, 11 pages.
Deposition of Deborah Lucy Hay, Ph. D., *Eli Lilly and Company* v. *Teva Pharmaceuticals International GMBH*, Case Nos. IPR2022-00738, IPR2022-00739, and IPR2022-00796, May 20, 2023, 221 pages.

(56) References Cited

OTHER PUBLICATIONS

Deposition Transcript of Brian M. Grosberg, M.D., *Eli Lilly and Company* v. *Teva Pharmaceuticals International GMBH*, Case Nos. IPR2022-00738, Mar. 28, 2023, 273 pages.

Errata to the Transcript of the Deposition of Dr. Brian M. Grosberg, Mar. 28, 2023, 2 pages.

FDA, "IND Application Reporting: Safety Reports," retrieved on Mar. 17, 2023, retrieved from URL <https://www.fda.gov/drugs/investigational-new-drug-ind-application/ind-application-reporting-safety-reports>, 3 pages.

Hay, "CGRP Receptor Biology: Is There More Than One Receptor?" Handb. Exp. Pharmacol., Aug. 2019, 255:13-22.

Hendrikse et al., "Molecular studies of CGRP and the CGRP family of peptides in the central nervous system," Cephalalgia, 39(3):403-419, 2019, 17 pages.

Hong et al., "Calcitonin gene-related peptide monoclonal antibody for preventive treatment of episodic migraine: A meta analysis," Clinical Neurology & Neurosurgery, Mar. 2017, 154:74-78.

ICH Harmonised Guideline, "Integrated Addendum to ICH E6(R1): Guideline for Good Clinical Practice E6(R2)," Current Step 4 version, Nov. 9, 2016, retrieved from URL <https://database.ich.org/sites/default/files/E6_R2_Addendum.pdf>, 66 pages.

Lopez et al., "Cardiovascular Disease," NCBI Bookshelf, retrieved on Mar. 22, 2023, retrieved from URL <https://www.ncbi.nlm.nih.gov/books/NBK535419/?report=printable>, 12 pages.

Mitsikostas et al., "Calcitonin gene-related peptide monoclonal antibodies for migraine prevention: comparisons across randomized controlled studies," Current Op. Neurol., Jun. 2017, 30(3):272-280.

Pan et al., "Antagonism of CGRP Signaling by Rimegepant at Two Receptors," Frontiers in Pharmacology, Aug. 2020, 11:1240, 1-5.

Procter, "Low Blood Pressure (Hypotension)," Merck Manuals Consumer Version (Modified Sep. 2022), retrieved on Mar. 22, 2023, retrieved from URL <https://www.merckmanuals.com/home/heart-and-blood-vessel-disorders/low-blood-pressure-and-shock/low-blood-pressure>, 6 pages.

Robbins et al., "Trigger Point Injections for Headache Disorders: Expert Consensus Methodology and Narrative Review," Headache, Oct. 2014, 54:1441-1459.

Russo et al., "CGRP Physiology, Pharmacology, and Therapeutic Targets: Migraine and Beyond," Physiological Reviews, Mar. 2023, 103:1565-1644, 81 pages.

Supplementary webappendix to Bigal et al., "Safety, tolerability, and efficacy of TEV-48125 for preventive treatment of high-frequency episodic migraine: a multicentre, randomised, double-blind, placebo-controlled, phase 2b study," Lancet Neurol., Sep. 2015, 5 pages.

Supplementary webappendix to Sun et al., "Safety and efficacy of AMG334 for prevention of episodic migraine: a randomised, double-blind, placebo-controlled, phase 2 trial," Lancet Neurol., Feb. 2016, 8 pages.

Supplementary webappendix to Tepper et al., "Safety and efficacy of erenumab for preventive treatment of chronic migraine: a randomised, double-blind, placebo-controlled phase 2 trial," Lancet Neurol., Apr. 2017, 6 pages.

U.S. Department of Health and Human Services, Food and Drug Administration, Center for Drug Evaluation and Research, Center for Biologics Evaluation and Research, "Guidance for Industry and Investigators: Safety Reporting Requirements for INDs and BA/BE Studies," Drug Safety, Dec. 2012, retrieved from URL <https://www.fda.gov/media/79394/download>, 32 pages.

Yeh et al., "Monoclonal antibodies for chronic pain: A practical review of mechanisms and clinical applications," Molecular Pain, Jan. 2017, 13:1-14.

Youdim, "Obesity," Merck Manuals Consumer Version (Modified Sep. 2022), retrieved on Mar. 23, 2023, retrieved from URL <https://www.merckmanuals.com/home/disorders-of-nutrition/obesity-and-the-metabolic-syndrome/obesity?query=obesity>, 13 pages.

Young, Jr., "Endocrine Disorders," Merck Manuals Consumer Version (Modified Sep. 2022), retrieved on Mar. 23, 2023, retrieved from URL <https://www.merckmanuals.com/home/hormonal-and-metabolic-disorders/biology-of-the-endocrine-system/endocrine-disorders>, 3 pages.

*Eli Lilly and Company*, Petitioner, v. *Teva Pharmaceuticals International GMBH*, Patent Owner, Case No. IPR2022-00738; U.S. Pat. No. 11,028, 160, Patent Owner's Sur-Reply, filed on Jun. 2, 2023, 42 pages.

*Eli Lilly and Company*, Petitioner, v. *Teva Pharmaceuticals International GMBH*, Patent Owner, Case No. IPR2022-00738; U.S. Pat. No. 11,028, 160, Patent Owner's Updated Exhibit List as of Jun. 2, 2023, dated Jun. 2, 2023, 11 pages.

*Eli Lilly and Company*, Petitioner, v. *Teva Pharmaceuticals International GMBH*, Patent Owner, Case No. IPR2022-00738; U.S. Pat. No. 11,028,160, Petitioner's Reply to Patent Owner's Response, filed May 11, 2023, 35 pages.

*Eli Lilly and Company*, Petitioner, v. *Teva Pharmaceuticals International GMBH*, Patent Owner, Case No. IPR2022-00738; U.S. Pat. No. 11,028, 160, Petitioner's Updated Exhibit List as of May 11, 2023, filed May 11, 2023, 23 pages.

*Eli Lilly and Company*, Petitioner, v. *Teva Pharmaceuticals International GMBH*, Patent Owner, Case No. IPR2022-00738; U.S. Pat. No. 11,028, 160, Petitioner's Updated Exhibit List as of May 18, 2023, filed May 18, 2023, 23 pages.

*Eli Lilly and Company*, Petitioner, v. *Teva Pharmaceuticals International GMBH*, Patent Owner, Case No. IPR2022-00738; U.S. Pat. No. 11,028, 160, Petitioner's Updated Exhibit List as of May 25, 2023, dated May 25, 2023, 24 pages.

*Eli Lilly and Company*, Petitioner, v. *Teva Pharmaceuticals International GMBH*, Patent Owner, Case No. IPR2022-00739; U.S. Pat. No. 11,028,161, Patent Owner's Sur-Reply, filed on Jun. 2, 2023, 42 pages.

*Eli Lilly and Company*, Petitioner, v. *Teva Pharmaceuticals International GMBH*, Patent Owner, Case No. IPR2022-00739; U.S. Pat. No. 11,028,161, Patent Owner's Updated Exhibit List as of Jun. 2, 2023, dated Jun. 2, 2023, 11 pages.

*Eli Lilly and Company*, Petitioner, v. *Teva Pharmaceuticals International GMBH*, Patent Owner, Case No. IPR2022-00739; U.S. Pat. No. 11,028,161, Petitioner's Reply to Patent Owner's Response, filed May 11, 2023, 35 pages.

*Eli Lilly and Company*, Petitioner, v. *Teva Pharmaceuticals International GMBH*, Patent Owner, Case No. IPR2022-00739; U.S. Pat. No. 11,028, 161, Petitioner's Updated Exhibit List as of May 11, 2023, filed May 11, 2023, 23 pages.

*Eli Lilly and Company*, Petitioner, v. *Teva Pharmaceuticals International GMBH*, Patent Owner, Case No. IPR2022-00739; U.S. Pat. No. 11,028, 161, Petitioner's Updated Exhibit List as of May 18, 2023, filed May 18, 2023, 23 pages.

*Eli Lilly and Company*, Petitioner, v. *Teva Pharmaceuticals International GMBH*, Patent Owner, Case No. IPR2022-00739; U.S. Pat. No. 11,028, 161, Petitioner's Updated Exhibit List as of May 25, 2023, dated May 25, 2023, 24 pages.

*Eli Lilly and Company*, Petitioner, v. *Teva Pharmaceuticals International GMBH*, Patent Owner, Case No. IPR2022-00796; U.S. Pat. No. 10,392,434, Patent Owner's Sur-Reply, filed on Jun. 2, 2023, 36 pages.

*Eli Lilly and Company*, Petitioner, v. *Teva Pharmaceuticals International GMBH*, Patent Owner, Case No. IPR2022-00796; U.S. Pat. No. 10,392,434, Patent Owner's Updated Exhibit List as of Jun. 2, 2023, dated Jun. 2, 2023, 8 pages.

*Eli Lilly and Company*, Petitioner, v. *Teva Pharmaceuticals International GMBH*, Patent Owner, Case No. IPR2022-00796; U.S. Pat. No. 10,392,434, Petitioner's Reply to Patent Owner's Response, filed May 11, 2023, 35 pages.

*Eli Lilly and Company*, Petitioner, v. *Teva Pharmaceuticals International GMBH*, Patent Owner, Case No. IPR2022-00796; U.S. Pat. No. 10,392,434, Petitioner's Updated Exhibit List as of May 11, 2023, filed May 11, 2023, 21 pages.

*Eli Lilly and Company*, Petitioner, v. *Teva Pharmaceuticals International GMBH*, Patent Owner, Case No. IPR2022-00796; U.S. Pat. No. 10,392,434, Petitioner's Updated Exhibit List as of May 18, 2023, filed May 18, 2023, 21 pages.

*Eli Lilly and Company*, Petitioner, v. *Teva Pharmaceuticals International GMBH*, Patent Owner, Case No. IPR2022-00796; U.S. Pat.

(56) References Cited

OTHER PUBLICATIONS

No. 10,392,434, Petitioner's Updated Exhibit List as of May 25, 2023, dated May 25, 2023, 23 pages.
*Eli Lilly and Company*, Petitioner, v. *Teva Pharmaceuticals International GMBH*, Patent Owner, Case Nos. IPR2022-00738, IPR2022-00739, and IPR2022-00796; Telephonic Conference, dated May 17, 2023, 34 pages.
*Eli Lilly and Co.* v. *Teva Pharmaceuticals International GMBH*, "Patent Owner's Oral Hearing Demonstratives," cases IPR2022-00738, IPR2022-00739, IPR2022-00796, Jul. 19, 2023, 104 pages.
*Eli Lilly and Co.* v. *Teva Pharmaceuticals Intl. GMBH*, "Petitioner's Demonstratives," cases IPR2022-00738, IPR2022-00739, IPR2022-00796, Jul. 19, 2023, 121 pages.
*Eli Lilly and Company*, Petitioner, v. *Teva Pharmaceuticals International GMBH*, Patent Owner, "DECISION, Final Written Decision, Determining All Challenged Claims Unpatentable," Case No. IPR2022-00738, U.S. Pat. No. 11,028,160, filed Sep. 25, 2023, 113 pages.
*Eli Lilly and Company*, Petitioner, v. *Teva Pharmaceuticals International GMBH*, Patent Owner, "DECISION, Final Written Decision, Determining All Challenged Claims Unpatentable," Case No. IPR2022-00739, U.S. Pat. No. 11,028,161, filed Sep. 25, 2023, 113 pages.
*Eli Lilly and Company*, Petitioner, v. *Teva Pharmaceuticals International GMBH*, Patent Owner, "Record of Oral Hearing," Case Nos. IPR2022-00738, IPR2022-00739, and IPR2022-00796, dated Sep. 21, 2023, 74 pages.
*Eli Lilly and Company*, Petitioner, v. *Teva Pharmaceuticals International GMBH*, Patent Owner, "DECISION, Final Written Decision, Determining All Challenged Claims Unpatentable," Case No. IPR2022-00796, U.S. Pat. No. 10,392,434, filed Oct. 11, 2023, 108 pages.
Inter Partes Review Certificate, Case No. IPR2022-00738, U.S. Pat. No. 11,028,160 K1, issued Jan. 3, 2024, Aycardi et al., 2 pages.
Inter Partes Review Certificate, Case No. IPR2022-00739, U.S. Pat. No. 11,028,161 K1, issued Jan. 2, 2024, Bigal et al., 2 pages.
"Definition of the Different Classes of Evidence (CoE)," Evidence-Based Spine-Care Journal, 2013, 4(2), 1 page.
American Headache Society, "57th Annual Scientific Meeting," American Headache Society, Jun. 18-21, 2015, Washington, DC, 127-187.
American Headache Society, "Late-Breaking Abstracts: 57th Annual Scientific Meeting of the American Headache Society, " Headache, 2015, 17 pages.
American Headache Society, "Program Abstracts: The 59th Annual American Headache Society Meeting, " Headache, Jun. 2017, 57(S3), 117 pages.
Andreou et al., "Topiramate in the Treatment of Migraine: A Kainate (Glutamate) Receptor Antagonist Within the Trigeminothalamic Pathway," Cephalalgia, Sep. 2011, 31(13):1343-1358.
Aurora et al., "Factors Associated with Significant Reduction in Migraine Headache Days: A Post Hoc Analysis of a Phase II Placebo-Controlled Trial in Patients Treated with Galcanezumab," Neurology, 2017, 88(16), 6 pages.
Bigal et al., "Memantine in the Preventive Treatment of Refractory Migraine," Headache, 2008, 48:1337-1342.
Bigal et al., "Monoclonal Antibodies for Migraine: Preventing Calcitonin Gene- Related Peptide Activity," CNS Drugs, 2014, 28:389-399.
Binder et al., "Botulinum Toxin Type A (Botox) for Treatment of Migraine," Dis. Mon., May 2002, 48:323-335.
Blumenfeld et al., "Patterns of Use and Reasons for Discontinuation of Prophylactic Medications for Episodic Migraine and Chronic Migraine: Results From the Second International Burden of Migraine Study (IBMS-II)," Headache, 2013, 53:644-55.
Bordini et al., "Propranolol vs Flunarizine vs Flunarizine Plus Propranolol In Migraine Without Aura Prophylaxis," Arq Neuropsiquiair, 1997, 55(3-B):536-541.

ClinicalTrials.gov identifier NCT02021773 "Assessment of LBR-101 in Chronic Migraine," dated Dec. 27, 2013, retrieved from URL <https://clinicaltrials.gov/ct2/show/NCT02021773>, 7 pages.
Complaint, *Teva Pharmaceuticals International GmbH* v. *Eli Lilly and Company*, No. 1:21-cv-10954, dated Jun. 8, 2021, 31 pages.
Curriculum Vitae of Brian M. Grosberg, M.D., Jan. 27, 2023, 25 pages.
Curriculum Vitae of Pamela Blake, MD, FAHS, May 11, 2022, 12 pages.
Declaration of Brian M. Grosberg, M.D., *Eli Lilly and Company*, Petitioner, v. *Teva Pharmaceuticals International GmBH*, Patent Owner, Case No. IPR2022-00738, U.S. Pat. No. 11,028,160, Jan. 27, 2023, 177 pages.
Declaration of Brian M. Grosberg, M.D., *Eli Lilly and Company*, Petitioner, v. *Teva Pharmaceuticals International GmBH*, Patent Owner, Case No. IPR2022-00739, U.S. Pat. No. 11,028,161, Jan. 27, 2023, 177 pages.
Declaration of Brian M. Grosberg, M.D., *Eli Lilly and Company*, Petitioner, v. *Teva Pharmaceuticals International GmBH*, Patent Owner, Case No. IPR2022-00796, U.S. Pat. No. 10,392,434, Jan. 27, 2023, 213 pages.
Declaration of Dr. Stefan Evers, MD, Ph. D., *Eli Lilly and Company*, Petitioner, v. *Teva Pharmaceuticals International GmBH*, Patent Owner, U.S. Pat. No. 10,392,434, dated Apr. 11, 2022, 158 pages.
Declaration of Dr. Stefan Evers, MD, Ph. D., *Eli Lilly and Company*, Petitioner, v. *Teva Pharmaceuticals International GmBH*, Patent Owner, U.S. Pat. No. 11,028,160, dated Mar. 21, 2022, 173 pages.
Declaration of Dr. Stefan Evers, MD, Ph. D., *Eli Lilly and Company*, Petitioner, v. *Teva Pharmaceuticals International GmBH*, Patent Owner, U.S. Pat. No. 11,028,161, dated Mar. 21, 2022, 170 pages.
Declaration of Pamela Blake, Md, Fahs, *Eli Lilly and Company*, Petitioner, v. *Teva Pharmaceuticals International GmBH*, Patent Owner, Case No. IPR2022-00738, U.S. Pat. No. 11,028,160, dated Jun. 30, 2022, 82 pages.
Declaration of Pamela Blake, Md, Fahs, *Eli Lilly and Company*, Petitioner, v. *Teva Pharmaceuticals International GmBH*, Patent Owner, Case No. IPR2022-00739, U.S. Pat. No. 11,028,161, dated Jun. 30, 2022, 82 pages.
Declaration of Pamela Blake, Md, Fahs, *Eli Lilly and Company*, Petitioner, v. *Teva Pharmaceuticals International GmBH*, Patent Owner, Case No. IPR2022-00796 U.S. Pat. No. 10,392,434, dated Jul. 18, 2022, 109 pages.
Declaration of Shauna L. Wiest, *Eli Lilly and Company*, Petitioner, v. *Teva Pharmaceuticals International GmBH*, Patent Owner, U.S. Pat. No. 10,392,434, dated Apr. 11, 2022, 104 pages.
Declaration of Shauna L. Wiest, *Eli Lilly and Company*, Petitioner, v. *Teva Pharmaceuticals International GmBH*, Patent Owner, U.S. Pat. No. 11,028,160, dated Mar. 22, 2022, 104 pages.
Declaration of Shauna L. Wiest, *Eli Lilly and Company*, Petitioner, v. *Teva Pharmaceuticals International GmBH*, Patent Owner, U.S. Pat. No. 11,028,161, dated Mar. 22, 2022, 104 pages.
Demaagd, "The Pharmacological Management of Migraine, Part 1: Overview and Abortive Therapy," Pharmacy & Therapeutics, 2008, 33(7):404-419.
Demaagd, "The Pharmacological Management of Migraine, Part 2: Preventive Therapy," Pharmacy & Therapeutics, 2008, 33(8):480-487.
Deposition Transcript of Dr. Stefan Evers, *Eli Lilly and Company* v. *Teva Pharmaceuticals International GMBH*, Case Nos. IPR2022-00738, IPR2022-00739, IPR2022-00796, Dec. 13, 2022, 163 pages.
Durham et al., "Regulation of Calcitonin Gene-Related Peptide Secretion From Trigeminal Nerve Cells by Botulinum Toxin Type A: Implications for Migraine Therapy," Headache, Jan. 2004, 44:35-43.
Durham et al., "Repression of Stimulated Calcitonin Gene-Related Peptide Secretion by Topiramate," Headache, Sep. 2006, 46:1291-1295.
Edvinsson et al., "New Drugs in Migraine Treatment and Prophylaxis: Telcagepant and Topiramate," Lancet, Aug. 2010, 376:645-655.
Evers et al., "EFNS guideline on the drug treatment of migraine—revised report of an EFNS task force," European Journal of Neurology, 2009, 16:968-81.

(56) References Cited

OTHER PUBLICATIONS

Form 6-K Teva Pharmaceutical Industries Ltd., Press Release, "Teva to Present New Findings at the American Headache Society (AHS) Meeting," dated Jun. 18, 2015, 9 pages.
Giamberardino et al., "Anti-CGRP monoclonal antibodies in migraine: current perspectives," Intern. Emerg. Med., 2016, 11:1045-1057, 13 pages.
Ho et al., "Antimigraine Efficacy of Telcagepant Based on Patient's Historical Triptan Response," Headache, 2011, 51:64-72.
Ho et al., "Randomized Controlled Trial of the CGRP Receptor Antagonist Telcagepant for Migraine Prevention," Neurology, Sep. 2014, 83: 958-966, 11 pages.
Ho et al., "Randomized Controlled Trial of The CGRP Receptor Antagonist Telcagepant For Prevention of Headache in Women with Perimenstrual Migraine," Cephalalgia, Feb. 2016, 36(2):148-161.
Hou et al., "The effect and safety of monoclonal antibodies to calcitonin gene-related peptide and its receptor on migraine: a systematic review and meta-analysis," The Journal of Headache and Pain, 2017, 18:42, 12 pages.
Hou et al., "The effect and safety of monoclonal antibodies to calcitonin gene-related peptide and its receptor on migraine: a systematic review and meta-analysis," The Journal of Headache and Pain, 2017, 18:42, retrieved from URL <https://thejournalofheadacheandpain.biomedcentral.com/articles/10.1186/s10194-017-0750-1>, 40 pages.
International Headache Society, "Abstracts of the 18th International Headache Congress," Cephalalgia, Sep. 2017, 37(1), 382 pages.
Jackisch et al., "Subcutaneous Administration of Monoclonal Antibodies in Oncology," Geburtsh Frauenheilk, 2014, 74:343-349.
Joshi et al., "A Narrative Review of the Importance of Pharmacokinetics and Drug-Drug Interactions of Preventive Therapies in Migraine Management," Headache, Feb. 2021, 61:838-853.
Karadas et al., "The Effects of Topiramate Therapy on Cerebral Metabolism in Migraine with Aura Patients," Turk Neurosurg, 2014, 24(5):704-709.
Katori et al., "Calcitonin Gene-Related Peptide In Vivo Positive Inotropy Is Attributable to Regional Sympatho-Stimulation and Is Blunted in Congestive Heart Failure," Circulation Research, Feb. 2005, 96:234-243.
Katsarava et al., "Defining the Differences Between Episodic Migraine and Chronic Migraine," Curr. Pain Headache Rep., 2012, 16:86-92.
Keskinbora et al., "A double-blind randomized controlled trial of topiramate and amitriptyline either alone or in combination for the prevention of migraine," Clinical Neurology & Neurosurgery, 2008, 110:979-84.
Kim et al., "Transforming Clinical Trial Eligibility Criteria to Reflect Practical Clinical Application," ASCO Educational Book, 2016, 36:83-90, 34 pages.
Kunz et al., "Calcitonin Gene-Related Peptide-Evoked Sustained Tachycardia in Calcitonin Receptor-Like Receptor Transgenic Mice is Mediated by Sympathetic Activity," Am. J. Physio.1 Heart Circ. Physiol., Oct. 2007, 293:H2155-H2160.
Luo et al., "The Pharmacological Mechanism of Gastrodin on Calcitonin Gene-Related Peptide of Cultured Rat Trigeminal Ganglion," Acta Pharmaceutica Sinica, Dec. 2011, 46(12): 1451-1456.
Mansfield et al., "Patient Preferences for Preventive Migraine Treatments: A Discrete-Choice Experiment," Headache, 2019, 59:715-26.
Martelletti et al., "Refractory chronic migraine: a Consensus Statement on clinical definition from the European Headache Federation," The Journal of Headache and Pain, 2014, 15:47, 6 pages.
Mathew, "Pathophysiology of Chronic Migraine and Mode of Action of Preventive Medications," Headache, Jul. 2011, 51(Suppl 2):84-92.
May et al., "Chronic Migraine: Risk Factors, Mechanisms, and Treatment," Neurology, Aug. 2016, 12:455-464.
Memorandum and Order on Motion to Dismiss, *Teva Pharmaceuticals International GmbH v. Eli Lilly and Company*, No. 1:21-cv-10954-ADB, dated Mar. 15, 2022, 12 pages.

Merriam-Webster, "Contraindication," retrieved on Jun. 27, 2022, retrieved from URL <https://web.archive.org/web/20160911214253/https://www.merriamwebster.com/dictionary/contraindication>, 5 pages.
Merriam-Webster, "Refractory," retrieved on Jun. 27, 2022, retrieved from URL <https://web.archive.org/web/20160830152812/https://www.merriamwebster.com/dic tionary/refractory>, 8 pages.
Mulleners et al., "Safety and efficacy of galcanezumab in patients for whom previous migraine preventive medication from two to four categories had failed (CONQUER): a multicentre, randomised, double-blind, placebo-controlled, phase 3b trial," Lancet Neurol., Oct. 2020, 19(10):814-825, Supplementary appendix, 27 pages.
Neeb et al., "Methylprednisolone Blocks Interleukin 1 Beta Induced Calcitonin Gene Related Peptide Release In Trigeminal Ganglia Cells," The Journal of Headache and Pain, Mar. 2016, 17(19):1-6.
Negro et al., "Chronic migraine treatment: from OnabotulinumtoxinA onwards," Expert Review of Neurotherapeutics, 2016, 16(10):1217-1227.
Paemeleire et al., "Diagnosis, pathophysiology and management of chronic migraine: a proposal of the Belgian Headache Society," Acta Neurol. Belg., 2015, 115:1-17.
Peroutka, "Calcitonin Gene-Related Peptide Targeted Immunotherapy for Migraine: Progress and Challenges in Treating Headache," BioDrugs, Jun. 2014, 28:237-244.
Peroutka, "Clinical Trials Update 2014: Year in Review," Headache, Jan. 2015, 55:149-157.
Peroutka, "Clinical Trials Update 2015: Year in Review," Headache, Jan. 2016, 56:178-184.
Piche-Nicholas et al., "Changes in complementarity-determining regions significantly alter IgG binding to the neonatal Fc receptor (FcRn) and pharmacokinetics," Taylor & Francis, MABS vol. 10, No. 1, 81-94, Jan. 2018, 14 pages.
Pinkney et al., "Vasorelaxation To The Nitroxyl Donor Isopropylamine NONOate in Resistance Arteries Does Not Require Perivascular Calcitonin Gene-Related Peptide," Hypertension, Sep. 2017, 70:587-593.
Press Release, "Teva to Present New Findings at the American Headache Society (AHS) Meeting—Analysis of Migraine Phase Iib Studies Provides Novel Insights into TEV-48125 Efficacy and Safety in Both Episodic & Chronic Migraine," Jun. 18, 2015, retrieved from URL <https://www.tevapharm.com/news-and-media/latest-news/teva-to-present-new-findings-at-the-american-headache-society-ahs-meeting--analysis-of-migraine-phase-/>, 5 pages.
Press Release, "Teva to Present New Findings at the American Headache Society (AHS) Meeting" Business Wire, dated Jun. 18, 2015, 6 pages.
Ramadan, "Current Trends in Migraine Prophylaxis," Headache, Apr. 2007, 47(Suppl 1):S52-S57.
Recober et al., "Calcitonin gene-related peptide: an update on the biology," Current Opinion in Neuro, Rapid Science Publishes, London, vol. 22, No. 3, Jun. 1, 2009, 6 pages.
Refractory Migraine: Mechanisms and Management, Schulman et al. (eds.), 2010, 484 pages.
Reichert, "Antibodies to watch in 2017," mAbs, 2017, 9(2): 167-181.
Schellenberg et al., "Nebivolol and Metoprolol for Treating Migraine: An Advance on ß-Blocker Treatment?" Headache, Jan. 2008, 48:118-125.
Schulman et al., "Defining Refractory Migraine: Results of the RHSIS Survey of American Headache Society Members," Headache, 2009, 49:509-18.
Schulman, "Refractory Migraine—A Review," Headache, 2013, 53:599-613.
Schuster et al., "New strategies for the treatment and prevention of primary headache disorders," Nat. Rev. Neurol., Nov. 2016, 12:635-650.
Schwedt, "Chronic Migraine," BMJ, Mar. 2014, 348:1-11.
Shi et al., "Pharmacologic Characterization of AMG 334, a Potent and Selective Human Monoclonal Antibody against the Calcitonin Gene-Related Peptide Receptor," Journal of Pharmacology and Experimental Therapeutics, Jan. 2016, 356:223-231.

(56) References Cited

OTHER PUBLICATIONS

Silberstein et al., "Evidence-based guideline update: Pharmacologic treatment for episodic migraine prevention in adults," Neurology, 2012, 78:1337-45 (2012); Correction, Neurology, 2013, 80:871, 17 pages.
Silberstein et al., "Guidelines for controlled trials of prophylactic treatment of chronic migraine in adults," Cephalalgia, 2008, 28:484-95.
Silberstein et al., "Pharmacological Approaches to Managing Migraine and Associated Comorbidities—Clinical Considerations for Monotherapy Versus Polytherapy," Headache, Apr. 2007, 47:585-599.
Silberstein et al., "Randomized, placebo-controlled trial of propranolol added to topiramate in chronic migraine," Neurology, 2012, 78:976-84.
Silberstein, "Practice parameter: Evidence-based guidelines for migraine headache (an evidence-based review): Report of the Quality Standards Subcommittee of the American Academy of Neurology," Neurology, 2000, 55:754-762.
Silberstein, "Preventive Migraine Treatment," Neurol. Clin., 2009, 27:429-443.
*Speedtrack, Inc*, Plaintiff, v. *Amazon, Inc.*, et al., Defendants, Claim Construction Order, Case No. 4:09-cv-04479-JSW, Nov. 8, 2019, 18 pages.
Starling et al., "Best Practices for Patients With Chronic Migraine: Burden, Diagnosis, and Management in Primary Care," Mayo Clin Proc., Mar. 2015, 90(3):408-414.
Stedman's Medical Dictionary For Health Professionals and Nursing, 7th ed., Wolters Kluwer Health and Lippincott Williams & Wilkins, 2012, 391, 1441, and 1539, 5 pages.
Supplementary Appendix to Goadsby et al., "A Controlled Trial of Erenumab for Episodic Migraine," N. Engl. J Med., 2017, 77:2123-2132, 21 pages.
Supplementary Appendix to Marcelo E. Bigal et al., "Safety, tolerability, and efficacy of TEV-48125 for preventive treatment of high-frequency episodic migraine: a multicentre, randomised, doubleblind, placebo-controlled, phase 2b study," Lancet Neurol., 2015, 14:1081-90, 5 pages.
Supplementary appendix to S.D. Silberstein et al., "Evidence-based guideline update: Pharmacologic treatment for episodic migraine prevention in adults," Neurology, 2012, 78:1337-45; Correction, Neurology, 2013, 80:871, 3 pages.
Supplementary webappendix to David W. Dodick et al., "Safety and efficacy of LY2951742, a monoclonal antibody to calcitonin gene-related peptide, for the preventio of migraine: a phase 2, randomised, double-blind, placebo-controlled study," Lancet Neurol., 2014, 13:885-92, 10 pages.
Supplementary webappendix to Marcelo E. Bigal et al., "Safety, tolerability, and efficacy of TEV-48125 for preventive treatment of chronic migraine: a multicentre, randomised, double-blind, placebocontrolled, phase 2b study," Lancet Neurol., 2015, 14:1091-1100, 4 pages.
Tepper et al., "Clinical and Preclinical Rationale for CGRP-Receptor Antagonists in the Treatment of Migraine," Headache Currents, Sep. 2008, 1259-1268, 12 pages.
U.S. Food & Drug Administration, "What is a Serious Adverse Event?," retrieved on Jun. 27, 2022, retrieved from URL <https://www.fda.gov/safety/reporting-serious-problemsfda/what-serious-adverse-event>, 2 pages.
Usan, "Statement On A Nonproprietary Name Adopted By The USAN Council: Galcanezumab," dated Aug. 26, 2015, retrieved from URL <https://searchusan.ama-assn.org/usan/documentDownload?uri=/unstructured/binary/usan/galcanezumab.pdf>, 2 pages.
Walker et al., "A Second Trigeminal CCRP Receptor: Function and Expression of the AMY1 Receptor," Annals of Clinical and Translational Neurology, Jun. 2015, 2(6):595-608.
Wang et al., "Comorbidities of migraine," Frontiers in Neurology, Aug. 2010, 1(16):1-9.
Weatherall, "Drug therapy in headache," Clinical Medicine, 2015, 15(3):273-279.

*Eli Lilly and Company*, Petitioner, v. *Teva Pharmaceuticals International GMBH*, "Federal Circuit Decision," IPR2018-01710 (U.S. Pat. No. 8,586,045 B2), IPR2018-01711 (U.S. Pat. No. 9,884,907 B2), IPR2018-01712 (U.S. Pat. No. 9,884,908 B2), filed on Sep. 23, 2021, 31 pages.
*Eli Lilly and Company* v *Teva Pharmaceuticals International GMBH*, "Decision Granting Institution of Inter Partes Review," Case No. IPR2022-00738, U.S. Pat. No. 11,028,160, Sep. 27, 2022, 53 pages.
*Eli Lilly and Company* v *Teva Pharmaceuticals International GMBH*, "Decision Granting Institution of Inter Partes Review," Case No. IPR2022-00739, U.S. Pat. No. 11,028,161, Sep. 27, 2022, 53 pages.
*Eli Lilly and Company* v *Teva Pharmaceuticals International GMBH*, "Decision Granting Institution of Inter Partes Review," Case No. IPR2022-00796, U.S. Pat. No. 10,392,434, dated Oct. 14, 2022, 63 pages.
*Eli Lilly and Company* v *Teva Pharmaceuticals International GMBH*, "Patent Owner Response," Case No. IPR2022-00738, U.S. Pat. No. 11,028,160, filed Jan. 27, 2023, 74 pages.
*Eli Lilly and Company* v *Teva Pharmaceuticals International GMBH*, "Patent Owner Response," Case No. IPR2022-00739, U.S. Pat. No. No. 11,028,161, filed Jan. 27, 2023, 74 pages.
*Eli Lilly and Company* v *Teva Pharmaceuticals International GMBH*, "Patent Owner Response," Case No. IPR2022-00796, U.S. Pat. No. 10,392,434, filed Jan. 27, 2023, 75 pages.
*Eli Lilly and Company* v *Teva Pharmaceuticals International GMBH*, "Patent Owner's Exhibit List as of Jul. 19, 2022," Case No. IPR2022-00796 U.S. Pat. No. 10,392,434, filed Jul. 19, 2022, 2 pages.
*Eli Lilly and Company* v *Teva Pharmaceuticals International GMBH*, "Patent Owner's Exhibit List as of Jun. 30, 2022," Case No. IPR2022-00738, U.S. Pat. No. 11,028,160, filed Jun. 30, 2022, 4 pages.
*Eli Lilly and Company* v *Teva Pharmaceuticals International GMBH*, "Patent Owner's Exhibit List as of Jun. 30, 2022," Case No. IPR2022-00739, U.S. Pat. No. 11,028,161, filed Jun. 30, 2022, 4 pages.
*Eli Lilly and Company* v *Teva Pharmaceuticals International GMBH*, "Patent Owner's Updated Exhibit List as of Feb. 17, 2023," Case No. IPR2022-00738, U.S. Pat. No. 11,028,160, filed Feb. 17, 2023, 13 pages.
*Eli Lilly and Company* v *Teva Pharmaceuticals International GMBH*, "Patent Owner's Updated Exhibit List as of Feb. 17, 2023," Case No. IPR2022-00739, U.S. Pat. No. 11,028,161, filed Feb. 17, 2023, 13 pages.
*Eli Lilly and Company* v *Teva Pharmaceuticals International GMBH*, "Patent Owner's Updated Exhibit List as of Feb. 17, 2023," Case No. IPR2022-00796, U.S. Pat. No. 10,392,434, filed Feb. 17, 2023, 10 pages.
*Eli Lilly and Company* v *Teva Pharmaceuticals International GMBH*, "Patent Owner's Updated Exhibit List as of Jan. 27, 2023," Case No. IPR2022-00738, U.S. Pat. No. 11,028,160, filed Jan. 27, 2023, 9 pages.
*Eli Lilly and Company* v *Teva Pharmaceuticals International GMBH*, "Patent Owner's Updated Exhibit List as of Jan. 27, 2023," Case No. IPR2022-00739, U.S. Pat. No. 11,028,161, filed Jan. 27, 2023, 9 pages.
*Eli Lilly and Company* v *Teva Pharmaceuticals International GMBH*, "Patent Owner's Updated Exhibit List as of Jan. 27, 2023," Case No. IPR2022-00796, U.S. Pat. No. 10,392,434, filed Jan. 27, 2023, 7 pages.
*Eli Lilly and Company* v *Teva Pharmaceuticals International GMBH*, "Petition for Inter Partes Review," Case No. IPR2022-00738, U.S. Pat. No. 11,028,160, filed Mar. 23, 2022, 91 pages.
*Eli Lilly and Company* v *Teva Pharmaceuticals International GMBH*, "Petition for Inter Partes Review," Case No. IPR2022-00739, U.S. Pat. No. 11,028,161, filed Mar. 23, 2022, 91 pages.
*Eli Lilly and Company* v *Teva Pharmaceuticals International GMBH*, "Petition for Inter Partes Review," Case No. IPR2022-00796, U.S. Pat. No. 10,392,434, filed Apr. 11, 2022, 87 pages.
*Eli Lilly and Company* v *Teva Pharmaceuticals International GMBH*, "Petitioner's Exhibit List as of Apr. 11, 2022," Case No. IPR2022-00796, U.S. Pat. No. 10,392,434, filed Apr. 11, 2022, 7 pages.

(56) References Cited

OTHER PUBLICATIONS

*Eli Lilly and Company* v *Teva Pharmaceuticals International GMBH*, "Petitioner's Exhibit List as of Mar. 23, 2022," Case No. IPR2022-00738, U.S. Pat. No. 11,028,160, filed Mar. 23, 2022, 7 pages.
*Eli Lilly and Company* v *Teva Pharmaceuticals International GMBH*, "Petitioner's Exhibit List as of Mar. 23, 2022," Case No. IPR2022-00739, U.S. Pat. No. 11,028,161, filed Mar. 23, 2022, 7 pages.
*Eli Lilly and Company,* Petitioner, v. *Teva Pharmaceuticals International GMBH*, Patent Owner, Case No. IPR2022-00738; U.S. Pat. No. 11,028, 160, Patent Owner's Preliminary Response, filed on Jun. 30, 2022, 71 pages.
*Eli Lilly and Company,* Petitioner, v. *Teva Pharmaceuticals International GMBH*, Patent Owner, Case No. IPR2022-00738; U.S. Pat. No. 11,028,160, Patent Owner's Sur-Reply to Petitioner's Reply, filed on Aug. 10, 2022, 9 pages.
*Eli Lilly and Company,* Petitioner, v. *Teva Pharmaceuticals International GMBH*, Patent Owner, Case No. IPR2022-00738; U.S. Pat. No. 11,028,160, Petitioner's Reply to Patent Owner's Preliminary Response, filed Jul. 27, 2022, 9 pages.
*Eli Lilly and Company,* Petitioner, v. *Teva Pharmaceuticals International GMBH*, Patent Owner, Case No. IPR2022-00739; U.S. Pat. No. 11,028,161, Patent Owner's Preliminary Response, filed Jun. 30, 2022, 71 pages.
*Eli Lilly and Company,* Petitioner, v. *Teva Pharmaceuticals International GMBH*, Patent Owner, Case No. IPR2022-00739; U.S. Pat. No. 11,028, 161, Patent Owner's Sur-Reply to Petitioner's Reply, filed on Aug. 10, 2022, 9 pages.
*Eli Lilly and Company,* Petitioner, v. *Teva Pharmaceuticals International GMBH*, Patent Owner, Case No. IPR2022-00739; U.S. Pat. No. 11,028, 161, Petitioner's Reply to Patent Owner's Preliminary Response, filed Jul. 27, 2022, 9 pages.
*Eli Lilly and Company,* Petitioner, v. *Teva Pharmaceuticals International GMBH*, Patent Owner, Case No. IPR2022-00796; U.S. Pat. No. 10,392,434, Patent Owner's Preliminary Response, dated Jul. 19, 2022, 74 pages.
*Eli Lilly and Company,* Petitioner, v. *Teva Pharmaceuticals International GMBH*, Patent Owner, Case No. IPR2022-00796; U.S. Pat. No. 10,392,434, Patent Owner's Sur-Reply to Petitioner's Reply, filed on Aug. 15, 2022, 9 pages.
*Eli Lilly and Company,* Petitioner, v. *Teva Pharmaceuticals International GMBH*, Patent Owner, Case No. IPR2022-00796; U.S. Pat. No. 10,392,434, Petitioner's Reply to Patent Owner's Preliminary Response, filed Aug. 1, 2022, 9 pages.
Inter Partes Review Certificate, Case No. IPR2018-01422, U.S. Pat. No. 9,340,614 K1, issued Mar. 4, 2022, Zeller et al., 2 pages.
Inter Partes Review Certificate, Case No. IPR2018-01423, U.S. Pat. No. 9,266,951 K1, issued Mar. 7, 2022, Poulsen et al., 2 pages.
Inter Partes Review Certificate, Case No. IPR2018-01424, U.S. Pat. No. 9,346,881 K1, issued Mar. 9, 2022, Poulsen et al., 2 pages.
Inter Partes Review Certificate, Case No. IPR2018-01425, U.S. Pat. No. 9,890,210 K1, issued Mar. 4, 2022, Zeller et al., 2 pages.
Inter Partes Review Certificate, Case No. IPR2018-01426, U.S. Pat. No. 9,890,211 K1, issued Mar. 4, 2022, Zeller et al., 2 pages.
Inter Partes Review Certificate, Case No. IPR2018-01427, U.S. Pat. No. 8,597,649 K1, issued Mar. 4, 2022, Zeller et al., 2 pages.
Inter Partes Review Certificate, Case No. IPR2018-01710, U.S. Pat. No. 8,586,045 K1, issued Mar. 4, 2022, Zeller et al., 2 pages.
Inter Partes Review Certificate, Case No. IPR2018-01711, U.S. Pat. No. 9,884,907 K1, issued Mar. 7, 2022, Zeller et al., 2 pages.
Inter Partes Review Certificate, Case No. IPR2018-01712, U.S. Pat. No. 9,884,908 K1, issued Mar. 4, 2022, Zeller et al., 2 pages.
*Teva Pharmaceuticals International GMBD* v. *Eli Lilly and Company*, "Federal Circuit Opinion," IPR2018-01422, IPR2018-01423, IPR2018- 01425, filed on Aug. 16, 2021, 25 pages.
*Teva Pharmaceuticals International GMBD* v. *Eli Lilly and Company*, "Federal Circuit Opinion," IPR2018-01424, IPR2018-01426, IPR2018- 01427, filed on Aug. 16, 2021, 4 pages.
*Teva Pharmaceuticals International GMBH and Teva Pharmaceuticals USA, Inc.,* v. *Eli Lilly and Company*, 1:21-cv-10954-ABD, D.I. 32, Plaintiff's Surreply in Opposition to Eli Lilly and Company's Motion to Dismiss, Nov. 9, 2021, 13 pages.
*Teva Pharmaceuticals International GMBH*, Appellant, v. *Eli Lilly and Company*, Appellee, Case Nos. IPR2018-01424, IPR2018-01426, and IPR2018-01427, Mandate, filed Oct. 7, 2021, 2 pages.
Duan et al., "The Levels of Calcitonin Gene-Related Peptide and Substance P in the Plasma of Rats with Traumatic Brain Injury and the Role of Neurogenic Inflammation in the Pathogenesis of TBI," The FASEB Journal, Apr. 2009, 23, Abstract No. 926.2, 2 pages.
Lucas et al., "A prospective study of prevalence and characterization of headache following mild traumatic brain injury, " Cephalalgia, Feb. 2014, 34(2):93-102.
Inter Partes Review Certificate, Case No. IPR2022-00796, U.S. Pat. No. 10,392,434 K1, issued Feb. 2, 2024, Bigal et al., 2 pages.

Figure 1

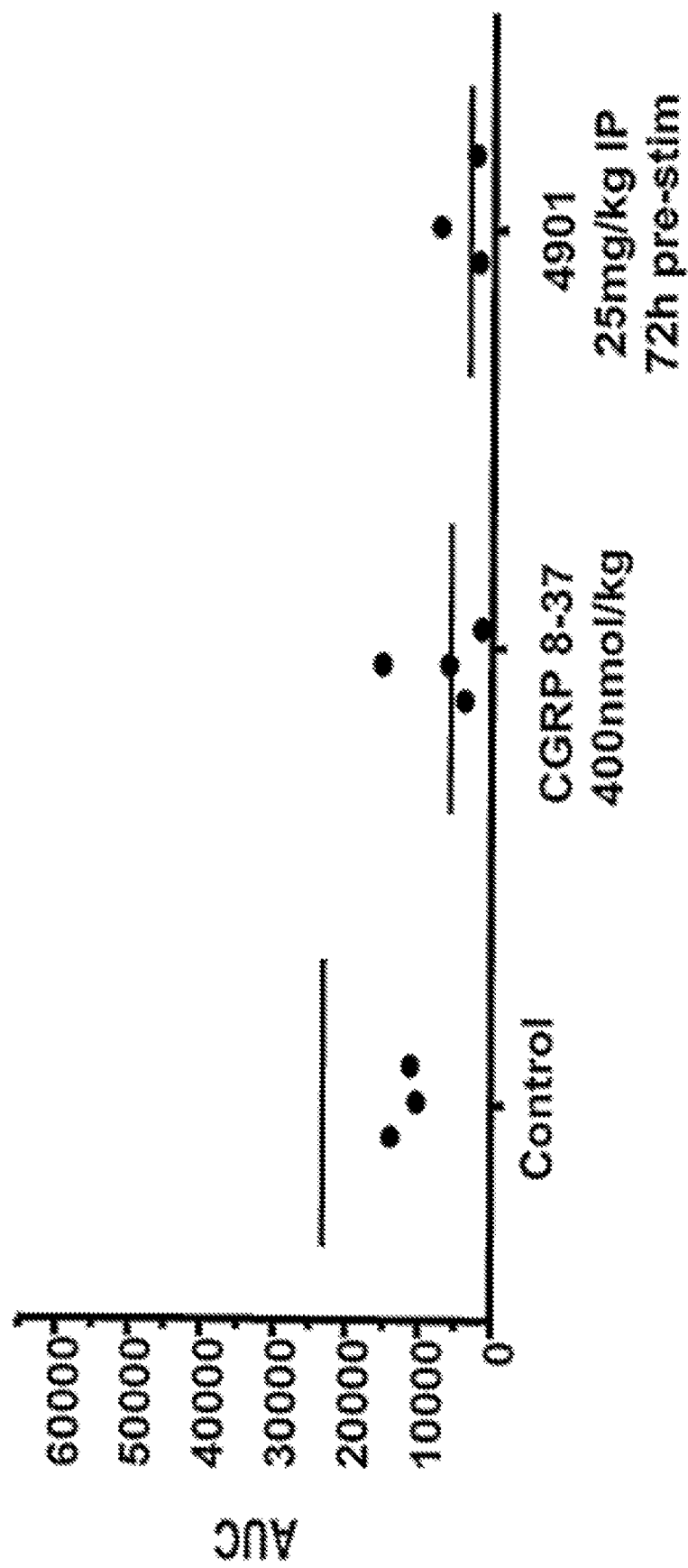

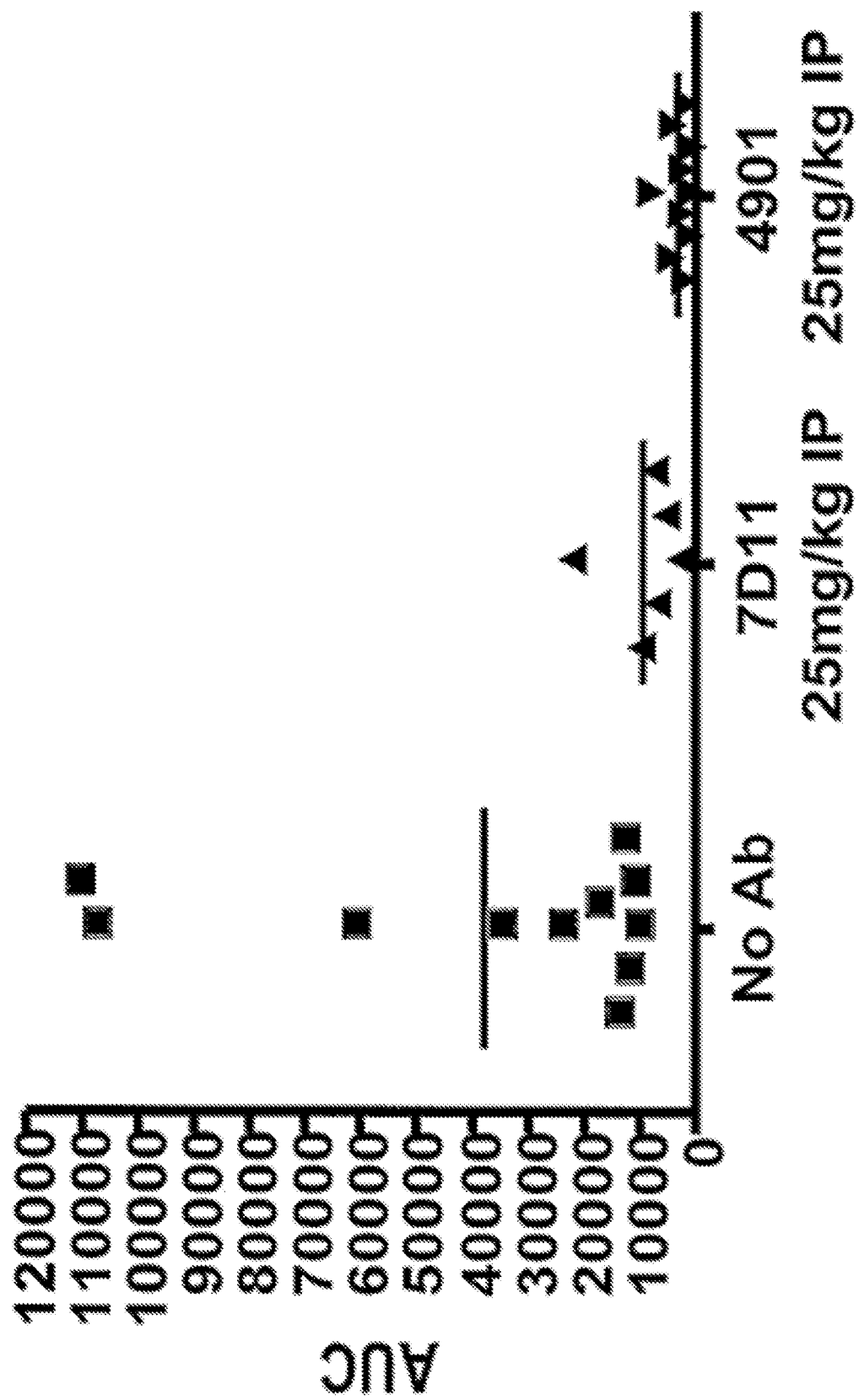

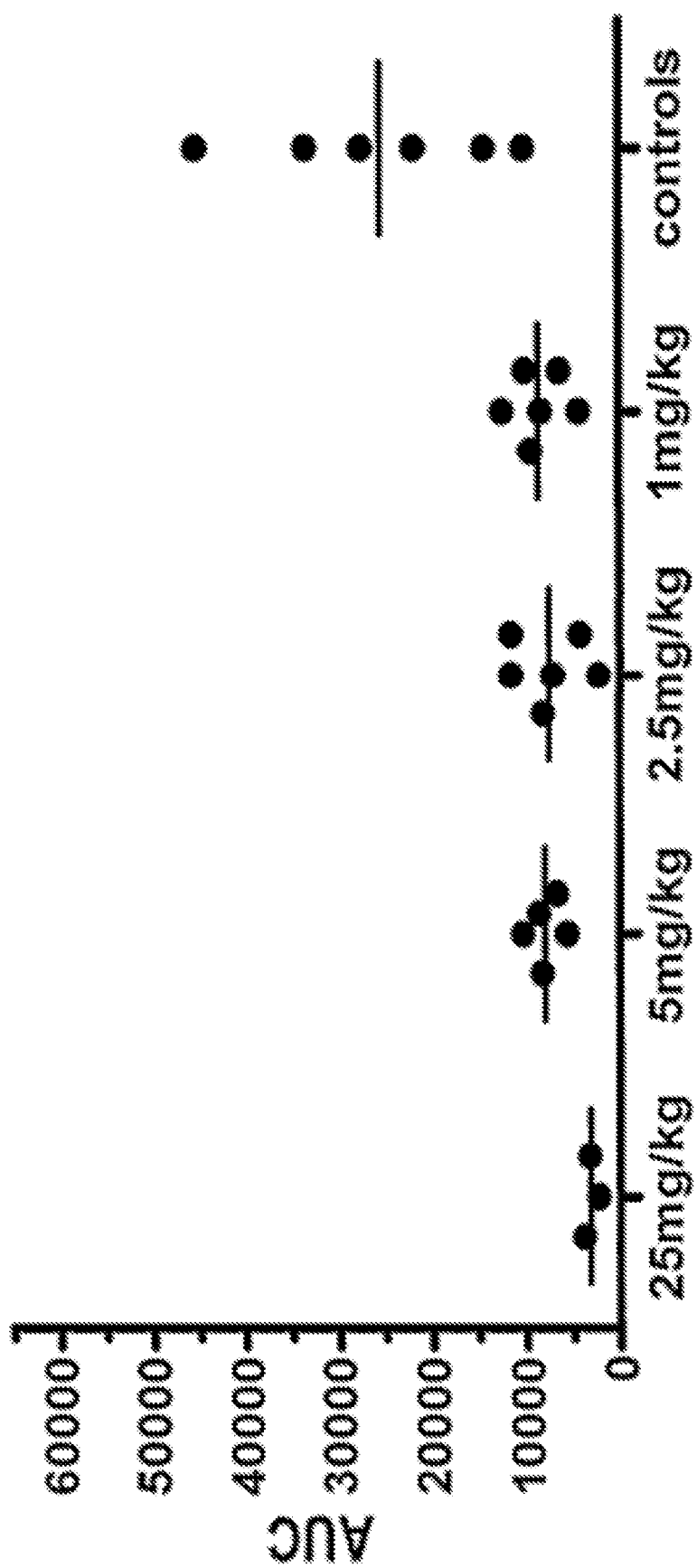

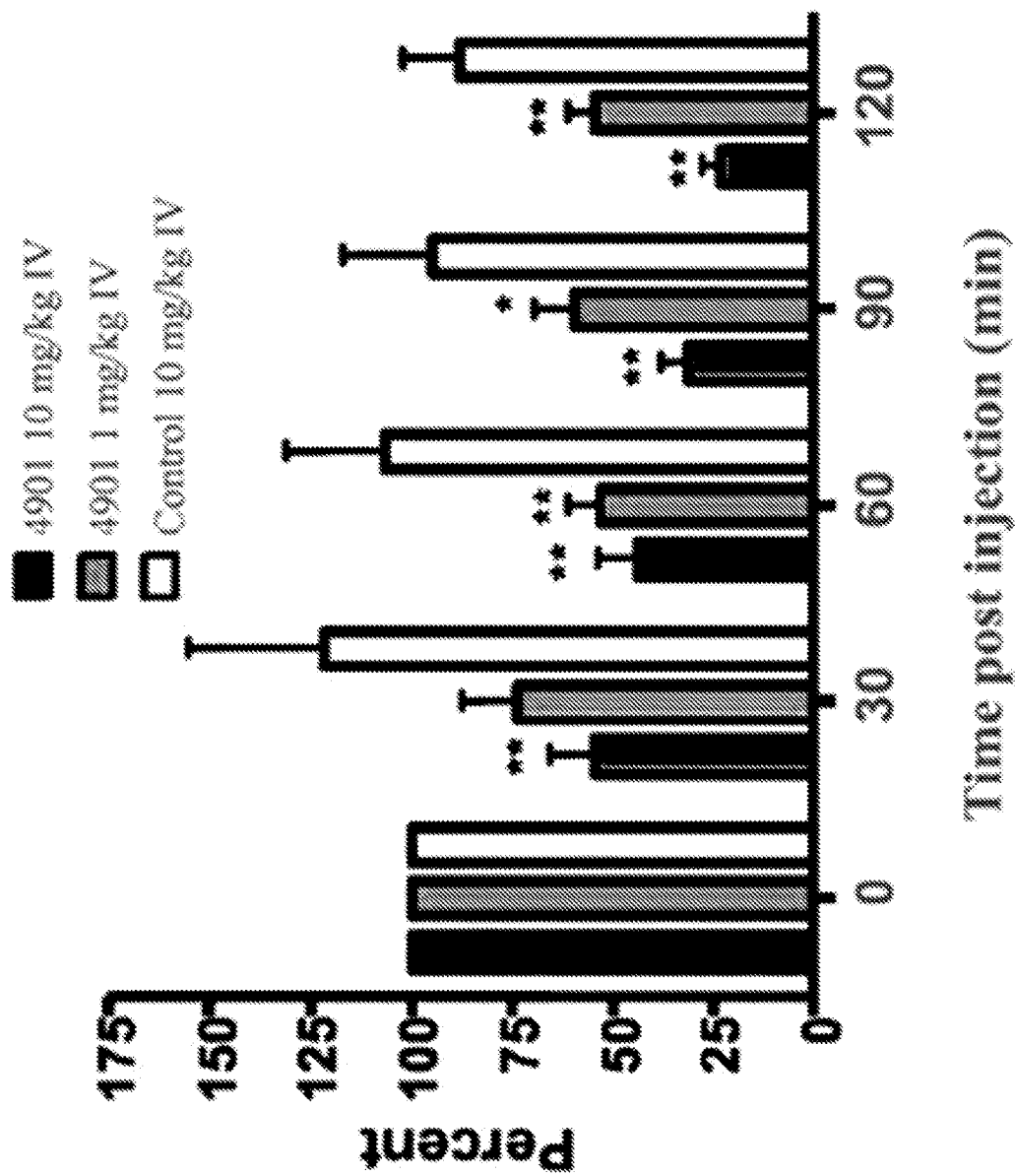

Figure 5

Bold=Kabat CDR
Underline=Chothia CDR

G1 Heavy chain

```
         1               10              20              30
         E V Q L V E S G G G L V Q P G G S L R L S C A A S G F T F S
                                                              H1
         35              40              50              60
         N Y W M S W V R Q A P G K G L E W V A E I R S D A S A I
                                               H2
         65              70              80              90
         H Y A E A V K G R F T I S R D N A K N S L Y L Q M N S L R A
         95              100             110             120
         E D T A V Y Y C L A Y F D Y G L A I D M Y W G Q G T L V T V
                                H3
         121 122
         S S
```

G1 Light chain

```
         1               10              20              30
         E I V L T Q S P A T L S L S P G E R A T L S C K A S K R V T
                                                          L1
         35              40              50              60
         T Y V S W Y Q Q K P G Q A P R L L I Y G A S N R Y L G I P A
                                               L2
         65              70              80              90
         R F S G S G S G T D F T L T I S S L E P E D F A V Y Y C S Q
         95              100             107
         S Y N Y P Y T F G Q G T K L E I K
              L3
```

TREATING REFRACTORY MIGRAINE

CROSS REFERENCE TO RELATED APPLICATIONS

This application is a continuation application of U.S. application Ser. No. 17/308,580, filed on May 5, 2021, which is a continuation of application U.S. application Ser. No. 17/076,759, filed on Oct. 21, 2020, now U.S. Pat. No. 11,028,160, which is a continuation application of U.S. application Ser. No. 16/508,574, filed on Jul. 11, 2019, now abandoned, which is a continuation application of U.S. application Ser. No. 15/712,444, filed on Sep. 22, 2017, now U.S. Pat. No. 10,392,434, which claims the benefit of priority of U.S. Application No. 62/399,180, filed on Sep. 23, 2016 and U.S. Application No. 62/558,557, filed on Sep. 14, 2017. The contents of these prior applications are hereby incorporated by reference in their entireties.

SEQUENCE LISTING

This application contains a Sequence Listing that has been submitted electronically as an XML file named "43612-0013006_SL_ST26.xml." The XML file, created on Feb. 16, 2023, is 146,898 bytes in size. The material in the XML file is hereby incorporated by reference in its entirety.

BACKGROUND

Migraine is a prevalent neurological condition characterized by attacks of headache and associated symptoms, such as nausea, vomiting, photophobia, and/or phonophobia. In US and Western Europe, the overall prevalence of migraine sufferers is 11% of the general population (6% males; 15-18% females). The two most common forms of migraine, migraine without aura and migraine with aura, occur on less than 15 days per month and are referred to as episodic forms of migraine (EM) (Lipton et al, Neurology 68(5): 343-349, 2007). However, 3% to 6% of individuals with EM evolve, in any given year, to a significantly more disabling condition called chronic migraine (CM) (Scher et al, Pain 106(1-2): 81-89, 2003). Individuals with CM present with headaches of any severity on 15 or more days per month and have full-blown migraine on at least 8 days per month. A sizable proportion of individuals with CM experience daily headaches and, therefore, faces considerable disability (Bigal and Lipton, Neurology 71(11):848-855, 2008).

Preventive drug treatment of migraine may be appropriate in a number of instances, including where frequency of attacks per month is two or higher, or where a patient's quality of life is severely impaired (Evers et al., Europ. J. Neurol. 16:968-981, 2009). A number of drugs from different pharmacological categories (e.g. beta blockers, anticonvulsants) have been approved for migraine prevention or have class A evidence to support their use. However, patient response and tolerance to some of these medications varies, and compliance and adherence to these medications can be poor (Puledda et al., J. Neurol. March 20. doi: 10.1007/s00415-017-8434, 2017).

Calcitonin gene-related peptide (CGRP) is a neuropeptide that has been found to be involved in migraine processes, both centrally and peripherally (Eftekhari and Edvinsson, Ther. Adv. Neurol. Disord. 3(6):369-378, 2010, Olesen, Cephalagia 31(5):638, 2011). Jugular levels of CGRP are increased during migraine attacks, and intravenous (iv) CGRP administration induces migraine-like headache in most individuals with migraine (Ashina et al., Neurology 55(9): 1335-1340, 2000, Hansen et al., Cephalagia 30(1): 1179-1186, 2010). CGRP is involved in the pathophysiology of migraine at all levels, peripherally (vasodilation, inflammation, and protein extravasation), at the trigeminal ganglion, and inside the brain (Ho et al., Nat. Rev. Neurol. 6(10):573-582, 2010). Studies have shown that inhibition of CGRP or antagonizing CGRP receptor has demonstrated efficacy in the treatment of EM (Bigal et al., Lancet Neurol. 14:1081-1090, 2015a, Hewitt et al., Cephalagia 31(6):712-722, 2011, Ho et al., Lancet 372(9656):2115-2123, 2008, Olesen et al., N. Engl. J. Med. 350(11):1104-1110, 2004) and CM (Bigal et al., Lancet Neurol. 14:1091-1100, 2015b).

Monoclonal antibodies that modulate the CGRP pathway thus represent a class of promising therapeutic candidates for patients who failed prior preventative treatment for CM and EM.

SUMMARY

Disclosed herein are anti-CGRP antagonist antibodies and methods of using the same for preventing, treating, or reducing incidence of migraine in a subject having refractory migraine (i.e., a subject who does not respond favorable to prior preventative migraine treatments). Also disclosed herein are methods of preventing, treating, or reducing incidence of migraine in a subject having refractory migraine comprising administering to the subject a monoclonal antibody that modulates the CGRP pathway.

Methods of preventing, treating, or reducing incidence of at least one secondary symptom associated with refractory migraine in a subject comprising administering to the subject a monoclonal antibody that modulates the CGRP pathway are also provided. In some embodiments, the amount of the monoclonal antibody administered to the patient can be about 225 mg to about 1000 mg, e.g., about 675 mg or about 900 mg. Accordingly, in some aspects, the methods of preventing, treating, or reducing incidence of migraine in a subject having refractory migraine can comprise administering to the subject a monoclonal antibody that modulates the CGRP pathway, wherein the amount of the monoclonal antibody administered to the patient can be about 225 mg to about 1000 mg, e.g., about 675 mg or about 900 mg. In other aspects, the methods of preventing, treating, or reducing incidence of at least one secondary symptom associated with refractory migraine in a subject can comprise administering to the subject a monoclonal antibody that modulates the CGRP pathway are also provided, wherein the amount of the monoclonal antibody administered to the patient can be about 225 mg to about 1000 mg, e.g., about 675 mg or about 900 mg. In one embodiment, the dosing regimen comprises administering an initial antibody dose (or starting antibody dose) of about 675 mg subcutaneously, followed by a monthly antibody dose of about 225 mg subcutaneously for, e.g., about two months, three months, four months, five months, six months, seven months, eight months, nine months, ten months, 11 months, or 12 months, or even a period of greater than one year (e.g., 18 months, two years, or three years). Yet another dosing regimen comprises administering an initial or starting dose of about 900 mg intravenously in an infusion over about 60 minutes, followed by doses of about 900 mg administered intravenously in an infusion over about 60 minutes every quarter for, e.g., about one year, two years, three years, four years, or five years. Yet another dosing regimen comprises administering an initial or starting dose of about 675 mg administered subcutaneously, followed by doses of about 675 mg administered subcutaneously every quarter for, e.g., about one year, two years, three years, four years, or five years.

Suitable administration schedules include, but are not limited to, monthly or quarterly doses, or a single dose. In some embodiments, the monoclonal antibody can be administered monthly. For example, the monoclonal antibody can be administered monthly for 1, 2, 3, 4, 5, 6, 7, 8, 9, 10, 11, 12, or more months. In some aspects, the monoclonal antibody can be administered monthly for three or more months. When administered monthly, the dose of the monoclonal antibody administered to the patient can be about 225 mg to about 900 mg.

The monoclonal antibody can be administered as a single dose. When administered as a single dose, the dose of the monoclonal antibody administered to the patient can be about 675 mg to about 1000 mg.

The treating or reducing can comprise reducing the number of headache hours of any severity, reducing the number of monthly headache days of any severity, reducing the use of any acute headache medications (e.g., migraine-specific acute headache medications), reducing a 6-item Headache Impact Test (HIT-6) disability score, improving 12-Item Short Form Health Survey (SF-12) score (Ware et al., Med Care 4:220-233, 1996), reducing Patient Global Impression of Change (PGIC) score (Hurst et al., J Manipulative Physiol Ther 27:26-35, 2004), improving Sport ConCuSSion ASSeSment tool 3 (SCAT-3) score (McCrory et al. British Journal of Sports Medicine 47:263-266, 2013), or any combination thereof. In some embodiments, the number of monthly headache days can be reduced for at least seven days after a single administration.

In some embodiments, monthly headache hours experienced by the subject after said administering is reduced by 40 or more hours (e.g., 45, 50, 55, 60, 65, 70, 75, 80, or more) from a pre-administration level in the subject. Monthly headache hours may be reduced by more than 60 hours. In some embodiments, monthly headache hours experienced by the subject after said administering are reduced by 25% or more (e.g., 30%, 35%, 40%, 45%, 50%, or more) relative to a pre-administration level in the subject. Monthly headache hours may be reduced by 40% or more. In some embodiments, monthly headache days experienced by the subject after said administering is reduced by three or more days (e.g., 3, 4, 5, 6, 7, 8, 9, 10, 11, 12, 13, 14, 15, 16, 17, 18, 19, 20, or more days) from a pre-administration level in the subject. In some embodiments, the number of monthly headache days can be reduced by at least about 50% from a pre-administration level in the subject. Thus, in some aspects, the number of monthly headache days can be reduced by at least about 50%, at least about 55%, at least about 60%, at least about 65%, at least about 70%, at least about 75%, at least about 80%, or at least about 90%.

In some embodiments, the administering can be subcutaneous administration. In some embodiments, the administering can be intravenous administration. In some embodiments, the administering can comprise utilizing a pre-filled syringe, pre-filled syringe with a needle safety device, injection pen, or auto-injector comprising a dose of the monoclonal antibody. In some embodiments, the monoclonal antibody can be formulated at a concentration of at least 150 mg/mL. In some embodiments, the monoclonal antibody can be administered in a volume of less than 2 mL, e.g., about 1.5 mL.

In some embodiments, the method further comprises administering to the subject a second agent simultaneously or sequentially with the monoclonal antibody. In an embodiment, the second agent is an acute headache treatment (e.g., a migraine-specific acute headache treatment). Accordingly, the second agent can be any of analgesics (e.g., acetylsalicylic acid, ibuprofen, naproxen, diclofenac, paracetamol, acetylsalicylic acid plus paracetamol plus caffeine, metamizol, phenazon, or tolfenamic acid); antiemetics (e.g., metoclopramide or domperidone); ergot alkaloids (e.g., ergotamine tartrate or dihydroergotamine); and triptans, i.e., 5-HT1 agonists (e.g., sumatriptan, zolmitriptan, naratriptan, rizatriptan, almotriptan, eletriptan, or frovatriptan).

In some embodiments, monthly use of the second agent by the subject is decreased by at least about 15%, e.g., at least 16%, 17%, 18%, 20%, 22%, 25%, 28%, 30%, 35%, 40%, 45%, 50%, 55%, 60%, 65%, 70%, 75%, 80%, 85%, 90%, or at least about 95%, after administering the monoclonal antibody. In some embodiments, the second agent is a triptan.

In some embodiments, the subject is a human.

The monoclonal antibody can be an anti-CGRP antagonist antibody. In some embodiments, the monoclonal antibody is a human or humanized monoclonal antibody. In some embodiments, the monoclonal antibody comprises (a) an antibody having a CDR H1 as set forth in SEQ ID NO:3; a CDR H2 as set forth in SEQ ID NO:4; a CDR H3 as set forth in SEQ ID NO:5; a CDR L1 as set forth in SEQ ID NO:6; a CDR L2 as set forth in SEQ ID NO:7; and a CDR L3 as set forth in SEQ ID NO:8; or (b) a variant of an antibody according to (a) as shown in Table 6.

Also disclosed are methods of decreasing a number of monthly headache hours experienced by a subject having refractory migraine. In one embodiment, the method comprises administering to the subject an amount of a monoclonal antibody that modulates the CGRP pathway, wherein the monoclonal antibody is in an amount effective to decrease the number of monthly headache hours by at least 20 (e.g., 25, 30, 35, 40, 45, 50, 55, 60, 65, 70 or more headache hours) after a single dose. In some embodiments, the number of monthly headache hours is reduced by at least about 50 hours. In one embodiment, the method comprises administering to the subject an amount of a monoclonal antibody that modulates the CGRP pathway, wherein the monoclonal antibody is in an amount effective to decrease the number of monthly headache hours by at least 15% (e.g., 20%, 25%, 30%, 35%, 40%, or more) after a single dose. In some embodiments, the number of monthly headache hours is reduced by at least about 30%. In some embodiments, the monoclonal antibody is an anti-CGRP antagonist antibody. In some embodiments, the amount of the monoclonal antibody administered to the patient is about 225 mg to about 1000 mg. In some embodiments, the monoclonal antibody is administered monthly. In some embodiments, the monoclonal antibody is administered as a single dose. In some embodiments, the administering is subcutaneous or intravenous administration. In some embodiments, the monoclonal antibody is formulated at a concentration of at least 150 mg/mL. In some embodiments, the monoclonal antibody is administered in a volume of less than 2 mL, e.g., about 1.5 mL. In some embodiments, the subject is human. In some embodiments, the monoclonal antibody is human or humanized. In some embodiments, the monoclonal antibody comprises (a) an antibody having a CDR H1 as set forth in SEQ ID NO:3; a CDR H2 as set forth in SEQ ID NO:4; a CDR H3 as set forth in SEQ ID NO:5; a CDR L1 as set forth in SEQ ID NO:6; a CDR L2 as set forth in SEQ ID NO:7; and a CDR L3 as set forth in SEQ ID NO:8; or (b) a variant of an antibody according to (a) as shown in Table 6.

Also disclosed are methods of decreasing a number of monthly headache days experienced by a subject having refractory migraine. In one embodiment, the method comprises administering to the subject an amount of a monoclonal antibody that modulates the CGRP pathway, wherein the monoclonal antibody is in an amount effective to decrease the number of monthly headache days by at least 3 (e.g., 3, 4, 5, 6, 7, 8, 9, 10, 11, 12, 13, 14, 15, 16, 17, 18, 19, 20 or more headache days) after a single dose. In some embodiments, the number of monthly headache days is reduced by at least about 6 headache days. In some embodiments, the number of monthly headache days can be reduced by at least about 50% from a pre-administration level in the subject. Thus, in some aspects, the number of monthly headache days can be reduced by at least about 50%, at least about 55%, at least about 60%, at least about 65%, at least about 70%, at least about 75%, at least about 80%, or at least about 90%. In some embodiments, the monoclonal antibody is an anti-CGRP antagonist antibody. In some embodiments, the amount of the monoclonal antibody administered to the patient is about 225 mg to about 1000 mg. In some embodiments, the monoclonal antibody is administered monthly. In some embodiments, the monoclonal antibody is administered as a single dose. In some embodiments, the administering is subcutaneous or intravenous administration. In some embodiments, the monoclonal antibody is formulated at a concentration of at least 150 mg/mL. In some embodiments, wherein the monoclonal antibody is administered in a volume of less than 2 mL, e.g., about 1.5 mL. In some embodiments, the subject is human. In some embodiments, the monoclonal antibody is human or humanized. In some embodiments, the monoclonal antibody comprises (a) an antibody having a CDR H1 as set forth in SEQ ID NO:3; a CDR H2 as set forth in SEQ ID NO:4; a CDR H3 as set forth in SEQ ID NO:5; a CDR L1 as set forth in SEQ ID NO:6; a CDR L2 as set forth in SEQ ID NO:7; and a CDR L3 as set forth in SEQ ID NO:8; or (b) a variant of an antibody according to (a) as shown in Table 6.

Also disclosed are methods of decreasing use of any acute headache medication in a subject having refractory migraine, comprising administering to the subject a monoclonal antibody (e.g., anti-CGRP antagonist antibody) that modulates the CGRP pathway, wherein the monoclonal antibody is in an amount effective to decrease monthly use of the headache medication by the subject by at least 15% (e.g., 20%, 25%, 30%, 35%, 40%, or more). In some embodiments, the acute headache medication is selected from the group consisting of 5-HT1 agonists, triptans, opiates, ergot alkaloids, and non-steroidal anti-inflammatory drugs (NSAIDs). In some embodiments, the acute headache medication is selected from analgesics (e.g., acetylsalicylic acid, ibuprofen, naproxen, diclofenac, paracetamol, acetylsalicylic acid plus paracetamol plus caffeine, metamizol, phenazon, or tolfenamic acid); antiemetics (e.g., metoclopramide or domperidone); ergot alkaloids (e.g., ergotamine tartrate or dihydroergotamine); and triptans, i.e., 5-HT1 agonists (e.g., sumatriptan, zolmitriptan, naratriptan, rizatriptan, almotriptan, eletriptan, or frovatriptan). In some embodiments, the acute headache medication is a triptan. In some embodiments, the amount of the monoclonal antibody administered to the patient is about 225 mg to about 1000 mg, e.g., about 675 mg or about 900 mg. In some embodiments, the monoclonal antibody is administered monthly. In some embodiments, the monoclonal antibody is administered as a single dose. In some embodiments, the administering is subcutaneous or intravenous administration. In some embodiments, the monoclonal antibody is formulated at a concentration of at least 150 mg/mL. In some embodiments, wherein the monoclonal antibody is administered in a volume of less than 2 mL, e.g., about 1.5 mL. In some embodiments, the subject is human. In some embodiments, the monoclonal antibody is human or humanized. In some embodiments, the monoclonal antibody comprises (a) an antibody having a CDR H1 as set forth in SEQ ID NO:3; a CDR H2 as set forth in SEQ ID NO:4; a CDR H3 as set forth in SEQ ID NO:5; a CDR L1 as set forth in SEQ ID NO:6; a CDR L2 as set forth in SEQ ID NO:7; and a CDR L3 as set forth in SEQ ID NO:8; or (b) a variant of an antibody according to (a) as shown in Table 6.

In one aspect, the invention provides a method of preventing, treating, or reducing incidence of migraine in a subject having refractory migraine comprising subcutaneously administering to the subject a loading dose of a monoclonal antibody (e.g., monoclonal anti-CGRP-antagonist antibody) in an amount that modulates the CGRP pathway, wherein the amount of the monoclonal antibody is about 225 mg to about 1000 mg, e.g., about 675 mg (e.g., three subcutaneous injections of 225 mg each), followed by monthly subcutaneous injections of about 100 mg to about 1000 mg, e.g., about 225 mg, for about one to 12 consecutive months, e.g., five consecutive months.

In some embodiments, the methods include selecting a subject who does not respond favorably to a migraine treatment selected from the group consisting of topiramate, carbamazepine, divalproex sodium, sodium valproate, valproic acid, flunarizine, candesartan, pizotifen, amitriptyline, venlafaxine, nortriptyline, duloxetine, atenolol, nadolol, metoprolol, propranolol, bisoprolol, timolol, and onabotulinumtoxinA. In some embodiments, the methods include selecting a subject who does not respond favorably to a migraine treatment selected from the group consisting of topiramate, carbamazepine, divalproex sodium, sodium valproate, flunarizine, pizotifen, amitriptyline, venlafaxine, nortriptyline, duloxetine, atenolol, nadolol, metoprolol, propranolol, timolol, and onabotulinumtoxinA. In some embodiments, the methods include selecting a subject who does not respond favorably to a migraine treatment selected from the group consisting of propranolol, metoprolol, atenolol, bisoprolol, topiramate, amitriptyline, flunarizine, candesartan, onabotulinumtoxinA, and valproic acid. In some embodiments, the methods include selecting a subject who does not respond favorably to a migraine treatment selected from propranolol/metoprolol, topiramate, flunarizine, valproate/divalproex, amitriptyline, venlafaxine, lisinopril, candesartan, and locally approved products (e.g. oxetorone or pizotifen). In other embodiments, the methods include selecting a subject who does not respond favorably to one or more migraine treatments of the following classes: beta-blockers, anticonvulsants, tricyclics, calcium channel blockers, angiotensin II receptor antagonists. For example, the subject may have documented inadequate response (in a medical chart or by treating physician's confirmation) to at least two preventive medications (from different clusters, as defined below). Or, the subject may have documented inadequate response (in a medical chart or by treating physician's confirmation) to two to four classes of prior preventive medications (from, e.g., different clusters, as defined below). As another example, the subject may have documented inadequate response (in a medical chart or by treating physician's confirmation) to two to three classes of prior preventive medications (from different clusters, as defined below) and a valproate (e.g., divalproex sodium, sodium valproate, or valproic acid).

Inadequate response is defined as: no clinically meaningful improvement per treating physician's judgement, after at least three months of therapy at a stable dose considered appropriate for migraine prevention according to accepted country guidelines, or when treatment has to be interrupted because of adverse events that made it intolerable by the patient or the drug is contraindicated or not suitable for the patient. The three month period may not apply if the drug is intolerable or contraindicated or not suitable for the patient. For onabotulinumtoxinA, an inadequate response is defined as: no clinically meaningful improvement per treating physician's judgement, after at least six months of therapy at a stable dose considered appropriate for migraine prevention according to accepted country guidelines, or when treatment has to be interrupted because of adverse events that made it intolerable by the patient. Or, if onabotulinumtoxinA is a previous preventative medication, at least two sets of injections and three months should have passed since the last set of injections.

In some embodiments, the clusters are as follows:
cluster A: topiramate, carbamazepine, divalproex sodium, and sodium valproate
cluster B: flunarizine and pizotifen
cluster C: amitriptyline, venlafaxine, nortriptyline, and duloxetine
cluster D: atenolol, nadolol, metoprolol, propranolol, and timolol
cluster E: onabotulinumtoxinA In some embodiments, the clusters are as follows:
cluster A: beta-blockers: propranolol, metoprolol, atenolol, and bisoprolol
cluster B: anticonvulsants: topiramate
cluster C: tricyclics: amitriptyline
cluster D: calcium channel blocker: flunarizine
cluster E: angiotensin II receptor antagonist: candesartan
cluster F: onabotulinumtoxinA
cluster G: valproic acid Additional clusters (which may be included with either of the groups of clusters above include:
cluster a: an angiotensin-converting enzyme (ACE) inhibitor, such as lisinopril
cluster b: a benzocycloheptene-based drug, such as pizotifen
cluster c: an antidepressant, such as amitriptyline (Elavil), trazodone (Desyrel), and imipramine (Tofranil), and venlafaxine
cluster d: an anticonvulsant such as phenytoin (Dilantin) or carbamazepine (Tegretol)
cluster e: oxetorone In one aspect, the invention provides a method of preventing, treating, or reducing incidence of migraine in a subject having refractory migraine comprising administering to the subject a single dose of a monoclonal antibody (e.g., monoclonal anti-CGRP-antagonist antibody) in an amount that modulates the CGRP pathway, wherein the amount of the monoclonal antibody is about 225 mg to about 1000 mg, e.g., about 675 mg or about 900 mg. In an embodiment, the subject is refractory to at least two different preventative treatments selected from topiramate, onabotulinumtoxinA, and valproic acid. In an embodiment, the subject is refractory to preventative treatment with topiramate, onabotulinumtoxinA, and valproic acid.

In one aspect, the invention provides a method of preventing, treating, or reducing incidence of migraine in a subject having refractory migraine comprising administering to the subject a monoclonal antibody (e.g., monoclonal anti-CGRP-antagonist antibody) in an amount that modulates the CGRP pathway, wherein the amount of the monoclonal antibody is about 225 mg to about 1000 mg, e.g., about 675 mg or about 900 mg. In an embodiment, the subject is refractory to at least two different preventative treatments selected from topiramate, onabotulinumtoxinA, and valproic acid. In an embodiment, the subject is refractory to preventative treatment with topiramate, onabotulinumtoxinA, and valproic acid. In some embodiments, the monoclonal antibody is administered as a single dose.

In a further embodiment, the invention provides methods for preventing, treating, ameliorating, controlling, reducing incidence of, or delaying the development or progression of migraine in an individual diagnosed with refractory migraine (see, e.g., the criteria described herein) comprising administering to the individual an effective amount of an anti-CGRP antagonist antibody in combination with at least one additional acute headache medication or agent useful for treating migraine. Such additional agents include, e.g., 5-HT1-like agonists (and agonists acting at other 5-HT1 sites), triptans, opiates, ergot alkaloids, and non-steroidal anti-inflammatory drugs (NSAIDs). In some embodiments, the acute headache medication is selected from analgesics (e.g., acetylsalicylic acid, ibuprofen, naproxen, diclofenac, paracetamol, acetylsalicylic acid plus paracetamol plus caffeine, metamizol, phenazon, or tolfenamic acid); antiemetics (e.g., metoclopramide or domperidone); ergot alkaloids (e.g., ergotamine tartrate or dihydroergotamine); and triptans, i.e., 5-HT1 agonists (e.g., sumatriptan, zolmitriptan, naratriptan, rizatriptan, almotriptan, eletriptan, or frovatriptan).

Non-limiting examples of 5-HT1 agonists that can be used in combination with an anti-CGRP antibody include a class of compounds known as triptans, such as sumatriptan, zolmitriptan, naratriptan, rizatriptan, eletriptan, almotriptan, and frovatriptan. Ergot alkaloids and related compounds are also known to have 5-HT agonist activity and have been used to treat headaches. Included among these compounds are ergotamine tartrate, ergonovine maleate, and ergoloid mesylates (e.g., dihydroergocornine, dihydroergocristine, dihydroergokryptine, and dihydroergotamine mesylate (DHE 45)).

Non-limiting examples of NSAIDs (as an acute headache medication) that can be used in combination with an anti-CGRP antibody include aspirin, diclofenac, diflunisal, etodolac, fenbufen, fenoprofen, flufenisal, flurbiprofen, ibuprofen, indomethacin, ketoprofen, ketorolac, meclofenamic acid, mefenamic acid, nabumetone, naproxen, oxaprozin, phenylbutazone, piroxicam, sulindac, tolmetin or zomepirac, cyclooxygenase-2 (COX-2) inhibitors, celecoxib; rofecoxib; meloxicam; JTE-522; L-745,337; NS398; or a pharmaceutically acceptable salt thereof.

In one embodiment, the anti-CGRP antagonist antibody used in any of the methods described above is any of the antibodies as described herein.

In some embodiments, the anti-CGRP antagonist antibody recognizes a human CGRP. In some embodiments, the anti-CGRP antagonist antibody binds to both human α-CGRP and β-CGRP. In some embodiments, the anti-CGRP antagonist antibody binds human and rat CGRP. In some embodiments, the anti-CGRP antagonist antibody binds the C-terminal fragment having amino acids 25-37 of CGRP. In some embodiments, the anti-CGRP antagonist antibody binds a C-terminal epitope within amino acids 25-37 of CGRP.

In some embodiments, the anti-CGRP antagonist antibody is a monoclonal antibody. In some embodiments, the anti-CGRP antagonist antibody is humanized. In some embodiments, the antibody is human. In some embodiments, the anti-CGRP antagonist is antibody G1 (as described herein). In some embodiments, the anti-CGRP antagonist antibody comprises one or more CDR(s) (such as one, two, three, four, five, or, in some embodiments, all six CDRs) of antibody G1 or variants of G1 shown in Table 6. In still other embodiments, the anti-CGRP antagonist antibody comprises the amino acid sequence of the heavy chain variable region shown in FIG. 5 (SEQ ID NO:1) and the amino acid sequence of the light chain variable region shown in FIG. 5 (SEQ ID NO:2).

In some embodiments, the antibody comprises a modified constant region, such as a constant region that is immunologically inert (including partially immunologically inert), e.g., does not trigger complement mediated lysis, does not stimulate antibody-dependent cell mediated cytotoxicity (ADCC), does not activate microglia, or having reduced one or more of these activities. In some embodiments, the constant region is modified as described in Eur. J. Immunol. (1999) 29:2613-2624; PCT Application No. PCT/GB99/01441; and/or UK Patent Application No. 9809951.8. In other embodiments, the antibody comprises a human heavy chain IgG2 constant region comprising the following mutations: A330P331 to S330S331 (amino acid numbering with reference to the wildtype IgG2 sequence). Eur. J. Immunol. (1999) 29:2613-2624. In some embodiments, the heavy chain constant region of the antibody is a human heavy chain IgG1 with any of the following mutations: 1) A327A330P331 to G327S330S331; 2) E233L234L235G236 (SEQ ID NO:48) to P233V234A235 with G236 deleted; 3) E233L234L235 to P233V234A235; 4) E233L234L235G236A327A330P331 (SEQ ID NO:49) to P233V234A235G327S330S331 (SEQ ID NO:50) with G236 deleted; 5) E233L234L235A327A330P331 (SEQ ID NO:51) to P233V234A235G327S330S331 (SEQ ID NO:50); and 6) N297 to A297 or any other amino acid except N. In some embodiments, the heavy chain constant region of the antibody is a human heavy chain IgG4 with any of the following mutations: E233F234L235G236 (SEQ ID NO:52) to P233V234A235 with G236 deleted; E233F234L235 to P233V234A235; and S228L235 to P228E235.

In still other embodiments, the constant region is aglycosylated for N-linked glycosylation. In some embodiments, the constant region is aglycosylated for N-linked glycosylation by mutating the oligosaccharide attachment residue (such as Asn297) and/or flanking residues that are part of the N-glycosylation recognition sequence in the constant region. In some embodiments, the constant region is aglycosylated for N-linked glycosylation. The constant region may be aglycosylated for N-linked glycosylation enzymatically or by expression in a glycosylation deficient host cell.

The binding affinity ($K_D$) of an anti-CGRP antagonist antibody to CGRP (such as human α-CGRP as measured by surface plasmon resonance at an appropriate temperature, such as 25 or 37° C.) can be about 0.02 to about 200 nM. In some embodiments, the binding affinity is any of about 200 nM, about 100 nM, about 50 nM, about 10 nM, about 1 nM, about 500 pM, about 100 pM, about 60 pM, about 50 pM, about 20 pM, about 15 pM, about 10 pM, about 5 pM, or about 2 pM. In some embodiments, the binding affinity is less than any of about 250 nM, about 200 nM, about 100 nM, about 50 nM, about 10 nM, about 1 nM, about 500 pM, about 100 pM, or about 50 pM. In some embodiments, the binding affinity is less than about 50 nM.

The anti-CGRP antagonist antibody may be administered prior to, during, and/or after a migraine in the subject having refractory migraine. In some embodiments, the anti-CGRP antagonist antibody is administered prior to the subject experiencing symptoms of a migraine. Administration of an anti-CGRP antagonist antibody can be by any means known in the art, including: orally, intravenously, subcutaneously, intraarterially, intramuscularly, intranasally (e.g., with or without inhalation), intracardially, intraspinally, intrathoracically, intraperitoneally, intraventricularly, sublingually, transdermally, and/or via inhalation. Administration may be systemic, e.g., intravenously, or localized. In some embodiments, an initial or starting dose and one or more additional doses are administered the same way, i.e., subcutaneously or intravenously. In some embodiments, the one or more additional doses are administered in a different way than the initial dose, i.e., the initial dose may be administered intravenously and the one or more additional doses may be administered subcutaneously.

In another aspect, the invention provides use of an anti-CGRP antagonist antibody for the manufacture of a medicament for use in any of the methods described herein.

In another aspect, the invention provides a pharmaceutical composition for preventing, treating, or reducing migraine in a subject having refractory migraine comprising an effective amount of an anti-CGRP antagonist antibody, in combination with one or more pharmaceutically acceptable excipients.

In another aspect, the invention provides a kit for use in any of the methods described herein. In some embodiments, the kit comprises a container, a composition comprising an anti-CGRP antagonist antibody described herein, in combination with a pharmaceutically acceptable carrier, and instructions for using the composition in any of the methods described herein.

In some embodiments, the methods provided herein utilize anti-CGRP antagonist antibodies and polypeptides derived from antibody G1 or its variants shown in Table 6. Accordingly, in one aspect, the invention provides an antibody G1 (interchangeably termed "G1" and "TEV-48125") that is produced by expression vectors having ATCC Accession Nos. PTA-6866 and PTA-6867. For example, in one embodiment is an antibody comprising a heavy chain produced by the expression vector with ATCC Accession No. PTA-6867. In a further embodiment is an antibody comprising a light chain produced by the expression vector with ATCC Accession No. PTA-6866. The amino acid sequences of the heavy chain and light chain variable regions of G1 are shown in FIG. 5. The complementarity determining region (CDR) portions of antibody G1 (including Chothia and Kabat CDRs) are also shown in FIG. 5. It is understood that reference to any part of or entire region of G1 encompasses sequences produced by the expression vectors having ATCC Accession Nos. PTA-6866 and PTA-6867, and/or the sequences depicted in FIG. 5. In some embodiments, the invention also provides antibody variants of G1 with amino acid sequences depicted in Table 6.

In some embodiments, the antibody comprises a $V_H$ domain that is at least 85%, at least 86%, at least 87%, at least 88%, at least 89%, at least 90%, at least 91%, at least 92%, at least 93%, at least 94%, at least 95%, at least 96%, at least 97% at least 98%, at least 99% or 100% identical in amino acid sequence to SEQ ID NO:1.

In some embodiments, the antibody comprises a $V_L$ domain that is at least 85%, at least 86%, at least 87%, at least 88%, at least 89%, at least 90%, at least 91%, at least 92%, at least 93%, at least 94%, at least 95%, at least 96%, at least 97% at least 98%, at least 99% or 100% identical in amino acid sequence to SEQ ID NO:2.

In some embodiments, the antibody comprises a heavy chain sequence that is at least 85%, at least 86%, at least 87%, at least 88%, at least 89%, at least 90%, at least 91%, at least 92%, at least 93%, at least 94%, at least 95%, at least 96%, at least 97% at least 98%, at least 99% or 100% identical in amino acid sequence to SEQ ID NO:11.

In some embodiments, the antibody comprises a light chain sequence that is at least 85%, at least 86%, at least 87%, at least 88%, at least 89%, at least 90%, at least 91%, at least 92%, at least 93%, at least 94%, at least 95%, at least 96%, at least 97% at least 98%, at least 99% or 100% identical in amino acid sequence to SEQ ID NO: 12.

In some embodiments, the antibody comprises a fragment or a region of the antibody G1 or its variants shown in Table 6. In one embodiment, the fragment is a light chain of the antibody G1. In another embodiment, the fragment is a heavy chain of the antibody G1. In yet another embodiment, the fragment contains one or more variable regions from a light chain and/or a heavy chain of the antibody G1. In yet another embodiment, the fragment contains one or more variable regions from a light chain and/or a heavy chain shown in FIG. 5. In yet another embodiment, the fragment contains one or more CDRs from a light chain and/or a heavy chain of the antibody G1.

In some embodiments, the polypeptide (such as an antibody) comprises the amino acid sequence of KASKXaaVXaaTYVS (SEQ ID NO:53), wherein Xaa at position 5 is R, W, G, L, or N; and wherein Xaa at position 7 is T, A, D, G, R, S, W, or V. In some embodiments, the amino acid sequence of KASKXaaVXaaTYVS (SEQ ID NO:53) is CDR1 of an antibody light chain.

In some embodiments, the polypeptide (such as an antibody) comprises the amino acid sequence of XaaXaaSN-RYXaa (SEQ ID NO:54), wherein Xaa at position 1 is G or A; wherein Xaa at position 2 is A or H; and wherein Xaa at position 7 is L, T, I, or S. In some embodiments, the amino acid sequence of XaaXaaSNRYXaa (SEQ ID NO:54) is CDR2 of an antibody light chain.

In some embodiments, the polypeptide (such as an antibody) comprises the amino acid sequence of EIRSXaaSDXaaXaaATXaaYAXaaAVKG (SEQ ID NO:55), wherein Xaa at position 5 is E, R, K, Q, or N; wherein Xaa at position 8 is A, G, N, E, H, S, L, R, C, F, Y, V, D, or P; wherein Xaa at position 9 is S, G, T, Y, C, E, L, A, P, I, N, R, V, D, or M; wherein Xaa at position 12 is H or F; wherein Xaa at position 15 is E or D. In some embodiments, the amino acid sequence of EIRSXaaSDXaaXaaATXaaYAXaaAVKG (SEQ ID NO:55) is CDR2 of an antibody heavy chain.

In some embodiments, the antibody is a human antibody. In other embodiments, the antibody a humanized antibody. In some embodiments, the antibody is monoclonal. In some embodiments, the antibody (or polypeptide) is isolated. In some embodiments, the antibody (or polypeptide) is substantially pure.

The heavy chain constant region of the antibodies may be from any types of constant region, such as IgG, IgM, IgD, IgA, and IgE; and any isotypes, such as IgG1, IgG2, IgG3, and IgG4.

In some embodiments, the antibody comprises a modified constant region as described herein.

In one aspect, the invention provides a composition for use in decreasing a number of monthly headache hours experienced by a subject with refractory migraine. In one embodiment, the use comprises administering to the subject an amount of a monoclonal antibody that modulates the CGRP pathway, wherein the monoclonal antibody is in an amount effective to decrease the number of monthly headache hours by at least 20 (e.g., 25, 30, 35, 40, 45, 50, 55, 60, 65, 70 or more headache hours) after a single dose. In some embodiments, the number of monthly headache hours is reduced by at least about 50 hours. In one embodiment, the use comprises administering to the subject an amount of a monoclonal antibody that modulates the CGRP pathway, wherein the monoclonal antibody is in an amount effective to decrease the number of monthly headache hours by at least 15% (e.g., 20%, 25%, 30%, 35%, 40%, or more) after a single dose. In some embodiments, the number of monthly headache hours is reduced by at least about 30%. In some embodiments, the monoclonal antibody is an anti-CGRP antagonist antibody. In some embodiments, the amount of the monoclonal antibody administered to the patient is about 675 mg to about 1000 mg. In some embodiments, the monoclonal antibody is administered monthly. In some embodiments, the monoclonal antibody is administered as a single dose. In some embodiments, the administering is subcutaneous or intravenous administration. In some embodiments, the monoclonal antibody is formulated at a concentration of at least 150 mg/mL. In some embodiments, wherein the monoclonal antibody is administered in a volume of less than 2 mL. In some embodiments, the subject is human. In some embodiments, the monoclonal antibody is human or humanized. In some embodiments, the monoclonal antibody comprises (a) an antibody having a CDR H1 as set forth in SEQ ID NO:3; a CDR H2 as set forth in SEQ ID NO:4; a CDR H3 as set forth in SEQ ID NO:5; a CDR L1 as set forth in SEQ ID NO:6; a CDR L2 as set forth in SEQ ID NO:7; and a CDR L3 as set forth in SEQ ID NO:8; or (b) a variant of an antibody according to (a) as shown in Table 6.

In one aspect, the invention provides a composition for use in decreasing a number of monthly headache days experienced by a subject with refractory migraine. In one embodiment, the use comprises administering to the subject an amount of a monoclonal antibody that modulates the CGRP pathway, wherein the monoclonal antibody is in an amount effective to decrease the number of monthly headache days by at least 3 (e.g., 3, 4, 5, 6, 7, 8, 9, 10, 11, 12, 13, 14, 15, 16, 17, 18, 19, 20 or more headache days) after a single dose. In some embodiments, the number of monthly headache days is reduced by at least about 6 headache days. In some embodiments, the monoclonal antibody is an anti-CGRP antagonist antibody. In some embodiments, the amount of the monoclonal antibody administered to the patient is about 675 mg to about 1000 mg. In some embodiments, the monoclonal antibody is administered monthly. In some embodiments, the monoclonal antibody is administered as a single dose. In some embodiments, the administering is subcutaneous or intravenous administration. In some embodiments, the monoclonal antibody is formulated at a concentration of at least 150 mg/mL. In some embodiments, wherein the monoclonal antibody is administered in a volume of less than 2 mL, e.g., about 1.5 mL. In some embodiments, the subject is human. In some embodiments, the monoclonal antibody is human or humanized. In some embodiments, the monoclonal antibody comprises (a) an antibody having a CDR H1 as set forth in SEQ ID NO:3; a CDR H2 as set forth in SEQ ID NO:4; a CDR H3 as set forth in SEQ ID NO:5; a CDR L1 as set forth in SEQ ID NO:6; a CDR L2 as set forth in SEQ ID NO:7; and a CDR L3 as set forth in SEQ ID NO:8; or (b) a variant of an antibody according to (a) as shown in Table 6.

In one aspect, the invention provides a composition for use in decreasing use of any acute headache medication in a subject with refractory migraine, comprising administering to the subject a monoclonal antibody (e.g., anti-CGRP antagonist antibody) that modulates the CGRP pathway, wherein the monoclonal antibody is in an amount effective to decrease monthly use of the acute headache medication by the subject by at least 15% (e.g., 20%, 25%, 30%, 35%, 40%, or more). In some embodiments, the headache medication is selected from the group consisting of 5-HT1 agonists, triptans, opiates, ergot alkaloids, and non-steroidal anti-inflammatory drugs (NSAIDs). In some embodiments, the headache medication is a triptan or ergot compound. In some embodiments, the acute headache medication is selected from the group consisting of analgesics (e.g., acetylsalicylic acid, ibuprofen, naproxen, diclofenac, paracetamol, acetylsalicylic acid plus paracetamol plus caffeine, metamizol, phenazon, or tolfenamic acid); antiemetics (e.g., metoclopramide or domperidone); ergot alkaloids (e.g., ergotamine tartrate or dihydroergotamine); and triptans, i.e., 5-HT1 agonists (e.g., sumatriptan, zolmitriptan, naratriptan, rizatriptan, almotriptan, eletriptan, or frovatriptan). In some embodiments, the amount of the monoclonal antibody administered to the patient is about 675 mg to about 1000 mg. In some embodiments, the monoclonal antibody is administered monthly. In some embodiments, the monoclonal antibody is administered as a single dose. In some embodiments, the administering is subcutaneous or intravenous administration. In some embodiments, the monoclonal antibody is formulated at a concentration of at least 150 mg/mL. In some embodiments, wherein the monoclonal antibody is administered in a volume of less than 2 mL, e.g., about 1.5 mL. In some embodiments, the subject is human. In some embodiments, the monoclonal antibody is human or humanized. In some embodiments, the monoclonal antibody comprises (a) an antibody having a CDR H1 as set forth in SEQ ID NO:3; a CDR H2 as set forth in SEQ ID NO:4; a CDR H3 as set forth in SEQ ID NO:5; a CDR L1 as set forth in SEQ ID NO:6; a CDR L2 as set forth in SEQ ID NO:7; and a CDR L3 as set forth in SEQ ID NO:8; or (b) a variant of an antibody according to (a) as shown in Table 6.

In one aspect, the invention provides a composition for use in of preventing, treating, or reducing incidence of migraine in a subject having refractory migraine comprising administering to the subject a single dose of a monoclonal antibody (e.g., monoclonal anti-CGRP-antagonist antibody) in an amount that modulates the CGRP pathway, wherein the amount of the monoclonal antibody administered to the patient is about 675 mg to about 1000 mg.

BRIEF DESCRIPTION OF THE DRAWINGS

FIG. 1 is a table showing binding affinities of 12 murine antibodies for different alanine substituted human α-CGRP fragments. Binding affinities were measured at 25° C. using Biacore by flowing Fabs across CGRPs on the chip. The boxed values represent the loss in affinity of alanine mutants relative to parental fragment, 25-37 (italic), except K35A, which was derived from a 19-37 parent. "$^{a}$" indicates affinities for 19-37 and 25-37 fragments are the mean average±standard deviation of two independent measurements on different sensor chips. "$^{b}$" indicates these interactions deviated from a simple bimolecular interaction model due to a biphasic offrate, so their affinities were determined using a conformational change model. Grey-scale key: white (1.0) indicates parental affinity; light grey (less than 0.5) indicates higher affinity than parent; dark grey (more than 2) indicates lower affinity than parent; and black indicates that no binding was detected.

FIGS. 2A and 2B show the effect of administering CGRP 8-37 (400 nmol/kg), antibody 4901 (25 mg/kg), and antibody 7D11 (25 mg/kg) on skin blood flow measured as blood cell flux after electrical pulse stimulation for 30 seconds. CGRP 8-37 was administered intravenously (iv) 3-5 min before electrical pulse stimulation. Antibodies were administered intraperitoneal (IP) 72 hours before electrical pulse stimulation. Each point in the graphs represents AUC of one rat treated under the conditions as indicated. Each line in the graphs represents average AUC of rats treated under the condition as indicated. AUC (area under the curve) equals to Δflux×Δtime. "Δflux" represents the change of flux units after the electrical pulse stimulation; and "Δtime" represents the time period taken for the blood cell flux level to return to the level before the electrical pulse stimulation.

FIG. 3 shows the effect of administering different dosage of antibody 4901 (25 mg/kg, 5 mg/kg, 2.5 mg/kg, or 1 mg/kg) on skin blood flow measured as blood cell flux after electrical pulse stimulation for 30 seconds. Antibodies were administered intravenously (IV) 24 hours before electrical pulse stimulation. Each point in the graph represents AUC of one rat treated under the conditions as indicated. The line in the graph represents average AUC of rats treated under the condition as indicated.

FIGS. 4A and 4B show the effect of administering antibody 4901 (1 mg/kg or 10 mg/kg, i.v.), antibody 7E9 (10 mg/kg, i.v.), and antibody 8B6 (10 mg/kg, i.v.) on skin blood flow measured as blood cell flux after electrical pulse stimulation for 30 seconds. Antibodies were administered intravenously (i.v.) followed by electrical pulse stimulation at 30 min, 60 min, 90 min, and 120 min after antibody administration. Y axis represents percent of AUC as compared to level of AUC when no antibody was administered (time 0). X axis represents time (minutes) period between the administration of antibodies and electrical pulse stimulation. "*" indicates P<0.05, and "**" indicates P<0.01, as compared to time 0. Data were analyzed using one-way ANOVA with a Dunnett's Multiple comparison test.

FIG. 5 shows the amino acid sequence of the heavy chain variable region (SEQ ID NO: 1) and light chain variable region (SEQ ID NO:2) of antibody G1. The Kabat CDRs are in bold text, and the Chothia CDRs are underlined. The amino acid residues for the heavy chain and light chain variable region are numbered sequentially.

DETAILED DESCRIPTION

Figure 4B:
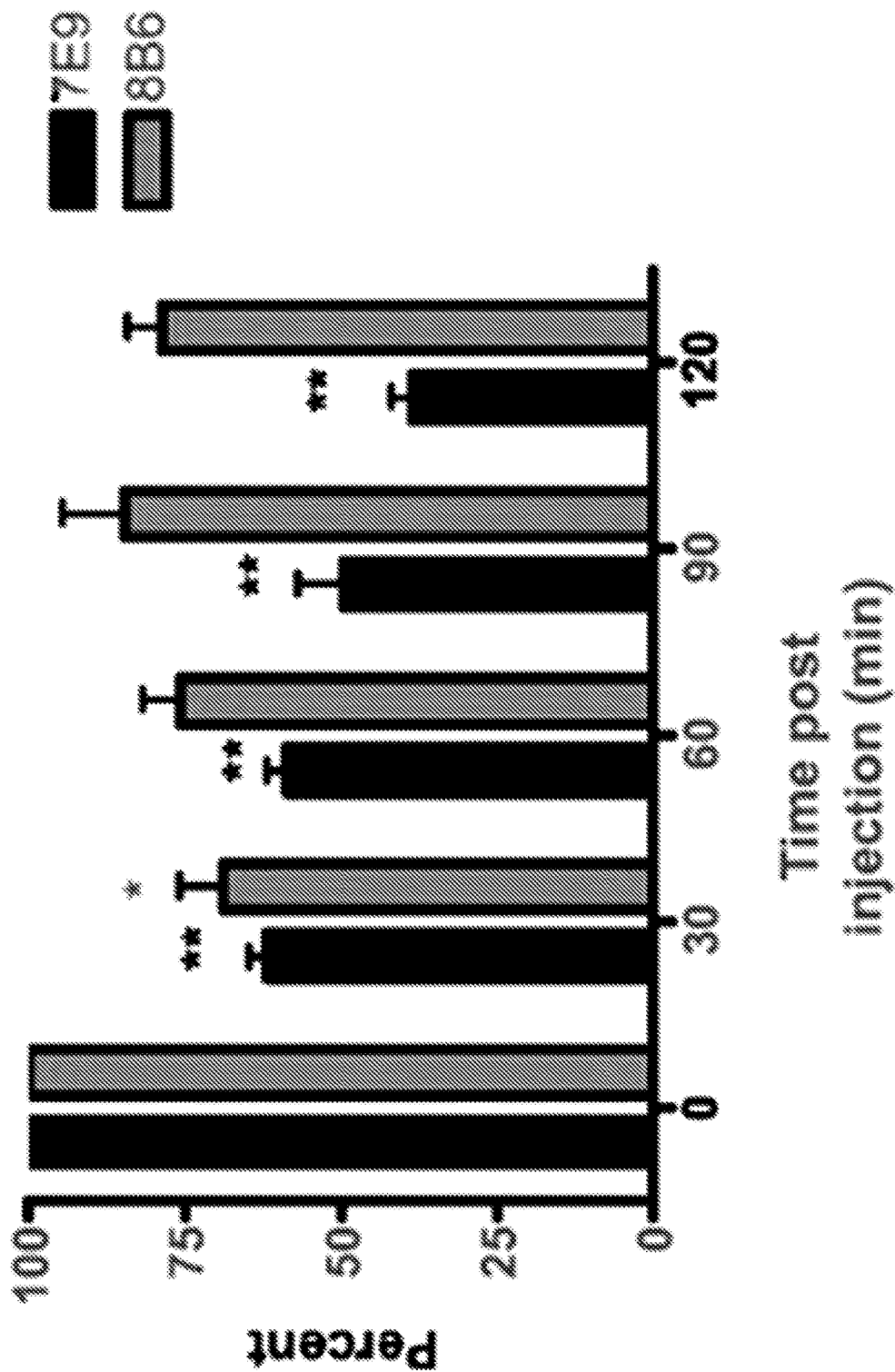

In some aspects, the invention disclosed herein provides methods for preventing, treating, and/or reducing incidence of migraine in an in a subject having refractory migraine by administering to the individual a therapeutically effective amount of an anti-CGRP antagonist antibody.

In some aspects, the invention disclosed herein also provides anti-CGRP antagonist antibodies and polypeptides derived from G1 or its variants shown in Table 6, or compositions thereof, for use in treating and/or reducing incidence of migraine in a subject having refractory migraine.

General Techniques

The practice of the various aspects of the present invention will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, second edition (Sambrook et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-1998) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel et al., eds., 1987); PCR: The Polymerase Chain Reaction, (Mullis et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practical approach (D. Catty, ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds., Harwood Academic Publishers, 1995).

Definitions

As used herein, "about" when used in reference to numerical ranges, cutoffs, or specific values is used to indicate that the recited values may vary by up to as much as 10% from the listed value. Thus, the term "about" is used to encompass variations of ±10% or less, variations of ±5% or less, variations of ±1% or less, variations of ±0.5% or less, or variations of ±0.1% or less from the specified value.

An "antibody" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term encompasses not only intact polyclonal or monoclonal antibodies, but also fragments thereof (such as Fab, Fab', F(ab')$_2$, Fv), single chain (ScFv), mutants thereof, fusion proteins comprising an antibody portion (such as domain antibodies), and any other modified configuration of the immunoglobulin molecule that comprises an antigen recognition site. An antibody includes an antibody of any class, such as IgG, IgA, or IgM (or sub-class thereof), and the antibody need not be of any particular class. Depending on the antibody amino acid sequence of the constant domain of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1, and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known.

As used herein, "monoclonal antibody" refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. Furthermore, in contrast to polyclonal antibody preparations, which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler and Milstein, 1975, Nature, 256:495, or may be made by recombinant DNA methods such as described in U.S. Pat. No. 4,816,567. The monoclonal antibodies may also be isolated from phage libraries generated using the techniques described in McCafferty et al., 1990, Nature, 348:552-554, for example.

As used herein, "humanized" antibodies refer to forms of non-human (e.g., murine) antibodies that are specific chimeric immunoglobulins, immunoglobulin chains, or fragments thereof (such as Fv, Fab, Fab', F(ab')$_2$ or other antigen-binding subsequences of antibodies) that contain minimal sequence derived from non-human immunoglobulin. For the most part, humanized antibodies are human immunoglobulins (recipient antibody) in which residues from a complementarity determining region (CDR) of the recipient are replaced by residues from a CDR of a non-human species (donor antibody) such as mouse, rat, or rabbit having the desired specificity, affinity, and, biological activity. In some instances, Fv framework region (FR) residues of the human immunoglobulin are replaced by corresponding non-human residues. Furthermore, the humanized antibody may comprise residues that are found neither in the recipient antibody nor in the imported CDR or framework sequences, but are included to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region or domain (Fc), typically that of a human immunoglobulin. Antibodies may have Fc regions modified as described in WO 99/58572. Other forms of humanized antibodies have one or more CDRs (one, two, three, four, five, six) which are altered with respect to the original antibody, which are also termed one or more CDRs "derived from" one or more CDRs from the original antibody.

As used herein, "human antibody" means an antibody having an amino acid sequence corresponding to that of an antibody produced by a human and/or has been made using any of the techniques for making human antibodies known in the art or disclosed herein. This definition of a human antibody includes antibodies comprising at least one human heavy chain polypeptide or at least one human light chain polypeptide. One such example is an antibody comprising murine light chain and human heavy chain polypeptides. Human antibodies can be produced using various techniques known in the art. In one embodiment, the human antibody is selected from a phage library, where that phage library expresses human antibodies (Vaughan et al., 1996, Nature Biotechnology, 14:309-314; Sheets et al., 1998, PNAS, (USA) 95:6157-6162; Hoogenboom and Winter, 1991, J. Mol. Biol., 227:381; Marks et al., 1991, J. Mol. Biol., 222:581). Human antibodies can also be made by introducing human immunoglobulin loci into transgenic animals, e.g., mice in which the endogenous immunoglobulin genes have been partially or completely inactivated. This approach is described in U.S. Pat. Nos. 5,545,807; 5,545,806; 5,569,825; 5,625,126; 5,633,425; and 5,661,016. Alternatively, the human antibody may be prepared by immortalizing human B lymphocytes that produce an antibody directed against a target antigen (such B lymphocytes may be recovered from an individual or may have been immunized in vitro). See, e.g., Cole et al., Monoclonal Antibodies and Cancer Therapy, Alan R. Liss, p. 77 (1985); Boerner et al., 1991, J. Immunol., 147 (1):86-95; and U.S. Pat. No. 5,750,373.

As used herein, the term "calcitonin gene-related peptide" and "CGRP" refers to any form of calcitonin gene-related peptide and variants thereof that retain at least part of the activity of CGRP. For example, CGRP may be α-CGRP or β-CGRP. As used herein, CGRP includes all mammalian species of native sequence CGRP, e.g., human, canine, feline, equine, and bovine.

As used herein, an "anti-CGRP antagonist antibody" (interchangeably termed "anti-CGRP antibody") refers to an antibody that is able to bind to CGRP and inhibit CGRP biological activity and/or downstream pathway(s) mediated by CGRP signaling. An anti-CGRP antagonist antibody encompasses antibodies that modulate, block, antagonize, suppress or reduce (including significantly) CGRP biological activity, or otherwise antagonize the CGRP pathway, including downstream pathways mediated by CGRP signaling, such as receptor binding and/or elicitation of a cellular response to CGRP. For purpose of the present invention, it will be explicitly understood that the term "anti-CGRP antagonist antibody" encompasses all the previously identified terms, titles, and functional states and characteristics whereby CGRP itself, CGRP biological activity (including but not limited to its ability to mediate any aspect of headache), or the consequences of the biological activity, are substantially nullified, decreased, or neutralized in any meaningful degree. In some embodiments, an anti-CGRP antagonist antibody binds CGRP and prevents CGRP binding to a CGRP receptor. In other embodiments, an anti-CGRP antibody binds CGRP and prevents activation of a CGRP receptor. Examples of anti-CGRP antagonist antibodies are provided herein.

As used herein, the terms "G1," "antibody G1," "TEV-48125," and fremanezumab are used interchangeably to refer to an anti-CGRP antagonist antibody produced by expression vectors having deposit numbers of ATCC PTA-6867 and ATCC PTA-6866. The amino acid sequence of the heavy chain and light chain variable regions are shown in FIG. 5. The CDR portions of antibody G1 (including Chothia and Kabat CDRs) are diagrammatically depicted in FIG. 5. The polynucleotides encoding the heavy and light chain variable regions are shown in SEQ ID NO:9 and SEQ ID NO:10. The G1 heavy chain full antibody amino acid sequence is shown in SEQ ID NO:11. The G1 light chain full antibody amino acid sequence is shown in SEQ ID NO:12. The characterization and processes for making antibody G1 (and variants thereof) are described in Examples 1-4 infra, as well as PCT Application No. PCT/IB2006/003181, which is hereby incorporated by reference in its entirety The terms "polypeptide", "oligopeptide", "peptide" and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that, because the polypeptides of this invention are based upon an antibody, the polypeptides can occur as single chains or associated chains.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after polymerization, such as by conjugation with a labeling component. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, α-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), (O)NR$_2$ ("amidate"), P(O)R, P(O)OR', CO or CH$_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

As used herein, refractory migraine patients (or "subject having refractory migraine") are considered refractory if they have a documented inadequate response (in a medical chart or by treating physician's confirmation) to at least two preventive medications (from a different cluster, defined below). Refractory migraine patients can also be considered refractory if they have a documented inadequate response (in a medical chart or by treating physician's confirmation) to two to four classes of prior preventive medications (from different cluster, as defined below), e.g., inadequate response to two classes of prior preventive medications, inadequate response to three classes of prior preventative medications, or an inadequate response to four classes of prior preventative medications.

Inadequate response is defined as: no clinically meaningful improvement per treating physician's judgement, after at least three months of therapy at a stable dose considered appropriate for migraine prevention according to accepted country guidelines, or when treatment has to be interrupted because of adverse events that made it intolerable by the patient or the drug is contraindicated or not suitable for the patient. The three-month period may not apply if the drug is intolerable or contraindicated or not suitable for the patient. For onabotulinumtoxinA, an inadequate response is defined as: no clinically meaningful improvement per treating physician's judgement, after at least six months of therapy at a stable dose considered appropriate for migraine prevention according to accepted country guidelines, or when treatment has to be interrupted because of adverse events that made it intolerable by the patient. Or, if onabotulinumtoxinA is a previous preventative medication, at least two sets of injections and three months should have passed since the last set of injections.

In some embodiments, the clusters are as follows:
cluster A: topiramate, carbamazepine, divalproex sodium, and sodium valproate
cluster B: flunarizine and pizotifen
cluster C: amitriptyline, venlafaxine, nortriptyline, and duloxetine
cluster D: atenolol, nadolol, metoprolol, propranolol, and timolol
cluster E: onabotulinumtoxinA In some embodiments, the clusters are as follows:
cluster A: beta-blockers: propranolol, metoprolol, atenolol, and bisoprolol
cluster B: anticonvulsants: topiramate
cluster C: tricyclics: amitriptyline
cluster D: calcium channel blocker: flunarizine
cluster E: angiotensin II receptor antagonist: candesartan
cluster F: onabotulinumtoxinA
cluster G: valproic acid Within this group of clusters, a subject has refractory migraine if the patient has an inadequate response to two to four classes of preventative headache medications. For example, a subject has refractory migraine if the patient has an inadequate response to two or three medications each from different clusters (A, B, C, D, E, F) and valproic acid (cluster G).

Additional clusters include:
cluster a: an angiotensin-converting enzyme (ACE) inhibitor, such as lisinopril,
cluster b: a benzocycloheptene-based drug, such as pizotifen
cluster c: an antidepressant, such as amitriptyline (Elavil), trazodone (Desyrel), and imipramine (Tofranil), and venlafaxine
cluster d: an anticonvulsant such as phenytoin (Dilantin) or carbamazepine (Tegretol)
cluster e: oxetorone A skilled practitioner will be readily able to recognize and/or diagnose a subject with a refractory migraine.

As used herein, "preventing" is an approach to stop migraine from occurring or existing in a subject, who is not already experiencing migraine. As used herein, "treatment" is an approach for obtaining beneficial or desired clinical results. For purposes of this invention, beneficial or desired clinical results include, but are not limited to, one or more of the following: improvement in any aspect of a refractory migraine, including lessening severity, alleviation of pain intensity, and other associated symptoms, reducing frequency of recurrence, reducing the number of monthly headache days or hours, increasing the quality of life of those suffering from refractory migraine, and decreasing dose of other medications (e.g., acute headache medication) required to treat the refractory migraine.

"Reducing incidence" of migraine means any of reducing severity (which can include reducing need for and/or amount of (e.g., exposure to) other drugs and/or therapies generally used for this condition, including, for example, ergotamine, dihydroergotamine, or triptans), duration, and/or frequency (including, for example, delaying or increasing time to next episodic attack in an individual). As is understood by those skilled in the art, individuals may vary in terms of their response to treatment, and, as such, for example, a "method of reducing incidence of migraine in an individual" reflects administering the anti-CGRP antagonist antibody based on a reasonable expectation that such administration may likely cause such a reduction in incidence of migraine in that particular individual.

"Ameliorating" migraine or one or more symptoms of refractory migraine means a lessening or improvement of one or more symptoms of migraine in a subject having refractory migraine as compared to not administering an anti-CGRP antagonist antibody. "Ameliorating" also includes shortening or reduction in duration of a symptom.

As used herein, "controlling refractory migraine" refers to maintaining or reducing severity or duration of one or more symptoms of migraine, e.g., the frequency of migraine attacks in an individual having refractory migraine (as compared to the level before treatment). For example, the duration or severity of head pain, or frequency of attacks is reduced by at least about any of 10%, 20%, 30%, 40%, 50%, 60%, or 70% in the individual as compared to the level before treatment.

As used herein, a "headache hour" refers to an hour during which a subject experiences headache. Headache hours can be expressed in terms of whole hours (e.g., one headache hour, two headache hours, three headache hours, etc.) or in terms of whole and partial hours (e.g., 0.5 headache hours, 1.2 headache hours, 2.67 headache hours, etc.). One or more headache hours may be described with respect to a particular time interval. For example, "daily headache hours" may refer to the number of headache hours a subject experiences within a day interval (e.g., a 24-hour period). In another example, "weekly headache hours" may refer to the number of headache hours a subject experiences within a week interval (e.g., a 7-day period). As can be appreciated, a week interval may or may not correspond to a calendar week. In another example, "monthly headache hours" may refer to the number of headache hours a subject experiences within a month interval. As can be appreciated, a month interval (e.g., a period of 28, 29, 30, or 31 days) may vary in terms of number of days depending upon the particular month and may or may not correspond to a calendar month. In yet another example, "yearly headache hours" may refer to the number of headache hours a subject experiences within a year interval. As can be appreciated, a year interval (e.g., a period of 365 or 366 days) may vary in terms of number of days depending upon the particular year and may or may not correspond to a calendar year.

As used herein, a "headache day" refers to a day during which a subject experiences headache. Headache days can be expressed in terms of whole days (e.g., one headache day, two headache days, three headache days, etc.) or in terms of whole and partial days (e.g., 0.5 headache days, 1.2 headache days, 2.67 headache days, etc.). One or more headache days may be described with respect to a particular time interval. For example, "weekly headache days" may refer to the number of headache days a subject experiences within a week interval (e.g., a 7-day period). As can be appreciated, a week interval may or may not correspond to a calendar week. In another example, "monthly headache days" may refer to the number of headache days a subject experiences within a month interval. As can be appreciated, a month interval (e.g., a period of 28, 29, 30, or 31 days) may vary in terms of number of days depending upon the particular month and may or may not correspond to a calendar month. In yet another example, "yearly headache days" may refer to the number of headache days a subject experiences within a year interval. As can be appreciated, a year interval (e.g., a period of 365 or 366 days) may vary in terms of number of days depending upon the particular year and may or may not correspond to a calendar year.

As used therein, "delaying" the development of migraine means to defer, hinder, slow, retard, stabilize, and/or postpone progression of the disease in a subject having refractory migraine. This delay can be of varying lengths of time, depending on the history of the disease and/or individuals being treated. As is evident to one skilled in the art, a sufficient or significant delay can, in effect, encompass prevention, in that the individual does not develop migraine, especially after being diagnosed with refractory migraine due to inadequate response to prior preventative treatments. A method that "delays" development of the symptom is a method that reduces probability of developing the symptom in a given time frame and/or reduces extent of the symptoms in a given time frame, when compared to not using the method. Such comparisons are typically based on clinical studies, using a statistically significant number of subjects.

"Development" or "progression" of migraine means initial manifestations and/or ensuing progression of the disorder in a subject having refractory migraine. Development of migraine can be detectable and assessed using standard clinical techniques as well known in the art.

As used herein, an "effective dosage" or "effective amount" of drug, compound, or pharmaceutical composition is an amount sufficient to effect beneficial or desired results. For prophylactic use, beneficial or desired results include results such as eliminating or reducing the risk, lessening the severity, or delaying the onset of the disease, including biochemical, histological and/or behavioral symptoms of the disease, its complications and intermediate pathological phenotypes presenting during development of the disease. For therapeutic use, beneficial or desired results include clinical results such as reducing pain intensity, duration, or frequency of refractory migraine attack, and decreasing one or more symptoms resulting from refractory migraine (biochemical, histological and/or behavioral), including its complications and intermediate pathological phenotypes presenting during development of the disease, increasing the quality of life of those suffering from the disease, decreasing the dose of other medications required to treat the disease, enhancing effect of another medication, and/or delaying the progression of the disease of patients. An effective dosage can be administered in one or more administrations. For purposes of this disclosure, an effective dosage of drug, compound, or pharmaceutical composition is an amount sufficient to accomplish prophylactic or therapeutic treatment either directly or indirectly. As is understood in the clinical context, an effective dosage of a drug, compound, or pharmaceutical composition may or may not be achieved in conjunction with another drug, compound, or pharmaceutical composition. Thus, an "effective dosage" may be considered in the context of administering one or more therapeutic agents, and a single agent may be considered to be given in an effective amount if, in conjunction with one or more other agents, a desirable result may be or is achieved.

An "individual" or a "subject" is a mammal, more preferably a human. Mammals also include, but are not limited to, farm animals, sport animals, pets, primates, horses, dogs, cats, mice and rats.

A. Methods for Preventing, Treating, or Reducing Refractory Migraine and/or at Least One Secondary Symptom Associated with Refractory Migraine In one aspect, the invention provides methods of preventing, treating, or reducing incidence of migraine in a subject having refractory migraine. In another aspect, the invention provides a method of treating or reducing incidence of at least one secondary symptom associated with refractory migraine in a subject. In some embodiments, the method comprises administering to the individual an effective amount of an antibody or polypeptides derived from the antibody that modulates the CGRP pathway (e.g., a monoclonal anti-CGRP antagonist antibody).

In another aspect, the invention provides methods for preventing, ameliorating, controlling, reducing incidence of, or delaying the progression of migraine in an individual having refractory migraine or symptoms associated with the diagnosis of refractory migraine comprising administering to the individual an effective amount of an antibody that modulates the CGRP pathway or an anti-CGRP antagonist antibody in combination with additional agent(s) useful for treating migraine, for example, the additional agent(s) can be an acute headache medication.

Such additional agents include, but are not limited to, 5-HT agonists, triptans, NSAIDs, analgesics, antiemetics, ergot alkaloids. For example, the antibody and the at least one additional acute migraine medication can be concomitantly administered, i.e., they can be given in close enough temporal proximity to allow their individual therapeutic effects to overlap.

Additional non-limiting examples of additional acute migraine agents that may be administered in combination with an anti-CGRP antagonist antibody include one or more of:
(i) an opioid analgesic, e.g., morphine, heroin, hydromorphone, oxymorphone, levorphanol, levallorphan, methadone, meperidine, fentanyl, cocaine, codeine, dihydrocodeine, oxycodone, hydrocodone, propoxyphene, nalmefene, nalorphine, naloxone, naltrexone, buprenorphine, butorphanol, nalbuphine or pentazocine;
(ii) a nonsteroidal antiinflammatory drug (NSAID), e.g., aspirin, diclofenac, diflunisal, etodolac, fenbufen, fenoprofen, flufenisal, flurbiprofen, ibuprofen, indomethacin, ketoprofen, ketorolac, meclofenamic acid, mefenamic acid, nabumetone, naproxen, oxaprozin, phenylbutazone, piroxicam, sulindac, tolmetin or zomepirac, cyclooxygenase-2 (COX-2) inhibitors, celecoxib; rofecoxib; meloxicam; JTE-522; L-745,337; NS398; or a pharmaceutically acceptable salt thereof;

(iii) a barbiturate sedative, e.g., amobarbital, aprobarbital, butabarbital, butalbital (including butalbital combinations, e.g., butalbital/aspirin/caffeine (Fiorinal®, Actavis) or butalbital/paracetamol/caffeine (Fioricet®, Cardinal Health)), mephobarbital, metharbital, methohexital, pentobarbital, phenobarbital, secobarbital, talbutal, theamylal or thiopental; or a pharmaceutically acceptable salt thereof;

(iv) a barbiturate analgesic, e.g., butalbital or a pharmaceutically acceptable salt thereof or a composition comprising butalbital.

(v) a benzodiazepine having a sedative action, e.g., chlordiazepoxide, clorazepate, diazepam, flurazepam, lorazepam, oxazepam, temazepam, or triazolam or a pharmaceutically acceptable salt thereof;

(vi) an $H_1$ antagonist having a sedative action, e.g., diphenhydramine, pyrilamine, promethazine, chlorpheniramine, or chlorcyclizine or a pharmaceutically acceptable salt thereof;

(vii) a sedative such as glutethimide, meprobamate, methaqualone or dichloralphenazone or a pharmaceutically acceptable salt thereof;

(viii) a skeletal muscle relaxant, e.g., baclofen, carisoprodol, chlorzoxazone, cyclobenzaprine, methocarbamol or orphenadrine or a pharmaceutically acceptable salt thereof;

(ix) an NMDA receptor antagonist, e.g., dextromethorphan ((+)-3-hydroxy-N-methylmorphinan) or its metabolite dextrorphan ((+)-3-hydroxy-N-methylmorphinan), ketamine, memantine, pyrroloquinoline quinone or cis-4-(phosphonomethyl)-2-piperidinecarboxylic acid or a pharmaceutically acceptable salt thereof;

(x) an alpha-adrenergic, e.g., doxazosin, tamsulosin, clonidine or 4-amino-6,7-dimethoxy-2-(5-methanesulfonamido-1,2,3,4-tetrahydroisoquinol-2-yl)-5-(2-pyridyl) quinazoline;

(xi) a COX-2 inhibitor, e.g., celecoxib, rofecoxib or valdecoxib;

(xii) a coal-tar analgesic, in particular paracetamol;

(xiii) a neuroleptic such as droperidol;

(xiv) a vanilloid receptor agonist (e.g., resiniferatoxin) or antagonist (e.g., capsazepine);

(xv) a local anaesthetic, such as mexiletine;

(xxii) a corticosteroid, such as dexamethasone;

(xxiii) a serotonin receptor agonist or antagonist;

(xxiv) a cholinergic (nicotinic) analgesic;

(xxv) tramadol;

(xxvi) a PDEV inhibitor, such as sildenafil, vardenafil or tadalafil;

(xxvii) an alpha-2-delta ligand such as gabapentin or pregabalin; and (xxviii) a cannabinoid.

Those skilled in the art will recognize the difference between administration of a drug for the acute treatment of migraine and for migraine prophylaxis (i.e., for the preventative treatment of migraine).

Those skilled in the art will be able to determine appropriate dosage amounts for particular agents to be used in combination with an anti-CGRP antibody. For example, sumatriptan may be administered in a dosage from about 0.01 to about 300 mg. In some cases, sumatriptan may be administered in a dosage from about 2 mg to about 300 mg, e.g., about 5 mg to about 250 mg, about 5 mg to about 200 mg, about 5 mg to about 100 mg, about 5 mg to about 50 mg, or about 5 mg to about 25 mg. When administered non-parenterally, the typical dosage of sumatriptan is from about 25 to about 100 mg with about 50 mg being generally preferred, e.g., about 45 mg, about 55 mg, or about 60 mg. When sumatriptan is administered parenterally, the preferred dosage is about 6 mg, e.g., about 5 mg, about 7 mg, or about 8 mg. However, these dosages may be varied according to methods standard in the art so that they are optimized for a particular patient or for a particular combination therapy. Further, for example, celecoxib may be administered in an amount of between 50 and 500 mg, e.g., about 50 mg to about 400 mg, about 50 mg to about 300 mg, about 50 mg to about 200 mg, about 50 mg to about 100 mg, about 100 mg to about 400 mg, or about 200 mg to about 300 mg. Further, the label for any approved acute headache medication can also provide appropriate dosage amounts for the desired result.

In another aspect, the disclosure provides a method of preventing, treating, or reducing incidence of migraine in a subject having refractory migraine comprising administering to the subject a monoclonal antibody (e.g., a monoclonal, anti-CGRP antagonist antibody) that modulates the CGRP pathway. In some embodiments, the amount of the monoclonal antibody administered on each of the plurality of days may be between 0.1 mg-5000 mg, 1 mg-5000 mg, 10 mg-5000 mg, 100 mg-5000 mg, 1000 mg-5000 mg, 0.1 mg-4000 mg, 1 mg-4000 mg, 10 mg-4000 mg, 100 mg-4000 mg, 1000 mg-4000 mg, 0.1 mg-3000 mg, 1 mg-3000 mg, 10 mg-3000 mg, 100 mg-3000 mg, 1000 mg-3000 mg, 0.1 mg-2000 mg, 1 mg-2000 mg, 10 mg-2000 mg, 100 mg-2000 mg, 1000 mg-2000 mg, 0.1 mg-1000 mg, 1 mg-1000 mg, 10 mg-1000 mg, or 100 mg-1000 mg. In some embodiments, the amount is between about 225 mg and about 1000 mg, e.g., about 675 mg or about 900 mg. An exemplary dosing regimen comprises administering an initial antibody dose of about 675 mg subcutaneously, followed by a monthly antibody dose of about 225 mg subcutaneously for, e.g., about two months, three months, four months, five months, six months, seven months, eight months, nine months, ten months, 11 months, or 12 months, or even a period of greater than one year (e.g., 18 months, two years, or three years). Another exemplary dosing regimen comprises administering an initial antibody dose of about 225 mg subcutaneously, followed by a monthly antibody dose of about 225 mg subcutaneously for, e.g., about two months, three months, four months, five months, six months, seven months, eight months, nine months, ten months, 11 months, or 12 months, or even a period of greater than one year (e.g., 18 months, two years, or three years). Yet another dosing regimen comprises administering an initial antibody dose of about 900 mg intravenously in an infusion over about 60 minutes, followed by doses of about 900 mg administered intravenously in an infusion over about 60 minutes every quarter for, e.g., one year, two years, three years, four years, or five years. Yet another dosing regimen comprises administering an initial or starting dose of about 675 mg administered subcutaneously, followed by doses of about 675 mg administered subcutaneously every quarter for, e.g., about one year, two years, three years, four years, or five years. However, other dosage regimens may be useful, depending on the pattern of pharmacokinetic decay that the practitioner wishes to achieve. In some embodiments, the initial dose (i.e., starting dose) and one or more of the additional doses are administered the same way, e.g., subcutaneously or intravenously. In some embodiments, the one or more additional doses are administered in a different way than the initial or starting dose, e.g., the initial dose may be administered intravenously and the one or more additional doses may be administered subcutaneously.

In another aspect, the disclosure provides a method of preventing, treating, or reducing incidence of migraine in a subject having refractory migraine comprising administering to the subject a single dose of a monoclonal antibody (e.g., a monoclonal, anti-CGRP antagonist antibody) in an amount that modulates the CGRP pathway. In some embodiments, the single dose may be an amount of antibody between 0.1 mg-5000 mg, 1 mg-5000 mg, 10 mg-5000 mg, 100 mg-5000 mg, 1000 mg-5000 mg, 0.1 mg-4000 mg, 1 mg-4000 mg, 10 mg-4000 mg, 100 mg-4000 mg, 1000 mg-4000 mg, 0.1 mg-3000 mg, 1 mg-3000 mg, 10 mg-3000 mg, 100 mg-3000 mg, 1000 mg-3000 mg, 0.1 mg-2000 mg, 1 mg-2000 mg, 10 mg-2000 mg, 100 mg-2000 mg, 1000 mg-2000 mg, 0.1 mg-1000 mg, 1 mg-1000 mg, 10 mg-1000 mg or 100 mg-1000 mg. In some embodiments, the single dose may be an amount of antibody between 225 mg and about 1000 mg, e.g., about 225 mg, about 675 mg or about 900 mg. In another embodiment, the single dose may be an amount of antibody between 675 mg and 900 mg.

In another aspect, the disclosure provides a method of preventing, treating, or reducing incidence of migraine in a subject having refractory migraine comprising administering to the subject a monthly dose of a monoclonal antibody (e.g., a monoclonal, anti-CGRP antagonist antibody) in an amount that modulates the CGRP pathway. In some embodiments, the single dose may be an amount of antibody between 0.1 mg-5000 mg, 1 mg-5000 mg, 10 mg-5000 mg, 100 mg-5000 mg, 1000 mg-5000 mg, 0.1 mg-4000 mg, 1 mg-4000 mg, 10 mg-4000 mg, 100 mg-4000 mg, 1000 mg-4000 mg, 0.1 mg-3000 mg, 1 mg-3000 mg, 10 mg-3000 mg, 100 mg-3000 mg, 1000 mg-3000 mg, 0.1 mg-2000 mg, 1 mg-2000 mg, 10 mg-2000 mg, 100 mg-2000 mg, 1000 mg-2000 mg, 0.1 mg-1000 mg, 1 mg-1000 mg, 10 mg-1000 mg or 100 mg-1000 mg. In some embodiments, the monthly dose may be an amount of antibody between about 225 mg and about 1000 mg, e.g., about 225 mg, about 675 mg or about 900 mg. An exemplary dosing regimen comprises administering an initial antibody dose of about 675 mg subcutaneously, followed by a monthly antibody dose of about 225 mg subcutaneously for, e.g., about two months, three months, four months, five months, six months, seven months, eight months, nine months, ten months, 11 months, or 12 months, or even a period of greater than one year (e.g., 18 months, two years, or three years). Another exemplary dosing regimen comprises administering an initial antibody dose of about 225 mg subcutaneously, followed by a monthly antibody dose of about 225 mg subcutaneously for, e.g., about two months, three months, four months, five months, six months, seven months, eight months, nine months, ten months, 11 months, or 12 months, or even a period of greater than one year (e.g., 18 months, two years, or three years). Yet another dosing regimen comprises administering an initial antibody dose of about 900 mg intravenously in an infusion over about 60 minutes, followed by doses of about 900 mg administered intravenously in an infusion over about 60 minutes every quarter for, e.g., one year, two years, three years, four years, or five years. Yet another dosing regimen comprises administering an initial or starting dose of about 675 mg administered subcutaneously, followed by doses of about 675 mg administered subcutaneously every quarter for, e.g., about one year, two years, three years, four years, or five years. However, other dosage regimens may be useful, depending on the pattern of pharmacokinetic decay that the practitioner wishes to achieve. In some embodiments, the initial dose (i.e., starting dose) and one or more of the additional doses are administered the same way, e.g., subcutaneously or intravenously. In some embodiments, the one or more additional doses are administered in a different way than the initial or starting dose, e.g., the initial dose may be administered intravenously and the one or more additional doses may be administered subcutaneously.

In another aspect, the disclosure provides a method of decreasing a number of monthly headache hours experienced by a subject having refractory migraine, comprising administering to the subject an amount of a monoclonal antibody (e.g., a monoclonal, anti-CGRP antagonist antibody) that modulates the CGRP pathway. In some embodiments, the monoclonal antibody can be in an amount effective to decrease the number of monthly headache hours by at least 0.1, 1, 5, 10, 15, 20, 25, 30, 35, 40, 45, 50, 55, 60, 65, 70, 75, 80, 85, 90, 95, 100 or more headache hours after a single dose, monthly dose, or quarterly dose. In some embodiments, the monoclonal antibody can be in an amount effective to decrease the number of monthly headache hours by at least 20 headache hours after a single dose, monthly dose, or quarterly dose. In some embodiments, the monoclonal antibody can be in an amount effective to decrease the number of monthly headache hours by at least 40, 45, 50, 55, 60, 65, 70, 75, 80, 85, 90, 95, 100, 105, 110, 115, 120, 125, or more headache hours. In some embodiments, the monoclonal antibody can be in an amount effective to decrease the number of monthly headache hours by at least 0.1%, 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 99%, or more after a single dose. In some embodiments, the monoclonal can be in an amount effective to decrease the number of monthly headache hours by at least 15%, 20%, 25%, 30%, 35%, 40%, 45%, 50%, 55%, 60%, 65%, 70%, 75%, 80%, 85%, 90%, 95%, 99%, or more after a single dose, monthly dose, or quarterly dose.

In another aspect, the disclosure provides a method of decreasing a number of monthly headache days experienced by a subject having refractory migraine, comprising administering to the subject an amount of a monoclonal antibody (e.g., a monoclonal, anti-CGRP antagonist antibody) that modulates the CGRP pathway. In some embodiments, the monoclonal antibody can be in an amount effective to decrease the number of monthly headache days by at least 3, 4, 5, 6, 7, 8, 9, 10, 11, 12, 13, 14, 15, 16, 17, 18, 19, 20, or more headache days after a single dose. In some embodiments, the monoclonal antibody can be in an amount effective to decrease the number of monthly headache days by at least 3, 4, 5, 6, 7, 8, 9, 10, 11, 12, 13, 14, 15, 16, 17, 18, 19, 20, or more headache days after a monthly dose or quarterly dose. In some embodiments, the monoclonal antibody can be in an amount effective to decrease the number of monthly headache days by at least 0.1%, 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 99%, or more after a single dose, monthly dose, or quarterly dose.

In another aspect, the disclosure provides a method of decreasing use of an acute headache medication in a subject having refractory migraine, comprising administering to the subject a monoclonal antibody (e.g., a monoclonal anti-CGRP antagonist antibody) that modulates the CGRP pathway. In some embodiments, the monoclonal antibody can be in an amount effective to decrease daily, monthly, quarterly, and/or yearly use of the anti-headache medication by the subject by at least 0.1%, 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 99%, or more. In some embodiments, the monoclonal antibody can be in an amount effective to decrease monthly use of the anti-headache medication by the subject by at least 15%, 20%, 25%, 30%, 35%, 40%, 45%, 50%, 55%, 60%, 65%, 70%, 75%, 80%, 85%, 90%, 95%, 99%, or more. The anti-headache medication can be any type of acute headache medication described herein. The acute headache medication can be migraine-specific headache medications, which are identifiable to one of skill in the art (e.g., triptans and ergot compounds). Non-limiting examples of acute headache medications include, for example, 5-HT1 agonists (and agonists acting at other 5-HT1 sites), triptans (e.g., sumatriptan, zolmitriptan, naratriptan, rizatriptan, eletriptan, almotriptan, afrovatriptan), ergot alkaloids (e.g., ergotamine tartrate, ergonovine maleate, and ergoloid mesylates (e.g., dihydroergocornine, dihydroergocristine, dihydroergokryptine, and dihydroergotamine mesylate (DHE 45)) and non-steroidal anti-inflammatory drugs (NSAIDs) (e.g., aspirin, diclofenac, diflunisal, etodolac, fenbufen, fenoprofen, flufenisal, flurbiprofen, ibuprofen, indomethacin, ketoprofen, ketorolac, meclofenamic acid, mefenamic acid, nabumetone, naproxen, oxaprozin, phenylbutazone, piroxicam, sulindac, tolmetin or zomepirac, cyclooxygenase-2 (COX-2) inhibitors, celecoxib; rofecoxib; meloxicam; JTE-522; L-745,337; NS398; or a pharmaceutically acceptable salt thereof), opiates/opioids (e.g., codeine, oxycodone), and barbiturates.

In another aspect, the disclosure provides a method of decreasing the monthly average number of days of use of a migraine-specific acute headache medication in a subject having refractory migraine, comprising administering to the subject a monoclonal antibody (e.g., a monoclonal anti-CGRP antagonist antibody) that modulates the CGRP pathway. In some embodiments, the monoclonal antibody can be in an amount effective to decrease the monthly average number of days of use of the acute headache medication by at least 3, 4, 5, 6, 7, 8, 9, 10, 11, 12, 13, 14, 15, 16, 17, 18, 19, 20, or more days after a single dose. In some embodiments, the monoclonal antibody can be in an amount effective to decrease the monthly average number of days of use of the acute headache medication by at least 3, 4, 5, 6, 7, 8, 9, 10, 11, 12, 13, 14, 15, 16, 17, 18, 19, 20, or more days after a monthly dose or quarterly dose. In some embodiments, the migraine-specific acute headache medication is a triptan or ergot compound.

In another aspect, the disclosure provides a method of decreasing the monthly average number of days with nausea and/or vomiting experienced by a subject having refractory migraine, comprising administering to the subject an amount of a monoclonal antibody (e.g., a monoclonal, anti-CGRP antagonist antibody) that modulates the CGRP pathway. In some embodiments, the monoclonal antibody can be in an amount effective to decrease the number of monthly nausea and/or vomiting days by at least 3, 4, 5, 6, 7, 8, 9, 10, 11, 12, 13, 14, 15, 16, 17, 18, 19, 20, or more nausea and/or vomiting days after a single dose. In some embodiments, the monoclonal antibody can be in an amount effective to decrease the number of monthly nausea and/or vomiting days by at least 3, 4, 5, 6, 7, 8, 9, 10, 11, 12, 13, 14, 15, 16, 17, 18, 19, 20, or more nausea and/or vomiting days after a monthly dose or quarterly dose. In some embodiments, the monoclonal antibody can be in an amount effective to decrease the number of monthly nausea and/or vomiting days by at least 0.1%, 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 99%, or more after a single dose, monthly dose, or quarterly dose.

In another aspect, the disclosure provides a method of decreasing the monthly average number of days with photophobia and/or phonophobia experienced by a subject having refractory migraine, comprising administering to the subject an amount of a monoclonal antibody (e.g., a monoclonal, anti-CGRP antagonist antibody) that modulates the CGRP pathway. In some embodiments, the monoclonal antibody can be in an amount effective to decrease the number of monthly photophobia and/or phonophobia days by at least 3, 4, 5, 6, 7, 8, 9, 10, 11, 12, 13, 14, 15, 16, 17, 18, 19, 20, or more photophobia and/or phonophobia days after a single dose. In some embodiments, the monoclonal antibody can be in an amount effective to decrease the number of monthly photophobia and/or phonophobia days by at least 3, 4, 5, 6, 7, 8, 9, 10, 11, 12, 13, 14, 15, 16, 17, 18, 19, 20, or more photophobia and/or phonophobia days after a monthly dose or quarterly dose. In some embodiments, the monoclonal antibody can be in an amount effective to decrease the number of monthly photophobia and/or phonophobia days by at least 0.1%, 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 99%, or more after a single dose, monthly dose, or quarterly dose.

In another aspect, the disclosure provides a method of improving the quality of life of a subject having refractory migraine, comprising administering to the subject a monoclonal antibody (e.g., a monoclonal anti-CGRP antagonist antibody) that modulates the CGRP pathway. In some embodiments, changes in quality of life are self-reported by the subject. In some embodiments, changes in the quality of life of a subject are measured using a Migraine-Specific Quality of Life (MSQOL) questionnaire. The MSQOL questionnaire, and various versions thereof, are known in the art.

In another aspect, the disclosure provides a method of improving the health-related quality of life of a subject, comprising administering to the subject a monoclonal antibody (e.g., a monoclonal anti-CGRP antagonist antibody) that modulates the CGRP pathway. In some embodiments, changes in health-related quality of life are self-reported by the subject. In some embodiments, changes in the health-related quality of life of a subject are measured using a EuroQol-5 Dimension (EQ 5D) questionnaire. The EQ 5D questionnaire, and various versions thereof, are known in the art.

In another aspect, the disclosure provides a method of reducing the disability due to migraine of a subject having refractory migraine, comprising administering to the subject a monoclonal antibody (e.g., a monoclonal anti-CGRP antagonist antibody) that modulates the CGRP pathway. In some embodiments, changes in disability due to migraine are self-reported by the subject. In some embodiments, changes in disability due to migraine of a subject are measured using a 6-item Headache Impact Test (HIT-6). The HIT-6, and various versions thereof, are known in the art.

In another aspect, the disclosure provides a method of reducing the disability due to migraine of a subject having refractory migraine, comprising administering to the subject a monoclonal antibody (e.g., a monoclonal anti-CGRP antagonist antibody) that modulates the CGRP pathway. In some embodiments, changes in disability due to migraine are self-reported by the subject. In some embodiments, changes in disability due to migraine of a subject are measured using a Migraine Disability Assessment (MIDAS)

questionnaire. The MIDAS questionnaire, and various versions thereof, are known in the art.

In another aspect, the disclosure provides a method of reducing depression in a subject, comprising administering to the subject having refractory migraine a monoclonal antibody (e.g., a monoclonal anti-CGRP antagonist antibody) that modulates the CGRP pathway. In some embodiments, changes in depression status are self-reported by the subject. In some embodiments, changes in the depression status of a subject are measured using the two-item Patient Health Questionnaire (PHQ-2) or the nine-item Patient Health Questionnaire (PHQ-9). In some embodiments, changes in the depression status of a subject are measured using the two-item Patient Health Questionnaire (PHQ-2) and the nine-item Patient Health Questionnaire (PHQ-9).

In another aspect, the disclosure provides a method of improving the work productivity and activity of a subject having refractory migraine, comprising administering to the subject a monoclonal antibody (e.g., a monoclonal anti-CGRP antagonist antibody) that modulates the CGRP pathway. In some embodiments, changes in work productivity and activity are self-reported by the subject. In some embodiments, changes in the work productivity and activity of a subject are measured using the Work Productivity and Activity Impairment (WPAI) questionnaire. The WPAI questionnaire, and various versions thereof, are known in the art.

With respect to all methods described herein, references to antibodies (e.g., monoclonal antibodies that modulate the CGRP pathway, anti-CGRP antagonist antibodies, monoclonal anti-CGRP antagonist antibodies) also include compositions comprising one or more of these agents. Accordingly, such a composition may be used according to a method referring to an antibody described herein. These compositions may further comprise suitable excipients, such as pharmaceutically acceptable excipients as described elsewhere herein.

An antibody described herein (e.g., a monoclonal antibody, an anti-CGRP antagonist antibody, a monoclonal anti-CGRP antagonist antibody) can be administered to an individual or subject in any therapeutic dose, via any suitable route and in any suitable formulation. It should be apparent to a person skilled in the art that the examples described herein are not intended to be limiting but to be illustrative of the techniques available. Accordingly, in some embodiments, an antibody described herein can be administered to a subject in accord with known methods, such as intravenous administration, e.g., as a bolus or by continuous infusion over a period of time, e.g., about 10 minutes, about 20 minutes, about 30 minutes, about 40 minutes, about 50 minutes, about 60 minutes, about 90 minutes, about 120 minutes, about 180 minutes, or about 240 minutes. The antibody described herein can also be administered to the subject by subcutaneous, intramuscular, intraperitoneal, intracerebrospinal, intra-articular, sublingually, intra-arterial, intrasynovial, via insufflation, intrathecal, oral, inhalation, intranasal (e.g., with or without inhalation), buccal, rectal, transdermal, intracardiac, intraosseous, intradermal, transmucosal, vaginal, intravitreal, peri-articular, local, epicutaneous, or topical routes. Administration can be systemic, e.g., intravenous administration, or localized. Commercially available nebulizers for liquid formulations, including jet nebulizers and ultrasonic nebulizers are useful for administration. Liquid formulations can be directly nebulized and lyophilized powder can be nebulized after reconstitution. Alternatively, an antibody described herein can be aerosolized using a fluorocarbon formulation and a metered dose inhaler, or inhaled as a lyophilized and milled powder.

In some embodiments, an antibody described herein can be administered via site-specific or targeted local delivery techniques. Examples of site-specific or targeted local delivery techniques include various implantable depot sources of the antibody or local delivery catheters, such as infusion catheters, an indwelling catheter, or a needle catheter, synthetic grafts, adventitial wraps, shunts and stents or other implantable devices, site specific carriers, direct injection, or direct application. See e.g., PCT Publication No. WO 00/53211 and U.S. Pat. No. 5,981,568, which are hereby incorporated by reference in their entireties.

Various formulations of an antibody described herein may be used for administration. In some embodiments, an antibody may be administered neat. In some embodiments, antibody and a pharmaceutically acceptable excipient may be in various formulations. Pharmaceutically acceptable excipients are known in the art, and are relatively inert substances that facilitate administration of a pharmacologically effective substance. For example, an excipient can give form or consistency, or act as a diluent. Suitable excipients include but are not limited to stabilizing agents, wetting and emulsifying agents, salts for varying osmolarity, encapsulating agents, buffers, and skin penetration enhancers. Excipients as well as formulations for parenteral and nonparenteral drug delivery are set forth in Remington, The Science and Practice of Pharmacy 20th Ed. Mack Publishing (2000).

In some embodiments, these agents, including antibodies described herein, may be formulated for administration by injection (e.g., intravenously, subcutaneously, intraperitoneally, intramuscularly, etc.). Accordingly, these agents can be combined with pharmaceutically acceptable vehicles such as saline, Ringer's solution, dextrose solution, and the like. The particular dosage regimen, i.e., dose, timing and repetition, will depend on the particular individual and that individual's medical history.

In some embodiments, these agents, including antibodies described herein, may be formulated for peripheral administration. Such formulations can be administered peripherally via any suitable peripheral route, including intravenously and subcutaneously. An agent prepared for peripheral administration can include a substance, medicament, and/or antibody that is not delivered centrally, spinally, intrathecally, or directly into the CNS. Non-limiting examples of peripheral administration routes include a route which is oral, sublingual, buccal, topical, rectal, via inhalation, transdermal, subcutaneous, intravenous, intra-arterial, intramuscular, intracardiac, intraosseous, intradermal, intraperitoneal, transmucosal, vaginal, intravitreal, intra-articular, peri-articular, local, or epicutaneous.

Therapeutic formulations of the antibodies used in accordance with the present disclosure can be prepared for storage and/or use by mixing an antibody having the desired degree of purity with optional pharmaceutically acceptable carriers, excipients or stabilizers (Remington, The Science and Practice of Pharmacy 20th Ed. Mack Publishing (2000)), and can in some cases be in the form of lyophilized formulations or aqueous solutions. Acceptable carriers, excipients, or stabilizers are nontoxic to recipients at the dosages and concentrations employed. A therapeutic formulation of an antibody may comprise one or more pharmaceutically acceptable carriers, excipients or stabilizes with non-limiting examples of such species that include buffers such as phosphate, citrate, and other organic acids; salts such as sodium chloride; antioxidants including ascorbic acid and methionine;

preservatives (such as octadecyldimethylbenzyl ammonium chloride; hexamethonium chloride; benzalkonium chloride, benzethonium chloride; phenol, butyl or benzyl alcohol; alkyl parabens, such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids (e.g., at concentrations of 0.1 mM to 100 mM, 0.1 mM to 1 mM, 0.01 mM to 50 mM, 1 mM to 50 mM, 1 mM to 30 mM, 1 mM to 20 mM, 10 mM to 25 mM) such as glycine, glutamine, methionine, asparagine, histidine, arginine, or lysine; monosaccharides, disaccharides, and other carbohydrates including glucose, mannose, or dextrins; chelating agents (e.g., at concentrations of 0.001 mg/mL to 1 mg/mL, 0.001 mg/mL to 1 mg/mL, 0.001 mg/mL to 0.1 mg/mL, 0.001 mg/mL to 0.01 mg/mL, 0.01 mg/mL to 0.1 mg/mL) such as EDTA (e.g., disodium EDTA dihydrate); sugars (e.g., at concentrations of 1 mg/mL to 500 mg/mL, 10 mg/ml to 200 mg/mL, 10 mg/mL to 100 mg/mL, 50 mg/mL to 150 mg/mL) such as sucrose, mannitol, trehalose or sorbitol; salt-forming counter-ions such as sodium; metal complexes (e.g., Zn-protein complexes); and/or nonionic surfactants (e.g., at concentrations of 0.01 mg/ml to 10 mg/mL, 0.01 mg/ml to 1 mg/mL, 0.1 mg/mL to 1 mg/mL, 0.01 mg/mL to 0.5 mg/mL) such as TWEEN™ (e.g., polysorbate (e.g., polysorbate 20, polysorbate 40, polysorbate 60, polysorbate 80)), PLURONICS™ or polyethylene glycol (PEG).

An antibody formulation may be characterized in terms of any of a variety of physical properties. For example, a liquid antibody formulation may have any suitable pH for therapeutic efficacy, safety and storage. For example, the pH of a liquid antibody formulation may be from pH 4 to about pH 9, from about pH 5 to about pH 8, from about pH 5 to about pH 7 or from about pH 6 to about pH 8. In some embodiments, a liquid antibody formulation may have a pH of about 3.0, 3.5, 4.0, 4.5, 5.0, 5.5, 6.0, 6.5, 7.0, 7.5, 8.0, 8.5, 9.0, 9.5, or about 10 or higher or lower.

In another example, a liquid antibody formulation may have any suitable viscosity for therapeutic efficacy, safety and storage. For example, the viscosity of a liquid antibody formulation may be from about 0.5 centipoise (cP) to about 100 cP, about 1 cP to about 50 cP, about 1 cP to about 20 cP, about 1 cP to about 15 cP, or about 5 cP to about 15 cP at 25° C. In some embodiments, a liquid antibody formulation may have a viscosity of about 0.5 cP, 1 cP, 1.2 cP, 1.4 cP, 1.6 cP, 1.8 cP, 2.0 cP, 2.2 cP, 2.4 cP, 2.6 cP, 2.8 cP, 3.0 cP, 3.2 cP, 3.4 cP, 3.6 cP, 3.8 cP, 4.0 cP, 4.2 cP, 4.4 cP, 4.6 cP, 4.8 cP, 5.0 cP, 5.2 CP, 5.4 cP, 5.6 cP, 5.8 cP, 6.0 cP, 6.2 cP, 6.4 cP, 6.6 cP, 6.8 cP, 7.0 cP, 7.2 cP, 7.4 cP, 7.6 cP, 7.8 cP, 8.0 cP, 8.2 cP, 8.4 cP, 8.6 cP, 8.8 cP, 9.0 cP, 9.2 cP, 9.4 cP, 9.6 cP, 9.8 CP, 10.0 cP, 10.2 cP, 10.4 cP, 10.6 cP, 10.8 cP, 11.0 cP, 11.2 cP, 11.4 cP, 11.6 cP, 11.8 CP, 12.0 cP, 12.2 cP, 12.4 cP, 12.6 cP, 12.8 cP, 13.0 cP, 13.2 cP, 13.4 cP, 13.6 cP, 13.8 CP, 14.0 cP, 14.2 cP, 14.4 cP, 14.6 cP, 14.8 cP, or about 15.0 cP at 25° C. or the viscosity may be higher or lower.

In another example, a liquid antibody formulation may have any suitable conductivity for therapeutic efficacy, safety and storage. For example, the conductivity of a liquid antibody formulation may be from about 0.1 millisiemens per centimeter (mS/cm) to about 15 mS/cm, 0.1 mS/cm to 10 mS/cm, 0.1 mS/cm to 5 mS/cm, 0.1 mS/cm to 2 mS/cm or 0.1 mS/cm to 1.5 mS/cm. In some embodiments, a liquid antibody formulation may have a conductivity of 0.19 mS/cm, 0.59 mS/cm, 1.09 mS/cm, 1.19 mS/cm, 1.29 mS/cm, 1.39 mS/cm, 1.49 mS/cm, 1.59 mS/cm, 1.69 mS/cm, 1.79 mS/cm, 1.89 mS/cm, 1.99 mS/cm, 2.09 mS/cm, 2.19 mS/cm, 2.29 mS/cm, 2.39 mS/cm, 2.49 mS/cm, 2.59 mS/cm, 2.69 mS/cm, 2.79 mS/cm, 2.89 mS/cm, 2.99 mS/cm, 3.09 mS/cm, 3.19 mS/cm, 3.29 mS/cm, 3.39 mS/cm, 3.49 mS/cm, 3.59 mS/cm, 3.69 mS/cm, 3.79 mS/cm, 3.89 mS/cm, 3.99 mS/cm, 4.09 mS/cm, 4.19 mS/cm, 4.29 mS/cm, 4.39 mS/cm, 4.49 mS/cm, 4.59 mS/cm, 4.69 mS/cm, 4.79 mS/cm, 4.89 mS/cm, 4.99 mS/cm, 5.09 mS/cm, 6.09 mS/cm, 6.59 mS/cm, 7.09 mS/cm, 7.59 mS/cm, 8.09 mS/cm, 8.59 mS/cm, 9.09 mS/cm, 9.59 mS/cm, 10.09 mS/cm, 10.59 mS/cm, 11.09 mS/cm, 11.59 mS/cm, 12.09 mS/cm, 12.59 mS/cm, 13.09 mS/cm, 13.59 mS/cm, 14.09 mS/cm, 14.59 mS/cm, or about 15.09 mS/cm or the conductivity may be higher or lower.

In another example, a liquid antibody formulation may have any suitable osmolality for therapeutic efficacy, safety, and storage. For example, the osmolality of a liquid antibody formulation may be from about 50 milliosmole per kilogram (mOsm/kg) to about 5000 mOsm/kg, about 50 mOsm/kg to about 2000 mOsm/kg, about 50 mOsm/kg to about 1000 mOsm/kg, about 50 mOsm/kg to about 750 mOsm/kg, or about 50 mOsm/kg to about 500 mOsm/kg. In some embodiments, a liquid antibody formulation may have an osmolality of about 50 mOsm/kg, 60 mOsm/kg, 70 mOsm/kg, 80 mOsm/kg, 90 mOsm/kg, 100 mOsm/kg 120 mOsm/kg, 140 mOsm/kg, 160 mOsm/kg, 180 mOsm/kg, 200 mOsm/kg, 220 mOsm/kg, 240 mOsm/kg, 260 mOsm/kg, 280 mOsm/kg, 300 mOsm/kg, 320 mOsm/kg, 340 mOsm/kg, 360 mOsm/kg, 380 mOsm/kg, 400 mOsm/kg, 420 mOsm/kg, 440 mOsm/kg, 460 mOsm/kg, 480 mOsm/kg, 500 mOsm/kg, 520 mOsm/kg, 540 mOsm/kg, 560 mOsm/kg, 580 mOsm/kg, 600 mOsm/kg, 620 mOsm/kg, 640 mOsm/kg, 660 mOsm/kg, 680 mOsm/kg, 700 mOsm/kg, 720 mOsm/kg, 740 mOsm/kg, 760 mOsm/kg, 780 mOsm/kg, 800 mOsm/kg, 820 mOsm/kg, 840 mOsm/kg, 860 mOsm/kg, 880 mOsm/kg, 900 mOsm/kg, 920 mOsm/kg, 940 mOsm/kg, 960 mOsm/kg, 980 mOsm/kg, 1000 mOsm/kg, 1050 mOsm/kg, 1100 mOsm/kg, 1150 mOsm/kg, 1200 mOsm/kg, 1250 mOsm/kg, 1300 mOsm/kg, 1350 mOsm/kg, 1400 mOsm/kg, 1450 mOsm/kg, about 1500 mOsm/kg, or the osmolality may be higher or lower.

Liposomes containing antibody can be prepared by methods known in the art, such as described in Epstein, et al., Proc. Natl. Acad. Sci. USA 82:3688 (1985); Hwang, et al., Proc. Natl Acad. Sci. USA 77:4030 (1980); and U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington, The Science and Practice of Pharmacy 20th Ed. Mack Publishing (2000).

Sustained-release preparations may be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or 'poly(vinylalcohol)), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(−)-3-hydroxybutyric acid.

The formulations to be used for in vivo administration should generally be sterile. This is readily accomplished by, for example, filtration through sterile filtration membranes. Therapeutic antibody compositions are generally placed into a container having a sterile access port, for example, an intravenous solution bag or vial having a stopper pierceable by a hypodermic injection needle.

The compositions according to the present invention may be in unit dosage forms such as tablets, pills, capsules, powders, granules, solutions or suspensions, or suppositories, for oral, parenteral or rectal administration, or administration by inhalation or insufflation. In some cases, a unit dosage form may be supplied in a prefilled receptacle (e.g., a prefilled syringe) useful in administering the unit dosage to a subject.

In some embodiments, a formulation comprising an antibody (e.g., monoclonal antibody that modulates the CGRP pathway, anti-CGRP antagonist antibody, monoclonal anti-CGRP antagonist antibody) described herein may be prepared for any suitable route of administration with an antibody amount ranging from about 0.1 mg to about 3000 mg, about 1 mg to about 1000 mg, about 100 mg to about 1000 mg, or about 100 mg to about 500 mg, about 200 mg to about 800 mg, about 500 mg to about 1500 mg, about 1500 mg to about 2500 mg, or about 2000 mg to about 3000 mg. In some cases, a formulation comprising an antibody (e.g., monoclonal antibody that modulates the CGRP pathway, anti-CGRP antagonist antibody, monoclonal anti-CGRP antagonist antibody) described herein may comprise an antibody amount of, at most, or at least about 0.1 mg, 1 mg, 100 mg, 1 mg, 10 mg, 25 mg, 50 mg, 75 mg, 100 mg, 125 mg, 150 mg, 175 mg, 200 mg, 225 mg, 250 mg, 275 mg, 300 mg, 325 mg, 350 mg, 375 mg, 400 mg, 450 mg, 475 mg, 500 mg, 525 mg, 550 mg, 575 mg, 600 mg, 625 mg, 650 mg, 675 mg, 700 mg, 725 mg, 750 mg, 775 mg, 800 mg, 825 mg, 850 mg, 875 mg, 900 mg, 925 mg, 950 mg, 975 mg, 1000 mg, 1100 mg, 1200 mg, 1300 mg, 1400 mg, 1500 mg, 1600 mg, 1700 mg, 1800 mg, 1900 mg, 2000 mg, or about 3000 mg.

In some embodiments, a liquid formulation comprising an antibody (e.g., monoclonal antibody that modulates the CGRP pathway, anti-CGRP antagonist antibody, monoclonal anti-CGRP antagonist antibody) described herein may be prepared for any suitable route of administration with an antibody concentration ranging from about 0.1 mg/mL to about 500 mg/mL, about 0.1 mg/mL to about 375 mg/mL, about 0.1 mg/mL to about 250 mg/mL, about 0.1 to about 175 mg/mL, about 0.1 to 100 mg/mL, about 1 mg/mL to about 500 mg/mL, about 1 mg/mL to about 375 mg/mL, about 1 mg/mL to about 300 mg/mL, about 1 mg/mL to 250 mg/mL, about 1 mg/mL to about 200 mg/mL, about 1 mg/mL to 150 mg/mL, about 1 mg/mL to about 100 mg/mL, about 10 mg/mL to 500 mg/mL, about 10 mg/mL to about 375 mg/mL, about 10 mg/mL to about 250 mg/mL, about 10 mg/mL to about 150 mg/mL, about 10 mg/mL to about 100 mg/mL, about 100 mg/mL to 500 mg/mL, about 100 mg/mL to 450 mg/mL, about 100 mg/mL to 400 mg/mL, about 100 mg/mL to about 350 mg/mL, about 100 mg/mL to about 300 mg/mL, about 100 mg/mL to about 250 mg/mL, 100 mg/mL to 200 mg/mL, or about 100 mg/mL to about 150 mg/mL. In some embodiments, a liquid formulation may comprise an antibody described herein at a concentration of, of at most, of at least, or less than about 0.1, 0.5, 1, 5, 10, 15 20, 25, 30, 35, 40, 45, 50, 55, 60, 65, 70, 75, 80, 85, 90, 95, 100, 105 110, 115, 120, 125, 130, 135, 140, 145, 150, 155, 160, 165, 170, 175, 180, 185, 190, 195, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, or about 500 mg/mL.

An antibody formulation may comprise one or more components including the antibody and other species described elsewhere herein. The antibody and other components may be in any suitable amount and/or any suitable concentration for therapeutic efficacy of the antibody, safety and storage. In one example, an antibody formulation may be a solution comprising about 51.4 mg/mL antibody (e.g., antibody G1, another anti-CGRP antagonist antibody, or a monoclonal antibody that modulates the CGRP pathway), 16-20 mM histidine, 0.1 mg/ml methionine, 84 mg/mL trehalose dihydrate, 0.05 mg/ml disodium EDTA dihydrate, and 0.2 mg/mL polysorbate 80.

In another example, an antibody formulation may comprise about 200 mg/ml antibody (e.g., antibody G1, another anti-CGRP antagonist antibody, or a monoclonal antibody that modulates the CGRP pathway), 15 mM arginine, 78 mg/ml sucrose, 0.3 mg/mL EDTA, and 0.1 mg/mL polysorbate 80.

In another example, an antibody formulation may comprise about 175 mg/ml antibody (e.g., antibody G1, another anti-CGRP antagonist antibody, or a monoclonal antibody that modulates the CGRP pathway), 20 mM glycine, 88 mg/mL trehalose dihydrate, 0.015 mg/mL EDTA, and 0.25 mg/mL polysorbate 80.

In another example, an antibody formulation may comprise about 225 mg/ml antibody (e.g., antibody G1, another anti-CGRP antagonist antibody, or a monoclonal antibody that modulates the CGRP pathway), 23 mM asparagine, 84 mg/mL sorbitol, 0.1 mg/mL EDTA, and 0.15 mg/mL polysorbate 60.

In another example, an antibody formulation may comprise about 150 mg/ml antibody (e.g., antibody G1, another anti-CGRP antagonist antibody, or a monoclonal antibody that modulates the CGRP pathway), 17 mM asparagine, 74 mg/mL mannitol, 0.025 mg/mL EDTA, and 0.2 mg/mL polysorbate 80.

In another example, an antibody formulation may comprise about 100 mg/ml antibody (e.g., antibody G1, another anti-CGRP antagonist antibody, or a monoclonal antibody that modulates the CGRP pathway), 16 mM arginine, 87 mg/mL mannitol, 0.025 mg/mL EDTA, and 0.15 mg/mL polysorbate 20.

In another example, an antibody formulation may comprise about 250 mg/ml antibody (e.g., antibody G1, another anti-CGRP antagonist antibody, or a monoclonal antibody that modulates the CGRP pathway), 25 mM histidine, 74 mg/mL mannitol, 0.025 mg/mL EDTA, and 0.25 mg/mL polysorbate 20.

In another example, an antibody formulation may comprise about 50 mg/ml antibody (e.g., antibody G1, another anti-CGRP antagonist antibody, or a monoclonal antibody that modulates the CGRP pathway), 19 mM arginine, 84 mg/ml sucrose, 0.05 mg/mL EDTA, and 0.3 mg/mL polysorbate 80.

In another example, an antibody formulation may comprise about 125 mg/mL antibody (e.g., antibody G1, another anti-CGRP antagonist antibody, or a monoclonal antibody that modulates the CGRP pathway), 22 mM glycine, 79 mg/mL trehalose dihydrate, 0.15 mg/mL EDTA, and 0.15 mg/mL polysorbate 80.

In another example, an antibody formulation may be a solution comprising about 175 mg/mL antibody (e.g., antibody G1, another anti-CGRP antagonist antibody, or a monoclonal antibody that modulates the CGRP pathway), 20 mM histidine, 0.1 mg/mL methionine, 84 mg/mL trehalose dihydrate, 0.05 mg/mL disodium EDTA dihydrate, and 0.2 mg/mL polysorbate 80.

In another example, an antibody formulation may comprise about 200 mg/mL antibody (e.g., antibody G1, another anti-CGRP antagonist antibody, or a monoclonal antibody that modulates the CGRP pathway), 30 mM arginine, 78 mg/mL sucrose, 0.3 mg/mL EDTA, and 0.1 mg/mL polysorbate 80.

In another example, an antibody formulation may comprise about 175 mg/ml antibody (e.g., antibody G1, another anti-CGRP antagonist antibody, or a monoclonal antibody that modulates the CGRP pathway), 20 mM glycine, 88 mg/mL trehalose dihydrate, 0.015 mg/mL EDTA, and 0.15 mg/mL polysorbate 80.

In another example, an antibody formulation may comprise about 150 mg/mL antibody (e.g., antibody G1, another anti-CGRP antagonist antibody, or a monoclonal antibody that modulates the CGRP pathway), 20 mM histidine, 84 mg/mL sucrose, 0.05 mg/mL EDTA, and 0.2 mg/mL polysorbate 80.

In another example, an antibody formulation may comprise about 225 mg/ml antibody (e.g., antibody G1, another anti-CGRP antagonist antibody, or a monoclonal antibody that modulates the CGRP pathway), 23 mM histidine, 84 mg/mL sorbitol, 0.1 mg/mL EDTA, and 0.15 mg/mL polysorbate 60.

In another example, an antibody formulation may comprise about 150 mg/ml antibody (e.g., antibody G1, another anti-CGRP antagonist antibody, or a monoclonal antibody that modulates the CGRP pathway), 17 mM asparagine, 74 mg/mL mannitol, 0.3 mg/mL EDTA, and 0.2 mg/mL polysorbate 80.

In another example, an antibody formulation may comprise about 100 mg/mL antibody (e.g., antibody G1, another anti-CGRP antagonist antibody, or a monoclonal antibody that modulates the CGRP pathway), 16 mM arginine, 87 mg/mL mannitol, 0.025 mg/mL EDTA, and 0.25 mg/mL polysorbate 20.

In another example, an antibody formulation may comprise about 250 mg/mL antibody (e.g., antibody G1, another anti-CGRP antagonist antibody, or a monoclonal antibody that modulates the CGRP pathway), 25 mM histidine, 89 mg/mL mannitol, 0.025 mg/mL EDTA, and 0.25 mg/mL polysorbate 20.

In another example, an antibody formulation may comprise 125 mg/mL antibody (e.g., antibody G1, another anti-CGRP antagonist antibody, or a monoclonal antibody that modulates the CGRP pathway), 29 mM arginine, 84 mg/mL sucrose, 0.05 mg/ml EDTA, and 0.3 mg/mL polysorbate 80.

In another example, an antibody formulation may comprise 150 mg/mL antibody (e.g., antibody G1, another anti-CGRP antagonist antibody, or a monoclonal antibody that modulates the CGRP pathway), 25 mM asparagine, 84 mg/ml mannitol, 0.05 mg/mL EDTA, and 0.2 mg/mL polysorbate 80.

In another example, an antibody formulation may comprise 145 mg/mL antibody (e.g., antibody G1, another anti-CGRP antagonist antibody, or a monoclonal antibody that modulates the CGRP pathway), 22 mM histidine, 72 mg/mL trehalose dihydrate, 0.05 mg/mL EDTA, and 0.1 mg/mL polysorbate 80.

An antibody described herein can be administered using any suitable method, including by injection (e.g., intravenously, subcutaneously, intraperitoneally, intramuscularly, etc.). Antibodies can also be administered via inhalation, as described herein. In some cases, an antibody may be administered nasally with or without inhalation. Generally, for administration of an antibody described herein, an initial candidate dosage can be about 2 mg/kg. For the purpose of the present invention, a typical daily dosage might range from about any of 3 µg/kg to 30 µg/kg to 300 µg/kg to 3 mg/kg, to 30 mg/kg to 100 mg/kg or more, depending on the factors mentioned above. For example, dosage of about 1 mg/kg, about 2.5 mg/kg, about 5 mg/kg, about 10 mg/kg, about 25 mg/kg, and about 30 mg/kg may be used. For repeated administrations over several days or longer, depending on the condition, the treatment is sustained until a desired suppression of symptoms occurs or until sufficient therapeutic levels are achieved, for example, to reduce pain. An exemplary dosing regimen comprises administering an initial or starting dose of about 8.5 mg/kg, or about 10 mg/kg, followed by a maintenance dose of about 2.8 mg/kg of an antibody, or followed by a maintenance dose of about 2.8 mg/kg every other week. Another exemplary dosing regimen comprises administering a dose of about 100 mg, 125 mg, 150 mg, 200 mg, 225 mg, 250 mg, 275 mg, 300 mg, 350 mg, 400 mg, 450 mg, 500 mg, 550 mg, 600 mg, about 675 mg, or about 900 mg to a subject once per month (e.g., approximately every 28 days) intravenously in an infusion over about one hour, or subcutaneously. For example, an exemplary dosing regimen can comprise administering an initial antibody dose of about 225 mg subcutaneously, followed by a monthly antibody dose of about 225 mg subcutaneously for, e.g., about two months, three months, four months, five months, six months, seven months, eight months, nine months, ten months, 11 months, or 12 months, or even a period of greater than one year (e.g., 18 months, two years, or three years). Another exemplary dosing regimen comprises administering an initial antibody dose of about 675 mg subcutaneously, followed by a monthly antibody dose of about 225 mg subcutaneously for, e.g., about two months, three months, four months, five months, six months, seven months, eight months, nine months, ten months, 11 months, or 12 months, or even a period of greater than one year (e.g., 18 months, two years, or three years). Yet another dosing regimen comprises administering an initial or starting dose of about 900 mg intravenously in an infusion over about 60 minutes, followed by doses of about 900 mg administered intravenously in an infusion over about 60 minutes every quarter for, e.g., one year, two years, three years, four years, or five years. Yet another dosing regimen comprises administering an initial or starting dose of about 675 mg administered subcutaneously, followed by doses of about 675 mg administered subcutaneously every quarter for, e.g., about one year, two years, three years, four years, or five years. However, other dosage regimens may be useful, depending on the pattern of pharmacokinetic decay that the practitioner wishes to achieve. For example, in some embodiments, dosing from about one to about four times a week is contemplated. The progress of this therapy is easily monitored by conventional techniques and assays. The dosing regimen (including the CGRP antagonist(s) used) can vary over time.

In some embodiments, the dose or amount of an antibody (e.g., monoclonal antibody that modulates the CGRP pathway, anti-CGRP antagonist antibody, monoclonal anti-CGRP antagonist antibody) described herein and administered to a subject may range from about 0.1 µg to about 3000 mg, 1 mg to 1000 mg, 100 mg to 1000 mg, 100 mg to 500 mg, 0.1 mg to 5000 mg, 1 mg to 4000 mg, 250 mg to 1000 mg, 500 mg to 1000 mg, 100 mg to 900 mg, 400 mg to 900 mg, 10 mg to 3000 mg, 10 mg to 2000 mg, 100 mg to 2000 mg, 150 mg to 2000 mg, 200 mg to 2000 mg, 250 mg to 2000 mg, 300 mg to 2000 mg, 350 mg to 2000 mg, 400 mg to 2000 mg, 450 mg to 2000 mg, 500 mg to 2000 mg, 550 mg to 2000 mg, 600 mg to 2000 mg, 650 mg to 2000 mg, 700 mg to 2000 mg, 750 mg to 2000 mg, 800 mg to 2000 mg, 850 mg to 2000 mg, 900 mg to 2000 mg, 950 mg to 2000 mg, or 1000 mg to 2000 mg. In some embodiments, the dose or amount of an antibody described herein and administered to a subject may be, may be at most, may be less than, or may be at least about 0.1 µg, 1 µg, 100 µg, 1 mg, 10 mg, 25 mg, 50 mg, 75 mg, 100 mg, 125 mg, 150 mg, 175 mg, 200 mg, 225 mg, 250 mg, 275 mg, 300 mg, 325 mg, 350 mg, 375 mg, 400 mg, 450 mg, 475 mg, 500 mg, 525 mg, 550 mg, 575 mg, 600 mg, 625 mg, 650 mg, 675 mg, 700 mg, 725 mg, 750 mg, 775 mg, 800 mg, 825 mg, 850 mg, 875 mg, 900 mg, 925 mg, 950 mg, 975 mg, 1000 mg, 1100 mg, 1200 mg, 1300 mg, 1400 mg, 1500 mg, 1600 mg, 1700 mg, 1800 mg, 1900 mg, 2000 mg, or about 3000 mg. In some embodiments, the amount is between about 225 mg to about 1000 mg, e.g., about 225 mg, about 675 mg or about 900 mg. An exemplary dosing regimen comprises administering an initial antibody dose of about 225 mg subcutaneously, followed by a monthly antibody dose of about 225 mg subcutaneously for, e.g., about two months, three months, four months, five months, six months, seven months, eight months, nine months, ten months, 11 months, or 12 months, or even a period of greater, than one year (e.g., 18 months, two years, or three years). An exemplary dosing regimen comprises administering an initial antibody dose of about 675 mg subcutaneously, followed by a monthly antibody dose of about 225 mg subcutaneously for, e.g., about two months, three months, four months, five months, six months, seven months, eight months, nine months, ten months, 11 months, or 12 months, or even a period of greater than one year (e.g., 18 months, two years, or three years). Yet another dosing regimen comprises administering an initial or starting dose of about 900 mg intravenously in an infusion over about 60 minutes, followed by doses of about 900 mg administered intravenously in an infusion over about 60 minutes every quarter for, e.g., one year, two years, three years, four years, or five years. Yet another dosing regimen comprises administering an initial or starting dose of about 675 mg administered subcutaneously, followed by doses of about 675 mg administered subcutaneously every quarter for, e.g., about one year, two years, three years, four years, or five years. However, other dosage regimens may be useful, depending on the pattern of pharmacokinetic decay that the practitioner wishes to achieve.

In some embodiments, the dose or amount of an antibody (e.g., monoclonal antibody that modulates the CGRP pathway, anti-CGRP antagonist antibody, monoclonal anti-CGRP antagonist antibody) described herein and administered to a subject may range from about 0.1 to 500, 0.1 to 100, 0.1 to 50, 0.1 to 20, 0.1 to 10, 1 to 10, 1 to 7, 1 to 5 or 0.1 to 3 mg/kg of body weight. In some embodiments, the dose or amount of an antibody (e.g., monoclonal antibody that modulates the CGRP pathway, anti-CGRP antagonist antibody, monoclonal anti-CGRP antagonist antibody) described herein and administered to a subject may be, may be at most, may be less than, or may be at least about 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, 200, 225, 250, 275, 300, 325, 350, 375, 400, 425, 450, 475, or about 500 mg/kg of body weight.

In some embodiments, the frequency at which a dose or amount of an antibody (e.g., monoclonal antibody that modulates the CGRP pathway, anti-CGRP antagonist antibody, monoclonal anti-CGRP antagonist antibody) described herein is administered to a subject may vary. In some embodiments, a single dose of antibody may be given to a subject across therapy. In some embodiments, the frequency at which a dose or amount of an antibody is administered to a subject is constant (e.g., administered about once per month or about once per quarter). In some embodiments, the frequency at which a dose or amount of an antibody is administered to a subject is about every quarter for about one year, two years, three years, four years, or five years. In some embodiments, the frequency at which a dose or amount of an antibody described herein is administered to a subject is variable (e.g., an initial or starting dose followed by a dose at once per month, followed by additional doses at about three months and about seven months). In some embodiments, the frequency at which an antibody is administered to a subject is, is at least, is less than, or is at most about one, two, three, four, five, or six time(s) per day. In some embodiments, the frequency at which an antibody (e.g., monoclonal antibody that modulates the CGRP pathway, anti-CGRP antagonist antibody, monoclonal anti-CGRP antagonist antibody) is administered to a subject is, is at least, is less than, or is at most about one, two, three, four, five, or six dose(s) per day.

In some embodiments, the frequency at which a dose or amount of an antibody (e.g., monoclonal antibody that modulates the CGRP pathway, anti-CGRP antagonist antibody, monoclonal anti-CGRP antagonist antibody) described herein is administered to a subject is, is at least, is less than, or is at most one, two, three, four, five, six, seven, eight, nine, ten, eleven, twelve, thirteen, fourteen, fifteen, sixteen, seventeen, eighteen, nineteen, or twenty time(s) per every one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two, forty-three, forty-four, forty-five, forty-six, forty-seven, forty-eight, forty-nine, fifty, fifty-five, sixty, sixty-five, seventy, seventy-five, eighty, eighty-five, ninety, ninety-five, one-hundred, one-hundred twenty-five, one-hundred fifty, one-hundred eighty, or two-hundred day(s).

In some embodiments, the frequency at which a dose or amount of an antibody (e.g., monoclonal antibody that modulates the CGRP pathway, anti-CGRP antagonist antibody, monoclonal anti-CGRP antagonist antibody) described herein is administered to a subject is, is at least, is less than, or is at most one, two, three, four, five, six, seven, eight, nine, ten, eleven, twelve, thirteen, fourteen, fifteen, sixteen, seventeen, eighteen, nineteen, or twenty time(s) per every one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two, forty-three, forty-four, forty-five, forty-six, forty-seven, forty-eight, forty-nine, fifty, fifty-five, sixty, sixty-five, seventy, seventy-five, eighty, eighty-five, ninety, ninety-five, or one-hundred week(s). In some embodiments, the frequency at which an antibody (e.g., monoclonal antibody that modulates the CGRP pathway, anti-CGRP antagonist antibody, monoclonal anti-CGRP antagonist antibody) described herein is administered to a subject is less than one, two, three, four, five, six, seven, eight, nine, ten, eleven, twelve, thirteen, fourteen, or fifteen dose(s) per week.

In some embodiments, the frequency at which a dose or amount of an antibody (e.g., monoclonal antibody that modulates the CGRP pathway, anti-CGRP antagonist antibody, monoclonal anti-CGRP antagonist antibody) is administered to a subject is, is at least, is less than, or is at most about one, two, three, four, five, six, seven, eight, nine, ten, eleven, twelve, thirteen, fourteen, fifteen, sixteen, seventeen, eighteen, nineteen, or twenty time(s) per every month, every two months, every three months, every four months, every five months, every six months, every seven months, every eight months, every nine months, every ten months, every eleven months, every twelve months, every thirteen months, every fourteen months, every fifteen months, every sixteen months, every seventeen months, or every eighteen month(s). In some embodiments, the frequency at which a dose or amount of an antibody (e.g., monoclonal antibody that modulates the CGRP pathway, anti-CGRP antagonist antibody, monoclonal anti-CGRP antagonist antibody) is administered to a subject is about one time per every one month. In some embodiments, the frequency at which a dose or amount of an antibody (e.g., monoclonal antibody that modulates the CGRP pathway, anti-CGRP antagonist antibody, monoclonal anti-CGRP antagonist antibody) is administered to a subject is about one time per every three months. In some embodiments, the frequency at which an antibody (e.g., monoclonal antibody that modulates the CGRP pathway, anti-CGRP antagonist antibody, monoclonal anti-CGRP antagonist antibody) described herein is administered to a subject is less than about one, two, three, four, five, six, seven, eight, nine, ten, eleven, twelve, thirteen, fourteen, or fifteen dose(s) per month. In some embodiments, a dose or amount of an antibody may be administered (e.g., subcutaneously or intravenously in an infusion) to a subject one time, two times, three times, four times, five times, six times, seven times, eight times, nine times, ten times or more per month.

In some embodiments, an antibody in a dose or amount of about 50 mg, 100 mg 150 mg, 200 mg, 225 mg, 250 mg, 300 mg, 350 mg, 400 mg, 450 mg, 500 mg, 550 mg, 600 mg, 650 mg, 675 mg, 700 mg, 750 mg, 800 mg, 850 mg, 900 mg, 950 mg, 1000 mg, 1050 mg, 1100 mg, 1150 mg, 1200 mg, 1250 mg, 1300 mg, 1350 mg, 1400 mg, 1450 mg, 1500 mg, 1550 mg, 1600 mg, 1650 mg, 1700 mg, 1750 mg, 1800 mg, 1850 mg, 1900 mg, 1950 mg, 2000 mg, 2050 mg, 2100 mg, 2150 mg, 2200 mg, 2250 mg, 2300 mg, 2350 mg, 2400 mg, 2450 mg, 2500 mg, 2550 mg, 2600 mg, 2650 mg, 2700 mg, 2750 mg, 2800 mg, 2850 mg, 2900 mg, 2950 mg, 3000 mg, or more may be administered (e.g., subcutaneously or intravenously in an infusion) to a subject once per month. In some embodiments, an antibody in a dose or amount of between about 0.1 mg to 5000 mg, 1 mg to 4000 mg, 10 mg to 3000 mg, 10 mg to 2000 mg, 100 mg to 2000 mg, 150 mg to 2000 mg, 200 mg to 2000 mg, 250 mg to 2000 mg, 300 mg to 2000 mg, 350 mg to 2000 mg, 400 mg to 2000 mg, 450 mg to 2000 mg, 500 mg to 2000 mg, 550 mg to 2000 mg, 600 mg to 2000 mg, 650 mg to 2000 mg, 700 mg to 2000 mg, 750 mg to 2000 mg, 800 mg to 2000 mg, 850 mg to 2000 mg, 900 mg to 2000 mg, 950 mg to 2000 mg, or about 1000 mg to 2000 mg may be administered (e.g., subcutaneously or intravenously in an infusion) to a subject once per month. In some embodiments, between about 225 mg and about 1000 mg, e.g., about 225 mg of antibody are administered once per month. An exemplary dosing regimen comprises administering an initial antibody dose of about 675 mg subcutaneously, followed by a monthly antibody dose of about 225 mg subcutaneously for, e.g., about two months, three months, four months, five months, six months, seven months, eight months, nine months, ten months, 11 months, or 12 months, or even a period of greater than one year (e.g., 18 months, two years, or three years). However, other dosage regimens may be useful, depending on the pattern of pharmacokinetic decay that the practitioner wishes to achieve.

In some embodiments, an antibody in a dose or amount of about 50 mg, 100 mg 150 mg, 200 mg, 225 mg, 250 mg, 300 mg, 350 mg, 400 mg, 450 mg, 500 mg, 550 mg, 600 mg, 650 mg, 675 mg, 700 mg, 750 mg, 800 mg, 850 mg, 900 mg, 950 mg, 1000 mg, 1050 mg, 1100 mg, 1150 mg, 1200 mg, 1250 mg, 1300 mg, 1350 mg, 1400 mg, 1450 mg, 1500 mg, 1550 mg, 1600 mg, 1650 mg, 1700 mg, 1750 mg, 1800 mg, 1850 mg, 1900 mg, 1950 mg, 2000 mg, 2050 mg, 2100 mg, 2150 mg, 2200 mg, 2250 mg, 2300 mg, 2350 mg, 2400 mg, 2450 mg, 2500 mg, 2550 mg, 2600 mg, 2650 mg, 2700 mg, 2750 mg, 2800 mg, 2850 mg, 2900 mg, 2950 mg, 3000 mg, or more may be administered (e.g., subcutaneously or intravenously in an infusion) to a subject every three months. In some embodiments, an antibody in a dose or amount of between about 0.1 mg to 5000 mg, 1 mg to 4000 mg, 10 mg to 3000 mg, 10 mg to 2000 mg, 100 mg to 2000 mg, 150 mg to 2000 mg, 200 mg to 2000 mg, 250 mg to 2000 mg, 300 mg to 2000 mg, 350 mg to 2000 mg, 400 mg to 2000 mg, 450 mg to 2000 mg, 500 mg to 2000 mg, 550 mg to 2000 mg, 600 mg to 2000 mg, 650 mg to 2000 mg, 700 mg to 2000 mg, 750 mg to 2000 mg, 800 mg to 2000 mg, 850 mg to 2000 mg, 900 mg to 2000 mg, 950 mg to 2000 mg, or 1000 mg to 2000 mg may be administered (e.g., subcutaneously or intravenously in an infusion) to a subject every three months. In some embodiments, between about 225 mg to about 1000 mg is administered once every three months or less, e.g., about 675 mg is administered subcutaneously about every three months or about 900 mg is administered about every three months intravenously in an infusion. An exemplary dosing regimen comprises administering an initial or starting dose of about 900 mg intravenously in an infusion over about 60 minutes, followed by doses of about 900 mg administered intravenously in an infusion over about 60 minutes every three months for one year, two years, three years, four years, or five years. Another exemplary dosing regimen comprises administering an initial or starting dose of about 675 mg administered subcutaneously, followed by doses of about 675 mg administered subcutaneously every three months for about one year, two years, three years, four years, or five years. However, other dosage regimens may be useful, depending on the pattern of pharmacokinetic decay that the practitioner wishes to achieve.

In some embodiments, an antibody in a dose or amount of about 50 mg, 100 mg 150 mg, 200 mg, 225 mg, 250 mg, 300 mg, 350 mg, 400 mg, 450 mg, 500 mg, 550 mg, 600 mg, 650 mg, 675 mg, 700 mg, 750 mg, 800 mg, 850 mg, 900 mg, 950 mg, 1000 mg, 1050 mg, 1100 mg, 1150 mg, 1200 mg, 1250 mg, 1300 mg, 1350 mg, 1400 mg, 1450 mg, 1500 mg, 1550 mg, 1600 mg, 1650 mg, 1700 mg, 1750 mg, 1800 mg, 1850 mg, 1900 mg, 1950 mg, 2000 mg, 2050 mg, 2100 mg, 2150 mg, 2200 mg, 2250 mg, 2300 mg, 2350 mg, 2400 mg, 2450 mg, 2500 mg, 2550 mg, 2600 mg, 2650 mg, 2700 mg, 2750 mg, 2800 mg, 2850 mg, 2900 mg, 2950 mg, 3000 mg, or more may be administered (e.g., subcutaneously or intravenously in an infusion) to a subject every six months. In some embodiments, an antibody in a dose or amount of between about 0.1 mg to 5000 mg, 1 mg to 4000 mg, 10 mg to 3000 mg, 10 mg to 2000 mg, 100 mg to 2000 mg, 150 mg to 2000 mg, 200 mg to 2000 mg, 250 mg to 2000 mg, 300 mg to 2000 mg, 350 mg to 2000 mg, 400 mg to 2000 mg, 450 mg to 2000 mg, 500 mg to 2000 mg, 550 mg to 2000 mg, 600 mg to 2000 mg, 650 mg to 2000 mg, 700 mg to 2000 mg, 750 mg to 2000 mg, 800 mg to 2000 mg, 850 mg to 2000 mg, 900 mg to 2000 mg, 950 mg to 2000 mg, or 1000 mg to 2000 mg may be administered (e.g., subcutaneously or intravenously in an infusion) to a subject every six months. In some embodiments, between 225 mg to 1000 mg is administered once every six months or less. However, other dosage regimens may be useful, depending on the pattern of pharmacokinetic decay that the practitioner wishes to achieve.

In some embodiments, the frequency at which a dose or amount of an antibody (e.g., monoclonal antibody that modulates the CGRP pathway, anti-CGRP antagonist antibody, monoclonal anti-CGRP antagonist antibody) is administered to a subject (e.g., subcutaneously or intravenously) is, is at least, is less than, or is at most one, two, three, four, five, six, seven, eight, nine, ten, eleven, twelve, thirteen, fourteen, fifteen, sixteen, seventeen, eighteen, nineteen, or twenty time(s) per every quarter. As can be appreciated, a "quarter" can refer to a time period of a quarter year or may also refer to a calendar quarter such as a time period of January 1-March 31, April 1-June 30, July 1-September 30, or October 1-December 31. In some cases, a "quarter" may refer to a time period of approximately three months.

In some embodiments, an antibody in a dose or amount of about 50 mg, 100 mg 150 mg, 200 mg, 225 mg, 250 mg, 300 mg, 350 mg, 400 mg, 450 mg, 500 mg, 550 mg, 600 mg, 650 mg, 675 mg, 700 mg, 750 mg, 800 mg, 850 mg, 900 mg, 950 mg, 1000 mg, 1050 mg, 1100 mg, 1150 mg, 1200 mg, 1250 mg, 1300 mg, 1350 mg, 1400 mg, 1450 mg, 1500 mg, 1550 mg, 1600 mg, 1650 mg, 1700 mg, 1750 mg, 1800 mg, 1850 mg, 1900 mg, 1950 mg, 2000 mg, 2050 mg, 2100 mg, 2150 mg, 2200 mg, 2250 mg, 2300 mg, 2350 mg, 2400 mg, 2450 mg, 2500 mg, 2550 mg, 2600 mg, 2650 mg, 2700 mg, 2750 mg, 2800 mg, 2850 mg, 2900 mg, 2950 mg, 3000 mg, or more may be administered (e.g., subcutaneously or intravenously in an infusion) to a subject every quarter. In some embodiments, an antibody in a dose or amount of between about 0.1 mg to 5000 mg, 1 mg to 4000 mg, 10 mg to 3000 mg, 10 mg to 2000 mg, 100 mg to 2000 mg, 150 mg to 2000 mg, 200 mg to 2000 mg, 250 mg to 2000 mg, 300 mg to 2000 mg, 350 mg to 2000 mg, 400 mg to 2000 mg, 450 mg to 2000 mg, 500 mg to 2000 mg, 550 mg to 2000 mg, 600 mg to 2000 mg, 650 mg to 2000 mg, 700 mg to 2000 mg, 750 mg to 2000 mg, 800 mg to 2000 mg, 850 mg to 2000 mg, 900 mg to 2000 mg, 950 mg to 2000 mg, or 1000 mg to 2000 mg may be administered (e.g., subcutaneously or intravenously in an infusion) to a subject every quarter. An exemplary dosing regimen comprises administering an initial or starting dose of about 900 mg intravenously in an infusion over about 60 minutes, followed by doses of about 900 mg administered intravenously in an infusion over about 60 minutes every quarter for one year, two years, three years, four years, or five years. Another exemplary dosing regimen comprises administering an initial or starting dose of about 675 mg administered subcutaneously, followed by doses of about 675 mg administered subcutaneously every quarter for about one year, two years, three years, four years, or five years. However, other dosage regimens may be useful, depending on the pattern of pharmacokinetic decay that the practitioner wishes to achieve.

In some embodiments, the frequency at which a dose or amount of an antibody (e.g., monoclonal antibody that modulates the CGRP pathway, anti-CGRP antagonist antibody, monoclonal anti-CGRP antagonist antibody) is administered is, is at least, is less than, or is at most about one, two, three, four, five, six, seven, eight, nine, ten, eleven, twelve, thirteen, fourteen, fifteen, sixteen, seventeen, eighteen, nineteen, or twenty time(s) per every year, every two years, every three years, every four years, or every five years. In some embodiments, the frequency at which an antibody (e.g., monoclonal antibody that modulates the CGRP pathway, anti-CGRP antagonist antibody, monoclonal anti-CGRP antagonist antibody) is administered to a subject is less than one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four or twenty-five dose(s) per year.

In some embodiments, an antibody in a dose or amount of about 50 mg, 100 mg 150 mg, 200 mg, 225 mg, 250 mg, 300 mg, 350 mg, 400 mg, 450 mg, 500 mg, 550 mg, 600 mg, 650 mg, 675 mg, 700 mg, 750 mg, 800 mg, 850 mg, 900 mg, 950 mg, 1000 mg, 1050 mg, 1100 mg, 1150 mg, 1200 mg, 1250 mg, 1300 mg, 1350 mg, 1400 mg, 1450 mg, 1500 mg, 1550 mg, 1600 mg, 1650 mg, 1700 mg, 1750 mg, 1800 mg, 1850 mg, 1900 mg, 1950 mg, 2000 mg, 2050 mg, 2100 mg, 2150 mg, 2200 mg, 2250 mg, 2300 mg, 2350 mg, 2400 mg, 2450 mg, 2500 mg, 2550 mg, 2600 mg, 2650 mg, 2700 mg, 2750 mg, 2800 mg, 2850 mg, 2900 mg, 2950 mg, 3000 mg, or more may be administered to a subject once per year. In some embodiments, an antibody in a dose or amount of between about 0.1 mg to 5000 mg, 1 mg to 4000 mg, 10 mg to 3000 mg, 10 mg to 2000 mg, 100 mg to 2000 mg, 150 mg to 2000 mg, 200 mg to 2000 mg, 250 mg to 2000 mg, 300 mg to 2000 mg, 350 mg to 2000 mg, 400 mg to 2000 mg, 450 mg to 2000 mg, 500 mg to 2000 mg, 550 mg to 2000 mg, 600 mg to 2000 mg, 650 mg to 2000 mg, 700 mg to 2000 mg, 750 mg to 2000 mg, 800 mg to 2000 mg, 850 mg to 2000 mg, 900 mg to 2000 mg, 950 mg to 2000 mg, or 1000 mg to 2000 mg may be administered to a subject every once per year. In some embodiments, between about 450 mg and about 2000 mg is administered once every year or less.

In some embodiments, a method may comprise administering an antibody (e.g., monoclonal antibody that modulates the CGRP pathway, anti-CGRP antagonist antibody, monoclonal anti-CGRP antagonist antibody) described herein to a subject on a plurality of days. Two, three, four, five, six, seven, eight or more days of the plurality of days may be more than 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75 or more days apart. In some embodiments, two of the plurality of days are more than one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty or more days apart. Moreover, in some embodiments, the amount of antibody administered on a first day of the plurality of days may be different (e.g., higher or lower) than the amount of the antibody administered on a second day.

In some embodiments, an initial dose (which can also be referred to as a loading dose or a starting dose) of an antibody (e.g., monoclonal antibody that modulates the CGRP pathway, anti-CGRP antagonist antibody, monoclonal anti-CGRP antagonist antibody) described herein may be administered to a subject, followed by administration of one or more additional doses at desired intervals. In some embodiments, the initial dose (or starting dose) and one or more of the additional doses are the same dose. In some embodiments, the one or more additional doses are a different dose than the initial or starting dose. In some embodiments, the initial dose and one or more of the additional doses are administered the same way, i.e., subcutaneously or intravenously. In some embodiments, the one or more additional doses are administered in a different way than the initial dose, e.g., the initial dose may be administered intravenously and the one or more additional doses may be administered subcutaneously. In some embodiments, the frequency at which the one or more additional doses are administered is constant (e.g., every month or every three months). In some embodiments, the frequency at which the one or more additional doses are administered is variable (e.g., one additional dose administered at one month following the initial dose, followed by another additional dose at three months following the initial dose). Any desirable and/or therapeutic regimen of initial loading dose, additional doses, and frequency (e.g., including those described herein) of additional doses may be used. An exemplary regimen includes an initial loading dose of about 225 mg anti CGRP antagonist antibody administered subcutaneously, followed by subsequent maintenance doses of about 225 mg of the antibody administered subcutaneously at one month intervals. An exemplary regimen includes an initial loading dose of about 675 mg anti-CGRP antagonist antibody administered subcutaneously, followed by subsequent maintenance doses of about 225 mg of the antibody administered subcutaneously at one month intervals. Yet another exemplary regimen includes an initial dose of about 900 mg anti-CGRP antagonist antibody administered intravenously in an infusion over about 60 minutes, followed by subsequent maintenance doses of about 900 mg anti-CGRP antagonist antibody administered intravenously in an infusion over about 60 minutes at three month intervals. Another exemplary regimen comprises an initial or starting dose of about 675 mg anti-CGRP antagonist antibody administered subcutaneously, followed by subsequent maintenance doses of about 675 mg anti CGRP antagonist antibody administered subcutaneously at three month intervals.

In some embodiments, an initial dose (or starting dose) of an antibody (e.g., monoclonal antibody that modulates the CGRP pathway, anti-CGRP antagonist antibody, monoclonal anti-CGRP antagonist antibody) of about 0.1 µg, 1 µg, 100 µg, 1 mg, 10 mg, 25 mg, 50 mg, 75 mg, 100 mg, 125 mg, 150 mg, 175 mg, 200 mg, 225 mg, 250 mg, 275 mg, 300 mg, 325 mg, 350 mg, 375 mg, 400 mg, 450 mg, 475 mg, 500 mg, 525 mg, 550 mg, 575 mg, 600 mg, 625 mg, 650 mg, 675 mg, 700 mg, 725 mg, 750 mg, 775 mg, 800 mg, 825 mg, 850 mg, 875 mg, 900 mg, 925 mg, 950 mg, 975 mg, 1000 mg, 1500 mg, 2000 mg, or about 3000 mg may be administered to a subject followed by one or more additional doses of the antibody of about 0.1 µg. 1 µg, 100 µg, 1 mg, 10 mg, 25 mg, 50 mg, 75 mg, 100 mg, 125 mg, 150 mg, 175 mg, 200 mg, 225 mg, 250 mg, 275 mg, 300 mg, 325 mg, 350 mg, 375 mg, 400 mg, 450 mg, 475 mg, 500 mg, 525 mg, 550 mg, 575 mg, 600 mg, 625 mg, 650 mg, 675 mg, 700 mg, 725 mg, 750 mg, 775 mg, 800 mg, 825 mg, 850 mg, 875 mg, 900 mg, 925 mg, 950 mg, 975 mg, 1000 mg, 1500 mg, 2000 mg, or about 3000 mg. An exemplary regimen includes an initial loading dose of about 225 mg anti CGRP antagonist antibody administered subcutaneously, followed by subsequent maintenance doses of about 225 mg of the antibody administered subcutaneously at one month intervals. An exemplary regimen includes an initial loading dose of about 675 mg anti-CGRP antagonist antibody administered subcutaneously, followed by subsequent maintenance doses of about 225 mg of the antibody administered subcutaneously at one month intervals. Yet another exemplary regimen includes an initial dose of about 900 mg anti-CGRP antagonist antibody administered intravenously in an infusion over about 60 minutes, followed by subsequent maintenance doses of about 900 mg anti-CGRP antagonist antibody administered intravenously in an infusion over about 60 minutes at three month intervals. Another exemplary regimen comprises an initial or starting dose of about 675 mg anti-CGRP antagonist antibody administered subcutaneously, followed by subsequent maintenance doses of about 675 mg anti-CGRP antagonist antibody administered subcutaneously at three month intervals.

In some embodiments, a dose or amount of antibody (e.g., monoclonal antibody that modulates the CGRP pathway, anti-CGRP antagonist antibody, monoclonal anti-CGRP antagonist antibody) described herein may be divided into sub-doses and administered as multiple sub-doses, depending, for example, on the route of administration and/or particular formulation administered. For example, in cases where a dose is administered subcutaneously, the subcutaneous dose may be divided into multiple sub-doses and each sub-dose administered at a different site in order to avoid, for example, a larger, single subcutaneous injection at a single site. For example, an intravenous dose of 900 mg may be divided into four sub-doses of 225 mg each. As another example, a subcutaneous dose of 675 mg may be divided into three sub-doses of 225 mg each and each 225 mg dose may be administered at a different site, which can help minimize the volume injected at each site. The division of sub-doses may be equal (e.g., three equal sub-doses) or may be unequal (e.g., three sub-doses, two of the sub-doses twice as large as the other sub-doses).

In some embodiments, the number of doses of antibody administered to a subject over the course of treatment may vary depending upon, for example, achieving reduced incidence of a refractory migraine and/or secondary symptom associated with a refractory migraine in the subject. For example, the number of doses administered over the course of treatment may be, may be at least, or may be at most 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or treatment may be given indefinitely. In some cases, treatment may be acute such that at most 1, 2, 3, 4, 5, or 6 doses are administered to a subject for treatment.

In some embodiments, a dose (or sub-dose) or amount of an antibody (e.g., monoclonal antibody that modulates the CGRP pathway, anti-CGRP antagonist antibody, monoclonal anti-CGRP antagonist antibody) described herein may be formulated in a liquid formulation and administered (e.g., via subcutaneous injection, via intravenous injection) to a subject. In such cases, the volume of liquid formulation comprising antibody may vary depending upon, for example, the concentration of antibody in the liquid formulation, the desired dose of antibody, and/or the route of administration used. For example, the volume of liquid formulation comprising an antibody described herein and administered (e.g., via an injection, such as, for example, a subcutaneous injection or an intravenous infusion) to a subject may be from about 0.001 mL to about 10.0 mL, about 0.01 mL to about 5.0 mL, about 0.1 mL to about 5 mL, about 0.1 mL to about 3 mL, about 0.5 mL to about 2.5 mL, or about 1 mL to about 2.5 mL. For example, the volume of liquid formulation comprising an antibody (e.g., monoclonal antibody that modulates the CGRP pathway, anti-CGRP antagonist antibody, monoclonal anti-CGRP antagonist antibody) described herein and administered (e.g., via an injection, such as, for example, a subcutaneous injection, or an intravenous infusion) to a subject may be, may be at least, may be less than, or may be at most about 0.001, 0.005, 0.01, 0.02, 0.03, 0.04, 0.05, 0.06, 0.07, 0.08, 0.09, 0.10, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.5, 6.0, 6.5, 7.0, 7.5, 8.0, 8.5, 9.0, 9.5, or about 10.0 mL.

In some embodiments, a dose (or sub-dose) or amount of an antibody (e.g., monoclonal antibody that modulates the CGRP pathway, anti-CGRP antagonist antibody, monoclonal anti-CGRP antagonist antibody) described herein may be supplied in prefilled receptacles useful in administering antibody to a subject. Such prefilled receptacles may be designed for self-administration or for administration by another. For example, a dose (or sub-dose) or amount of antibody described herein may be supplied as a liquid formulation in pre-filled syringes, pre-filled syringes with a needle safety device, injection pens, or auto-injectors. In such examples, the pre-filled syringes may be designed for self-administration or for administration by another. In some cases, the pre-filled syringes or auto-injectors may be designed for subcutaneous administration and/or intravenous administration.

For the purpose of the present invention, the appropriate dosage of an antibody may depend on the antibody (or compositions thereof) employed, the type and severity of the secondary symptom, the type and severity of the refractory migraine or other condition to be treated, whether the agent is administered for preventive or therapeutic purposes, previous therapy, the patient's clinical history and response to the agent, and the discretion of the attending physician. Typically, the clinician will administer an antibody, until a dosage is reached that achieves the desired result. Dose and/or frequency can vary over course of treatment.

Empirical considerations, such as the half-life, generally will contribute to the determination of the dosage. For example, antibodies that are compatible with the human immune system, such as humanized antibodies or fully human antibodies, may be used to prolong half-life of the antibody and to prevent the antibody being attacked by the host's immune system. Frequency of administration may be determined and adjusted over the course of therapy, and is generally, but not necessarily, based on treatment and/or suppression and/or amelioration and/or delay of refractory migraine or other condition. Alternatively, sustained continuous release formulations of antibodies may be appropriate. Various formulations and devices for achieving sustained release are known in the art.

In one embodiment, dosages for an antibody (e.g., monoclonal antibody that modulates the CGRP pathway, anti-CGRP antagonist antibody, monoclonal anti-CGRP antagonist antibody) described herein may be determined empirically in individuals who have been given one or more administration(s) of the antibody. Individuals are given incremental dosages of an antibody. To assess efficacy of an antibody, an indicator of the disease can be followed.

Administration of an antibody (e.g., monoclonal antibody that modulates the CGRP pathway, anti-CGRP antagonist antibody, monoclonal anti-CGRP antagonist antibody) in accordance with the methods of the present invention can be continuous or intermittent, depending, for example, upon the recipient's physiological condition, whether the purpose of the administration is therapeutic or prophylactic, and other factors known to skilled practitioners. The administration of an antibody may be essentially continuous over a preselected period of time or may be in a series of spaced dose, e.g., either before, during, or after developing refractory migraine; before; during; before and after; during and after; before and during; or before, during, and after developing refractory migraine. Administration can be before, during and/or after any event likely to give rise to refractory migraine.

In some embodiments, more than one antibody may be present. At least one, at least two, at least three, at least four, at least five different, or more antibodies can be present. Generally, those antibodies may have complementary activities that do not adversely affect each other. An antibody (e.g., monoclonal antibody that modulates the CGRP pathway, anti-CGRP antagonist antibody, monoclonal anti-CGRP antagonist antibody) described herein can also be used in conjunction with other CGRP antagonists or CGRP receptor antagonists. For example, one or more of the following CGRP antagonists may be used: an anti-sense molecule directed to a CGRP (including an anti-sense molecule directed to a nucleic acid encoding CGRP), a CGRP inhibitory compound, a CGRP structural analog, a dominant-negative mutation of a CGRP receptor that binds a CGRP, and an anti-CGRP receptor antibody. An antibody can also be used in conjunction with other agents that serve to enhance and/or complement the effectiveness of the agents.

Diagnosis or assessment of refractory migraine is well-established in the art. Assessment may be performed based on subjective measures, such as patient characterization of symptoms and medical history documenting inadequate response to prior preventative treatments. In some embodiments, assessment of refractory migraine may be via headache hours, as described elsewhere herein. For example, assessment of refractory migraine may be in terms of daily headache hours, weekly headache hours, monthly headache hours and/or yearly headache hours. In some cases, headache hours may be as reported by the subject.

Treatment efficacy can be assessed by methods well-known in the art. For example, pain relief may be assessed. Accordingly, in some embodiments, pain relief is subjectively observed after 1, 2, or a few hours after administering an anti-CGRP antibody. In some embodiments, frequency of refractory migraine attacks is subjectively observed after administering an anti-CGRP antibody.

In some embodiments, a method for preventing, treating, or reducing incidence of migraine in a subject having refractory migraine as described herein may reduce incidence of migraine after a single administration of an antibody (e.g., monoclonal antibody that modulates the CGRP pathway, anti-CGRP antagonist antibody, monoclonal anti-CGRP antagonist antibody) described herein for an extended period of time. For example, incidence of migraine may be reduced for at least 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more days after a single administration.

In some embodiments, a method for treating or reducing incidence of migraine in a subject as described herein (i.e., having refractory migraine) may reduce the number of headache hours experienced by a subject from a pre-administration level after administration of one or more doses of an antibody (e.g., monoclonal antibody that modulates the CGRP pathway, anti-CGRP antagonist antibody, monoclonal anti-CGRP antagonist antibody) described herein to the subject. For example, daily headache hours experienced by the subject after administering one or more doses of an antibody to the subject may be reduced by 0.5, 1, 2, 3, 4, 5, 6, 7, 8, 9, 10, 11, 12, 13, 14, 15, 16, 17, 18, 19, 20, 21, 22, 23, or 24 headache hours from a pre-administration level in the subject. In some cases, daily headache hours experienced by the subject after administering one or more doses of an antibody to the subject may be reduced by 0.5%, 1%, 5%, 10%, 15%, 20%, 25%, 30%, 35%, 40%, 45%, 50%, 55%, 60%, 65%, 70%, 75%, 80%, 85%, 90%, 95%, 99%, or more relative to a pre-administration level in the subject. In another example, weekly headache hours experienced by the subject after administering one or more doses of an antibody to the subject may be reduced by 0.5, 1, 5, 10, 15, 20, 25, 30, 35, 40, 45, 50, 55, 60, 65, 70, 75 or more headache hours from a pre-administration level in the subject. In some cases, weekly headache hours experienced by the subject after administering one or more doses of an antibody to the subject may be reduced by 0.5%, 1%, 5%, 10%, 15%, 20%, 25%, 30%, 35%, 40%, 45%, 50%, 55%, 60%, 65%, 70%, 75%, 80%, 85%, 90%, 95%, 99%, or more relative to a pre-administration level in the subject. In another example, monthly headache hours experienced by the subject after administering one or more doses of an antibody to the subject may be reduced by 0.5, 1, 5, 10, 15, 20, 25, 30, 35, 40, 45, 50, 55, 60, 65, 70, 75, 80, 85, 90, 95, 100, 105, 110, 115, 120, 125, or more headache hours from a pre-administration level. In some cases, monthly headache hours experienced by the subject after administering one or more doses of an antibody to the subject may be reduced by 0.5%, 1%, 5%, 10%, 15%, 20%, 25%, 30%, 35%, 40%, 45%, 50%, 55%, 60%, 65%, 70%, 75%, 80%, 85%, 90%, 95%, 99% or more relative to a pre-administration level in the subject.

In some embodiments, a method for treating or reducing incidence of migraine in a subject having refractory migraine as described herein may reduce the number of headache days experienced by a subject from a pre-administration level after administration of one or more doses of an antibody (e.g., monoclonal antibody that modulates the CGRP pathway, anti-CGRP antagonist antibody, monoclonal anti-CGRP antagonist antibody) described herein to the subject. For example, weekly headache days experienced by the subject after administering one or more doses of an antibody to the subject may be reduced by 0.5, 1, 1.5, 2, 2.5, 3, 3.5, 4, 4.5, 5, 5.5, 6, 6.5, or 7 headache days from a pre-administration level in the subject. In some cases, weekly headache days experienced by the subject after administering one or more doses of an antibody to the subject may be reduced by 0.5%, 1%, 5%, 10%, 15%, 20%, 25%, 30%, 35%, 40%, 45%, 50%, 55%, 60%, 65%, 70%, 75%, 80%, 85%, 90%, 95%, 99% or more relative to a pre-administration level in the subject. In another example, monthly headache days experienced by the subject after administering one or more doses of an antibody to the subject may be reduced by 0.5, 1, 2, 3, 4, 5, 6, 7, 8, 9, 10, 15, 20 or more headache days from a pre-administration level.

In some embodiments, a method may comprise administering to a subject one or more additional agent(s) simultaneously or sequentially with an antibody (e.g., monoclonal antibody that modulates the CGRP pathway, anti-CGRP antagonist antibody, monoclonal anti-CGRP antagonist antibody). In some embodiments, an additional agent may be an acute headache medication such as 5-HT1 agonists, triptans, ergot alkaloids, opiates, and NSAIDs) described elsewhere herein. In some embodiments, a therapeutic effect may be greater as compared to use of an antibody or one or more additional agent(s) alone. Accordingly, a synergistic effect between an antibody and the one or more additional agents may be achieved.

B. Anti-CGRP Antagonist Antibodies

In some embodiments, the methods of the invention use an antibody, which can be an anti-CGRP antagonist antibody. An anti-CGRP antagonist antibody can refer to any antibody molecule that blocks, suppresses or reduces (including significantly) CGRP biological activity, including downstream pathways mediated by CGRP signaling, such as receptor binding and/or elicitation of a cellular response to CGRP.

An anti-CGRP antagonist antibody can exhibit any one or more of the following characteristics: (a) bind to CGRP; (b) block CGRP from binding to its receptor(s); (c) block or decrease CGRP receptor activation (including, but not limited to, cAMP activation); (d) inhibit CGRP biological activity or downstream pathways mediated by CGRP signaling function; (e) prevent, ameliorate, or treat any aspect of refractory migraine; (f) increase clearance of CGRP; and (g) inhibit (reduce) CGRP synthesis, production or release. Anti-CGRP antagonist antibodies are known in the art. See e.g., Tan et al., Clin. Sci. (Lond). 89:565-73, 1995; Sigma (Missouri, US), product number C7113 (clone #4901); Plourde et al., Peptides 14:1225-1229, 1993.

In some embodiments, the antibody reacts with CGRP in a manner that inhibits CGRP, and/or the CGRP pathway, including downstream pathways mediated by the CGRP signaling function. In some embodiments, the anti-CGRP antagonist antibody recognizes human CGRP. In some embodiments, the anti-CGRP antagonist antibody binds to both human $\alpha$-CGRP and $\beta$-CGRP. In some embodiments, the anti-CGRP antagonist antibody binds human and rat CGRP. In some embodiments, the anti-CGRP antagonist antibody binds the C-terminal fragment having amino acids 25-37 of CGRP. In some embodiments, the anti-CGRP antagonist antibody binds a C-terminal epitope within amino acids 25-37 of CGRP.

The antibodies useful in the present invention can encompass monoclonal antibodies, polyclonal antibodies, antibody fragments (e.g., Fab, Fab', F(ab')2, Fv, Fc, etc.), chimeric antibodies, bispecific antibodies, heteroconjugate antibodies, single chain (ScFv), mutants thereof, fusion proteins comprising an antibody portion (e.g., a domain antibody), humanized antibodies, and any other modified configuration of the immunoglobulin molecule that comprises an antigen recognition site of the required specificity, including glycosylation variants of antibodies, amino acid sequence variants of antibodies, and covalently modified antibodies. The antibodies may be murine, rat, human, or any other origin (including chimeric or humanized antibodies).

In some embodiments, the anti-CGRP antagonist antibody is a monoclonal antibody. In some embodiments, the anti-CGRP antagonist antibody is humanized. In some embodiments, the antibody is human. In some embodiments, the anti-CGRP antagonist antibody is antibody G1 (as described herein). In some embodiments, the anti-CGRP antagonist antibody comprises one or more CDR(s) (such as one, two, three, four, five, or, in some embodiments, all six CDRs) of antibody G1 or variants of G1 shown in Table 6. In still other embodiments, the anti-CGRP antagonist antibody comprises the amino acid sequence of the heavy chain variable region shown in FIG. 5 (SEQ ID NO:1) and the amino acid sequence of the light chain variable region shown in FIG. 5 (SEQ ID NO:2). In still other embodiments, the anti-CGRP antagonist antibody comprises a heavy chain full antibody amino acid sequence shown in SEQ ID NO: 11 and a light chain full antibody amino acid sequence shown in SEQ ID NO: 12.

In some embodiments, the antibody comprises a light chain variable region (LCVR) and a heavy chain variable region (HCVR) selected from the groups consisting of: (a) LCVR17 (SEQ ID NO:58) and HCVR22 (SEQ ID NO:59); (b) LCVR18 (SEQ ID NO:60) and HCVR23 (SEQ ID NO:61); (c) LCVR19 (SEQ ID NO:62) and HCVR24 (SEQ ID NO:63); (d) LCVR20 (SEQ ID NO:64) and HCVR25 (SEQ ID NO:65); (e) LCVR21 (SEQ ID NO:66) and HCVR26 (SEQ ID NO:67); (f) LCVR27 (SEQ ID NO:68) and HCVR28 (SEQ ID NO:69); (g) LCVR29 (SEQ ID NO:70) and HCVR30 (SEQ ID NO:71); (h) LCVR31 (SEQ ID NO:72) and HCVR32 (SEQ ID NO:73); (i) LCVR33 (SEQ ID NO:74) and HCVR34 (SEQ ID NO:75); (j) LCVR35 (SEQ ID NO:76) and HCVR36 (SEQ ID NO:77); and (k) LCVR37 (SEQ ID NO:78) and HCVR38 (SEQ ID NO:79). Sequences of these regions are provided herein. Other examples of anti-CGRP antibodies are described in US20110305711 (SEQ ID NOs:5, 6, 7, 12, 16, 19, 24, 29, 34, and 39), US20120294802, US20120294797 (SEQ ID NOs:51-60), which are hereby incorporated by reference in their entireties. For example, antibodies with any of the following sequences may be used.

```
Ab6 Variable region Light chain (humanized)
protein sequence (US20120294797)
                                        (SEQ ID NO: 80)
QVLTQSPSSLSASVGDRVTINCQASQSVYHNTYLAWYQQKPGKVPKQLI

YDASTLASGVPSRFSGSGSGTDFTLTISSLQPEDVATYYCLGSYDCTNG

DCFVFGGGTKVEIKR

Ab6 Light chain (humanized) Full length protein
sequence (US20120294797)
                                        (SEQ ID NO: 81)
QVLTQSPSSLSASVGDRVTINCQASQSVYHNTYLAWYQQKPGKVPKQLI

YDASTLASGVPSRFSGSGSGTDFTLTISSLQPEDVATYYCLGSYDCTNG

DCFVFGGGTKVEIKRTVAAPSVFIFPPSDEQLKSGTASVVCLLNNFYPR

EAKVQWKVDNALQSGNSQESVTEQDSKDSTYSLSSTLTLSKADYEKHKV

YACEVTHQGLSSPVTKSFNRGEC

Ab6 Variable region heavy chain (humanized)
protein sequence (US20120294797)
                                        (SEQ ID NO: 82)
EVQLVESGGGLVQPGGSLRLSCAVSGIDLSGYYMNWVRQAPGKGLEWVG

VIGINGATYYASWAKGRFTISRDNSKTTVYLQMNSLRAEDTAVYFCARG

DIWGQGTLVTVSS

Ab6 Heavy chain (humanized) Full length protein
sequence-yeast produced (US20120294797)
                                        (SEQ ID NO: 83)
EVQLVESGGGLVQPGGSLRLSCAVSGIDLSGYYMNWVRQAPGKGLEWVG

VIGINGATYYASWAKGRFTISRDNSKTTVYLQMNSLRAEDTAVYFCARG

DIWGQGTLVTVSSASTKGPSVFPLAPSSKSTSGGTAALGCLVKDYFPEP

VTVSWNSGALTSGVHTFPAVLQSSGLYSLSSVVTVPSSSLGTQTYICNV

NHKPSNTKVDARVEPKSCDKTHTCPPCPAPELLGGPSVFLFPPKPKDTL

MISRTPEVTCVVVDVSHEDPEVKFNWYVDGVEVHNAKTKPREEQYASTY

RVVSVLTVLHQDWLNGKEYKCKVSNKALPAPIEKTISKAKGQPREPQVY

TLPPSREEMTKNQVSLTCLVKGFYPSDIAVEWESNGQPENNYKTTPPVL

DSDGSFFLYSKLTVDKSRWQQGNVFSCSVMHEALHNHYTQKSLSLSPGK

Ab6 Variable region Light chain (humanized)
protein sequence CDRI (US20120294797)
                                        (SEQ ID NO: 84)
QASQSVYHNTYLA Ab6 Variable region Light chain (humanized)
protein sequence CDR2 (US20120294797)
                                        (SEQ ID NO: 85)
DASTLAS Ab6 Variable region Light chain (humanized)
protein sequence CDR3 (US20120294797)
                                        (SEQ ID NO: 86)
LGSYDCTNGDCFV Ab6 Variable region heavy chain (humanized)
protein sequence CDRI (US20120294797)
                                        (SEQ ID NO: 87)
GYYMN Ab6 Variable region heavy chain (humanized)
protein sequence CDR2 (US20120294797)
                                        (SEQ ID NO: 88)
IGINGATYYASWAKG Ab6 Variable region heavy chain (humanized)
protein sequence CDR3 (US20120294797)
                                        (SEQ ID NO: 89)
GDI Light chain variable region protein sequence CDR3
(US20110305711)
                                        (SEQ ID NO: 90)
QQGDALPPT Light chain variable region protein sequence CDR1
(US20110305711)
                                        (SEQ ID NO: 91)
RASKDISKYL Light chain variable region protein sequence CDR2
(US20110305711)
                                        (SEQ ID NO: 92)
YTSGYSH Heavy chain variable region protein sequence CDR1
(US20110305711)
                                        (SEQ ID NO: 93)
GYTFGNYWMQ Heavy chain variable region protein sequence CDR2
(US20110305711)
                                        (SEQ ID NO: 94)
AIYEGTGKTVYIQKFAD Heavy chain variable region protein sequence CDR3
(US20110305711)
                                        (SEQ ID NO: 95)
LSDYVSGFGY
```

-continued

Light chain variable region protein sequence
(US20110305711)
(SEQ ID NO: 96)
DIQMTQSPSSLSASVGDRVTITCRASKDISKYLNWYQQKPGKAPKLLIY

YTSGYHSGVPSRFSGSGSGTDFTLTISSLQPEDFATYYCQQGDALPPTF

GGGTKVEIK

Heavy chain variable region protein sequence
(US20110305711)
(SEQ ID NO: 97)
QVQLVQSGAEVKKPGSSVKVSCKASGYTFGNYWMQWVRQAPGQGLEWMG

AIYEGTGKTVYIQKFADRVTITADKSTSTAYMELSSLRSEDTAVYYCAR

LSDYVSGFGYWGQGTTVTVSS

Light chain protein sequence (US20110305711)
(SEQ ID NO: 98)
DIQMTQSPSSLSASVGDRVTITCRASKDISKYLNWYQQKPGKAPKLLIY

YTSGYHSGVPSRFSGSGSGTDFTLTISSLQPEDFATYYCQQGDALPPTF

GGGTKVEIKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC

Heavy chain protein sequence (US20110305711)
(SEQ ID NO: 99)
QVQLVQSGAEVKKPGSSVKVSCKASGYTFGNYWMQWVRQAPGQGLEWMG

AIYEGTGKTVYIQKFADRVTITADKSTSTAYMELSSLRSEDTAVYYCAR

LSDYVSGFGYWGQGTTVTVSSASTKGPSVFPLAPCSRSTSESTAALGCL

VKDYFPEPVTVSWNSGALTSGVHTFPAVLQSSGLYSLSSVVTVPSSSLG

TKTYTCNVDHKPSNTKVDKRVESKYGPPCPPCPAPEAAGGPSVFLFPPK

PKDTLMISRTPEVTCVVVDVSQEDPEVQFNWYVDGVEVHNAKTKPREEQ

FNSTYRVVSVLTVLHQDWLNGKEYKCKVSNKGLPSSIEKTISKAKGQPR

EPQVYTLPPSQEEMTKNQVSLTCLVKGFYPSDIAVEWESNGQPENNYKT

TPPVLDSDGSFFLYSRLTVDKSRWQEGNVFSCSVMHEALHNHYTQKSLS

LSLG

In some embodiments, the antibody comprises a modified constant region, such as a constant region that is immunologically inert described herein. In some embodiments, the constant region is modified as described in Eur. J. Immunol. (1999) 29:2613-2624; PCT Application No. PCT/GB99/01441; and/or UK Patent Application No. 9809951.8. In other embodiments, the antibody comprises a human heavy chain IgG2 constant region comprising the following mutations: A330P331 to S330S331 (amino acid numbering with reference to the wildtype IgG2 sequence). Eur. J. Immunol. (1999) 29:2613-2624. In some embodiments, the antibody comprises a constant region of IgG4 comprising the following mutations: E233F234L235 to P233V234A235. In still other embodiments, the constant region is aglycosylated for N-linked glycosylation. In some embodiments, the constant region is aglycosylated for N-linked glycosylation by mutating the oligosaccharide attachment residue (such as Asn297) and/or flanking residues that are part of the N-glycosylation recognition sequence in the constant region. In some embodiments, the constant region is aglycosylated for N-linked glycosylation. The constant region may be aglycosylated for N-linked glycosylation enzymatically or by expression in a glycosylation deficient host cell.

The binding affinity ($K_D$) of an anti-CGRP antagonist antibody to CGRP (such as human α-CGRP) can be about 0.02 to about 200 nM. In some embodiments, the binding affinity is any of about 200 nM, about 100 nM, about 50 nM, about 10 nM, about 1 nM, about 500 pM, about 100 pM, about 60 pM, about 50 pM, about 20 pM, about 15 pM, about 10 pM, about 5 pM, or about 2 pM. In some embodiments, the binding affinity is less than any of about 250 nM, about 200 nM, about 100 nM, about 50 nM, about 10 nM, about 1 nM, about 500 pM, about 100 pM, or about 50 pM.

One way of determining binding affinity of antibodies to CGRP is by measuring binding affinity of monofunctional Fab fragments of the antibody. To obtain monofunctional Fab fragments, an antibody (for example, IgG) can be cleaved with papain or expressed recombinantly. The affinity of an anti-CGRP Fab fragment of an antibody can be determined by surface plasmon resonance (Biacore3000™ surface plasmon resonance (SPR) system, Biacore, INC, Piscataway NJ) equipped with pre-immobilized streptavidin sensor chips (SA) using HBS-EP running buffer (0.01M HEPES, pH 7.4, 0.15 NaCl, 3 mM EDTA, 0.005% v/v Surfactant P20). Biotinylated human CGRP (or any other CGRP) can be diluted into HBS-EP buffer to a concentration of less than 0.5 µg/mL and injected across the individual chip channels using variable contact times, to achieve two ranges of antigen density, either 50-200 response units (RU) for detailed kinetic studies or 800-1,000 RU for screening assays. Regeneration studies have shown that 25 mM NaOH in 25% v/v ethanol effectively removes the bound Fab while keeping the activity of CGRP on the chip for over 200 injections. Typically, serial dilutions (spanning concentrations of 0.1-10× estimated $K_D$) of purified Fab samples are injected for 1 min at 100 µL/minute and dissociation times of up to 2 hours are allowed. The concentrations of the Fab proteins are determined by ELISA and/or SDS-PAGE electrophoresis using a Fab of known concentration (as determined by amino acid analysis) as a standard. Kinetic association rates ($k_{on}$) and dissociation rates ($k_{off}$) are obtained simultaneously by fitting the data globally to a 1:1 Langmuir binding model (Karlsson, R. Roos, H. Fagerstam, L. Petersson, B. (1994). Methods Enzymology 6. 99-110) using the BIAevaluation program. Equilibrium dissociation constant ($K_D$) values are calculated as $k_{off}/k_{on}$. This protocol is suitable for use in determining binding affinity of an antibody to any CGRP, including human CGRP, CGRP of another mammalian (such as mouse CGRP, rat CGRP, primate CGRP), as well as different forms of CGRP (such as α and β form). Binding affinity of an antibody is generally measured at 25° C., but can also be measured at 37° C.

Antibodies, including anti-CGRP antagonist antibodies, may be made by any method known in the art. The route and schedule of immunization of the host animal are generally in keeping with established and conventional techniques for antibody stimulation and production, as further described herein. General techniques for production of human and mouse antibodies are known in the art and are described herein.

It is contemplated that any mammalian subject including humans or antibody producing cells therefrom can be manipulated to serve as the basis for production of mammalian, including human, hybridoma cell lines. Typically, the host animal is inoculated intraperitoneally, intramuscularly, orally, subcutaneously, intraplantar, and/or intradermally with an amount of immunogen, including as described herein.

Antibodies (e.g., anti-CGRP antagonist antibodies) and polypeptides derived from antibodies can be identified or characterized using methods known in the art, whereby reduction, amelioration, or neutralization of a CGRP biological activity is detected and/or measured. For example, anti-CGRP antagonist antibody can also be identified by incubating a candidate agent with CGRP and monitoring any one or more of the following characteristics: (a) bind to CGRP; (b) block CGRP from binding to its receptor(s); (c) block or decrease CGRP receptor activation (including CAMP activation); (d) inhibit CGRP biological activity or downstream pathways mediated by CGRP signaling function; (e) prevent, ameliorate, or treat any aspect of refractory migraine; (f) increase clearance of CGRP; and (g) inhibit (reduce) CGRP synthesis, production or release. In some embodiments, an anti-CGRP antagonist antibody or polypeptide is identified by incubating a candidate agent with CGRP and monitoring binding and/or attendant reduction or neutralization of a biological activity of CGRP. The binding assay may be performed with purified CGRP polypeptide(s), or with cells naturally expressing, or transfected to express, CGRP polypeptide(s). In one embodiment, the binding assay is a competitive binding assay, where the ability of a candidate antibody to compete with a known anti-CGRP antagonist for CGRP binding is evaluated. The assay may be performed in various formats, including the ELISA format. In other embodiments, an anti-CGRP antagonist antibody is identified by incubating a candidate agent with CGRP and monitoring binding and attendant inhibition of CGRP receptor activation expressed on the surface of a cell. In some embodiments, an anti-CGRP receptor antibody can be used in any of the methods described herein. For example, anti-CGRP receptor antibodies, as described in US20100172895 and U.S. Pat. No. 9,102,731, which are hereby incorporated by reference in their entireties, may be used. Therefore, antibodies with any of the following sequences may be used.

```
Light chain variable region protein sequence CDR1
(U.S. Pat. No. 9,102,731)
                                      (SEQ ID NO: 100)
SGSSSNIGNNYVS Light chain variable region protein sequence CDR2
(U.S. Pat. No. 9,102,731)
                                      (SEQ ID NO: 101)
DNNKRPS Light chain variable region protein sequence CDR3
(U.S. Pat. No. 9,102,731)
                                      (SEQ ID NO: 102)
GTWDSRLSAVV Heavy chain variable region protein sequence CDR1
(U.S. Pat. No. 9,102,731)
                                      (SEQ ID NO: 103)
SFGMH Heavy chain variable region protein sequence CDR2
(U.S. Pat. No. 9,102,731)
                                      (SEQ ID NO: 104)
VISFDGSIKYSVDSVKG Heavy chain variable region protein sequence CDR3
(U.S. Pat. No. 9,102,731)
                                      (SEQ ID NO: 105)
DRLNYYDSSGYYHYKYYGMAV Light chain variable region protein sequence
(U.S. Pat. No. 9,102,731)
                                      (SEQ ID NO: 106)
QSVLTQPPSVSAAPGQKVTISCSGSSSNIGNNYVSWYQQLPGTAPKWYD

NNKRPSGIPDRFSGSKSGTSTTLGITGLQTGDEADYYCGTWDSRLSAVV
FGGGTKLTVL
```

```
-continued

Heavy chain variable region protein sequence
(U.S. Pat. No. 9,102,731)
                                      (SEQ ID NO: 107)
QVQLVESGGGVVQPGRSLRLSCAASGFTFSSFGMHWVRQAPGKGLEWVA

VISFDGSIKYSVDSVKGRFTISRDNSKNTLFLQMNSLRAEDTAVYYCAR

DRLNYYDSSGYYHYKYYGMAVWGQGTTVTVSS

Light chain protein sequence
(U.S. Pat. No. 9,102,731)
                                      (SEQ ID NO: 108)
MDMRVPAQLLGLLLLWLRGARCQSVLTQPPSVSAAPGQKVTISCSGSSS

NIGNNYVSWYQQLPGTAPKWYDNNKRPSGIPDRFSGSKSGTSTTLGITG

LQTGDEADYYCGTWDSRLSAVVFGGGTKLTVLGQPKANPTVTLFPPSSE

ELQANKATLVCLISDFYPGAVTVAWKADGSPVKAGVETTKPSKQSNNKY

AASSYLSLTPEQWKSHRSYSCQVTHEGSTVEKTVAPTECS

Heavy chain protein sequence
(U.S. Pat. No. 9,102,731)
                                      (SEQ ID NO: 109)
MDMRVPAQLLGLLLLWLRGARCQVQLVESGGGVVQPGRSLRLSCAASGF

TFSSFGMHWVRQAPGKGLEWVAVISFDGSIKYSVDSVKGRFTISRDNSK

NTLFLQMNSLRAEDTAVYYCARDRLNYYDSSGYYHYKYYGMAVWGQGTT

VTVSSASTKGPSVFPLAPCSRSTSESTAALGCLVKDYFPEPVTVSWNSG

ALTSGVHTFPAVLQSSGLYSLSSVVTVPSSNFGTQTYTCNVDHKPSNTK

VDKTVERKCCVECPPCPAPPVAGPSVFLFPPKPKDTLMISRTPEVTCVV

VDVSHEDPEVQFNWYVDGVEVHNAKTKPREEQFNSTFRVVSVLTVVHQD

WLNGKEYKCKVSNKGLPAPIEKTISKTKGQPREPQVYTLPPSREEMTKN

QVSLTCLVKGFYPSDIAVEWESNGQPENNYKTTPPMLDSDGSFFLYSKL

TVDKSRWQQGNVFSCSVMHEALHNHYTQKSLSLSPGK
```

Following initial identification, the activity of a candidate antibody (e.g., anti-CGRP antagonist antibody) can be further confirmed and refined by bioassays, known to test the targeted biological activities. Alternatively, bioassays can be used to screen candidates directly. Some of the methods for identifying and characterizing anti-CGRP antagonist antibody or polypeptide are described in detail in the Examples.

Antibodies, including anti-CGRP antagonist antibodies, may be characterized using methods well known in the art. For example, one method is to identify the epitope to which it binds, or "epitope mapping." There are many methods known in the art for mapping and characterizing the location of epitopes on proteins, including solving the crystal structure of an antibody-antigen complex, competition assays, gene fragment expression assays, and synthetic peptide-based assays, as described, for example, in Chapter 11 of Harlow and Lane, Using Antibodies, a Laboratory Manual, Cold Spring Harbor Laboratory Press, Cold Spring Harbor, New York, 1999.

Yet another method which can be used to characterize an antibody, including an anti-CGRP antagonist antibody, is to use competition assays with other antibodies known to bind to the same antigen, i.e., various fragments on CGRP, to determine if the anti-CGRP antagonist antibody binds to the same epitope as other antibodies. Competition assays are well known to those of skill in the art.

C. Antibody G1 and Related Antibodies, Polypeptides, Polynucleotides, Vectors and Host Cells This invention encompasses compositions, including pharmaceutical compositions, comprising antibody G1 and its variants shown in Table 6 or polypeptide derived from antibody G1 and its variants shown in Table 6; and polynucleotides comprising sequences encoding G1 and its variants or the polypeptide. In some embodiments, compositions comprise one or more antibodies or polypeptides (which may or may not be an antibody) that bind to CGRP, and/or one or more polynucleotides comprising sequences encoding one or more antibodies or polypeptides that bind to CGRP. These compositions may further comprise suitable excipients, such as pharmaceutically acceptable excipients including buffers, which are well known in the art.

In some embodiments, the anti-CGRP antagonist antibodies and polypeptides of the invention are characterized by any (one or more) of the following characteristics: (a) bind to CGRP; (b) block CGRP from binding to its receptor(s); (c) block or decrease CGRP receptor activation (including cAMP activation); (d) inhibit CGRP biological activity or downstream pathways mediated by CGRP signaling function; (e) prevent, ameliorate, or treat any aspect of refractory migraine; (f) increase clearance of CGRP; and (g) inhibit (reduce) CGRP synthesis, production or release.

In some embodiments, the invention provides any of the following, or compositions (including pharmaceutical compositions) comprising any of the following: (a) antibody G1 or its variants shown in Table 6; (b) a fragment or a region of antibody G1 or its variants shown in Table 6; (c) a light chain of antibody G1 or its variants shown in Table 6; (d) a heavy chain of antibody G1 or its variants shown in Table 6; (e) one or more variable region(s) from a light chain and/or a heavy chain of antibody G1 or its variants shown in Table 6; (f) one or more CDR(s) (one, two, three, four, five or six CDRs) of antibody G1 or its variants shown in Table 6; (g) CDR H3 from the heavy chain of antibody G1; (h) CDR L3 from the light chain of antibody G1 or its variants shown in Table 6; (i) three CDRs from the light chain of antibody G1 or its variants shown in Table 6; (j) three CDRs from the heavy chain of antibody G1 or its variants shown in Table 6; (k) three CDRs from the light chain and three CDRs from the heavy chain, of antibody G1 or its variants shown in Table 6; and (l) an antibody comprising any one of (b) through (k). In some embodiments, the invention also provides polypeptides comprising any one or more of the above.

The CDR portions of antibody G1 (including Chothia and Kabat CDRs) are diagrammatically depicted in FIG. 5. Determination of CDR regions is well within the skill of the art. It is understood that in some embodiments, CDRs can be a combination of the Kabat and Chothia CDR (also termed "combined CDRs" or "extended CDRs"). In some embodiments, the CDRs are the Kabat CDRs. In other embodiments, the CDRs are the Chothia CDRs. In other words, in embodiments with more than one CDR, the CDRs may be any of Kabat, Chothia, combination CDRs, or combinations thereof.

In some embodiments, the invention provides a polypeptide (which may or may not be an antibody) which comprises at least one CDR, at least two, at least three, or at least four, at least five, or all six CDRs that are substantially identical to at least one CDR, at least two, at least three, at least four, at least five or all six CDRs of G1 or its variants shown in Table 6. Other embodiments include antibodies which have at least two, three, four, five, or six CDR(s) that are substantially identical to at least two, three, four, five or six CDRs of G1 or derived from G1. In some embodiments, the at least one, two, three, four, five, or six CDR(s) are at least about 85%, 86%, 87%, 88%, 89%, 90%, 95%, 96%, 97%, 98%, or 99% identical to at least one, two, three, four, five or six CDRs of G1 or its variants shown in Table 6. It is understood that, for purposes of this invention, binding specificity and/or overall activity is generally retained, although the extent of activity may vary compared to G1 or its variants shown in Table 6 (may be greater or lesser).

In some embodiments, the invention also provides a polypeptide (which may or may not be an antibody) which comprises an amino acid sequence of G1 or its variants shown in Table 6 that has any of the following: at least 5 contiguous amino acids, at least 8 contiguous amino acids, at least about 10 contiguous amino acids, at least about 15 contiguous amino acids, at least about 20 contiguous amino acids, at least about 25 contiguous amino acids, at least about 30 contiguous amino acids of a sequence of G1 or its variants shown in Table 6, wherein at least 3 of the amino acids are from a variable region of G1 (FIG. 5) or its variants shown in Table 6. In one embodiment, the variable region is from a light chain of G1. In another embodiment, the variable region is from a heavy chain of G1. An exemplary polypeptide has contiguous amino acid (lengths described above) from both the heavy and light chain variable regions of G1. In another embodiment, the 5 (or more) contiguous amino acids are from a complementarity determining region (CDR) of G1 shown in FIG. 5. In some embodiments, the contiguous amino acids are from a variable region of G1.

The binding affinity ($K_D$) of an anti-CGRP antagonist antibody and polypeptide to CGRP (such as human α-CGRP) can be about 0.06 to about 200 nM. In some embodiments, the binding affinity is any of about 200 nM, 100 nM, about 50 nM, about 10 nM, about 1 nM, about 500 pM, about 100 pM, about 60 pM, about 50 pM, about 20 pM, about 15 pM, about 10 pM, about 5 pM, or about 2 pM. In some embodiments, the binding affinity is less than any of about 250 nM, about 200 nM, about 100 nM, about 50 nM, about 10 nM, about 1 nM, about 500 pM, about 100 pM, or about 50 pM.

The antibodies provided herein can be made by procedures known in the art. The polypeptides can be produced by proteolytic or other degradation of the antibodies, by recombinant methods (i.e., single or fusion polypeptides) as described above or by chemical synthesis. Polypeptides of the antibodies, especially shorter polypeptides up to about 50 amino acids, are conveniently made by chemical synthesis. Methods of chemical synthesis are known in the art and are commercially available. For example, an antibody could be produced by an automated polypeptide synthesizer employing the solid phase method. See also, U.S. Pat. Nos. 5,807,715; 4,816,567; and 6,331,415.

In another alternative, the antibodies can be made recombinantly using procedures that are well known in the art. In one embodiment, a polynucleotide comprises a sequence encoding the heavy chain and/or the light chain variable regions of antibody G1 shown in SEQ ID NO:9 and SEQ ID NO:10. In another embodiment, the polynucleotide comprising the nucleotide sequence shown in SEQ ID NO:9 and SEQ ID NO: 10 are cloned into one or more vectors for expression or propagation. The sequence encoding the antibody of interest may be maintained in a vector in a host cell and the host cell can then be expanded and frozen for future use. Vectors (including expression vectors) and host cells are further described herein.

In some embodiments, the invention also encompasses single chain variable region fragments ("scFv") of antibodies of this invention, such as G1. Single chain variable region fragments are made by linking light and/or heavy chain variable regions by using a short linking peptide. Bird et al. (1988) Science 242:423-426. An example of a linking peptide is (GGGGS)3 (SEQ ID NO:57) which bridges approximately 3.5 nm between the carboxy terminus of one variable region and the amino terminus of the other variable region. Linkers of other sequences have been designed and used. Bird et al. (1988). Linkers can in turn be modified for additional functions, such as attachment of drugs or attachment to solid supports. The single chain variants can be produced either recombinantly or synthetically. For synthetic production of scFv, an automated synthesizer can be used. For recombinant production of scFv, a suitable plasmid containing polynucleotide that encodes the scFv can be introduced into a suitable host cell, either eukaryotic, such as yeast, plant, insect or mammalian cells, or prokaryotic, such as E. coli. Polynucleotides encoding the scFv of interest can be made by routine manipulations such as ligation of polynucleotides. The resultant scFv can be isolated using standard protein purification techniques known in the art.

Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) Proc. Natl. Acad Sci. USA 90:6444-6448; Poljak, R. J., et al. (1994) Structure 2:1121-1123).

For example, bispecific antibodies, monoclonal antibodies that have binding specificities for at least two different antigens, can be prepared using the antibodies disclosed herein. Methods for making bispecific antibodies are known in the art (see, e.g., Suresh et al., 1986, Methods in Enzymology 121:210). Traditionally, the recombinant production of bispecific antibodies was based on the coexpression of two immunoglobulin heavy chain-light chain pairs, with the two heavy chains having different specificities (Millstein and Cuello, 1983, Nature 305, 537-539).

According to one approach to making bispecific antibodies, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2 and CH3 regions. It is preferred to have the first heavy chain constant region (CH1), containing the site necessary for light chain binding, present in at least one of the fusions. DNAs encoding the immunoglobulin heavy chain fusions and, if desired, the immunoglobulin light chain, are inserted into separate expression vectors, and are cotransfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In one approach, the bispecific antibodies are composed of a hybrid immunoglobulin heavy chain with a first binding specificity in one arm, and a hybrid immunoglobulin heavy chain-light chain pair (providing a second binding specificity) in the other arm. This asymmetric structure, with an immunoglobulin light chain in only one half of the bispecific molecule, facilitates the separation of the desired bispecific compound from unwanted immunoglobulin chain combinations. This approach is described in PCT Publication No. WO 94/04690.

Heteroconjugate antibodies, comprising two covalently joined antibodies, are also within the scope of the invention. Such antibodies have been used to target immune system cells to unwanted cells (U.S. Pat. No. 4,676,980), and for treatment of HIV infection (PCT application publication Nos. WO 91/00360 and WO 92/200373; EP 03089). Heteroconjugate antibodies may be made using any convenient cross-linking methods. Suitable cross-linking agents and techniques are well known in the art, and are described in U.S. Pat. No. 4,676,980.

Chimeric or hybrid antibodies also may be prepared in vitro using known methods of synthetic protein chemistry, including those involving cross-linking agents. For example, immunotoxins may be constructed using a disulfide exchange reaction or by forming a thioether bond. Examples of suitable reagents for this purpose include iminothiolate and methyl-4-mercaptobutyrimidate.

Humanized antibody comprising one or more CDRs of antibody G1 or its variants shown in Table 6, or one or more CDRs derived from antibody G1 or its variants shown in Table 6 can be made using any methods known in the art. For example, four general steps may be used to humanize a monoclonal antibody.

In some embodiments, the invention encompasses modifications to antibody G1 or its variants shown in Table 6, including functionally equivalent antibodies which do not significantly affect their properties and variants which have enhanced or decreased activity and/or affinity. For example, the amino acid sequence of antibody G1 or its variants shown in Table 6 may be mutated to obtain an antibody with the desired binding affinity to CGRP. Modification of polypeptides is routine practice in the art and need not be described in detail herein. Modification of polypeptides is exemplified in the Examples. Examples of modified polypeptides include polypeptides with conservative substitutions of amino acid residues, one or more deletions or additions of amino acids which do not significantly deleteriously change the functional activity, or use of chemical analogs.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to an epitope tag. Other insertional variants of the antibody molecule include the fusion to the N- or C-terminus of the antibody of an enzyme or a polypeptide which increases the serum half-life of the antibody.

Substitution variants have at least one amino acid residue in the antibody molecule removed and a different residue inserted in its place. The sites of greatest interest for substitutional mutagenesis include the hypervariable regions, but FR alterations are also contemplated. Conservative substitutions are shown in Table 1 under the heading of "conservative substitutions". If such substitutions result in a change in biological activity, then more substantial changes, denominated "exemplary substitutions" in Table 1, or as further described below in reference to amino acid classes, may be introduced and the products screened.

TABLE 1

Amino Acid Substitutions

| Original Residue | Conservative Substitutions | Exemplary Substitutions |
|---|---|---|
| Ala (A) | Val | Val; Leu; Ile |
| Arg (R) | Lys | Lys; Gln; Asn |
| Asn (N) | Gln | Gln; His; Asp, Lys; Arg |
| Asp (D) | Glu | Glu; Asn |
| Cys (C) | Ser | Ser; Ala |
| Gln (Q) | Asn | Asn; Glu |
| Glu (E) | Asp | Asp; Gln |
| Gly (G) | Ala | Ala |
| His (H) | Arg | Asn; Gln; Lys; Arg |
| Ile (I) | Leu | Leu; Val; Met; Ala; Phe; Norleucine |
| Leu (L) | Ile | Norleucine; Ile; Val; Met; Ala; Phe |
| Lys (K) | Arg | Arg; Gln; Asn |
| Met (M) | Leu | Leu; Phe; Ile |
| Phe (F) | Tyr | Leu; Val; Ile; Ala; Tyr |
| Pro (P) | Ala | Ala |
| Ser (S) | Thr | Thr |
| Thr (T) | Ser | Ser |
| Trp (W) | Tyr | Tyr; Phe |
| Tyr (Y) | Phe | Trp; Phe; Thr; Ser |
| Val (V) | Leu | Ile; Leu; Met; Phe; Ala; Norleucine |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) Non-polar: Norleucine, Met, Ala, Val, Leu, Ile;
(2) Polar without charge: Cys, Ser, Thr, Asn, Gln;
(3) Acidic (negatively charged): Asp, Glu;
(4) Basic (positively charged): Lys, Arg;
(5) Residues that influence chain orientation: Gly, Pro; and
(6) Aromatic: Trp, Tyr, Phe, His.

Non-conservative substitutions are made by exchanging a member of one of these classes for another class.

Any cysteine residue not involved in maintaining the proper conformation of the antibody also may be substituted, generally with serine, to improve the oxidative stability of the molecule and prevent aberrant cross-linking. Conversely, cysteine bond(s) may be added to the antibody to improve its stability, particularly where the antibody is an antibody fragment such as an Fv fragment.

Amino acid modifications can range from changing or modifying one or more amino acids to complete redesign of a region, such as the variable region. Changes in the variable region can alter binding affinity and/or specificity. In some embodiments, no more than one to five conservative amino acid substitutions are made within a CDR domain. In other embodiments, no more than one to three conservative amino acid substitutions are made within a CDR domain. In still other embodiments, the CDR domain is CDR H3 and/or CDR L3.

Modifications also include glycosylated and nonglycosylated polypeptides, as well as polypeptides with other post-translational modifications, such as, for example, glycosylation with different sugars, acetylation, and phosphorylation. Antibodies are glycosylated at conserved positions in their constant regions (Jefferis and Lund, 1997, Chem. Immunol. 65:111-128; Wright and Morrison, 1997, TibTECH 15:26-32). The oligosaccharide side chains of the immunoglobulins affect the protein's function (Boyd et al., 1996, Mol. Immunol. 32:1311-1318; Wittwe and Howard, 1990, Biochem. 29:4175-4180) and the intramolecular interaction between portions of the glycoprotein, which can affect the conformation and presented three-dimensional surface of the glycoprotein (Hefferis and Lund, supra; Wyss and Wagner, 1996, Current Opin. Biotech. 7:409-416). Oligosaccharides may also serve to target a given glycoprotein to certain molecules based upon specific recognition structures. Glycosylation of antibodies has also been reported to affect antibody-dependent cellular cytotoxicity (ADCC). In particular, CHO cells with tetracycline-regulated expression of β(1,4)-N-acetylglucosaminyltransferase III (GnTIII), a glycosyltransferase catalyzing formation of bisecting GlcNAc, was reported to have improved ADCC activity (Umana et al., 1999, Mature Biotech. 17:176-180).

Glycosylation of antibodies is typically either N-linked or O-linked. N-linked refers to the attachment of the carbohydrate moiety to the side chain of an asparagine residue. The tripeptide sequences asparagine-X-serine, asparagine-X-threonine, and asparagine-X-cysteine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Other methods of modification include using coupling techniques known in the art, including, but not limited to, enzymatic means, oxidative substitution and chelation. Modifications can be used, for example, for attachment of labels for immunoassay. Modified G1 polypeptides can be made using established procedures in the art and can be screened using standard assays known in the art, some of which are described below and in the Examples.

In some embodiments of the invention, the antibody comprises a modified constant region, such as a constant region that is immunologically inert or partially inert, e.g., does not trigger complement mediated lysis, does not stimulate antibody-dependent cell mediated cytotoxicity (ADCC), or does not activate microglia; or have reduced activities (compared to the unmodified antibody) in any one or more of the following: triggering complement mediated lysis, stimulating antibody-dependent cell mediated cytotoxicity (ADCC), or activating microglia. Different modifications of the constant region may be used to achieve optimal level and/or combination of effector functions. See, for example, Morgan et al., Immunology 86:319-324 (1995); Lund et al., J. Immunology 157:4963-9 157:4963-4969 (1996); Idusogie et al., J. Immunology 164:4178-4184 (2000); Tao et al., J. Immunology 143: 2595-2601 (1989); and Jefferis et al., Immunological Reviews 163:59-76 (1998). In some embodiments, the constant region is modified as described in Eur. J. Immunol. (1999) 29:2613-2624; PCT Application No. PCT/GB99/01441; and/or UK Patent Application No. 9809951.8. In other embodiments, the antibody comprises a human heavy chain IgG2 constant region comprising the following mutations: A330P331 to S330S331 (amino acid numbering with reference to the wildtype IgG2 sequence). Eur. J. Immunol. (1999) 29:2613-2624. In still other embodiments, the constant region is aglycosylated for N-linked glycosylation. In some embodiments, the constant region is aglycosylated for N-linked glycosylation by mutating the glycosylated amino acid residue or flanking residues that are part of the N-glycosylation recognition sequence in the constant region. For example, N-glycosylation site N297 may be mutated to A, Q, K, or H. See, Tao et al., J. Immunology 143: 2595-2601 (1989); and Jefferis et al., Immunological Reviews 163:59-76 (1998). In some embodiments, the constant region is aglycosylated for N-linked glycosylation. The constant region may be aglycosylated for N-linked glycosylation enzymatically (such as removing carbohydrate by enzyme PNGase), or by expression in a glycosylation deficient host cell.

Other antibody modifications include antibodies that have been modified as described in PCT Publication No. WO 99/58572, published Nov. 18, 1999. These antibodies comprise, in addition to a binding domain directed at the target molecule, an effector domain having an amino acid sequence substantially homologous to all or part of a constant domain of a human immunoglobulin heavy chain. These antibodies are capable of binding the target molecule without triggering significant complement dependent lysis, or cell-mediated destruction of the target. In some embodiments, the effector domain is capable of specifically binding FcRn and/or FcγRIIb. These are typically based on chimeric domains derived from two or more human immunoglobulin heavy chain $C_H2$ domains. Antibodies modified in this manner are particularly suitable for use in chronic antibody therapy, to avoid inflammatory and other adverse reactions to conventional antibody therapy.

In some embodiments, the invention includes affinity matured embodiments. For example, affinity matured antibodies can be produced by procedures known in the art (Marks et al., 1992, Bio/Technology, 10:779-783; Barbas et al., 1994, Proc Nat. Acad. Sci, USA 91:3809-3813; Schier et al., 1995, Gene, 169:147-155; Yelton et al., 1995, J. Immunol., 155:1994-2004; Jackson et al., 1995, J. Immunol., 154(7):3310-9; Hawkins et al, 1992, J. Mol. Biol., 226:889-896; and WO2004/058184).

In some embodiments, the invention also encompasses fusion proteins comprising one or more fragments or regions from the antibodies (such as G1) or polypeptides of this invention. In one embodiment, a fusion polypeptide is provided that comprises at least 10 contiguous amino acids of the variable light chain region shown in SEQ ID NO:2 (FIG. 5) and/or at least 10 amino acids of the variable heavy chain region shown in SEQ ID NO:1 (FIG. 5). In other embodiments, a fusion polypeptide is provided that comprises at least about 10, at least about 15, at least about 20, at least about 25, or at least about 30 contiguous amino acids of the variable light chain region shown in SEQ ID NO:2 (FIG. 5) and/or at least about 10, at least about 15, at least about 20, at least about 25, or at least about 30 contiguous amino acids of the variable heavy chain region shown in SEQ ID NO:1 (FIG. 5). In another embodiment, the fusion polypeptide comprises a light chain variable region and/or a heavy chain variable region of G1, as shown in SEQ ID NO:2 and SEQ ID NO: 1 of FIG. 5. In another embodiment, the fusion polypeptide comprises one or more CDR(s) of G1. In still other embodiments, the fusion polypeptide comprises CDR H3 and/or CDR L3 of antibody G1. For purposes of this invention, an G1 fusion protein contains one or more G1 antibodies and another amino acid sequence to which it is not attached in the native molecule, for example, a heterologous sequence or a homologous sequence from another region. Exemplary heterologous sequences include, but are not limited to a "tag" such as a FLAG tag or a 6His tag (SEQ ID NO:56). Tags are well known in the art.

In some embodiments, the invention also provides compositions (including pharmaceutical compositions) and kits comprising antibody G1, and/or any or all of the antibodies or polypeptides described herein.

Preferably, the "percentage of sequence identity" is determined by comparing two optimally aligned sequences over a window of comparison of at least 20 positions, wherein the portion of the polynucleotide or polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residue occurs in both sequences to yield the number of matched positions, dividing the number of matched positions by the total number of positions in the reference sequence (i.e., the window size) and multiplying the results by 100 to yield the percentage of sequence identity.

Variants may also, or alternatively, be substantially homologous to a native gene, or a portion or complement thereof. Such polynucleotide variants are capable of hybridizing under moderately stringent conditions to a naturally occurring DNA sequence encoding a native antibody (or a complementary sequence).

D. Compositions

In some embodiments, compositions used in a method of the invention comprise an effective amount of an antibody (e.g., anti-CGRP antagonist antibody, monoclonal antibody that modulates the CGRP pathway) or an antibody derived polypeptide described herein. Examples of such compositions, as well as how to formulate, are also described in an earlier section and below. In one embodiment, the composition further comprises a CGRP antagonist. In some embodiments, the composition comprises one or more monoclonal antibodies that modulate the CGRP pathway. In some embodiments, the composition comprises one or more anti-CGRP antagonist antibodies. In some embodiments, the anti-CGRP antagonist antibody recognizes human CGRP. In some embodiments, the anti-CGRP antagonist antibody is humanized. In some embodiments, the anti-CGRP antagonist antibody comprises a constant region that does not trigger an unwanted or undesirable immune response, such as antibody-mediated lysis or ADCC. In some embodiments, the anti-CGRP antagonist antibody comprises one or more CDR(s) of antibody G1 (such as one, two, three, four, five, or, in some embodiments, all six CDRs from G1). In some embodiments, the anti-CGRP antagonist antibody is human.

It is understood that the compositions can comprise more than one antibody (e.g., more than one anti-CGRP antagonist antibody—a mixture of anti-CGRP antagonist antibodies that recognize different epitopes of CGRP). Other exemplary compositions comprise more than one anti-CGRP antagonist antibodies that recognize the same epitope(s), or different species of anti-CGRP antagonist antibodies that bind to different epitopes of CGRP.

A composition can further comprise pharmaceutically acceptable carriers, excipients, or stabilizers (Remington:

The Science and practice of Pharmacy 20th Ed. (2000) Lippincott Williams and Wilkins, Ed. K. E. Hoover). Acceptable carriers, excipients, or stabilizers are nontoxic to recipients at the dosages and concentrations employed. A therapeutic formulation of an antibody may comprise one or more pharmaceutically acceptable carriers, excipients or stabilizes with non-limiting examples of such species that include buffers such as phosphate, citrate, and other organic acids; salts such as sodium chloride; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens, such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids (e.g., at concentrations of 0.1 mM to 100 mM, 0.1 mM to 1 mM, 0.01 mM to 50 mM, 1 mM to 50 mM, 1 mM to 30 mM, 1 mM to 20 mM, 10 mM to 25 mM) such as glycine, glutamine, methionine, asparagine, histidine, arginine, or lysine; monosaccharides, disaccharides, and other carbohydrates including glucose, mannose, or dextrins; chelating agents (e.g., at concentrations of 0.001 mg/ml to 1 mg/mL, 0.001 mg/mL to 1 mg/mL, 0.001 mg/ml to 0.1 mg/mL, 0.001 mg/mL to 0.01 mg/mL) such as EDTA (e.g., disodium EDTA dihydrate); sugars (e.g., at concentrations of 1 mg/mL to 500 mg/mL, 10 mg/mL to 200 mg/mL, 10 mg/mL to 100 mg/mL, 50 mg/mL to 150 mg/mL) such as sucrose, mannitol, trehalose or sorbitol; salt-forming counter-ions such as sodium; metal complexes (e.g., Zn-protein complexes); and/or non-ionic surfactants (e.g., at concentrations of 0.01 mg/ml to 10 mg/mL, 0.01 mg/mL to 1 mg/mL, 0.1 mg/mL to 1 mg/mL, 0.01 mg/mL to 0.5 mg/mL) such as TWEEN™ (e.g., polysorbate (e.g., polysorbate 20, polysorbate 40, polysorbate 60, polysorbate 80)), PLURONICS™ or polyethylene glycol (PEG). Pharmaceutically acceptable excipients are further described herein.

An antibody (e.g., an anti-CGRP antagonist antibody) and compositions thereof can also be used in conjunction with other agents that serve to enhance and/or complement the effectiveness of the agents.

E. Kits

In one aspect, the invention also provides kits for use in the instant methods. Kits can include one or more containers comprising an antibody described herein (e.g., an anti-CGRP antagonist antibody (such as a humanized antibody)) or polypeptide described herein and instructions for use in accordance with any of the methods described herein. Generally, these instructions comprise a description of administration of the antibody to treat, ameliorate or prevent refractory migraine according to any of the methods described herein. The kit may further comprise a description of selecting an individual suitable for treatment based on identifying whether that individual has refractory migraine or whether the individual is at risk of having refractory migraine. In still other embodiments, the instructions comprise a description of administering an antibody (e.g., anti-CGRP antagonist antibody) to an individual at risk of having refractory migraine.

In some embodiments, the antibody is a humanized antibody. In some embodiments, the antibody is human. In other embodiments, the antibody is a monoclonal antibody. In some embodiments, the antibody comprises one or more CDR(s) of antibody G1 (such as one, two, three, four, five, or, in some embodiments, all six CDRs from G1).

The instructions relating to the use of an antibody (e.g., anti-CGRP antagonist antibody) generally include information as to dosage, dosing schedule, and route of administration for the intended treatment. The containers may be unit doses, bulk packages (e.g., multi-dose packages) or sub-unit doses. Instructions supplied in the kits are typically written instructions on a label or package insert (e.g., a paper sheet included in the kit), but machine-readable instructions (e.g., instructions carried on a magnetic or optical storage disk) are also acceptable.

The label or package insert indicates that the composition is used for treating, ameliorating and/or preventing migraine in a subject having refractory migraine. Instructions may be provided for practicing any of the methods described herein.

The kits of this invention are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). At least one active agent in the composition is an anti-CGRP antagonist antibody and/or a monoclonal antibody that modulates the CGRP pathway. The container may further comprise a second pharmaceutically active agent.

Kits may optionally provide additional components such as buffers and interpretive information. Normally, the kit comprises a container and a label or package insert(s) on or associated with the container.

Further aspects and embodiments of the present invention are set out in the following numbered paragraphs:

1. A method of treating a refractory migraine in a subject, the method comprising:
   selecting a subject who does not respond favorably to a migraine treatment selected from the group consisting of topiramate, carbamazepine, divalproex sodium, sodium valproate, flunarizine, pizotifen, amitriptyline, venlafaxine, nortriptyline, duloxetine, atenolol, nadolol, metoprolol, propranolol, timolol, and onabotulinumtoxinA; and
   administering to the subject a therapeutically effective amount of a monoclonal antibody that modulates the calcitonin gene-related peptide (CGRP) pathway.

2. The method of paragraph 1, wherein the subject does not respond favorably to the migraine treatment after about three months and/or develops adverse side effects.

3. The method of paragraph 1, wherein the monoclonal antibody is administered to the subject intravenously or subcutaneously.

4. The method of paragraph 1, wherein the monoclonal antibody is administered at a dose of about 675 mg.

5. The method of paragraph 4, wherein the monoclonal antibody is administered at a dose of about 225 mg in three separate injections.

6. The method of paragraph 1, wherein the monoclonal antibody is administered at a dose of about 675 mg followed by subsequent doses of about 225 mg at one month intervals.

7. The method of paragraph 1, wherein the monoclonal antibody is administered at a dose of about 675 mg followed by five subsequent doses of about 225 mg at one month intervals.

8. The method of paragraph 1, wherein the administering comprises administering the antibody to the subject from a pre-filled syringe, pre-filled syringe with a needle safety device, injection pen, or auto-injector comprising a dose of the monoclonal antibody.

9. The method of paragraph 1, wherein the monoclonal antibody is administered as a formulation comprising the antibody at a concentration of at least about 150 mg/mL.

10. The method of paragraph 1, wherein the monoclonal antibody is administered in a volume of less than 2 mL.

11. The method of paragraph 1, wherein the monoclonal antibody is an anti CGRP antagonist antibody.

12. The method of paragraph 1, wherein the monoclonal antibody is human or humanized.

13. The method of paragraph 1, wherein the monoclonal antibody is a humanized anti-CGRP antagonist antibody.

14. The method of paragraph 1, wherein the monoclonal antibody comprises a CDR H1 as set forth in SEQ ID NO:3; a CDR H2 as set forth in SEQ ID NO:4; a CDR H3 as set forth in SEQ ID NO:5; a CDR L1 as set forth in SEQ ID NO:6; a CDR L2 as set forth in SEQ ID NO:7; and a CDR L3 as set forth in SEQ ID NO:8.

15. The method of paragraph 1, wherein the monoclonal antibody is an IgG1, IgG2, IgG3, or IgG4 antibody.

16. The method of paragraph 1, wherein the subject is human.

17. The method of paragraph 1, comprising administering to the subject a second agent simultaneously or sequentially with the monoclonal antibody.

18. The method of paragraph 17, wherein monthly use of the second agent by the subject is decreased by at least 15% after administering the monoclonal antibody.

19. A composition for use in accordance with any of the preceding paragraphs.

The following Examples are provided to illustrate but not limit the invention. It is understood that the examples and embodiments described herein are for illustrative purposes only and that various modifications or changes in light thereof will be suggested to persons skilled in the art and are to be included within the spirit and purview of this application. All publications, patents, and patent applications cited herein are hereby incorporated by reference in their entirety for all purposes to the same extent as if each individual publication, patent or patent application were specifically and individually indicated to be so incorporated by reference.

EXAMPLES

Example 1: Generation and Characterization of Monoclonal Antibodies Directed Against CGRP Generation of anti-CGRP antibodies. To generate anti-CGRP antibodies that have cross-species reactivity for rat and human CGRP, mice were immunized with 25-100 µg of human α-CGRP or β-CGRP conjugated to KLH in adjuvant (50 µl per footpad, 100 µl total per mouse) at various intervals. Immunization was generally performed as described in Geerligs H J et al., 1989, J. Immunol. Methods 124:95-102; Kenney J S et al., 1989, J. Immunol. Methods 121:157-166; and Wicher K et al., 1989, Int. Arch. Allergy Appl. Immunol. 89:128-135. Mice were first immunized with 50 µg of human α-CGRP or β-CGRP conjugated to KLH in CFA (complete Freund's adjuvant). After 21 days, mice were secondly immunized with 25 µg of human β-CGRP (for mice first immunized with human α-CGRP) or α-CGRP (for mice first immunized with human β-CGRP) conjugated to KLH in IFA (incomplete Freund's adjuvant). Twenty-three days later after the second immunization, third immunization was performed with 25 µg of rat α-CGRP conjugated to KLH in IFA. Ten days later, antibody titers were tested using ELISA. Forth immunization was performed with 25 µg of the peptide (rat α-CGRP-KLH) in IFA 34 days after the third immunization. Final booster was performed with 100 µg soluble peptide (rat α-CGRP) 32 days after the forth immunization.

Splenocytes were obtained from the immunized mouse and fused with NSO myeloma cells at a ratio of 10:1, with polyethylene glycol 1500. The hybrids were plated out into 96-well plates in DMEM containing 20% horse serum and 2-oxaloacetate/pyruvate/insulin (Sigma), and hypoxanthine/aminopterin/thymidine selection was begun. On day 8, 100 µl of DMEM containing 20% horse serum was added to all the wells. Supernatants of the hybrids were screened by using antibody capture immunoassay. Determination of antibody class was done with class-specific second antibodies.

A panel of monoclonal antibody-producing cell lines was selected based on their binding to human and rat CGRP for further characterization. These antibodies and characteristics are shown below in Tables 2 and 3.

Purification and Fab fragment preparation. Monoclonal antibodies selected for further characterization were purified from supernatants of hybridoma cultures using protein A affinity chromatography. The supernatants were equilibrated to pH 8. The supernatants were then loaded to the protein A column MabSelect (Amersham Biosciences #17-5199-02) equilibrated with PBS to pH 8. The column was washed with 5 column volumes of PBS, pH 8. The antibodies were eluted with 50 mM citrate-phosphate buffer, pH 3. The eluted antibodies were neutralized with 1 M Phosphate Buffer, pH 8. The purified antibodies were dialyzed with PBS, pH 7.4. The antibody concentrations were determined by SDS-PAGE, using a murine monoclonal antibody standard curve.

Fabs were prepared by papain proteolysis of the full antibodies using Immunopure Fab kit (Pierce #44885) and purified by flow through protein A chromatography following manufacturer instructions. Concentrations were determined by ELISA and/or SDS-PAGE electrophoresis using a standard Fab of known concentration (determined by amino acid analysis), and by A280 using 1OD=0.6 mg/ml (or theoretical equivalent based on the amino acid sequence).

Affinity determination of the Fabs. Affinities of the anti-CGRP monoclonal antibodies were determined at either 25° C. or 37° C. using the BIACORE3000™ surface plasmon resonance (SPR) system (Biacore, INC, Piscataway NJ) with the manufacture's own running buffer, HBS-EP (10 mM HEPES pH 7.4, 150 mM NaCl, 3 mM EDTA, 0.005% v/v polysorbate P20). Affinity was determined by capturing N-terminally biotinylated CGRP peptides (custom ordered from GenScript Corporation, New Jersey or Global Peptide Services, Colorado) via pre-immobilized streptavidin on SA chip and measuring binding kinetics of antibody Fab titrated across the CGRP surface. Biotinylated CGRP was diluted into HBS-EP and injected over the chip at a concentration of less than 0.001 mg/ml. Using variable flow time across the individual chip channels, two ranges of antigen density were achieved: <50 response units (RU) for detailed kinetic studies and about 800 RU for concentration studies and screening. Two- or three-fold serial dilutions typically at concentrations spanning 1 µM-0.1 nM (aimed at 0.1-10× estimated $K_D$) of purified Fab fragments were injected for 1 minute at 100 µL/min and dissociation times of 10 minutes were allowed. After each binding cycle, surfaces were regenerated with 25 mM NaOH in 25% v/v ethanol, which was tolerated over hundreds of cycles. Kinetic association rate ($k_{on}$) and dissociation rate ($k_{off}$) were obtained simultaneously by fitting the data to a 1:1 Langmuir binding model (Karlsson, R. Roos, H. Fagerstam, L. Petersson, B. (1994). Methods Enzymology 6. 99-110) using the BIAevaluation program. Global equilibrium dissociation constants ($K_D$) or "affinities" were calculated from the ratio $K_D = k_{off}/k_{on}$. Affinities of the murine Fab fragments are shown in Tables 2 and 3.

Figure 1:
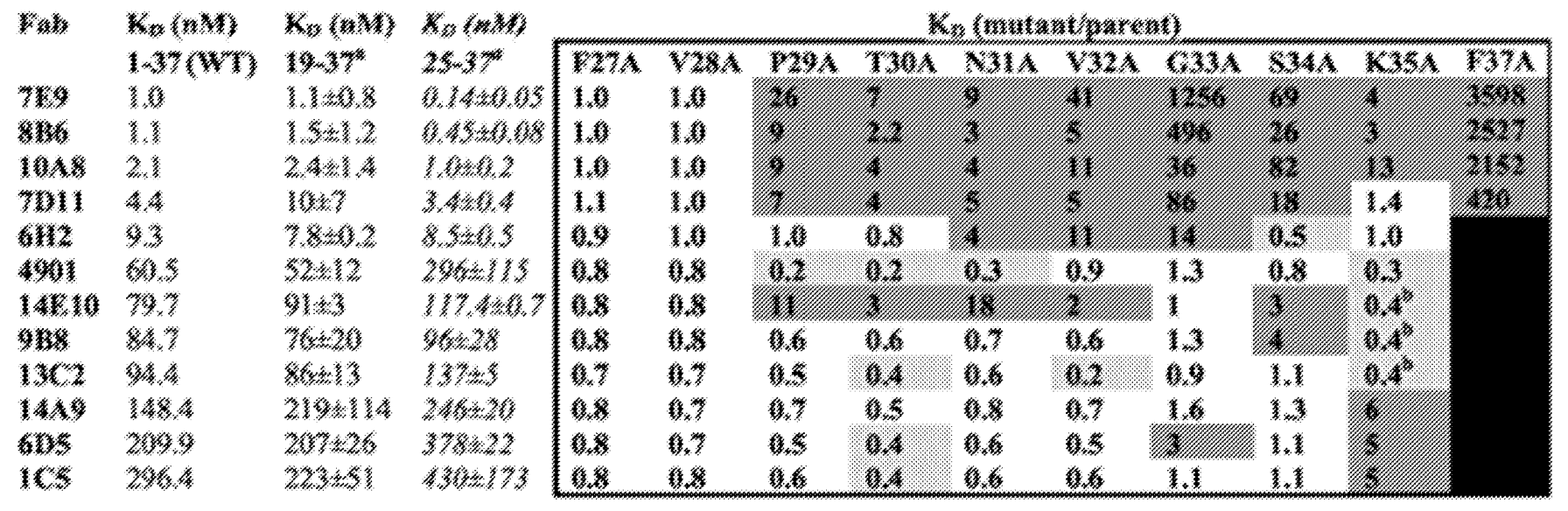

Epitope mapping of the murine anti-CGRP antibodies. To determine the epitope that anti-CGRP antibodies bind on human α-CGRP, binding affinities of the Fab fragments to various CGRP fragments were measured as described above by capturing N-terminally biotinylated CGRP fragments amino acids 19-37 and amino acids 25-37 on a SA sensor chip. FIG. 1 shows their binding affinities measured at 25° C. As shown in FIG. 1, all antibodies, except antibody 4901, bind to human α-CGRP fragments 19-37 and 25-37 with affinity similar to their binding affinity to full length human α-CGRP (1-37). Antibody 4901 binds to human α-CGRP fragment 25-37 with six-fold lower affinity than binding to full length human α-CGRP fragment, due mainly to a loss in off-rate. The data indicate that these anti-CGRP antibodies generally bind to the C-terminal end of CGRP.

Alanine scanning was performed to further characterize amino acids in human α-CGRP involved in binding of anti-CGRP antibodies. Different variants of human α-CGRP with single alanine substitutions were generated by peptide synthesis. Their amino acid sequences are shown in Table 4 along with all the other peptides used in the Biacore analysis. Affinities of Fab fragments of the anti-CGRP antibodies to these variants were determined using Biacore as described above. As shown in FIG. 1, all 12 antibodies target a C-terminal epitope, with amino acid F37 being the most crucial residue. Mutation of F37 to alanine significantly lowered the affinity or even completely knocked out binding of the anti-CGRP antibodies to the peptide. The next most important amino acid residue is G33, however, only the high affinity antibodies (7E9, 8B6, 10A8, and 7D11) were affected by alanine replacement at this position. Amino acid residue S34 also plays a significant, but lesser, role in the binding of these four high affinity antibodies.

TABLE 2

Characteristics of the anti-CGRP monoclonal antibodies' binding to human α-CGRP and their antagonist activity

| Antibodies | $K_D$ to human α-CGRP at 25° C. (nM) | $K_D$ to human α-CGRP at 37° C. (nM) | Cell-based blocking human α-CGRP binding to its receptor at 25° C. (measured by cAMP activation) | $IC_{50}$ (nM binding sites) at 25° C. (room temp.) measured in radioligand binding assay. |
|---|---|---|---|---|
| 7E9 | 1.0 | 0.9 | Yes | 2.5 |
| 8B6 | 1.1 | 1.2 | Yes | 4.0 |
| 10A8 | 2.1 | 3.0 | Yes | n.d. |
| 7D11 | 4.4 | 5.4 | Yes | n.d. |
| 6H2 | 9.3 | 42 | Yes | 12.9 |
| 4901 | 61 | 139 | Yes | 58 |
| 14E10 | 80 | 179 | Yes | n.d. |
| 9B8 | 85 | 183 | No | n.d. |
| 13C2 | 94 | 379 | No | n.d. |
| 14A9 | 148 | 581 | No | n.d. |
| 6D5 | 210 | 647 | No | n.d. |
| 1C5 | 296 | 652 | No | n.d. |

Note:
Antibody 4901 is commercially available (Sigma, Product No. C7113).
n.d. = not determined

TABLE 3

Characteristics of the anti-CGRP monoclonal antibodies' binding to rat α-CGRP and antagonist activity

| Antibodies | $K_D$ to rat α-CGRP at 37° C. (nM) | Cell-based blocking of binding of rat α-CGRP to its receptor at 25° C. (measured by cAMP activation) | In vivo blocking in saphenous nerve assay |
|---|---|---|---|
| 4901 | 3.4 | Yes | Yes |
| 7E9 | 47 | Yes | Yes |
| 6H2 | 54 | No | No |
| 8B6 | 75 | Yes | Yes |
| 7D11 | 218 | Yes | Yes |
| 10A8 | 451 | No | n.d. |
| 9B8 | 876 | No | n.d. |
| 14E10 | 922 | No | n.d. |
| 13C2 | >1000 | No | n.d. |
| 14A9 | >1000 | No | n.d. |
| 6D5 | >1000 | No | n.d. |
| 1C5 | >1000 | No | n.d. |

"n.d." indicates no test was performed for the antibody.

TABLE 4

Amino acid sequences of human α-CGRP fragments (SEQ ID NOS: 15-40) and related peptides (SEQ ID NOS: 41-47). All peptides are C-terminally amidated except SEQ ID NOS: 36-40. Residues in bold indicate point mutations.

| CGRP | Amino acid sequence | SEQ ID NO |
|---|---|---|
| 1-37 (WT) | ACDTATCVTHRLAGLLSRSGGVVKNNFVPTNVGSKAF | 15 |
| 8-37 | VTHRLAGLLSRSGGVVKNNFVPTNVGSKAF | 16 |
| 19-37 | SGGVVKNNFVPTNVGSKAF | 17 |
| P29A (19-37) | SGGVVKNNFVATNVGSKAF | 18 |

TABLE 4-continued

Amino acid sequences of human α-CGRP fragments (SEQ ID NOS: 15-40) and related peptides (SEQ ID NOS: 41-47). All peptides are C-terminally amidated except SEQ ID NOS: 36-40. Residues in bold indicate point mutations.

| CGRP | Amino acid sequence | SEQ ID NO |
|---|---|---|
| K35A (19-37) | SGGVVKNNFVPTNVGSAAF | 19 |
| K35E (19-37) | SGGVVKNNFVPTNVGSEAF | 20 |
| K35M (19-37) | SGGVVKNNFVPTNVGSMAF | 21 |
| K35Q (19-37) | SGGVVKNNFVPTNVGSQAF | 22 |
| F37A (19-37) | SGGVVKNNFVPTNVGSKAA | 23 |
| 25-38A | NNFVPTNVGSKAFA | 24 |
| 25-37 | NNFVPTNVGSKAF | 25 |
| F27A (25-37) | NNAVPTNVGSKAF | 26 |
| V28A (25-37) | NNFAPTNVGSKAF | 27 |
| P29A (25-37) | NNFVATNVGSKAF | 28 |
| T30A (25-37) | NNFVPANVGSKAF | 29 |
| N31A (25-37) | NNFVPTAVGSKAF | 30 |
| V32A (25-37) | NNFVPTNAGSKAF | 31 |
| G33A (25-37) | NNFVPTNVASKAF | 32 |
| S34A (25-37) | NNFVPTNVGAKAF | 33 |
| F37A (25-37) | NNFVPTNVGSKAA | 34 |
| 26-37 | NFVPTNVGSKAF | 35 |
| 19-37-COOH | SGGVVKNNFVPTNVGSKAF | 36 |
| 19-36-COOH | SGGVVKNNFVPTNVGSKA | 37 |
| 1-36-COOH | ACDTATCVTHRLAGLLSRSGGVVKNNFVPTNVGSKA | 38 |
| 1-19-COOH | ACDTATCVTHRLAGLLSRS | 39 |
| 1-13-COOH | ACDTATCVTHRLA | 40 |
| rat α (1-37) | SCNTATCVTHRLAGLLSRSGGVVKDNFVPTNVGSEAF | 41 |
| rat α (19-37) | SGGVVKDNFVPTNVGSEAF | 42 |
| human β (1-37) | ACNTATCVTHRLAGLLSRSGGMVKSNFVPTNVGSKAF | 43 |
| rat β (1-37) | SCNTATCVTHRLAGLLSRSGGVVKDNFVPTNVGSKAF | 44 |
| Human calcitonin (1-32) | CGNLSTCMLGTYTQDFNKFHTFPQTAIGVGAP | 45 |
| Human amylin (1-37) | KCNTATCATQRLANFLVHSSNNFGAILSSTNVGSNTY | 46 |
| Human adrenomedullin (1-52) | YRQSMNNFQGLRSFGCRFGTCTVQKLAHQIYQFTDKDKDNVAPRSKISPQGY | 47 |

Example 2: Screening of Anti-CGRP Antagonist Antibodies Using In Vitro Assays

Murine anti-CGRP antibodies were further screened for antagonist activity in vitro using cell based cAMP activation assay and binding assay.

Antagonist activity measured by cAMP assay. Five microliters of human or rat α-CGRP (final concentration 50 nM) in the presence or absence of an anti-CGRP antibody (final concentration 1-3000 nM), or rat α-CGRP or human α-CGRP (final concentration 0.1 nM-10 μM; as a positive control for c-AMP activation) was dispensed into a 384-well plate (Nunc, Cat. No. 264657). Ten microliters of cells (human SK-N-MC if human α-CGRP is used, or rat L6 from ATCC if rat α-CGRP is used) in stimulation buffer (20 mM HEPES, pH 7.4, 146 mM NaCl, 5 mM KCl, 1 mM $CaCl_2$), 1 mM $MgCl_2$, and 500 μM 3-Isobutyl-1-methylxanthine (IBMX)) were added into the wells of the plate. The plate was incubated at room temperature for 30 minutes.

After the incubation, cAMP activation was performed using HitHunter™ Enzyme Fragment Complementation Assay (Applied Biosystems) following manufacture's instruction. The assay is based on a genetically engineered β-galactosidase enzyme that consists of two fragments-termed Enzyme Acceptor (EA) and Enzyme Donor (ED). When the two fragments are separated, the enzyme is inactive. When the fragments are together they can recombine spontaneously to form active enzyme by a process called complementation. The EFC assay platform utilizes an ED-CAMP peptide conjugate in which CAMP is recognized by anti-cAMP. This ED fragment is capable of reassociation with EA to form active enzyme. In the assay, anti-cAMP antibody is optimally titrated to bind ED-CAMP conjugate and inhibit enzyme formation. Levels of CAMP in cell lysate samples compete with ED-CAMP conjugate for binding to the anti-cAMP antibody. The amount of free ED conjugate in the assay is proportional to the concentration of cAMP. Therefore, CAMP is measured by the formation of active enzyme that is quantified by the turnover of β-galactosidase luminescent substrate. The CAMP activation assay was performed by adding 10 µl of lysis buffer and anti-cAMP antibody (1:1 ratio) following by incubation at room temperature for 60 min. Then 10 µl of ED-CAMP reagent was added into each well and incubated for 60 minutes at room temperature. After the incubation, 20 µl of EA reagent and CL mixture (containing the substrate) (1:1 ratio) was added into each well and incubated for 1-3 hours or overnight at room temperature. The plate was read at 1 second/well on PMT instrument or 30 seconds/place on imager. The antibodies that inhibit activation of cAMP by α-CGRP were identified (referred to as "yes") in Tables 2 and 3 above. Data in Tables 2 and 3 indicate that antibodies that demonstrated antagonist activity in the assay generally have high affinity. For example, antibodies having $K_D$ (determined at 25° C.) of about 80 nM or less to human α-CGRP or having $K_D$ (determined at 37° C.) of about 47 nM or less to rat α-CGRP showed antagonist activity in this assay.

Radioligand binding assay. Binding assay was performed to measure the $IC_{50}$ of anti-CGRP antibody in blocking the CGRP from binding to the receptor as described previously. Zimmermann et al., Peptides 16:421-4, 1995; Mallee et al., J. Biol. Chem. 277:14294-8, 2002. Membranes (25 µg) from SK-N-MC cells were incubated for 90 min at room temperature in incubation buffer (50 mM Tris-HCl, pH 7.4, 5 mM $MgCl_2$, 0.1% BSA) containing 10 pM $^{125}$I-human α-CGRP in a total volume of 1 mL. To determine inhibition concentrations ($IC_{50}$), antibodies or unlabeled CGRP (as a control), from a about 100 fold higher stock solution were dissolved at varying concentrations in the incubation buffer and incubated at the same time with membranes and 10 pM $^{125}$I-human α-CGRP. Incubation was terminated by filtration through a glass microfiber filter (GF/B, 1 µm) which had been blocked with 0.5% polyethylenimine. Dose response curves were plotted and $K_i$ values were determined by using the equation: $K_i=IC_{50}/(1+([ligand]/K_D))$; where the equilibrium dissociation constant $K_D=8$ pM for human α-CGRP to CGRP1 receptor as present in SK-N-MC cells, and $B_{max}=0.025$ pmol/mg protein. The reported $IC_{50}$ value (in terms of IgG molecules) was converted to binding sites (by multiplying it by 2) so that it could be compared with the affinities ($K_D$) determined by Biacore (see Table 2).

Table 2 shows the $IC_{50}$ of murine antibodies 7E9, 8B6, 6H2 and 4901. Data indicate that antibody affinity generally correlates with $IC_{50}$: antibodies with higher affinity (lower $K_D$ values) have lower $IC_{50}$ in the radioligand binding assay.

Example 3: Effect of Anti-CGRP Antagonist Antibodies on Skin Vasodilatation Induced by Stimulation of Rat Saphenous Nerve To test antagonist activity of anti-CGRP antibodies, effect of the antibodies on skin vasodilatation by stimulation of rat saphenous nerve was tested using a rat model described previously. Escott et al., Br. J. Pharmacol. 110:772-776, 1993. In this rat model, electrical stimulation of saphenous nerve induces release of CGRP from nerve endings, resulting in an increase in skin blood flow. Blood flow in the foot skin of male Sprague Dawley rats (170-300 g, from Charles River Hollister) was measured after saphenous nerve stimulation. Rats were maintained under anesthesia with 2% isoflurane. Bretylium tosylate (30 mg/kg, administered i.v.) was given at the beginning of the experiment to minimize vasoconstriction due to the concomitant stimulation of sympathetic fibers of the saphenous nerve. Body temperature was maintained at 37° C. by the use of a rectal probe thermostatically connected to a temperature controlled heating pad. Compounds including antibodies, positive control (CGRP 8-37), and vehicle (PBS, 0.01% Tween 20) were given intravenously through the right femoral vein, except for the experiment shown in FIG. 3, the test compound and the control were injected through tail vein, and for experiments shown in FIGS. 2A and 2B, antibodies 4901 and 7D11 were injected intraperitoneally (IP). Positive control compound CGRP 8-37 (vasodilatation antagonist), due to its short half-life, was given 3-5 min before nerve stimulation at 400 nmol/kg (200 µl). Tan et al., Clin. Sci. 89:656-73, 1995. The antibodies were given in different doses (1 mg/kg, 2.5 mg/kg, 5 mg/kg, 10 mg/kg, and 25 mg/kg).

For experiments shown in FIGS. 2A and 2B, antibody 4901 (25 mg/kg), antibody 7D11 (25 mg/kg), or vehicle control (PBS with 0.01% Tween 20) was administered intraperitoneally (IP) 72 hours before the electrical pulse stimulation. For experiment shown in FIG. 3, antibody 4901 (1 mg/kg, 2.5 mg/kg, 5 mg/kg, or 25 mg/kg) or vehicle control (PBS with 0.01% Tween 20) was administered intravenously 24 hours before the electrical pulse stimulation. After administration of the antibodies or vehicle control, the saphenous nerve of the right hindlimb was exposed surgically, cut proximally and covered with plastic wrap to prevent drying. A laser Doppler probe was placed over the medio-dorsal side of the hindpaw skin, which is the region innervated by the saphenous nerve. Skin blood flow, measured as blood cell flux, was monitored with a laser Doppler flow meter. When a stable base-line flux (less than 5% variation) was established for at least 5 minutes, the nerve was placed over platinum bipolar electrodes and electrically stimulated with 60 pulses (2 Hz, 10 V, 1 ms, for 30 seconds) and then again 20 minutes later. Cumulative change in skin blood flow was estimated by the area under the flux-time curve (AUC, which is equal to change in flux multiplied by change in time) for each flux response to electrical pulse stimulation. The average of the blood flow response to the two stimulations was taken. Animals were kept under anesthesia for a period of one to three hours.

As shown in FIG. 2A and FIG. 2B, blood flow increase stimulated by applying electronic pulses on saphenous nerve was inhibited by the presence of CGRP 8-37 (400 nmol/kg, administered i.v.), antibody 4901 (25 mg/kg, administered ip), or antibody 7D11 (25 mg/kg, administered ip) as compared to the control. CGRP 8-37 was administered 3-5 minutes before the saphenous nerve stimulation; and antibodies were administered 72 hours before the saphenous nerve stimulation. As shown in FIG. 3, blood flow increase stimulated by applying electronic pulses on saphenous nerve was inhibited by the presence of antibody 4901 at different doses (1 mg/kg, 2.5 mg/kg, 5 mg/kg, and 25 mg/kg) administered intravenously at 24 hours before the saphenous nerve stimulation.

For experiments shown in FIGS. 4A and 4B, saphenous nerve was exposed surgically before antibody administration. The saphenous nerve of the right hindlimb was exposed surgically, cut proximally and covered with plastic wrap to prevent drying. A laser Doppler probe was placed over the medio-dorsal side of the hindpaw skin, which is the region innervated by the saphenous nerve. Skin blood flow, measured as blood cell flux, was monitored with a laser Doppler flow meter. Thirty to forty-five minutes after bretylium tosylate injection, when a stable base-line flux (less than 5% variation) was established for at least 5 minutes, the nerve was placed over platinum bipolar electrodes and electrically stimulated (2 Hz, 10V, 1 ms, for 30 seconds) and again 20 minutes later. The average of the blood flow flux response to these two stimulations was used to establish the baseline response (time 0) to electrical stimulation. Antibody 4901 (1 mg/kg or 10 mg/kg), antibody 7E9 (10 mg/kg), antibody 8B6 (10 mg/kg), or vehicle (PBS with 0.01% Tween 20) were then administered intravenously (i.v.). The nerve was subsequently stimulated (2 Hz, 10V, 1 ms, for 30 see) at 30 minutes, 60 minutes, 90 minutes, and 120 minutes after antibody or vehicle administration. Animals were kept under anesthesia for a period of approximately three hours. Cumulative change in skin blood flow was estimated by the area under the flux-time curve (AUC, which is equal to change in flux multiplied by change in time) for each flux response to electrical pulse stimulations.

As shown in FIG. 4A, blood flow increase stimulated by applying electronic pulses on saphenous nerve was significantly inhibited by the presence of antibody 4901 1 mg/kg administered i.v., when electronic pulse stimulation was applied at 60 minutes, 90 minutes, and 120 minutes after the antibody administration, and blood flow increase stimulated by applying electronic pulses on saphenous nerve was significantly inhibited by the presence of antibody 4901 10 mg/kg administered i.v., when electronic pulse stimulation was applied at 30 minutes, 60 minutes, 90 minutes, and 120 minutes after the antibody administration. FIG. 4B shows that blood flow increase stimulated by applying electronic pulses on saphenous nerve was significantly inhibited by the presence of antibody 7E9 (10 mg/kg, administered i.v.) when electronic pulse stimulation was applied at 30 min, 60 min, 90 min, and 120 min after antibody administration, and by the presence of antibody 8B6 (10 mg/kg, administered i.v.) when electronic pulse stimulation was applied at 30 min after antibody administration.

These data indicate that antibodies 4901, 7E9, 7D11, and 8B6 are effective in blocking CGRP activity as measured by skin vasodilatation induced by stimulation of rat saphenous nerve.

Example 4. Characterization of Anti-CGRP Antibody G1 and its Variants

Amino acid sequences for the heavy chain variable region and light chain variable region of anti-CGRP antibody G1 are shown in FIG. 5. The following methods were used for expression and characterization of antibody G1 and its variants.

Expression vector used. Expression of the Fab fragment of the antibodies was under control of an IPTG inducible lacZ promoter similar to that described in Barbas (2001) Phage display: a laboratory manual, Cold Spring Harbor, NY, Cold Spring Harbor Laboratory Press pg. 2.10. Vector pComb3X), however, modifications included addition and expression of the following additional domains: the human Kappa light chain constant domain and the CH1 constant domain of IgG2 human immunoglobulin, Ig gamma-2 chain C region, protein accession number P01859; Immunoglobulin kappa light chain (*Homo sapiens*), protein accession number CAA09181.

Small scale Fab preparation. From *E. coli* transformed (either using electroporation-competent TG1 cells or chemically-competent Top 10 cells) with a Fab library, single colonies were used to inoculate both a master plate (agar LB+carbenicillin (50 µg/mL)+2% glucose) and a working plate (2 mL/well, 96-well/plate) where each well contained 1.5 mL LB+carbenicillin (50 µg/mL)+2% glucose. A gas permeable adhesive seal (ABgene, Surrey, UK) was applied to the plate. Both plates were incubated at 30° C. for 12-16 hours; the working plate was shaken vigorously. The master plate was stored at 4° C. until needed, while the cells from the working plate were pelleted (4000 rpm, 4° C., 20 minutes) and resuspended in 1.0 mL LB+carbenicillin (50 µg/mL)+0.5 mM IPTG to induce expression of Fabs by vigorous shaking for 5 hours at 30° C. Induced cells were centrifuges at 4000 rpm, 4° C. for 20 minutes and resuspended in 0.6 mL Biacore HB-SEP buffer (10 mM HEPES pH 7.4, 150 mM NaCl, 3 mM EDTA, 0.005% v/v P20). Lysis of HB-SEP resuspended cells was accomplished by freezing (−80° C.) and then thawing at 37° C. Cell lysates were centrifuged at 4000 rpm, 4° C. for 1 hour to separate the debris from the Fab-containing supernatants, which were subsequently filtered (0.2 µm) using a Millipore MultiScreen Assay System 96-Well Filtration Plate and vacuum manifold. Biacore was used to analyze filtered supernatants by injecting them across CGRPs on the sensor chip. Affinity-selected clones expressing Fabs were rescued from the master plate, which provided template DNA for PCR, sequencing, and plasmid preparation.

Large scale Fab preparation. To obtain kinetic parameters, Fabs were expressed on a larger scale as follows. Erlenmeyer flasks containing 150 mL LB+carbenicillin (50 µg/mL)+2% glucose were inoculated with 1 mL of a "starter" overnight culture from an affinity-selected Fab-expressing *E. coli* clone. The remainder of the starter culture (~3 mL) was used to prepare plasmid DNA (QIAprep mini-prep, Qiagen kit) for sequencing and further manipulation. The large culture was incubated at 30° C. with vigorous shaking until an $OD_{600\ nm}$ of 1.0 was attained (typically 12-16 h). The cells were pelleted by centrifuging at 4000 rpm, 4° C. for 20 minutes, and resuspended in 150 mL LB+carbenicillin (50 µg/mL)+0.5 mM IPTG. After 5 hours expression at 30° C., cells were pelleted by centrifuging at 4000 rpm, 4° C. for 20 minutes, resuspended in 10 mL Biacore HBS-EP buffer, and lysed using a single freeze (−80° C.)/thaw (37° C.) cycle. Cell lysates were pelleted by centrifuging at 4000 rpm, 4° C. for one hour, and the supernatant was collected and filtered (0.2 µm). Filtered supernatants were loaded onto Ni-NTA superflow sepharose (Qiagen, Valencia, CA) columns equilibrated with PBS, pH 8, then washed with 5 column volumes of PBS, pH 8. Individual Fabs eluted in different fractions with PBS (pH 8)+300 mM Imidazole. Fractions containing Fabs were pooled and dialyzed in PBS, then quantified by ELISA prior to affinity characterization.

Full antibody preparation. For expression of full antibodies, heavy and light chain variable regions were cloned in mammalian expression vectors and transfected using lipofectamine into HEK 293 cells for transient expression. Antibodies were purified using protein A using standard methods.

Vector pDb.CGRP.hFcGI is an expression vector comprising the heavy chain of the G1 antibody, and is suitable for transient or stable expression of the heavy chain. Vector pDb.CGRP.hFcGI has nucleotide sequences corresponding to the following regions: the murine cytomegalovirus promoter region (nucleotides 7-612); a synthetic intron (nucleotides 613-1679); the DHFR coding region (nucleotides 688-1253); human growth hormone signal peptide (nucleotides 1899-1976); heavy chain variable region of G1 (nucleotides 1977-2621); human heavy chain IgG2 constant region containing the following mutations: A330P331 to S330S331 (amino acid numbering with reference to the wildtype IgG2 sequence; see Eur. J. Immunol. (1999) 29:2613-2624). Vector pDb.CGRP.hFcGI was deposited at the ATCC on Jul. 15, 2005, and was assigned ATCC Accession No. PTA-6867.

Vector pEb. CGRP.hKGI is an expression vector comprising the light chain of the G1 antibody, and is suitable for transient expression of the light chain. Vector pEb.CGRP.hKGI has nucleotide sequences corresponding to the following regions: the murine cytomegalovirus promoter region (nucleotides 2-613); human EF-1 intron (nucleotides 614-1149); human growth hormone signal peptide (nucleotides 1160-1237); antibody G1 light chain variable region (nucleotides 1238-1558); human kappa chain constant region (nucleotides 1559-1882). Vector pEb.CGRP.hKGI was deposited at the ATCC on Jul. 15, 2005, and was assigned ATCC Accession No. PTA-6866.

Biacore assay for affinity determination. Affinities of G1 monoclonal antibody and its variants were determined at either 25° C. or 37° C. using the BIACORE3000™ surface plasmon resonance (SPR) system (Biacore, INC, Piscataway NJ). Affinity was determined by capturing N-terminally biotinylated CGRP or fragments via pre-immobilized streptavidin (SA sensor chip) and measuring the binding kinetics of antibody G1 Fab fragments or variants titrated across the CGRP or fragment on the chip. All Biacore assays were conducted in HBS-EP running buffer (10 mM HEPES pH 7.4, 150 mM NaCl, 3 mM EDTA, 0.005% v/v polysorbate P20). CGRP surfaces were prepared by diluting the N-biotinylated CGRP to a concentration of less than 0.001 mg/mL into HBS-EP buffer and injecting it across the SA sensor chip using variable contact times. Low capacity surfaces, corresponding to capture levels <50 response units (RU) were used for high-resolution kinetic studies, whereas high capacity surfaces (about 800 RU of captured CGRP) were used for concentration studies, screening, and solution affinity determinations. Kinetic data were obtained by diluting antibody G1 Fab serially in two- or three-fold increments to concentrations spanning 1 uM-0.1 nM (aimed at 0.1-10× estimated $K_D$). Samples were typically injected for 1 minute at 100 μL/min and dissociation times of at least 10 minutes were allowed. After each binding cycle, surfaces were regenerated with 25 mM NaOH in 25% v/v ethanol, which was tolerated over hundreds of cycles. An entire titration series (typically generated in duplicate) was fit globally to a 1:1 Langmuir binding model using the BIAevaluation program. This returned a unique pair of association and dissociation kinetic rate constants (respectively, $k_{on}$ and $k_{off}$) for each binding interaction, whose ratio gave the equilibrium dissociation constant ($K_D = k_{off}/k_{on}$). Affinities ($K_D$ values) determined in this way are listed in Tables 6 and 7.

High-resolution analysis of binding interactions with extremely slow offrates. For interactions with extremely slow offrates (in particular, antibody G1 Fab binding to human α-CGRP on the chip at 25° C.), affinities were obtained in a two-part experiment. The protocol described above was used with the following modifications. The association rate constant ($k_{on}$) was determined by injecting a 2-fold titration series (in duplicate) spanning 550 nM-1 nM for 30 seconds at 100 L/min and allowing only a 30 second dissociation phase. The dissociation rate constant ($k_{off}$) was determined by injecting three concentrations (high, medium, and low) of the same titration series in duplicate for 30 seconds and allowing a 2-hour dissociation phase. The affinity ($K_D$) of each interaction was obtained by combining the $k_{on}$ and $k_{off}$ values obtained in both types of experiments, as shown in Table 5.

Determining solution affinity by Biacore. The solution affinity of antibody G1 for rat α-CGRP and F37A (19-37) human α-CGRP was measured by Biacore at 37° C. A high capacity CGRP chip surface was used (the high-affinity human α-CGRP was chosen for detection purposes) and HBS-EP running buffer was flowed at 5 μL/min. Antibody G1 Fab fragment at a constant concentration of 5 nM (aimed to be at or below the expected $K_D$ of the solution-based interaction) was pre-incubated with competing peptide, either rat α-CGRP or F37A (19-37) human α-CGRP, at final concentrations spanning 1 nM to 1 μM in 3-fold serial dilutions. Antibody G1 Fab solutions in the absence or presence of solution-based competing peptide, were injected across CGRP on the chip and the depletion of binding responses detected at the chip surface as a result of solution competition was monitored. These binding responses were converted to "free Fab concentrations" using a calibration curve, which was constructed by titrating antibody G1 Fab alone (5, 2.5, 1.25, 0.625, 0.325 and 0 nM) across the CGRP on the chip. "Free Fab concentrations" were plotted against the concentration of competing solution-based peptide used to generate each data point and fit to a solution affinity model using the BIAevaluation software. The solution affinities determined (indirectly) in this way are shown in Tables 5 and 7 and were used to validate the affinities obtained when Fabs are injected directly across N-biotinylated CGRPs on a SA chip. The close agreement between the affinities determined by these two methods confirms that tethering an N-biotinylated version of the CGRP to the chip does not alter its native solution binding activity.

Table 5 below shows the binding affinities of antibody G1 to human α-CGRP, human β-CGRP, rat α-CGRP, and rat β-CGRP determined by Biacore, by flowing Fab fragments across N-biotinylated CGRPs on a SA chip. To better resolve the affinities of binding interactions with extremely slow offrates, affinities were also determined in a two-part experiment to complement this assay orientation, the solution affinity of the rat α-CGRP interaction was also determined (as described above). The close agreement of the affinities measured in both assay orientations confirms that the binding affinity of the native rat α-CGRP in solution is not altered when it is N-biotinylated and tethered to a SA chip.

TABLE 5

Binding affinities of antibody G1 Fabs titrated across CGRPs on the chip

| CGRPs on chip | Temp. (° C.) | $k_{on}$ (1/Ms) | $k_{off}$ (1/s) | $K_D$ (nM) |
|---|---|---|---|---|
| Human α-CGRP | 25 | $1.86 \times 10^5$ | $7.80 \times 10^{-6}$ | 0.042 (7%, n = 4)* |
| Human α-CGRP | 37 | $5.78 \times 10^5$ | $3.63 \times 10^{-5}$ | 0.063 (4%, n = 2)* |
| Human β-CGRP | 37 | $4.51 \times 10^5$ | $6.98 \times 10^{-5}$ | 0.155 |
| Rat α-CGRP | 25 | $5.08 \times 10^4$ | $6.18 \times 10^{-5}$ | 1.22 (12%, n = 2)* |
| Rat α-CGRP | 37 | $1.55 \times 10^5$ | $3.99 \times 10^{-4}$ | 2.57* (Solution $K_D$ = 10 (50%, n = 4)**) |
| Rat β-CGRP | 37 | $5.16 \times 10^5$ | $7.85 \times 10^{-5}$ | 0.152 |

*Affinities for α-CGRPs (rat and human) were determined in a high-resolution two-part experiment, in which the dissociation phase was monitored for 2 hours (the values for $k_{on}$, $k_{off}$, and $K_D$ represent the average of n replicate experiments with the standard deviation expressed as a percent variance). Affinities for β-CGRPs (rat and human) were determined by global analysis using only a 20-min dissociation phase, which was not accurate enough to quantify their extremely offrates (their offrates are likely slower than stated here and therefore their affinities are likely even higher). Antibody G1 Fab dissociated extremely slowly from all CGRPs (except α-rat CGRP) with offrates that approached the resolution limit of the Biacore assay (especially at 25° C.).

**Solution affinity determined by measuring the depletion of binding responses detected at CGRP on the chip for antibody G1 Fab pre-incubated with solution-based rat-CGRP competitor.

Table 6 below shows antibodies having the amino acid sequence variation as compared to antibody G1 and their affinities to both rat α-CGRP and human α-CGRP. All amino acid substitutions of the variants shown in Table 6 are described relative to the sequence of G1. The binding affinities of Fab fragments were determined by Biacore by flowing them across CGRPs on a SA chip.

TABLE 6

Amino acid sequences and binding affinity data for antibody G1 variants determined at 37° C. by Biacore.

| Clone | L1 | L2 | H2 | HC-FW3 | α-rat $k_{off}$(1/s) | α-rat $K_D$ (nM) | α-human $k_{off}$(1/s) | α-human $K_D$ (nM) |
|---|---|---|---|---|---|---|---|---|
| G1 | | | | | $3.99 \times 10^{-4}$ | 2.57 | $3.63 \times 10^{-5}$ | 0.063 |
| M1 | | | | A100L | $1.10 \times 10^{-3}$ | | $1.73 \times 10^{-4}$ | |
| M2 | | | | L99A A100R | $2.6 \times 10^{-3}$ | 58 | $3.1 \times 10^{-4}$ | 3 |
| M3 | | | | L99A A100S | $2.0 \times 10^{-3}$ | 61 | $2.1 \times 10^{-4}$ | 1.7 |
| M4 | | | | L99A A100V | $1.52 \times 10^{-3}$ | 84.4 | $6.95 \times 10^{-5}$ | 0.43 |
| M5 | | | | L99A A100Y | $7.35 \times 10^{-4}$ | 40.8 | $3.22 \times 10^{-5}$ | 0.20 |
| M6 | | | | L99N | $7.84 \times 10^{-4}$ | 43.6 | $1.33 \times 10^{-4}$ | 0.83 |
| M7 | | | | L99N A100C | $9.18 \times 10^{-4}$ | 51.0 | $2.43 \times 10^{-4}$ | 1.52 |
| M8 | | | | L99N A100G | $7.45 \times 10^{-4}$ | 41.4 | $9.20 \times 10^{-5}$ | 0.58 |
| M9 | | | | L99N A100Y | n.d. | n.d. | $1.00 \times 10^{-5}$ | 0.06 |
| M10 | | | | L99S A100S | $1.51 \times 10^{-3}$ | 83.9 | $1.73 \times 10^{-4}$ | 1.08 |
| M11 | | | | L99S A100T | $4.83 \times 10^{-3}$ | 268.3 | $2.83 \times 10^{-4}$ | 1.77 |
| M12 | | | | L99S A100V | $1.94 \times 10^{-3}$ | 107.8 | $1.01 \times 10^{-4}$ | 0.63 |
| M13 | | | | L99T A100G | $1.84 \times 10^{-3}$ | 102.2 | $1.86 \times 10^{-4}$ | 1.16 |
| M14 | | | | L99T A100K | n.d. | n.d. | $1.00 \times 10^{-5}$ | 0.06 |
| M15 | | | | L99T A100P | $1.15 \times 10^{-3}$ | 63.9 | $1.58 \times 10^{-5}$ | 0.10 |
| M16 | | | | L99T A100S | $9.96 \times 10^{-4}$ | 55.3 | $1.65 \times 10^{-4}$ | 1.03 |
| M17 | | | | L99T A100V | $2.06 \times 10^{-3}$ | 114.4 | $1.85 \times 10^{-4}$ | 1.16 |
| M18 | | | | L99V A100G | $1.22 \times 10^{-3}$ | 67.8 | $7.03 \times 10^{-5}$ | 0.44 |
| M19 | | | | L99V A100R | n.d. | n.d. | $1.00 \times 10^{-5}$ | 0.06 |
| M20 | R28W | | | L99R A100L | $1.44 \times 10^{-3}$ | 80.0 | $1.36 \times 10^{-4}$ | 0.85 |
| M21 | R28W | | | L99S | $6.95 \times 10^{-4}$ | 15.2 | $1.42 \times 10^{-4}$ | 1.23 |
| M22 | R28W | | | L99T | $1.10 \times 10^{-3}$ | 61.1 | $1.16 \times 10^{-4}$ | 0.73 |
| M23 | R28G | | | L99T A100V | $7.99 \times 10^{-4}$ | 44.4 | $1.30 \times 10^{-4}$ | 0.81 |
| M24 | R28L | | | L99T A100V | $1.04 \times 10^{-3}$ | 57.8 | $1.48 \times 10^{-4}$ | 0.93 |
| M25 | R28N | | | L99T A100V | $1.4 \times 10^{-3}$ | 76 | $1.4 \times 10^{-4}$ | 1.3 |
| M26 | R28N | | A57G | L99T A100V | $9.24 \times 10^{-4}$ | 51.3 | $1.48 \times 10^{-4}$ | 0.93 |

TABLE 6-continued

Amino acid sequences and binding affinity data for antibody G1 variants determined at 37° C. by Biacore.

| Clone | L1 | L2 | H2 | HC-FW3 | α-rat $k_{off}$(1/s) | α-rat $K_D$ (nM) | α-human $k_{off}$(1/s) | α-human $K_D$ (nM) |
|---|---|---|---|---|---|---|---|---|
| M27 | R28N T30A | | | L99T A100V | $3.41 \times 10^{-3}$ | 189.4 | $3.57 \times 10^{-4}$ | 2.23 |
| M28 | R28N T30D | | E54R A57N | L99T A100V | $1.25 \times 10^{-3}$ | 69.4 | $9.96 \times 10^{-5}$ | 0.62 |
| M29 | R28N T30G | | | L99T A100V | $3.59 \times 10^{-3}$ | 199.4 | $3.80 \times 10^{-4}$ | 2.38 |
| M30 | R28N T30G | | E54K A57E | L99T A100V | $6.38 \times 10^{-3}$ | 354.4 | $5.90 \times 10^{-4}$ | 3.69 |
| M31 | R28N T30G | | E54K A57G | L99T A100V | $3.61 \times 10^{-3}$ | 200.6 | $3.47 \times 10^{-4}$ | 2.17 |
| M32 | R28N T30G | | E54K A57H | L99T A100V | $2.96 \times 10^{-3}$ | 164.4 | $2.71 \times 10^{-4}$ | 1.69 |
| M33 | R28N T30G | | E54K A57N S58G | L99T A100V | $9.22 \times 10^{-3}$ | 512.2 | $7.50 \times 10^{-4}$ | 4.69 |
| M34 | R28N T30G | | E54K A57N S58T | L99T A100V | $2.17 \times 10^{-3}$ | 120.6 | $6.46 \times 10^{-4}$ | 4.04 |
| M35 | R28N T30G | | E54K A57S | L99T A100V | $3.99 \times 10^{-3}$ | 221.7 | $3.39 \times 10^{-4}$ | 2.12 |
| M36 | R28N T30R | | | L99T A100V | $4.79 \times 10^{-3}$ | 266.1 | $2.39 \times 10^{-4}$ | 1.49 |
| M37 | R28N T30S | | A57G | L99T A100V | $1.45 \times 10^{-3}$ | 80.6 | $2.26 \times 10^{-4}$ | 1.41 |
| M38 | R28N T30W | | | L99T A100V | $5.11 \times 10^{-3}$ | 283.9 | $2.18 \times 10^{-4}$ | 1.36 |
| M39 | R28N | G50A L56T | A57N S58Y | L99T A100V | $9.95 \times 10^{-3}$ | 552.8 | $4.25 \times 10^{-4}$ | 2.66 |
| M40 | R28N | G50A L56T | E54K A57L | L99T A100V | 0.36 | 20000.0 | $1.28 \times 10^{-3}$ | 8.00 |
| M41 | R28N | G50A L56T | E54K A57N E64D | L99T A100V | $4.53 \times 10^{-3}$ | 251.7 | $2.10 \times 10^{-4}$ | 1.31 |
| M42 | R28N | G50A L56T | E54K A57N H61F | L99T A100V | $7.52 \times 10^{-3}$ | 417.8 | $4.17 \times 10^{-4}$ | 2.61 |
| M43 | R28N | G50A L56T | E54K A57N S58C | L99T A100V | $4.53 \times 10^{-3}$ | 251.7 | $2.63 \times 10^{-4}$ | 1.64 |
| M44 | R28N | G50A L56T | E54K A57N S58E | L99T A100V | $\underline{6.13 \times 10^{-3}}$ | $\underline{443}$ | $\underline{2.10 \times 10^{-4}}$ | $\underline{2.05}$ |
| M45 | R28N | G50A L56T | E54K A57N S58E E64D | L99T A100V | $\underline{5.58 \times 10^{-3}}$ | $\underline{259}$ | $\underline{2.11 \times 10^{-4}}$ | $\underline{1.85}$ |
| M46 | R28N | G50A L56T | E54K A57N S58E H61F | L99T A100V | $2.94 \times 10^{-3}$ | 163.3 | $5.39 \times 10^{-4}$ | 3.37 |
| M47 | R28N | G50A L56T | E54K A57N S58G | L99T A100V | $8.23 \times 10^{-3}$ | 457.2 | $3.32 \times 10^{-4}$ | 2.08 |
| M48 | R28N | G50A L56T | E54K A57N S58L | L99T A100V | 0.0343 | 1905.6 | $8.42 \times 10^{-4}$ | 5.26 |
| M49 | R28N | G50A L56T | E54K A57N S58Y H61F | L99T A100V | 0.0148 | 822.2 | $5.95 \times 10^{-4}$ | 3.72 |
| M50 | R28N | G50A L56T | E54K A57R | L99T A100V | $5.30 \times 10^{-3}$ | 294.4 | $4.06 \times 10^{-4}$ | 2.54 |
| M51 | R28N | L56I | E54K A57G | L99T A100V | $1.18 \times 10^{-3}$ | 65.6 | $1.31 \times 10^{-4}$ | 0.82 |
| M52 | R28N | L56I | E54K A57N S58A | L99T A100V | $2.29 \times 10^{-3}$ | 127.2 | $2.81 \times 10^{-4}$ | 1.76 |
| M53 | R28N | L56I | E54K A57N S58G | L99T A100V | $1.91 \times 10^{-3}$ | 106.1 | $3.74 \times 10^{-4}$ | 2.34 |
| M54 | R28N T30A | G50A | E54K A57N S58P | L99T A100V | $2.16 \times 10^{-3}$ | 120.0 | $1.79 \times 10^{-3}$ | 11.19 |

TABLE 6-continued

Amino acid sequences and binding affinity data for antibody G1 variants determined at 37° C. by Biacore.

| Clone | L1 | L2 | H2 | HC-FW3 | α-rat $k_{off}$(1/s) | α-rat $K_D$ (nM) | α-human $k_{off}$(1/s) | α-human $K_D$ (nM) |
|---|---|---|---|---|---|---|---|---|
| M55 | R28N T30A | L56S | E54K A57N S58E E64D | L99T A100V | $5.85 \times 10^{-3}$ | 325.0 | $4.78 \times 10^{-4}$ | 2.99 |
| M56 | R28N T30D | L56S | E54K A57N H61F | L99T A100V | $9.35 \times 10^{-3}$ | 519.4 | $4.79 \times 10^{-4}$ | 2.99 |
| M57 | R28N T30D | L56S | E54K A57N S58E | L99T A100V | 0.0104 | 1,200 | $3.22 \times 10^{-4}$ | 3.08 |
| M58 | R28N T30D | L56S | E54K A57N S58I H61F | L99T A100V | No binding | n.d. | $1.95 \times 10^{-3}$ | 12.19 |
| M59 | R28N T30D | L56S | E54K A57N S58N H61F | L99T A100V | 0.0123 | 683.3 | $5.24 \times 10^{-4}$ | 3.28 |
| M60 | R28N T30D | L56S | E54K A57N S58R H61F | L99T A100V | 0.0272 | 1511.1 | $9.11 \times 10^{-4}$ | 5.69 |
| M61 | R28N T30G | A51H | E54Q A57N H61F | L99T A100V | $5.21 \times 10^{-3}$ | 289.4 | $4.59 \times 10^{-4}$ | 2.87 |
| M62 | R28N T30G | A51H L56T | E54K A57N S58E | L99T A100V | $5.75 \times 10^{-3}$ | 242 | $5.57 \times 10^{-4}$ | 5.86 |
| M63 | R28N T30G | G50A | E54K A57N S58T | L99T A100V | $2.65 \times 10^{-3}$ | 147.2 | $1.50 \times 10^{-3}$ | 9.38 |
| M64 | R28N T30G | G50A | E54K A57N S58V | L99T A100V | 0.0234 | 1300.0 | $1.32 \times 10^{-3}$ | 8.25 |
| M65 | R28N T30G | G50A L56I | E54K A57C | L99T A100V | $4.07 \times 10^{-3}$ | 226.1 | $8.03 \times 10^{-4}$ | 5.02 |
| M66 | R28N T30G | L56I | E54K A57E | L99T A100V | $5.11 \times 10^{-3}$ | 283.9 | $5.20 \times 10^{-4}$ | 3.25 |
| M67 | R28N T30G | L56I | E54K A57F | L99T A100V | $1.71 \times 10^{-3}$ | 95.0 | $8.20 \times 10^{-4}$ | 5.13 |
| M68 | R28N T30G | L56I | E54K A57N S58D E64D | L99T A100V | $6.76 \times 10^{-3}$ | 375.6 | $4.28 \times 10^{-4}$ | 2.68 |
| M69 | R28N T30G | L56I | E54K A57N S58E | L99T A100V | $1.81 \times 10^{-3}$ | 100.6 | $7.33 \times 10^{-4}$ | 4.58 |
| M70 | R28N T30G | L56I | E54K A57S | L99T A100V | $6.07 \times 10^{-3}$ | 337.2 | $5.59 \times 10^{-4}$ | 3.49 |
| M71 | R28N T30G | L56I | E54K A57Y | L99T A100V | $2.12 \times 10^{-3}$ | 117.8 | $1.28 \times 10^{-3}$ | 8.00 |
| M72 | R28N T30G | L56S | E54K | L99T A100V | $3.95 \times 10^{-3}$ | 219.4 | $4.00 \times 10^{-4}$ | 2.50 |
| M73 | R28N T30G | L56S | E54K A57N S58Y E64D | L99T A100V | $3.00 \times 10^{-3}$ | 166.7 | $2.55 \times 10^{-4}$ | 1.59 |
| M74 | R28N T30G | L56S | E54K A57S | L99T A100V | $6.03 \times 10^{-3}$ | 335.0 | $5.97 \times 10^{-4}$ | 3.73 |
| M75 | R28N T30G | L56S | E54K A57V | L99T A100V | $1.87 \times 10^{-2}$ | 1038.9 | $1.16 \times 10^{-3}$ | 7.25 |
| M76 | R28N T30S | G50A L56T | A57G | L99T A100V | $1.16 \times 10^{-3}$ | 64.4 | $3.64 \times 10^{-4}$ | 2.28 |
| M77 | R28N T30S | G50A L56T | E54K A57D | L99T A100V | 0.0143 | 794.4 | $4.77 \times 10^{-4}$ | 2.98 |
| M78 | R28N T30S | G50A L56T | E54K A57N S58T | L99T A100V | 0.167 | 9277.8 | $1.31 \times 10^{-4}$ | 8.19 |
| M79 | R28N T30S | G50A L56T | E54K A57P | L99T A100V | 0.19 | 10555.6 | $1.29 \times 10^{-4}$ | 8.06 |
| M80 | R28N T30S | L56I | E54K A57N S58V | L99T A100V | 0.0993 | 5516.7 | $2.09 \times 10^{-4}$ | 13.06 |

TABLE 6-continued

Amino acid sequences and binding affinity data for antibody G1 variants determined at 37° C. by Biacore.

| Clone | L1 | L2 | H2 | HC-FW3 | α-rat $k_{off}$(1/s) | α-rat $K_D$ (nM) | α-human $k_{off}$(1/s) | α-human $K_D$ (nM) |
|---|---|---|---|---|---|---|---|---|
| M81 | R28N T30S | L56S | E54K A57N S58E | L99T A100V | $4.29 \times 10^{-3}$ | 238.3 | $4.90 \times 10^{-4}$ | 3.06 |
| M82 | R28N T30V | A51H L56T | A57N | L99T A100V | $6.99 \times 10^{-3}$ | 388.3 | $8.77 \times 10^{-4}$ | 5.48 |
| M83 | R28N T30V | A51H L56T | E54K A57N S58M H61F | L99T A100V | No binding | n.d. | $9.33 \times 10^{-4}$ | 5.83 |
| M84 | R28N T30V | A51H L56T | E54N A57N | L99T A100V | $1.76 \times 10^{-2}$ | 977.8 | $1.08 \times 10^{-3}$ | 6.75 |

Figure 6:
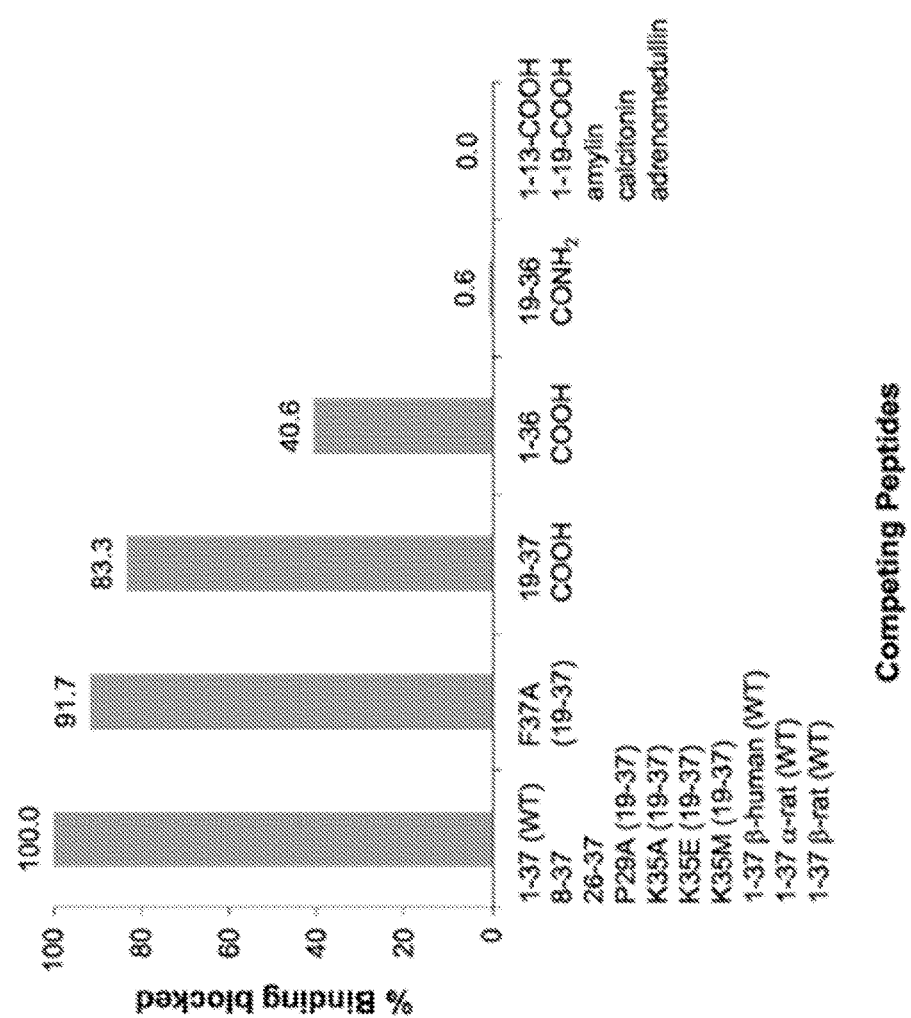
FIG. 6 shows epitope mapping of antibody G1 by peptide competition using Biacore. N-biotinylated human α-CGRP was captured on SA sensor chip. G1 Fab (50 nM) in the absence of a competing peptide or pre-incubated for 1 hour with 10 μM of a competing peptide was flowed onto the chip. Binding of G1 Fab to the human α-CGRP on the chip was measured. Y axis represents percentage of binding blocked by the presence of the competing peptide compared with the binding in the absence of the competing peptide.

All CDRs including both Kabat and Chothia CDRs. Amino acid residues are numbered sequentially (see FIG. 5). All clones have L3+H1+H3 sequences identical to G1. $K_D = k_{off}/k_{on}$. All $k_{off}$ values were determined in a screening mode except those that are underlined, which were obtained by global analysis of a Fab concentration series (G1 was analyzed in a high-resolution mode). Underlined $K_D$ values were therefore determined experimentally by measuring $k_{on}$. Other $k_{on}$ values were estimated to be the same as M25. n.d.=not determined To determine the epitope on human α-CGRP that is recognized by antibody G1, Biacore assays described above were used. Human α-CGRP was purchased as an N-biotinylated version to enable its high-affinity capture via SA sensor chips. The binding of G1 Fab fragment to the human α-CGRP on the chip in the absence or presence of a CGRP peptide was determined. Typically, a 2000:1 mol peptide/Fab solution (e.g., 10 µM peptide in 50 nM G1 Fab) was injected across human α-CGRP on the chip. FIG. 6 shows the percentage of binding blocked by competing peptide. Data shown in FIG. 6 indicate that peptides that block 100% binding of G1 Fab to human α-CGRP are 1-37 (WT), 8-37, 26-37, P29A (19-37), K35A (19-37), K35E (19-37), and K35M (19-37) of human α-CGRP; 1-37 of β-CGRP (WT); 1-37 of rat α-CGRP (WT); and 1-37 of rat β-CGRP (WT). All these peptides are amidated at the C-terminus. Peptides F37A (19-37) and 19-37 (the latter not amidated at the C-terminus) of human α-CGRP also blocked about 80% to 90% of binding of G1 Fab to human α-CGRP. Peptide 1-36 (not amidated at the C-terminus) of human α-CGRP blocked about 40% of binding of G1 Fab to human α-CGRP. Peptide fragment 19-36 (amidated at the C-terminus) of human α-CGRP; peptide fragments 1-13 and 1-19 of human α-CGRP (neither of which are amidated at the C-terminus); and human amylin, calcitonin, and adrenomedullin (all amidated at the C-terminus) did not compete with binding of G1 Fab to human α-CGRP on the chip. These data demonstrate that G1 targets a C-terminal epitope of CGRP and that both the identity of the most terminal residue (F37) and its amidation is important for binding.

Binding affinities of G1 Fab to variants of human α-CGRP (at 37° C.) was also determined. Table 7 below shows the affinities as measured directly by titrating G1 Fab across N-biotinylated human α-CGRP and variants on the chip. Data in Table 7 indicate that antibody G1 binds to a C-terminal epitope with F37 and G33 being the most important residues. G1 does not bind to CGRP when an extra amino acid residue (alanine) is added at the C-terminal (which is amidated).

TABLE 7

Binding affinities of G1 Fab to human α-CGRP and variants measured at 37° C. (see Table 4 for their amino acid sequences)

| CGRP on chip | $k_{on}$ (1/Ms) | $k_{off}$(1/s) | $K_D$ (nM) |
|---|---|---|---|
| 1-37 (WT) | $4.68 \times 10^5$ | $7.63 \times 10^{-5}$ | 0.16 (high resolution $K_D$ = 0.06) |
| 19-37 | $4.60 \times 10^5$ | $7.30 \times 10^{-5}$ | 0.16 |
| 25-37 | $3.10 \times 10^5$ | $8.80 \times 10^{-5}$ | 0.28 |
| F27A (25-37) | $3.25 \times 10^5$ | $1.24 \times 10^{-4}$ | 0.38 |
| V28A (25-37) | $3.32 \times 10^5$ | $9.38 \times 10^{-5}$ | 0.28 |
| P29A (25-37) | $2.26 \times 10^5$ | $1.78 \times 10^{-4}$ | 0.79 |
| T30A (25-37) | $1.79 \times 10^5$ | $8.41 \times 10^{-5}$ | 0.47 |
| N31A (25-37) | $2.17 \times 10^5$ | $1.14 \times 10^{-4}$ | 0.53 |
| V32A (25-37) | $2.02 \times 10^5$ | $3.46 \times 10^{-4}$ | 1.71 |
| G33A (25-37) | $2.07 \times 10^5$ | 0.0291 | 141 |
| S34A (25-37) | $2.51 \times 10^5$ | $7.64 \times 10^{-4}$ | 3.04 |
| K35A (19-37) | $2.23 \times 10^5$ | $2.97 \times 10^{-4}$ | 1.33 |
| K35E (19-37) | $5.95 \times 10^4$ | $5.79 \times 10^{-4}$ | 9.73 |
| K35M (19-37) | $2.63 \times 10^5$ | $1.34 \times 10^{-4}$ | 0.51 |
| K35Q (19-37) | $1.95 \times 10^5$ | $2.70 \times 10^{-4}$ | 1.38 |
| F37A (25-37) | $8.90 \times 10^4$ | $8.48 \times 10^{-3}$ | 95 (solution $K_D$ = 172 nM) |
| 38A (25-38A) | — | — | No binding detected |

The above data indicate that the epitope that antibody G1 binds is on the C-terminal end of human α-CGRP, and amino acids 33 and 37 on human α-CGRP are important for binding of antibody G1. Also, the amidation of residue F37 is important for binding.

Example 5. Clinical Study

A clinical study is conducted to evaluate the efficacy and safety of fremanezumab for prophylactic treatment of migraine in patients with inadequate response to prior preventive treatments. Fremanezumab (TEV-48125) is a fully humanized IgG 2a/kappa monoclonal antibody for administration by the subcutaneous route for the preventive treatment of migraine. Fremanezumab is a potent, selective calcitonin gene-related peptide (CGRP) binder that blocks both CGRP isoforms (α and β CGRP) from binding to the CGRP receptor.

Objectives

The primary objective of the study is to demonstrate the efficacy of fremanezumab administered as monthly and quarterly subcutaneous (sc) injections to adult patients with migraine with inadequate response to two to four classes of prior preventive treatments as compared with placebo.

The secondary objective of the study is to further evaluate the efficacy of fremanezumab administered as monthly and quarterly sc injections to adult patients with migraine with inadequate response to two to four classes of prior preventive treatments as compared with placebo.

A secondary objective of the study is to evaluate the safety and tolerability of fremanezumab administered as monthly and quarterly sc injections to adult patients with migraine with inadequate response to two to four classes of prior preventive treatments as compared with placebo.

The exploratory objectives are as follows:
- to further evaluate the efficacy of fremanezumab in adult migraine patients with inadequate response to two to four classes of prior preventive treatments
- to evaluate immunogenicity and impact of antidrug antibody (ADA) on clinical outcome
- to explore the correlation between pharmacokinetic parameters and efficacy of fremanezumab
- to explore the relationship between genetic polymorphisms, migraine onset/severity and efficacy and safety of fremanezumab Clinical Study Design A multicenter, randomized, double-blind, placebo-controlled, parallel-group study with an open-label period is conducted to evaluate the efficacy, safety, and tolerability of monthly and quarterly subcutaneous (sc) fremanezumab compared with placebo in patients with chronic migraine (CM) and episodic migraine (EM) with inadequate response to prior preventive treatments. The study will consist of a screening visit, a run-in period (28 days), a 12-week double-blind, placebo-controlled treatment period, a 12-week open-label period, and a follow-up visit 6.0 months after the last dose of fremanezumab for ADA blood sample collection. At the end of the open-label treatment period (4 weeks after the last dose) an end of treatment study visit (visit 8) will be scheduled and patients should return to the care of their treating physicians. Patients should be treated with standard of care after withdrawal from or termination of the 24-week treatment period/study, as appropriate.

Double-Blind Period

At the baseline visit (visit 2), patients are randomly assigned to a treatment group with fremanezumab (2 different dose regimens) or placebo in a 1:1:1 ratio as follows:
For patients with CM:
- sc administration of 675 mg of fremanezumab at visit 2 followed by monthly sc administration of 225 mg of fremanezumab for 2 months or
- sc administration of 675 mg of fremanezumab at visit 2 followed by monthly sc administration of matching placebo for 2 months or
- 3 monthly doses of matching placebo For patients with EM:
- sc administration of fremanezumab at 225 mg plus 2 matching placebo injections as first dose followed by monthly sc administration of 225 mg of fremanezumab for 2 months or
- sc administration of fremanezumab at 675 mg as first dose followed by monthly sc administration of matching placebo for 2 months or
- 3 monthly doses of matching placebo Open-Label Period After visit 4, all patients completing the double-blind period enter the open-label period. All patients (CM and EM) will receive sc 225 mg of fremanezumab monthly for 3 months. (visits 5, 6, and 7).

Randomization and treatment assignment for the double-blind period is performed using electronic interactive response technology (IRT). The study is stratified based on CM or EM, gender, country, and a special treatment failure group defined as patients who must have had inadequate response to valproic acid. In addition, patients in the special treatment failure group must have had inadequate response to 2 to 3 other classes of migraine preventive medications, as defined herein. The proportion of CM and EM patients in the study should be approximately 50:50 in each subgroup.

The open-label period will not be randomized as all patients will receive the same monthly dose (225 mg fremanezumab).

CM is Defined as:
Patient Fulfills the Following Criteria for CM in Prospectively Collected Baseline Information During the 28-Day Run-In Period:
  Headache occurring on ≥15 days
  On ≥8 days, fulfilling any of the following:
    ICHD-3 diagnostic criteria C and D for 1.1 Migraine without aura
    ICHD-3 criteria B and C for 1.2 Migraine with aura
    Probable migraine (a migraine subtype where only 1 migraine criterion is missing)
    The patient used a triptan or ergot derivative to treat established headache.

EM is Defined as:
The Patient Fulfills the Following Criteria for EM in Prospectively Collected Baseline Information During the 28-Day Run-In Period:
  Headache occurring ≥6 days but <15 days
  On ≥4 days, fulfilling any of the following:
    ICHD-3 diagnostic criteria C and D for 1.1 Migraine without aura
    ICHD-3 criteria B and C for 1.2 Migraine with aura
    Probable migraine (a migraine subtype where only 1 migraine criterion is missing)
    The patient used a triptan or ergot derivative to treat an established headache Blinded treatment is administered sc once a month (approximately every 28 days) for a total of 3 doses (visits 2, 3, and 4) and open-label treatment is administered for a total of 3 doses (visits 5, 6, and 7). Final study assessments are performed at visit 8 (end-of-treatment [EOT] visit), approximately 4 weeks after administration of last dose of fremanezumab. A follow-up visit is scheduled 6.0 months (>5 half-lives) after the last study drug administration for ADA blood sampling. Patients who discontinue early will have the follow-up visit 6.0 months after the last dose. The total duration of patient participation in the study is planned to be 50 weeks including a run-in period lasting 28 days, a double-blind treatment period lasting 12 weeks, an open-label period lasting 12 weeks, and 1 follow-up visit at week 46. Patients are expected to complete the entire duration of the study, including the open-label period and the follow-up visit.

The end of study is defined as the last visit of the last patient (follow-up visit, visit 9). However, an interim database lock occurs following the end of the double-blind treatment period of the last patient for analysis of that portion of the study data. A second interim lock will occur following the end of the open-label period. The total study duration, including the 6.0-month follow-up-period, is approximately 2 years.

Endpoints

The primary efficacy endpoint is the mean change from baseline (28-day run-in period) in the monthly average number of migraine days during the 12-week period after the 1st dose of fremanezumab.

Secondary Endpoints to Further Demonstrate Efficacy Include:
  The proportion of patients reaching at least 50% reduction in the monthly average number of migraine days during the 12-week period after the 1st dose of fremanezumab.

The mean change from baseline (28-day run-in period) in the monthly average number of headache days of at least moderate severity during the 12-week period after the 1st dose of fremanezumab.

The mean change from baseline (28-day run-in period) in the monthly average number of migraine days during the 4-week period after the 1st dose of fremanezumab.

The proportion of patients reaching at least 50% reduction in the monthly average number of migraine days during the 4-week period after the 1st dose of fremanezumab.

The mean change from baseline (28-day run-in period) in the monthly average number of days of use of any acute headache medications during the 12-week period after the 1st dose of fremanezumab.

The mean change from baseline (28-day run-in period) in the number of headache days of at least moderate severity during the 4-week period after the 1st dose of fremanezumab.

Secondary Endpoints to Demonstrate Safety and Tolerability Include:

The occurrence of adverse events throughout the study.

Analysis of clinical laboratory (serum chemistry, hematology, coagulation and urinalysis) test results at specified time points.

Analysis of vital signs (systolic and diastolic blood pressure, oral temperature, and pulse rate) measurements at each visit. Note: In addition, oxygen saturation and respiratory rate will be measured in cases of suspected anaphylaxis and severe hypersensitivity.

Analysis of 12-lead electrocardiogram (ECG) findings at specified time points.

The use of concomitant medication for adverse events during the study.

The number (%) of patients who did not complete the study due to adverse events.

Analysis of clinically significant changes in physical examinations, including body weight.

Occurrence of severe hypersensitivity/anaphylaxis reactions.

Suicidal ideations and behaviors as measured by the eC-SSRS.

Exploratory Objectives to Demonstrate Efficacy

To evaluate the efficacy of fremanezumab in adult migraine patients with inadequate response to two to four classes of prior preventative treatments Exploratory Endpoints for the Double-Blind Period are as Follows:

The proportion of patients reaching at least 75% reduction in the monthly average number of migraine days during the 12-week period after the 1st dose of study drug.

The proportion of patients reaching total (100%) response (no headache) during the 12-week period after the 1st dose of study drug.

The proportion of patients reaching total (100%) response (no headache) for at least one month during the 12-week period after the 4th dose of study drug The mean change from baseline (28-day run-in period) in the monthly average number of headache hours of at least moderate severity during the 12-week period after the (1st) dose of the study drug.

The proportion of patients reaching at least 50% reduction in the number of migraine days during the 4-week period after the 1st dose of study drug for whom this level of effect is sustained throughout the 12-week period after the 1st dose of study drug.

The proportion of patients reaching at least 75% reduction in the number of migraine days during the 4-week period after the 1st dose of study drug for whom this level of effect is sustained throughout the 12-week period after the 1st dose of study drug.

The mean change from baseline (28-day run-in period) in the monthly average number of days with nausea or vomiting during the 12-week period after the 1st dose of study drug.

The mean change from baseline (28-day run-in period) in the monthly average number of days with photophobia and phonophobia during the 12-week period after the 1st dose of study drug.

The mean change from baseline (28-day run-in period) in the monthly average number of days of use of migraine-specific acute headache medications (triptans and ergot compounds) during the 12-week period after the 1st dose of study drug.

The mean change from baseline (28-day run-in period) in the number of migraine days during the 12-week period after the 1st dose of study drug for patients who failed topiramate for migraine in the past.

The mean change from baseline (28-day run-in period) in the number of migraine days during the 12-week period after the 1st dose of study drug for patients who failed onabotulinumtoxinA for migraine in the past.

The mean change from baseline (28-day run-in period) in the number of migraine days during the 12-week period after the 1st dose of study drug for patients who failed valproic acid for migraine in the past.

The mean change from baseline (28-day run-in period) in the number of migraine days during the 12-week period after the 1st dose of study drug for the subset of patients who failed 2 to 3 classes of preventive medications and valproic acid for migraine in the past.

The proportion of patients reaching at least 50% reduction in the monthly average number of migraine days during the 12-week period after the 1st dose of fremanezumab for the subset of patients who failed 2 to 3 classes of preventive medications and valproic acid for migraine in the past The mean change from baseline (day 0) in disability score, as measured by the 6-item Headache Impact Test (HIT-6), at 4 weeks after administration of the 3rd dose of study drug.

The mean change from baseline (day 0) in disability score, as measured by the Migraine Disability Assessment (MIDAS) questionnaire, at 4 weeks after the administration of the 3rd dose of study drug.

The mean change from baseline (day 0) in quality of life, as measured by the MigraineSpecific Quality of Life (MSQOL) questionnaire, at 4 weeks after administration of the 3rd dose of study drug.

The mean change from baseline (day 0) in the health status, as measured by the EuroQol-5 Dimension (EQ-5D-5L) questionnaire at 4 weeks after administration of the 3rd dose of study drug.

The mean change from baseline (day 0) in patient depression status, as measured by the 2 item Patient Health Questionnaire (PHQ-2) and 9-item Patient Health Questionnaire (PHQ-9), at 4 weeks after administration of the 3rd dose of study drug.

The mean change from baseline (day 0) in patient work productivity and activity impairment, as measured by the Work Productivity and Activity Impairment (WPAI) questionnaire, at 4 weeks after administration of the 3rd dose of study drug.

The mean change from baseline (day 0) of patient satisfaction, as measured by the Patient Global Impression of Change (PGIC) scale, at 4 weeks after the 3rd dose of study drug.

Exploratory Endpoints for the Open-Label Period are:

The mean change from baseline (28-day run-in period) in the monthly average number of migraine days during the 12-week period after the 4th dose of fremanezumab.

The proportion of patients reaching at least 50% reduction from baseline (28-day run-in period) in the monthly average number of migraine days during the 12-week period after the 4th dose of fremanezumab.

The mean change from baseline (28-day run-in period) in the monthly average number of headache days of at least moderate severity during the 12-week period after the 4th dose of fremanezumab.

The mean change from baseline (28-day run-in period) in the monthly average number of days of use of any acute headache medications during the 12-week period after the 4th dose of fremanezumab.

The proportion of patients reaching at least 75% reduction from baseline (28-day run-in period) in the monthly average number of migraine days during the 12-week period after the 4th dose of study drug.

The proportion of patients reaching total (100%) response (no headache) during the 12-week period after the 4th dose of study drug.

The proportion of patients reaching total (100%) response (no headache) for at least one month during the 12-week period after the 4th dose of study drug.

The mean change from baseline (28-day run-in period) in the monthly average number of headache hours of at least moderate severity during the 12-week period after the 4th dose of the study drug.

The proportion of patients reaching at least 50% reduction from baseline (28-day run-in period) in the number of migraine days during the 4-week period after the 4th dose of study drug for whom this level of effect is sustained throughout the 12-week period after the 4th dose of study drug.

The proportion of patients reaching at least 75% reduction from baseline (28-day run-in period) in the number of migraine days during the 4-week period after the 4th dose of study drug for whom this level of effect is sustained throughout the 12-week period after the 4th dose of study drug.

The mean change from baseline (28-day run-in period) in the monthly average number of days with nausea or vomiting during the 12-week period after the 4th dose of study drug.

The mean change from baseline (28-day run-in period) in the monthly average number of days with photophobia and phonophobia during the 12-week period after the 4th dose of study drug.

The mean change from baseline (28-day run-in period) in the monthly average number of days of use of migraine-specific acute headache medications (triptans and ergot compounds) during the 12-week period after the 4th dose of study drug.

The mean change from baseline (28-day run-in period) in the number of migraine days during the 12-week period after the 4th dose of study drug for patients who failed topiramate for migraine in the past.

The mean change from baseline (28-day run-in period) in the number of migraine days during the 12-week period after the 4th dose of study drug for patients who failed onabotulinumtoxinA for migraine in the past.

The mean change from baseline (28-day run-in period) in the number of migraine days during the 12-week period after the 4th dose of study drug for patients who failed valproic acid for migraine in the past.

The mean change from baseline (28-day run-in period) in the number of migraine days during the 12-week period after the 4th dose of study drug for patients who failed 2 to 3 classes of preventive medications in addition to valproic acid for migraine in the past.

The proportion of patients reaching at least 50% reduction from baseline (28-day run-in period) in the monthly average number of migraine days during the 12-week period after the 4th dose of fremanezumab for patients who failed 2 to 3 classes of preventive medications in addition to valproic acid for migraine in the past.

The mean change from baseline (day 0) in disability score, as measured by the HIT-6, at 4 weeks after administration of the 6th dose of study drug.

The mean change from baseline (day 0) in disability score, as measured by the MIDAS questionnaire, at 4 weeks after the administration of the 6th dose of study drug.

The mean change from baseline (day 0) in quality of life, as measured by the MSQOL questionnaire, at 4 weeks after administration of the 6th dose of study drug.

The mean change from baseline (day 0) in the health status, as measured by the EQ-5D-5L questionnaire at 4 weeks after administration of the 6th dose of study drug.

The mean change from baseline (day 0) in patient depression status, as measured by the PHQ-2 and PHQ-9, at 4 weeks after administration of the 6th dose of study drug.

The mean change from baseline (day 0) in patient work productivity and activity impairment, as measured by the WPAI questionnaire, at 4 weeks after administration of the 6th dose of study drug.

The mean change from baseline (day 0) of patient satisfaction, as measured by the PGIC scale, at 4 weeks after the 6th dose of study drug.

Exploratory Endpoints for Both the Double-Blind and Open-Label Periods:

To evaluate the immunogenicity response of fremanezumab and the impact of ADAs on clinical outcomes in patients exposed to sc fremanezumab.

To explore the relationship between genetic polymorphisms (including those within the calcitonin gene-related peptide (CGRP) receptor-ligand complex, in migraine-associated susceptibility genes, and in as-yet undiscovered loci) versus migraine onset/severity, adverse events to medication and fremanezumab efficacy.

Study Population

The study population is composed of male and female patients, aged 18 to 70 years, inclusive, with a history of migraine (as defined by International Classification of Headache Disorders, 3rd revision [ICHD-3] criteria [IHS 2013]) for at least 12 months prior to screening and diagnosis of episodic or chronic migraine prospectively documented via a review of headache data recorded daily in an electronic daily headache diary device during a 28-day run-in period.

At the time of screening, patients must have documented inadequate response to two to four classes of prior preventive migraine medications within the past 10 years (in medical chart or by treating physician's confirmation).

A subset of these patients (at least 120 patients) must have documented inadequate response to 2 to 3 classes of prior preventive medications and in addition inadequate response to valproic acid. All inadequate responses must be within the past 10 years (in medical chart or by treating physician's confirmation).

Prior migraine preventive medications are as follows (see Martelletti et al., *J. Headache Pain,* 15(1):47, 2014):
- beta-blockers: propranolol, metoprolol, atenolol, and bisoprolol
- anticonvulsants: topiramate
- tricyclics: amitriptyline
- calcium channel blocker: flunarizine
- angiotensin II receptor antagonist: candesartan
- onabotulinumtoxinA
- valproic acid The use of the medications listed above on a daily basis for other indications is disallowed for the duration of the study. Any of the listed medications are allowed if given as topical or eye drops. Other medications in the same classes but not included in this list are allowed.

Inadequate Response to Prior Preventative Migraine Medications (Including Valproic Acid) is Defined as:

Patients must have documented inadequate response (in medical chart or by treating physician's confirmation) to two to four classes of prior preventive medications from the list above regardless of which class the medication belongs to.

Inadequate response is defined as: no clinically meaningful improvement per treating physician's judgment, after at least 3 months of therapy at a stable dose considered appropriate for migraine prevention according to accepted country guidelines, or when treatment has to be interrupted because of adverse events that made it intolerable by the patient or the drug is contraindicated or not suitable for the patient. The 3 month period does not apply if the drug is intolerable or contraindicated or not suitable for the patient.

If onabotulinumtoxinA is the previously failed preventive medication, at least 2 sets of injections and 3 months must have passed since the last set of injections prior to the screening visit.

Patient Inclusion Criteria

Patients are Included in the Study Only if they Meet all of the Following Criteria:

a. The patient is capable of giving signed informed consent.
b. Male or female patient aged 18 to 70 years, inclusive.
c. The patient has a diagnosis of migraine with onset at ≤50 years of age.
d. The patient is in good health in the opinion of the investigators as determined by medical history, physical examination, laboratory tests, and ECG.
e. Body weight ≥45 kg and body mass index (BMI) within the range 17.5 to 34.9 kg/m2 (inclusive).
f. The patient has a history of migraine (according to ICHD-3 criteria [IHS 2013]) or clinical judgment suggests a migraine diagnosis (not better accounted for by another ICHD-3 diagnosis) for ≥12 months prior to screening.
g. The patient fulfills the following criteria for migraine in prospectively collected baseline information during the 28-day run-in period:

For Patients with CM:
Headache occurring on ≥15 days
On ≥8 days, fulfilling any of the following:
  i. ICHD-3 diagnostic criteria C and D for 1.1 Migraine without aura
  ii. ICHD-3 criteria B and C for 1.2 Migraine with aura
  iii. Probable migraine (a migraine subtype where only 1 migraine criterion is missing)
  iv. The patient used a triptan or ergot derivative to treat an established headache For Patients with EM:
Headache occurring ≥6 days
On ≥4 days, fulfilling any of the following:
  i. ICHD-3 diagnostic criteria C and D for 1.1 Migraine without aura
  ii. ICHD-3 criteria B and C for 1.2 Migraine with aura
  iii. Probable migraine (a migraine subtype where only 1 migraine criterion is missing)
  iv. The patient used a triptan or ergot derivative to treat an established headache h. At the time of screening, the patient must have documented inadequate response to two to four classes of prior preventive migraine medications, as defined herein, within the past 10 years (in medical chart or by treating physician's confirmation). Inadequate response to prior preventive migraine medications (including valproic acid) is defined as: no clinically meaningful improvement per treating physician's judgment, after at least 3 months of therapy at a stable dose considered appropriate for migraine prevention according to accepted country guidelines, or when treatment has to be interrupted because of adverse events that made it intolerable for the patient, or the medication is contraindicated or unsuitable for the prophylactic treatment of migraine for the patient. The 3-month period does not apply if the drug is intolerable or contraindicated. If onabotulinumtoxinA is the previous preventive medication, at least 2 sets of injections and 3 months must have passed since the last set of injections prior to the screening visit.

i. The patient agrees not to initiate any migraine medications, as defined herein, during the run-in period, double-blind treatment period, and open-label period. At the screening visit, at least five half-lives of these medications must have passed since the patient has been on any migraine preventive medication, as defined herein.

j. Other prescription medications not defined as prior migraine preventive medication as defined herein must have been on stable doses for at least 2 months at the screening visit with no expectation to change during the double-blind treatment period of the study.

k. The patient demonstrated compliance with the electronic headache diary during the run-in period by entry of headache data on a minimum of 24 days cumulative during the run-in period (~85% diary compliance).

l. Women may be included only if they have a negative serum beta-human chorionic gonadotropin (β-HCG) test at screening, are sterile, or postmenopausal.

m. Women of childbearing potential (WOCBP) whose male partners are potentially fertile (e.g., no vasectomy) must use highly effective birth control methods for the duration of the study and the follow-up period (i.e., starting at screening) and for 6.0 months after discontinuation of IMP.

n. Men must be sterile, or if they are potentially fertile/reproductively competent (not surgically [eg, vasectomy] or congenitally sterile) and their female partners are of childbearing potential, must use, together with their female partners, acceptable birth control methods for the duration of the study and for 6.0 months after discontinuation of the IMP.

o. The patient must be willing and able to comply with study restrictions, to remain at the clinic for the required duration during the study period and to return to the clinic for the follow-up evaluations.

Patient Exclusion Criteria

Patients are Excluded from Participating in this Study if they Meet any of the Following Criteria:

a. At the time of screening visit, patient is receiving any preventive migraine medications, as defined herein, regardless of the medical indication for more than 5 days and expects to continue with these medications.

b. Patient has received onabotulinumtoxinA for migraine or for any medical or cosmetic reasons requiring injections in the head, face, or neck during the 3 months before screening visit.

c. The patient uses medications containing opioids (including codeine) or barbiturates (including butalbital/aspirin/caffeine [Fiorinal®, Actavis plc], butalbital/paracetamol/caffeine [Fioricet®, Cardinal Health], or any other combination containing butalbital) on more than 4 days during the run-in period for the treatment of migraine or for any other reason.

d. The patient has used an intervention/device (e.g., scheduled nerve blocks and transcranial magnetic stimulation) for migraine during the 2 months prior to screening.

e. The patient uses triptans/ergots as preventive therapies for migraine.

f. Patient uses non-steroidal anti-inflammatory drugs (NSAIDs) as preventive therapy for migraine on nearly daily basis for other indications. Note: Low dose aspirin (e.g., 81 mg) used for cardiovascular disease prevention is allowed.

g. The patient suffers from unremitting headaches, defined as having headaches for more than 80% of the time he/she is awake, and less than 4 days without headache per month. Daily headache is acceptable if the patient has headaches 80% or less of the time he/she is awake on most days.

h. The patient has a clinically significant hematological, cardiac, renal, endocrine, pulmonary, gastrointestinal, genitourinary, neurologic, hepatic, or ocular disease that, in the opinion of the investigator, could jeopardize or would compromise the patient's ability to participate in this study.

i. Evidence or medical history of clinically significant psychiatric issues that, in the opinion of the investigator, could jeopardize or would compromise the patient's ability to participate in this study including major depression, panic disorder, or generalized anxiety disorder, any suicide attempt in the past or suicidal ideation with a specific plan in the past two years prior to screening or current suicidal ideation as measured by eC-SSRS.

j. History of clinically significant cardiovascular disease or vascular ischemia (such as myocardial, neurological [e.g., cerebral ischemia], peripheral extremity ischemia, or other ischemic event) or thromboembolic events (arterial or venous thrombotic or embolic events), such as cerebrovascular accident (including transient ischemic attacks), deep vein thrombosis, or pulmonary embolism.

k. History of human immunodeficiency virus, tuberculosis, or chronic hepatitis B or C infection.

l. Past or current history of cancer, except for appropriately treated non-melanoma skin carcinoma in the last 5 years.

m. Pregnant or lactating female patients or female patients who plan to become pregnant during the study.

n. Participation in a clinical study of a new chemical entity or a prescription medicine within 2 months before screening (or 3 months in case of biologics if the half-life of the biologics is unknown) or 5 half-lives, whichever is longer, or is currently participating in another study of an IMP (or a medical device).

o. Any prior exposure to a monoclonal antibody targeting the CGRP pathway (such as AMG 334, ALD304, LY2951742, or fremanezumab).

p. Any finding in the baseline 12-lead ECG considered clinically significant in the judgment of the investigator.

q. Any finding that, in the judgment of the investigator, is a clinically significant abnormality, including serum chemistry, hematology, coagulation, and urinalysis test values (abnormal tests may be repeated for confirmation).

r. Hepatic enzymes (alanine aminotransferase, aspartate aminotransferase, and alkaline phosphatase)>1.5×the upper limit of the normal (ULN) range after confirmation in a repeat test or suspected hepatocellular damage that fulfills criteria for Hy's law at screening.

s. Serum creatinine>1.5×the ULN, clinically significant proteinuria, or evidence of renal disease at screening.

t. The patient has a history of alcohol abuse during the 2 years prior to screening.

u. The patient has a history of drug abuse during the past 2 years or drug dependence during the past 5 years.

v. The patient cannot participate or successfully complete the study, in the opinion of their healthcare provider or the investigator, for any of the following reasons:

mentally or legally incapacitated or unable to give consent for any reason in custody due to an administrative or a legal decision, under tutelage, or being admitted to a sanitarium or social institution unable to be contacted in case of emergency has any other condition, which, in the opinion of the investigator, makes the patient inappropriate for inclusion in the study w. The patient is a study center or sponsor employee who is directly involved in the study or the relative of such an employee.

x. The patient has been previously screen failed for the study.

Antibody Sequences

G1 heavy chain variable region amino acid sequence
(SEQ ID NO: 1)
EVQLVESGGGLVQPGGSLRLSCAASGFTFSNYWISWVRQAPGKGLEWVAE

IRSESDASATHYAEAVKGRFTISRDNAKNSLYLQMNSLRAEDTAVYYCLA

YFDYGLAIQNYWGQGTLVTVSS

G1 light chain variable region amino acid sequence
(SEQ ID NO: 2)
EIVLTQSPATLSLSPGERATLSCKASKRVTTYVSWYQQKPGQAPRLLIYG

ASNRYLGIPARFSGSGSGTDFTLTISSLEPEDFAVYYCSQSYNYPYTFGQ

GTKLEIK

G1 CDR H1 (extended CDR)
(SEQ ID NO: 3)
GFTFSNYWIS

G1 CDR H2 (extended CDR)
(SEQ ID NO: 4)
EIRSESDASATHYAEAVKG

G1 CDR H3
(SEQ ID NO: 5)
YFDYGLAIQNY

G1 CDR L1
(SEQ ID NO: 6)
KASKRVTTYVS

G1 CDR L2
(SEQ ID NO: 7)
GASNRYL

G1 CDR L3
(SEQ ID NO: 8)
SQSYNYPYT

G1 heavy chain variable region nucleotide sequence
(SEQ ID NO: 9)
GAAGTTCAGCTGGTTGAATCCGGTGGTGGTCTGGTTCAGCCAGGTGGTTC

CCTGCGTCTGTCCTGCGCTGCTTCCGGTTTCACCTTCTCCAACTACTGGA

TCTCCTGGGTTCGTCAGGCTCCTGGTAAAGGTCTGGAATGGGTTGCTGAA

ATCCGTTCCGAATCCGACGCGTCCGCTACCCATTACGCTGAAGCTGTTAA

AGGTCGTTTCACCATCTCCCGTGACAACGCTAAGAACTCCCTGTACCTGC

AGATGAACTCCCTGCGTGCTGAAGACACCGCTGTTTACTACTGCCTGGCT

TACTTTGACTACGGTCTGGCTATCCAGAACTACTGGGGTCAGGGTACCCT

GGTTACCGTTTCCTCC

G1 light chain variable region nucleotide sequence
(SEQ ID NO: 10)
GAAATCGTTCTGACCCAGTCCCCGGCTACCCTGTCCCTGTCCCCAGGTGA

ACGTGCTACCCTGTCCTGCAAAGCTTCCAAACGGGTTACCACCTACGTTT

CCTGGTACCAGCAGAAACCCGGTCAGGCTCCTCGTCTGCTGATCTACGGT

GCTTCCAACCGTTACCTCGGTATCCCAGCTCGTTTCTCCGGTTCCGGTTC

CGGTACCGACTTCACCCTGACCATCTCCTCCCTGGAACCCGAAGACTTCG

CTGTTTACTACTGCAGTCAGTCCTACAACTACCCCTACACCTTCGGTCAG

GGTACCAAACTGGAAATCAAA

G1 heavy chain full antibody amino acid sequence
(including modified IgG2 as described herein)
(SEQ ID NO: 11)
EVQLVESGGGLVQPGGSLRLSCAASGFTFSNYWISWVRQAPGKGLEWVAE

IRSESDASATHYAEAVKGRFTISRDNAKNSLYLQMNSLRAEDTAVYYCLA

YFDYGLAIQNYWGQGTLVTVSSASTKGPSVFPLAPCSRSTSESTAALGCL

VKDYFPEPVTVSWNSGALTSGVHTFPAVLQSSGLYSLSSVVTVPSSNFGT

QTYTCNVDHKPSNTKVDKTVERKCCVECPPCPAPPVAGPSVFLFPPKPKD

TLMISRTPEVTCVVVDVSHEDPEVQFNWYVDGVEVHNAKTKPREEQFNST

FRVVSVLTVVHQDWLNGKEYKCKVSNKGLPSSIEKTISKTKGQPREPQVY

TLPPSREEMTKNQVSLTCLVKGFYPSDIAVEWESNGQPENNYKTTPPMLD

SDGSFFLYSKLTVDKSRWQQGNVFSCSVMHEALHNHYTQKSLSLSPGK

G1 light chain full antibody amino acid sequence
(SEQ ID NO: 12)
EIVLTQSPATLSLSPGERATLSCKASKRVTTYVSWYQQKPGQAPRLLIYG

ASNRYLGIPARFSGSGSGTDFTLTISSLEPEDFAVYYCSQSYNYPYTFGQ

GTKLEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

G1 heavy chain full antibody nucleotide sequence
(including modified IgG2 as described herein)
(SEQ ID NO: 13)
GAAGTTCAGCTGGTTGAATCCGGTGGTGGTCTGGTTCAGCCAGGTGGTTC

CCTGCGTCTGTCCTGCGCTGCTTCCGGTTTCACCTTCTCCAACTACTGGA

TCTCCTGGGTTCGTCAGGCTCCTGGTAAAGGTCTGGAATGGGTTGCTGAA

ATCCGTTCCGAATCCGACGCGTCCGCTACCCATTACGCTGAAGCTGTTAA

AGGTCGTTTCACCATCTCCCGTGACAACGCTAAGAACTCCCTGTACCTGC

AGATGAACTCCCTGCGTGCTGAAGACACCGCTGTTTACTACTGCCTGGCT

TACTTTGACTACGGTCTGGCTATCCAGAACTACTGGGGTCAGGGTACCCT

GGTTACCGTTTCCTCCGCCTCCACCAAGGGCCCATCTGTCTTCCCACTGG

CCCCATGCTCCCGCAGCACCTCCGAGAGCACAGCCGCCCTGGGCTGCCTG

GTCAAGGACTACTTCCCAGAACCTGTGACCGTGTCCTGGAACTCTGGCGC

TCTGACCAGCGGCGTGCACACCTTCCCAGCTGTCCTGCAGTCCTCAGGTC

TCTACTCCCTCAGCAGCGTGGTGACCGTGCCATCCAGCAACTTCGGCACC

CAGACCTACACCTGCAACGTAGATCACAAGCCAAGCAACACCAAGGTCGA

CAAGACCGTGGAGAGAAAGTGTTGTGTGGAGTGTCCACCTTGTCCAGCCC

CTCCAGTGGCCGGACCATCCGTGTTCCTGTTCCCTCCAAAGCCAAAGGAC

ACCCTGATGATCTCCAGAACCCCAGAGGTGACCTGTGTGGTGGTGGACGT

GTCCCACGAGGACCCCGAGGTGCAGTTCAACTGGTATGTGGACGGAGTGG

AGGTGCACAACGCCAAGACCAAGCCAAGAGAGGAGCAGTTCAACTCCACC

TTCAGAGTGGTGAGCGTGCTGACCGTGGTGCACCAGGACTGGCTGAACGG

AAAGGAGTATAAGTGTAAGGTGTCCAACAAGGGACTGCCATCCAGCATCG

AGAAGACCATCTCCAAGACCAAGGGACAGCCAAGAGAGCCACAGGTGTAT

ACCCTGCCCCCATCCAGAGAGGAGATGACCAAGAACCAGGTGTCCCTGAC

CTGTCTGGTGAAGGGATTCTATCCATCCGACATCGCCGTGGAGTGGGAGT

CCAACGGACAGCCAGAGAACAACTATAAGACCACCCCTCCAATGCTGGAC

TCCGACGGATCCTTCTTCCTGTATTCCAAGCTGACCGTGGACAAGTCCAG

ATGGCAGCAGGGAAACGTGTTCTCTTGTTCCGTGATGCACGAGGCCCTGC

ACAACCACTATACCCAGAAGAGCCTGTCCCTGTCTCCAGGAAAGTAA

G1 light chain full antibody nucleotide sequence
(SEQ ID NO: 14)
GAAATCGTTCTGACCCAGTCCCCGGCTACCCTGTCCCTGTCCCCAGGTGA

ACGTGCTACCCTGTCCTGCAAAGCTTCCAAACGGGTTACCACCTACGTTT

CCTGGTACCAGCAGAAACCCGGTCAGGCTCCTCGTCTGCTGATCTACGGT

GCTTCCAACCGTTACCTCGGTATCCCAGCTCGTTTCTCCGGTTCCGGTTC

CGGTACCGACTTCACCCTGACCATCTCCTCCCTGGAACCCGAAGACTTCG

CTGTTTACTACTGCAGTCAGTCCTACAACTACCCCTACACCTTCGGTCAG

GGTACCAAACTGGAAATCAAACGCACTGTGGCTGCACCATCTGTCTTCAT

CTTCCCTCCATCTGATGAGCAGTTGAAATCCGGAACTGCCTCTGTTGTGT

```
GCCTGCTGAATAACTTCTATCCGCGCGAGGCCAAAGTACAGTGGAAGGTG

GATAACGCCCTCCAATCCGGTAACTCCCAGGAGAGTGTCACAGAGCAGGA

CAGCAAGGACAGCACCTACAGCCTCAGCAGCACCCTGACCCTGAGCAAAG

CAGACTACGAGAAACACAAAGTCTACGCCTGCGAAGTCACCCATCAGGGC

CTGAGTTCTCCAGTCACAAAGAGCTTCAACCGCGGTGAGTGCTAA
```

Amino acid sequence comparison of human and rat
CGRP (human α-CGRP (SEQ ID NO: 15); human β-CGRP
(SEQ ID NO: 43); rat α-CGRP (SEQ ID NO: 41); and
rat β-CGRP (SEQ ID NO: 44):
NH$_2$-AC☒TATCVTHRLAGLLSRSGGVVK☒NFVPTNVGSKAF-CONH$_2$
(human α-CGRP)

NH$_2$-AC☒TATCVTHRLAGLLSRSGG☒VK☒NFVPTNVGSKAF-CONH$_2$
(human β-CGRP)

NH$_2$-☒C☒TATCVTHRLAGLLSRSGGVVK☒NFVPTNVGS☒AF-CONH$_2$
(rat α-CGRP)

NH$_2$-☒C☒TATCVTHRLAGLLSRSGGVVK☒NFVPTNVGSKAF-CONH$_2$
(rat β-CGRP)

Light chain variable region LCVR17 amino acid
sequence
(SEQ ID NO: 58)
DIQMTQSPSSLSASVGDRVTITCRASQDIDNYLNWYQQKPGKAPKLLIYY

TSEYHSGVPSRFSGSGSGTDFTFTISSLQPEDIATYYCQQGDALPPTFGQ

GTKLEIK

Heavy chain variable region HCVR22 amino acid
sequence
(SEQ ID NO: 59)
QVQLVQSGAEVKKPGASVKVSCKASGYTFGNYWMQWVRQAPGQGLEWMGA

IYEGTGDTRYIQKFAGRVTMTRDTSTSTVYMELSSLRSEDTAVYYCARLS

DYVSGFSYWGQGTLVTVSS

Light chain variable region LCVR18 amino acid
sequence
(SEQ ID NO: 60)
DIQMTQSPSSLSASVGDRVTITCRASQDIDNYLNWYQQKPGKAPKLLIYY

TSEYHSGVPSRFSGSGSGTDFTFTISSLQPEDIATYYCQQGDALPPTFGQ

GTKLEIK

Heavy chain variable region HCVR23 amino acid
sequence
(SEQ ID NO: 61)
QVQLVQSGAEVKKPGASVKVSCKASGYTFGNYWMQWVRQAPGQGLEWMGA

IYEGTGKTVYIQKFAGRVTMTRDTSTSTVYMELSSLRSEDTAVYYCARLS

DYVSGFSYWGQGTLVTVSS

Light chain variable region LCVR19 amino acid
sequence
(SEQ ID NO: 62)
DIQMTQSPSSLSASVGDRVTITCRASKDISKYLNWYQQKPGKAPKLLIYY

TSGYHSGVPSRFSGSGSGTDFTLTISSLQPEDFATYYCQQGDALPPTFGG

GTKVEIK

Heavy chain variable region HCVR24 amino acid
sequence
(SEQ ID NO: 63)
QVQLVQSGAEVKKPGSSVKVSCKASGYTFGNYWMQWVRQAPGQGLEWMGA

IYEGTGKTVYIQKFADRVTITADKSTSTAYMELSSLRSEDTAVYYCARLS

DYVSGFGYWGQGTTVTVSS

Light chain variable region LCVR20 amino acid
sequence
(SEQ ID NO: 64)
DIQMTQSPSSLSASVGDRVTITCRASRPIDKYLNWYQQKPGKAPKLLIYY

TSEYHSGVPSRFSGSGSGTDFTFTISSLQPEDIATYYCQQGDALPPTFGQ

GTKLEIK

Heavy chain variable region HCVR25 amino acid
sequence
(SEQ ID NO: 65)
QVQLVQSGAEVKKPGASVKVSCKASGYTFGNYWMQWVRQAPGQGLEWMGA

IYEGTGKTVYIQKFAGRVTMTRDTSTSTVYMELSSLRSEDTAVYYCARLS

DYVSGFGYWGQGTLVTVSS

Light chain variable region LCVR21 amino acid
sequence
(SEQ ID NO: 66)
DIQMTQSPSSLSASVGDRVTITCRASQDIDKYLNWYQQKPGKAPKLLIYY

TSGYHSGVPSRFSGSGSGTDFTLTISSLQPEDFATYYCQQGDALPPTFGG

GTKVEIK

Heavy chain variable region HCVR26 amino acid
sequence
(SEQ ID NO: 67)
QVQLVQSGAEVKKPGSSVKVSCKASGYTFGNYWMQWVRQAPGQGLEWMGA

IYEGTGKTVYIQKFAGRVTITADKSTSTAYMELSSLRSEDTAVYYCARLS

DYVSGFGYWGQGTTVTVSS

Light chain variable region LCVR27 amino acid
sequence
(SEQ ID NO: 68)
QVLTQSPSSLSASVGDRVTINCQASQSVYHNTYLAWYQQKPGKVPKQLIY

DASTLASGVPSRFSGSGSGTDFTLTISSLQPEDVATYYCLGSYDCTNGDC

FVFGGGTKVEIKR

Heavy chain variable region HCVR28 amino acid
sequence
(SEQ ID NO: 69)
EVQLVESGGGLVQPGGSLRLSCAVSGIDLSGYYMNWVRQAPGKGLEWVGV

IGINGATYYASWAKGRFTISRDNSKTTVYLQMNSLRAEDTAVYFCARGDI

WGQGTLVTVSS

Light chain variable region LCVR29 amino acid
sequence
(SEQ ID NO: 70)
QVLTQSPSSLSASVGDRVTINCQASQSVYDNNYLAWYQQKPGKVPKQLIY

STSTLASGVPSRFSGSGSGTDFTLTISSLQPEDVATYYCLGSYDCSSGDC

FVFGGGTKVEIKR

Heavy chain variable region HCVR30 amino acid
sequence
(SEQ ID NO: 71)
EVQLVESGGGLVQPGGSLRLSCAVSGLDLSSYYMQWVRQAPGKGLEWVGV

IGINDNTYYASWAKGRFTISRDNSKTTVYLQMNSLRAEDTAVYFCARGDI

WGQGTLVTVSS

Light chain variable region LCVR31 amino acid sequence
(SEQ ID NO: 72)
QVLTQSPSSLSASVGDRVTINCQASQSVYDNNYLAWYQQKPGKVPKQLIY

STSTLASGVPSRFSGSGSGTDFTLTISSLQPEDVATYYCLGSYDCSSGDC

FVFGGGTKVEIKR

Heavy chain variable region HCVR32 amino acid sequence
(SEQ ID NO: 73)
EVQLVESGGGLVQPGGSLRLSCAVSGLDLSSYYMQWVRQAPGKGLEWVGV

IGINDNTYYASWAKGRFTISRDNSKTTVYLQMNSLRAEDTAVYFCARGDI

WGQGTLVTVSS

Light chain variable region LCVR33 amino acid sequence
(SEQ ID NO: 74)
QVLTQTPSPVSAAVGSTVTINCQASQSVYHNTYLAWYQQKPGQPPKQLIY

DASTLASGVPSRFSGSGSGTQFTLTISGVQCNDAAAYYCLGSYDCTNGDC

FVFGGGTEVVVKR

Heavy chain variable region HCVR34 amino acid sequence
(SEQ ID NO: 75)
QSLEESGGRLVTPGTPLTLTCSVSGIDLSGYYMNWVRQAPGKGLEWIGVI

GINGATYYASWAKGRFTISKTSSTTVDLKMTSLTTEDTATYFCARGDIWG

PGTLVTVSS

Light chain variable region LCVR35 amino acid sequence
(SEQ ID NO: 76)
QVLTQSPSSLSASVGDRVTINCQASQSVYHNTYLAWYQQKPGKVPKQLIY

DASTLASGVPSRFSGSGSGTDFTLTISSLQPEDVATYYCLGSYDCTNGDC

FVFGGGTKVEIKR

Heavy chain variable region HCVR36 amino acid sequence
(SEQ ID NO: 77)
EVQLVESGGGLVQPGGSLRLSCAVSGIDLSGYYMNWVRQAPGKGLEWVGV

IGINGATYYASWAKGRFTISRDNSKTTVYLQMNSLRAEDTAVYFCARGDI

WGQGTLVTVSS

Light chain variable region LCVR37 amino acid sequence
(SEQ ID NO: 78)
QSVLTQPPSVSAAPGQKVTISCSGSSSNIGNNYVSWYQQLPGTAPKLLIY

DNNKRPSGIPDRFSGSKSGTSTTLGITGLQTGDEADYYCGTWDSRLSAVV

FGGGTKLTVL

Heavy chain variable region HCVR38 amino acid sequence
(SEQ ID NO: 79)
QVQLVESGGGVVQPGRSLRLSCAASGFTFSSFGMHWVRQAPGKGLEWVAV

ISFDGSIKYSVDSVKGRFTISRDNSKNTLFLQMNSLRAEDTAVYYCARDR

LNYYDSSGYYHYKYYGMAVWGQGTTVTSS

---

What is claimed is:

1. A method of treating or preventing migraine in a subject, the method comprising:

selecting a subject that has had inadequate responses to at least two preventive medications, wherein the inadequate responses were (i) no clinically meaningful improvement after at least three months, or (ii) treatment had to be interrupted because of adverse events that made it intolerable to the subject, wherein the at least two preventive medications are selected from two or more different clusters, wherein the clusters are defined as follows:

cluster A: topiramate, carbamazepine, divalproex sodium, and sodium valproate cluster B: flunarizine and pizotifen cluster C: amitriptyline, venlafaxine, nortriptyline, and duloxetine cluster D: atenolol, nadolol, metoprolol, propranolol, and timolol cluster E: onabotulinumtoxinA;

and administering to the subject a therapeutically effective amount of a humanized monoclonal anti-calcitonin gene-related peptide (CGRP) antagonist antibody comprising the amino acid sequence of the heavy chain variable region set forth in SEQ ID NO: 1 and the amino acid sequence of the light chain variable region set forth in SEQ ID NO: 2.

2. The method of claim 1, wherein the monoclonal antibody is administered at a dose of about 225 mg.

3. The method of claim 1, wherein the monoclonal antibody is administered at a dose of about 675 mg.

4. The method of claim 3, wherein the dose of about 675 mg is administered as three separate injections of about 225 mg each.

5. The method of claim 3, wherein the monoclonal antibody is administered at a dose of about 675 mg followed by subsequent doses of about 675 mg administered every quarter.

6. The method of claim 2, wherein the administering to the subject a therapeutically effective amount of a humanized monoclonal anti-calcitonin gene-related peptide (CGRP) antagonist antibody comprises administering to the subject an initial dose of about 225 mg of the monoclonal antibody followed by administering to the subject subsequent doses of about 225 mg of the monoclonal antibody at about one month intervals.

7. The method of claim 1, wherein the monoclonal antibody is administered about once per month.

8. The method of claim 1, wherein the monoclonal antibody is administered as a liquid formulation comprising the monoclonal antibody at a concentration of at least about 150 mg/mL.

9. The method of claim 1, wherein the monoclonal antibody is administered at a volume of less than 2 mL.

10. The method of claim 1, wherein the administering comprises administering the monoclonal antibody to the subject from a pre-filled syringe, pre-filled syringe with a needle safety device, injection pen, or auto-injector comprising a dose of the monoclonal antibody.

11. The method of claim 1, wherein the monoclonal antibody is administered subcutaneously.

12. The method of claim 1, comprising selecting a subject that has had inadequate responses to at least three preventive medications.

13. A method of treating or preventing migraine in a subject in need thereof, wherein the subject has had inadequate responses to at least two preventive medications, wherein the inadequate responses were (i) no clinically meaningful improvement after at least three months, or (ii) treatment had to be interrupted because of adverse events that made it intolerable to the subject, wherein the at least two preventive medications are selected from two or more different clusters, wherein the clusters are defined as follows:
cluster A: topiramate, carbamazepine, divalproex sodium, and sodium valproate
cluster B: flunarizine and pizotifen
cluster C: amitriptyline, venlafaxine, nortriptyline, and duloxetine
cluster D: atenolol, nadolol, metoprolol, propranolol, and timolol
cluster E: onabotulinumtoxinA,
the method comprising administering to the subject a therapeutically effective amount of a humanized monoclonal anti-calcitonin gene-related peptide (CGRP) antagonist antibody comprising the amino acid sequence of the heavy chain variable region set forth in SEQ ID NO: 1 and the amino acid sequence of the light chain variable region set forth in SEQ ID NO: 2, wherein the monoclonal antibody is administered at a dose of about 675 mg followed by subsequent doses of about 675 mg administered every quarter.

14. The method of claim 13, wherein the dose of about 675 mg is administered as three separate injections of about 225 mg each.

15. The method of claim 13, wherein the monoclonal antibody is administered as a liquid formulation comprising the monoclonal antibody at a concentration of at least about 150 mg/mL.

16. The method of claim 13, wherein the monoclonal antibody is administered at a volume of less than 2 mL.

17. The method of claim 13, wherein the administering comprises administering the monoclonal antibody to the subject from a pre-filled syringe, pre-filled syringe with a needle safety device, injection pen, or auto-injector comprising a dose of the monoclonal antibody.

18. The method of claim 13, wherein the monoclonal antibody is administered subcutaneously.

19. The method of claim 13, wherein the subject has had inadequate responses to at least three preventive medications.

* * * * *

```
                         SEQUENCE LISTING

Sequence total quantity: 109
SEQ ID NO: 1            moltype = AA   length = 122
FEATURE                 Location/Qualifiers
REGION                  1..122
                        note = Description of Artificial Sequence: Synthetic
                         polypeptide
source                  1..122
                        mol_type = protein
                        organism = synthetic construct
SEQUENCE: 1
EVQLVESGGG LVQPGGSLRL SCAASGFTFS NYWISWVRQA PGKGLEWVAE IRSESDASAT   60
HYAEAVKGRF TISRDNAKNS LYLQMNSLRA EDTAVYYCLA YFDYGLAIQN YWGQGTLVTV  120
SS                                                                 122

SEQ ID NO: 2            moltype = AA   length = 107
FEATURE                 Location/Qualifiers
REGION                  1..107
                        note = Description of Artificial Sequence: Synthetic
                         polypeptide
source                  1..107
                        mol_type = protein
                        organism = synthetic construct
SEQUENCE: 2
EIVLTQSPAT LSLSPGERAT LSCKASKRVT TYVSWYQQKP GQAPRLLIYG ASNRYLGIPA   60
RFSGSGSGTD FTLTISSLEP EDFAVYYCSQ SYNYPYTFGQ GTKLEIK                107

SEQ ID NO: 3            moltype = AA   length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 3
GFTFSNYWIS                                                          10

SEQ ID NO: 4            moltype = AA   length = 19
FEATURE                 Location/Qualifiers
```

```
REGION                   1..19
                         note = Description of Artificial Sequence: Synthetic peptide
source                   1..19
                         mol_type = protein
                         organism = synthetic construct
SEQUENCE: 4
EIRSESDASA THYAEAVKG                                                         19

SEQ ID NO: 5             moltype = AA   length = 11
FEATURE                  Location/Qualifiers
REGION                   1..11
                         note = Description of Artificial Sequence: Synthetic peptide
source                   1..11
                         mol_type = protein
                         organism = synthetic construct
SEQUENCE: 5
YFDYGLAIQN Y                                                                 11

SEQ ID NO: 6             moltype = AA   length = 11
FEATURE                  Location/Qualifiers
REGION                   1..11
                         note = Description of Artificial Sequence: Synthetic peptide
source                   1..11
                         mol_type = protein
                         organism = synthetic construct
SEQUENCE: 6
KASKRVTTYV S                                                                 11

SEQ ID NO: 7             moltype = AA   length = 7
FEATURE                  Location/Qualifiers
REGION                   1..7
                         note = Description of Artificial Sequence: Synthetic peptide
source                   1..7
                         mol_type = protein
                         organism = synthetic construct
SEQUENCE: 7
GASNRYL                                                                       7

SEQ ID NO: 8             moltype = AA   length = 9
FEATURE                  Location/Qualifiers
REGION                   1..9
                         note = Description of Artificial Sequence: Synthetic peptide
source                   1..9
                         mol_type = protein
                         organism = synthetic construct
SEQUENCE: 8
SQSYNYPYT                                                                     9

SEQ ID NO: 9             moltype = DNA   length = 366
FEATURE                  Location/Qualifiers
misc_feature             1..366
                         note = Description of Artificial Sequence: Synthetic
                          polynucleotide
source                   1..366
                         mol_type = other DNA
                         organism = synthetic construct
SEQUENCE: 9
gaagttcagc tggttgaatc cggtggtggt ctggttcagc caggtggttc cctgcgtctg            60
tcctgcgctg cttccggttt caccttctcc aactactgga tctcctgggt tcgtcaggct           120
cctggtaaag gtctggaatg ggttgctgaa atccgttccg aatccgacgc gtccgctacc           180
cattacgctg aagctgttaa aggtcgtttc cacatctccc gtgacaacgc taagaactcc           240
ctgtacctgc agatgaactc cctgcgtgct gaagacaccg ctgtttacta ctgcctggct           300
tactttgact acgtctggc tatccagaac tactggggtc agggtaccct ggttaccgtt            360
tcctcc                                                                      366

SEQ ID NO: 10            moltype = DNA   length = 321
FEATURE                  Location/Qualifiers
misc_feature             1..321
                         note = Description of Artificial Sequence: Synthetic
                          polynucleotide
source                   1..321
                         mol_type = other DNA
                         organism = synthetic construct
SEQUENCE: 10
gaaatcgttc tgacccagtc cccggctacc ctgtccctgt cccaggtga acgtgctacc             60
ctgtcctgca aagcttccaa acgggttacc acctacgttt cctggtacca gcagaaaccc           120
ggtcaggctc tcgtctgct gatctacggt gcttccaacc gttacctcgg tatcccagct            180
cgtttctccg gttccggttc cggtaccgac ttcacccta ccatctcctc cctggaaccc            240
```

```
gaagacttcg ctgtttacta ctgcagtcag tcctacaact accccctacac cttcggtcag    300
ggtaccaaac tggaaatcaa a                                                321
```

| SEQ ID NO: 11 | moltype = AA   length = 448 |
|---|---|
| FEATURE | Location/Qualifiers |
| REGION | 1..448 |
|  | note = Description of Artificial Sequence: Synthetic polypeptide |
| source | 1..448 |
|  | mol_type = protein |
|  | organism = synthetic construct |

SEQUENCE: 11

```
EVQLVESGGG LVQPGGSLRL SCAASGFTFS NYWISWVRQA PGKGLEWVAE IRSESDASAT    60
HYAEAVKGRF TISRDNAKNS LYLQMNSLRA EDTAVYYCLA YFDYGLAIQN YWGQGTLVTV   120
SSASTKGPSV FPLAPCSRST SESTAALGCL VKDYFPEPVT VSWNSGALTS GVHTFPAVLQ   180
SSGLYSLSSV VTVPSSNFGT QTYTCNVDHK PSNTKVDKTV ERKCCVECPP CPAPPVAGPS   240
VFLFPPKPKD TLMISRTPEV TCVVVDVSHE DPEVQFNWYV DGVEVHNAKT KPREEQFNST   300
FRVVSVLTVV HQDWLNGKEY KCKVSNKGLP SSIEKTISKT KGQPREPQVY TLPPSREEMT   360
KNQVSLTCLV KGFYPSDIAV EWESNGQPEN NYKTTPPMLD SDGSFFLYSK LTVDKSRWQQ   420
GNVFSCSVMH EALHNHYTQK SLSLSPGK                                     448
```

| SEQ ID NO: 12 | moltype = AA   length = 214 |
|---|---|
| FEATURE | Location/Qualifiers |
| REGION | 1..214 |
|  | note = Description of Artificial Sequence: Synthetic polypeptide |
| source | 1..214 |
|  | mol_type = protein |
|  | organism = synthetic construct |

SEQUENCE: 12

```
EIVLTQSPAT LSLSPGERAT LSCKASKRVT TYVSWYQQKP GQAPRLLIYG ASNRYLGIPA    60
RFSGSGSGTD FTLTISSLEP EDFAVYYCSQ SYNYPYTFGQ GTKLEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214
```

| SEQ ID NO: 13 | moltype = DNA   length = 1347 |
|---|---|
| FEATURE | Location/Qualifiers |
| misc_feature | 1..1347 |
|  | note = Description of Artificial Sequence: Synthetic polynucleotide |
| source | 1..1347 |
|  | mol_type = other DNA |
|  | organism = synthetic construct |

SEQUENCE: 13

```
gaagttcagc tggttgaatc cggtggtggt ctggttcagc caggtggttc cctgcgtctg    60
tcctgcgctg cttccggttt caccttctcc aactactgga tctcctgggt tcgtcaggct   120
cctggtaaag gtctggaatg ggttgctgaa atccgttccg aatccgacgc gtccgctacc   180
cattacgctg aagctgttaa aggtcgtttc accatctccc gtgacaacgc taagaactcc   240
ctgtacctgc agatgaactc cctgcgtgct gaagacaccg ctgtttacta ctgcctggct   300
tactttgact acggtctggc tatccagaac tactggggtc agggtaccct ggttaccgtt   360
tcctccgcct ccaccaaggg cccatctgtc ttcccactgg cccatgctcc ccgcagcacc   420
tccgagagca cagccgccct gggctgcctg gtcaaggact acttcccaga acctgtgacc   480
gtgtcctgga actctggcgc tctgaccagc ggcgtgcaca ccttcccagc tgtcctgcag   540
tcctcaggtc tctactccct cagcagcgtg gtgaccgtgc catccagcaa cttcggcacc   600
cagacctaca cctgcaacgt agatcacaag ccaagcaaca ccaaggtgga caagaccgtg   660
gagagaaagt gttgtgtgga gtgtccacct tgtccagccc ctccagtggc cggaccatcc   720
gtgttcctgt tccctccaaa gccaaaggac accctgatga tctccagaac cccagaggtg   780
acctgtgtgg tggtggacgt gtcccacgag gacccagagg tgcagttcaa ctggtatgtg   840
gacggagtgg aggtgcacaa cgccaagacc aagccaagag aggagcagtt caactccacc   900
ttcagagtgg tgagcgtgct gaccgtggtg caccaggact ggctgaacgg aaaggagtat   960
aagtgtaagg tgtccaacaa gggactgcca tccagcatcg agaagaccat ctccaagacc  1020
aagggacagc caagagagcc acaggtgtat accctgcccc catccagaga ggagatgacc  1080
aagaaccagg tgtccctgac ctgtctggtg aagggattct atccatccga catcgccgtg  1140
gagtgggagt ccaacggaca gccagagaac aactataagc tcacccctcc aatgctggac  1200
tccgacggat cctt cttcct gtattccaag ctgaccgtgg acaagtccag atggcagcag  1260
ggaaacgtgt tctcttgttc cgtgatgcac gaggccctgc acaaccacta cccagaagag  1320
agcctgtccc tgtctccagg aaagtaa                                      1347
```

| SEQ ID NO: 14 | moltype = DNA   length = 645 |
|---|---|
| FEATURE | Location/Qualifiers |
| misc_feature | 1..645 |
|  | note = Description of Artificial Sequence: Synthetic polynucleotide |
| source | 1..645 |
|  | mol_type = other DNA |
|  | organism = synthetic construct |

SEQUENCE: 14

```
gaaatcgttc tgacccagtc cccggctacc ctgtccctgt ccccaggtga acgtgctacc    60
ctgtcctgca aagcttccaa acgggttacc acctacgttt cctggtacca gcagaaaccc   120
```

```
ggtcaggctc ctcgtctgct gatctacggt gcttccaacc gttacctcgg tatcccagct    180
cgtttctccg gttccggttc cggtaccgac ttcaccctga ccatctcctc cctggaaccc    240
gaagacttcg ctgtttacta ctgcagtcag tcctacaact accccctacac cttcggtcag   300
ggtaccaaac tggaaatcaa acgcactgtg gctgcaccat ctgtcttcat cttccctcca    360
tctgatgagc agttgaaatc cggaactgcc tctgttgtgt gcctgctgaa taacttctat    420
ccgcgcgagg ccaaagtaca gtggaaggtg gataacgccc tccaatccgg taactcccag    480
gagagtgtca cagagcagga cagcaaggac agcacctaca gcctcagcag cacccctgacc   540
ctgagcaaag cagactacga gaaacacaaa gtctacgcct gcgaagtcac ccatcagggc    600
ctgagttctc cagtcacaaa gagcttcaac cgcggtgagt gctaa                    645
```

```
SEQ ID NO: 15          moltype = AA   length = 37
FEATURE                Location/Qualifiers
REGION                 1..37
                       note = misc_feature - C-term amidated
source                 1..37
                       mol_type = protein
                       organism = Homo sapiens
SEQUENCE: 15
ACDTATCVTH RLAGLLSRSG GVVKNNFVPT NVGSKAF                              37

SEQ ID NO: 16          moltype = AA   length = 30
FEATURE                Location/Qualifiers
REGION                 1..30
                       note = misc_feature - C-term amidated
source                 1..30
                       mol_type = protein
                       organism = Homo sapiens
SEQUENCE: 16
VTHRLAGLLS RSGGVVKNNF VPTNVGSKAF                                      30

SEQ ID NO: 17          moltype = AA   length = 19
FEATURE                Location/Qualifiers
REGION                 1..19
                       note = misc_feature - C-term amidated
source                 1..19
                       mol_type = protein
                       organism = Homo sapiens
SEQUENCE: 17
SGGVVKNNFV PTNVGSKAF                                                  19

SEQ ID NO: 18          moltype = AA   length = 19
FEATURE                Location/Qualifiers
REGION                 1..19
                       note = misc_feature - C-term amidated
source                 1..19
                       mol_type = protein
                       organism = Homo sapiens
SEQUENCE: 18
SGGVVKNNFV ATNVGSKAF                                                  19

SEQ ID NO: 19          moltype = AA   length = 19
FEATURE                Location/Qualifiers
REGION                 1..19
                       note = misc_feature - C-term amidated
source                 1..19
                       mol_type = protein
                       organism = Homo sapiens
SEQUENCE: 19
SGGVVKNNFV PTNVGSAAF                                                  19

SEQ ID NO: 20          moltype = AA   length = 19
FEATURE                Location/Qualifiers
REGION                 1..19
                       note = misc_feature - C-term amidated
source                 1..19
                       mol_type = protein
                       organism = Homo sapiens
SEQUENCE: 20
SGGVVKNNFV PTNVGSEAF                                                  19

SEQ ID NO: 21          moltype = AA   length = 19
FEATURE                Location/Qualifiers
REGION                 1..19
                       note = misc_feature - C-term amidated
source                 1..19
                       mol_type = protein
                       organism = Homo sapiens
SEQUENCE: 21
SGGVVKNNFV PTNVGSMAF                                                  19
```

```
SEQ ID NO: 22              moltype = AA  length = 19
FEATURE                    Location/Qualifiers
REGION                     1..19
                           note = misc_feature - C-term amidated
source                     1..19
                           mol_type = protein
                           organism = Homo sapiens
SEQUENCE: 22
SGGVVKNNFV PTNVGSQAF                                                  19

SEQ ID NO: 23              moltype = AA  length = 19
FEATURE                    Location/Qualifiers
REGION                     1..19
                           note = misc_feature - C-term amidated
source                     1..19
                           mol_type = protein
                           organism = Homo sapiens
SEQUENCE: 23
SGGVVKNNFV PTNVGSKAA                                                  19

SEQ ID NO: 24              moltype = AA  length = 14
FEATURE                    Location/Qualifiers
REGION                     1..14
                           note = misc_feature - C-term amidated
source                     1..14
                           mol_type = protein
                           organism = Homo sapiens
SEQUENCE: 24
NNFVPTNVGS KAFA                                                       14

SEQ ID NO: 25              moltype = AA  length = 13
FEATURE                    Location/Qualifiers
REGION                     1..13
                           note = misc_feature - C-term amidated
source                     1..13
                           mol_type = protein
                           organism = Homo sapiens
SEQUENCE: 25
NNFVPTNVGS KAF                                                        13

SEQ ID NO: 26              moltype = AA  length = 13
FEATURE                    Location/Qualifiers
REGION                     1..13
                           note = misc_feature - C-term amidated
source                     1..13
                           mol_type = protein
                           organism = Homo sapiens
SEQUENCE: 26
NNAVPTNVGS KAF                                                        13

SEQ ID NO: 27              moltype = AA  length = 13
FEATURE                    Location/Qualifiers
REGION                     1..13
                           note = misc_feature - C-term amidated
source                     1..13
                           mol_type = protein
                           organism = Homo sapiens
SEQUENCE: 27
NNFAPTNVGS KAF                                                        13

SEQ ID NO: 28              moltype = AA  length = 13
FEATURE                    Location/Qualifiers
REGION                     1..13
                           note = misc_feature - C-term amidated
source                     1..13
                           mol_type = protein
                           organism = Homo sapiens
SEQUENCE: 28
NNFVATNVGS KAF                                                        13

SEQ ID NO: 29              moltype = AA  length = 13
FEATURE                    Location/Qualifiers
REGION                     1..13
                           note = misc_feature - C-term amidated
source                     1..13
                           mol_type = protein
                           organism = Homo sapiens
```

```
SEQUENCE: 29
NNFVPANVGS KAF                                                              13

SEQ ID NO: 30           moltype = AA  length = 13
FEATURE                 Location/Qualifiers
REGION                  1..13
                        note = misc_feature - C-term amidated
source                  1..13
                        mol_type = protein
                        organism = Homo sapiens
SEQUENCE: 30
NNFVPTAVGS KAF                                                              13

SEQ ID NO: 31           moltype = AA  length = 13
FEATURE                 Location/Qualifiers
REGION                  1..13
                        note = misc_feature - C-term amidated
source                  1..13
                        mol_type = protein
                        organism = Homo sapiens
SEQUENCE: 31
NNFVPTNAGS KAF                                                              13

SEQ ID NO: 32           moltype = AA  length = 13
FEATURE                 Location/Qualifiers
REGION                  1..13
                        note = misc_feature - C-term amidated
source                  1..13
                        mol_type = protein
                        organism = Homo sapiens
SEQUENCE: 32
NNFVPTNVAS KAF                                                              13

SEQ ID NO: 33           moltype = AA  length = 13
FEATURE                 Location/Qualifiers
REGION                  1..13
                        note = misc_feature - C-term amidated
source                  1..13
                        mol_type = protein
                        organism = Homo sapiens
SEQUENCE: 33
NNFVPTNVGA KAF                                                              13

SEQ ID NO: 34           moltype = AA  length = 13
FEATURE                 Location/Qualifiers
REGION                  1..13
                        note = misc_feature - C-term amidated
source                  1..13
                        mol_type = protein
                        organism = Homo sapiens
SEQUENCE: 34
NNFVPTNVGS KAA                                                              13

SEQ ID NO: 35           moltype = AA  length = 12
FEATURE                 Location/Qualifiers
REGION                  1..12
                        note = misc_feature - C-term amidated
source                  1..12
                        mol_type = protein
                        organism = Homo sapiens
SEQUENCE: 35
NFVPTNVGSK AF                                                               12

SEQ ID NO: 36           moltype = AA  length = 19
FEATURE                 Location/Qualifiers
source                  1..19
                        mol_type = protein
                        organism = Homo sapiens
SEQUENCE: 36
SGGVVKNNFV PTNVGSKAF                                                        19

SEQ ID NO: 37           moltype = AA  length = 18
FEATURE                 Location/Qualifiers
source                  1..18
                        mol_type = protein
                        organism = Homo sapiens
SEQUENCE: 37
SGGVVKNNFV PTNVGSKA                                                         18
```

```
SEQ ID NO: 38              moltype = AA   length = 36
FEATURE                    Location/Qualifiers
source                     1..36
                           mol_type = protein
                           organism = Homo sapiens
SEQUENCE: 38
ACDTATCVTH RLAGLLSRSG GVVKNNFVPT NVGSKA                                    36

SEQ ID NO: 39              moltype = AA   length = 19
FEATURE                    Location/Qualifiers
source                     1..19
                           mol_type = protein
                           organism = Homo sapiens
SEQUENCE: 39
ACDTATCVTH RLAGLLSRS                                                       19

SEQ ID NO: 40              moltype = AA   length = 13
FEATURE                    Location/Qualifiers
source                     1..13
                           mol_type = protein
                           organism = Homo sapiens
SEQUENCE: 40
ACDTATCVTH RLA                                                             13

SEQ ID NO: 41              moltype = AA   length = 37
FEATURE                    Location/Qualifiers
REGION                     1..37
                           note = misc_feature - C-term amidated
source                     1..37
                           mol_type = protein
                           organism = Rattus sp.
SEQUENCE: 41
SCNTATCVTH RLAGLLSRSG GVVKDNFVPT NVGSEAF                                   37

SEQ ID NO: 42              moltype = AA   length = 19
FEATURE                    Location/Qualifiers
REGION                     1..19
                           note = misc_feature - C-term amidated
source                     1..19
                           mol_type = protein
                           organism = Rattus sp.
SEQUENCE: 42
SGGVVKDNFV PTNVGSEAF                                                       19

SEQ ID NO: 43              moltype = AA   length = 37
FEATURE                    Location/Qualifiers
REGION                     1..37
                           note = misc_feature - C-term amidated
source                     1..37
                           mol_type = protein
                           organism = Homo sapiens
SEQUENCE: 43
ACNTATCVTH RLAGLLSRSG GMVKSNFVPT NVGSKAF                                   37

SEQ ID NO: 44              moltype = AA   length = 37
FEATURE                    Location/Qualifiers
REGION                     1..37
                           note = misc_feature - C-term amidated
source                     1..37
                           mol_type = protein
                           organism = Rattus sp.
SEQUENCE: 44
SCNTATCVTH RLAGLLSRSG GVVKDNFVPT NVGSKAF                                   37

SEQ ID NO: 45              moltype = AA   length = 32
FEATURE                    Location/Qualifiers
REGION                     1..32
                           note = misc_feature - C-term amidated
source                     1..32
                           mol_type = protein
                           organism = Homo sapiens
SEQUENCE: 45
CGNLSTCMLG TYTQDFNKFH TFPQTAIGVG AP                                        32

SEQ ID NO: 46              moltype = AA   length = 37
FEATURE                    Location/Qualifiers
REGION                     1..37
                           note = misc_feature - C-term amidated
```

```
source                  1..37
                        mol_type = protein
                        organism = Homo sapiens
SEQUENCE: 46
KCNTATCATQ RLANFLVHSS NNFGAILSST NVGSNTY                              37

SEQ ID NO: 47           moltype = AA  length = 52
FEATURE                 Location/Qualifiers
REGION                  1..52
                        note = misc_feature - C-term amidated
source                  1..52
                        mol_type = protein
                        organism = Homo sapiens
SEQUENCE: 47
YRQSMNNFQG LRSFGCRFGT CTVQKLAHQI YQFTDKDKDN VAPRSKISPQ GY             52

SEQ ID NO: 48           moltype = AA  length = 4
FEATURE                 Location/Qualifiers
REGION                  1..4
                        note = Description of Artificial Sequence: Synthetic peptide
source                  1..4
                        mol_type = protein
                        organism = synthetic construct
SEQUENCE: 48
ELLG                                                                   4

SEQ ID NO: 49           moltype = AA  length = 4
FEATURE                 Location/Qualifiers
REGION                  1..4
                        note = Description of Artificial Sequence: Synthetic peptide
source                  1..4
                        mol_type = protein
                        organism = synthetic construct
SEQUENCE: 49
ELLG                                                                   4

SEQ ID NO: 50           moltype =     length =
SEQUENCE: 50
000

SEQ ID NO: 51           moltype =     length =
SEQUENCE: 51
000

SEQ ID NO: 52           moltype = AA  length = 4
FEATURE                 Location/Qualifiers
REGION                  1..4
                        note = Description of Artificial Sequence: Synthetic peptide
source                  1..4
                        mol_type = protein
                        organism = synthetic construct
SEQUENCE: 52
EFLG                                                                   4

SEQ ID NO: 53           moltype = AA  length = 11
FEATURE                 Location/Qualifiers
REGION                  1..11
                        note = Description of Artificial Sequence: Synthetic peptide
MOD_RES                 5
                        note = Arg, Trp, Gly, Leu or Asn
MOD_RES                 7
                        note = Thr, Ala, Asp, Gly, Arg, Ser, Trp or Val
source                  1..11
                        mol_type = protein
                        organism = synthetic construct
SEQUENCE: 53
KASKXVXTYV S                                                          11

SEQ ID NO: 54           moltype = AA  length = 7
FEATURE                 Location/Qualifiers
REGION                  1..7
                        note = Description of Artificial Sequence: Synthetic peptide
MOD_RES                 1
                        note = Gly or Ala
MOD_RES                 2
                        note = Ala or His
MOD_RES                 7
                        note = Leu, Thr, Ile or Ser
```

```
source                   1..7
                         mol_type = protein
                         organism = synthetic construct
SEQUENCE: 54
XXSNRYX                                                              7

SEQ ID NO: 55            moltype = AA   length = 19
FEATURE                  Location/Qualifiers
REGION                   1..19
                         note = Description of Artificial Sequence: Synthetic peptide
MOD_RES                  5
                         note = Glu, Arg, Lys, Gln or Asn
MOD_RES                  8
                         note = Ala, Gly, Asn, Glu, His, Ser, Leu, Arg, Cys, Phe,
                          Tyr, Val, Aspor Pro
MOD_RES                  9
                         note = Ser, Gly, Thr, Tyr, Cys, Glu, Leu, Ala, Pro, Ile,
                          Asn, Arg, Val,Asp or Met
MOD_RES                  12
                         note = His or Phe
MOD_RES                  15
                         note = Glu or Asp
source                   1..19
                         mol_type = protein
                         organism = synthetic construct
SEQUENCE: 55
EIRSXSDXXA TXYAXAVKG                                                 19

SEQ ID NO: 56            moltype = AA   length = 6
FEATURE                  Location/Qualifiers
REGION                   1..6
                         note = Description of Artificial Sequence: Synthetic 6xHis
                          tag
source                   1..6
                         mol_type = protein
                         organism = synthetic construct
SEQUENCE: 56
HHHHHH                                                               6

SEQ ID NO: 57            moltype = AA   length = 15
FEATURE                  Location/Qualifiers
REGION                   1..15
                         note = Description of Artificial Sequence: Synthetic peptide
source                   1..15
                         mol_type = protein
                         organism = synthetic construct
SEQUENCE: 57
GGGGSGGGGS GGGGS                                                     15

SEQ ID NO: 58            moltype = AA   length = 107
FEATURE                  Location/Qualifiers
REGION                   1..107
                         note = Description of Artificial Sequence: Synthetic
                          polypeptide
source                   1..107
                         mol_type = protein
                         organism = synthetic construct
SEQUENCE: 58
DIQMTQSPSS LSASVGDRVT ITCRASQDID NYLNWYQQKP GKAPKLLIYY TSEYHSGVPS    60
RFSGSGSGTD FTFTISSLQP EDIATYYCQQ GDALPPTFGQ GTKLEIK                  107

SEQ ID NO: 59            moltype = AA   length = 119
FEATURE                  Location/Qualifiers
REGION                   1..119
                         note = Description of Artificial Sequence: Synthetic
                          polypeptide
source                   1..119
                         mol_type = protein
                         organism = synthetic construct
SEQUENCE: 59
QVQLVQSGAE VKKPGASVKV SCKASGYTFG NYWMQWVRQA PGQGLEWMGA IYEGTGDTRY    60
IQKFAGRVTM TRDTSTSTVY MELSSLRSED TAVYYCARLS DYVSGFSYWG QGTLVTVSS     119

SEQ ID NO: 60            moltype = AA   length = 107
FEATURE                  Location/Qualifiers
REGION                   1..107
                         note = Description of Artificial Sequence: Synthetic
                          polypeptide
```

```
source                  1..107
                        mol_type = protein
                        organism = synthetic construct
SEQUENCE: 60
DIQMTQSPSS LSASVGDRVT ITCRASQDID NYLNWYQQKP GKAPKLLIYY TSEYHSGVPS    60
RFSGSGSGTD FTFTISSLQP EDIATYYCQQ GDALPPTFGQ GTKLEIK                 107

SEQ ID NO: 61           moltype = AA   length = 119
FEATURE                 Location/Qualifiers
REGION                  1..119
                        note = Description of Artificial Sequence: Synthetic
                        polypeptide
source                  1..119
                        mol_type = protein
                        organism = synthetic construct
SEQUENCE: 61
QVQLVQSGAE VKKPGASVKV SCKASGYTFG NYWMQWVRQA PGQGLEWMGA IYEGTGKTVY    60
IQKFAGRVTM TRDTSTSTVY MELSSLRSED TAVYYCARLS DYVSGFSYWG QGTLVTVSS    119

SEQ ID NO: 62           moltype = AA   length = 107
FEATURE                 Location/Qualifiers
REGION                  1..107
                        note = Description of Artificial Sequence: Synthetic
                        polypeptide
source                  1..107
                        mol_type = protein
                        organism = synthetic construct
SEQUENCE: 62
DIQMTQSPSS LSASVGDRVT ITCRASKDIS KYLNWYQQKP GKAPKLLIYY TSGYHSGVPS    60
RFSGSGSGTD FTLTISSLQP EDFATYYCQQ GDALPPTFGG GTKVEIK                 107

SEQ ID NO: 63           moltype = AA   length = 119
FEATURE                 Location/Qualifiers
REGION                  1..119
                        note = Description of Artificial Sequence: Synthetic
                        polypeptide
source                  1..119
                        mol_type = protein
                        organism = synthetic construct
SEQUENCE: 63
QVQLVQSGAE VKKPGSSVKV SCKASGYTFG NYWMQWVRQA PGQGLEWMGA IYEGTGKTVY    60
IQKFADRVTI TADKSTSTAY MELSSLRSED TAVYYCARLS DYVSGFGYWG QGTTVTVSS    119

SEQ ID NO: 64           moltype = AA   length = 107
FEATURE                 Location/Qualifiers
REGION                  1..107
                        note = Description of Artificial Sequence: Synthetic
                        polypeptide
source                  1..107
                        mol_type = protein
                        organism = synthetic construct
SEQUENCE: 64
DIQMTQSPSS LSASVGDRVT ITCRASRPID KYLNWYQQKP GKAPKLLIYY TSEYHSGVPS    60
RFSGSGSGTD FTFTISSLQP EDIATYYCQQ GDALPPTFGQ GTKLEIK                 107

SEQ ID NO: 65           moltype = AA   length = 119
FEATURE                 Location/Qualifiers
REGION                  1..119
                        note = Description of Artificial Sequence: Synthetic
                        polypeptide
source                  1..119
                        mol_type = protein
                        organism = synthetic construct
SEQUENCE: 65
QVQLVQSGAE VKKPGASVKV SCKASGYTFG NYWMQWVRQA PGQGLEWMGA IYEGTGKTVY    60
IQKFAGRVTM TRDTSTSTVY MELSSLRSED TAVYYCARLS DYVSGFGYWG QGTLVTVSS    119

SEQ ID NO: 66           moltype = AA   length = 107
FEATURE                 Location/Qualifiers
REGION                  1..107
                        note = Description of Artificial Sequence: Synthetic
                        polypeptide
source                  1..107
                        mol_type = protein
                        organism = synthetic construct
SEQUENCE: 66
DIQMTQSPSS LSASVGDRVT ITCRASQDID KYLNWYQQKP GKAPKLLIYY TSGYHSGVPS    60
RFSGSGSGTD FTLTISSLQP EDFATYYCQQ GDALPPTFGG GTKVEIK                 107
```

```
SEQ ID NO: 67            moltype = AA  length = 119
FEATURE                  Location/Qualifiers
REGION                   1..119
                         note = Description of Artificial Sequence: Synthetic
                         polypeptide
source                   1..119
                         mol_type = protein
                         organism = synthetic construct
SEQUENCE: 67
QVQLVQSGAE VKKPGSSVKV SCKASGYTFG NYWMQWVRQA PGQGLEWMGA IYEGTGKTVY    60
IQKFAGRVTI TADKSTSTAY MELSSLRSED TAVYYCARLS DYVSGFGYWG QGTTVTVSS    119

SEQ ID NO: 68            moltype = AA  length = 113
FEATURE                  Location/Qualifiers
REGION                   1..113
                         note = Description of Artificial Sequence: Synthetic
                         polypeptide
source                   1..113
                         mol_type = protein
                         organism = synthetic construct
SEQUENCE: 68
QVLTQSPSSL SASVGDRVTI NCQASQSVYH NTYLAWYQQK PGKVPKQLIY DASTLASGVP    60
SRFSGSGSGT DFTLTISSLQ PEDVATYYCL GSYDCTNGDC FVFGGGTKVE IKR          113

SEQ ID NO: 69            moltype = AA  length = 111
FEATURE                  Location/Qualifiers
REGION                   1..111
                         note = Description of Artificial Sequence: Synthetic
                         polypeptide
source                   1..111
                         mol_type = protein
                         organism = synthetic construct
SEQUENCE: 69
EVQLVESGGG LVQPGGSLRL SCAVSGIDLS GYYMNWVRQA PGKGLEWVGV IGINGATYYA    60
SWAKGRFTIS RDNSKTTVYL QMNSLRAEDT AVYFCARGDI WGQGTLVTVS S            111

SEQ ID NO: 70            moltype = AA  length = 113
FEATURE                  Location/Qualifiers
REGION                   1..113
                         note = Description of Artificial Sequence: Synthetic
                         polypeptide
source                   1..113
                         mol_type = protein
                         organism = synthetic construct
SEQUENCE: 70
QVLTQSPSSL SASVGDRVTI NCQASQSVYD NNYLAWYQQK PGKVPKQLIY STSTLASGVP    60
SRFSGSGSGT DFTLTISSLQ PEDVATYYCL GSYDCSSGDC FVFGGGTKVE IKR          113

SEQ ID NO: 71            moltype = AA  length = 111
FEATURE                  Location/Qualifiers
REGION                   1..111
                         note = Description of Artificial Sequence: Synthetic
                         polypeptide
source                   1..111
                         mol_type = protein
                         organism = synthetic construct
SEQUENCE: 71
EVQLVESGGG LVQPGGSLRL SCAVSGLDLS SYYMQWVRQA PGKGLEWVGV IGINDNTYYA    60
SWAKGRFTIS RDNSKTTVYL QMNSLRAEDT AVYFCARGDI WGQGTLVTVS S            111

SEQ ID NO: 72            moltype = AA  length = 113
FEATURE                  Location/Qualifiers
REGION                   1..113
                         note = Description of Artificial Sequence: Synthetic
                         polypeptide
source                   1..113
                         mol_type = protein
                         organism = synthetic construct
SEQUENCE: 72
QVLTQSPSSL SASVGDRVTI NCQASQSVYD NNYLAWYQQK PGKVPKQLIY STSTLASGVP    60
SRFSGSGSGT DFTLTISSLQ PEDVATYYCL GSYDCSSGDC FVFGGGTKVE IKR          113

SEQ ID NO: 73            moltype = AA  length = 111
FEATURE                  Location/Qualifiers
REGION                   1..111
                         note = Description of Artificial Sequence: Synthetic
                         polypeptide
```

```
                        source               1..111
                                             mol_type = protein
                                             organism = synthetic construct
SEQUENCE: 73
EVQLVESGGG LVQPGGSLRL SCAVSGLDLS SYYMQWVRQA PGKGLEWVGV IGINDNTYYA    60
SWAKGRFTIS RDNSKTTVYL QMNSLRAEDT AVYFCARGDI WGQGTLVTVS S            111

SEQ ID NO: 74           moltype = AA  length = 113
FEATURE                 Location/Qualifiers
REGION                  1..113
                        note = Description of Artificial Sequence: Synthetic
                         polypeptide
source                  1..113
                        mol_type = protein
                        organism = synthetic construct
SEQUENCE: 74
QVLTQTPSPV SAAVGSTVTI NCQASQSVYH NTYLAWYQQK PGQPPKQLIY DASTLASGVP    60
SRFSGSGSGT QFTLTISGVQ CNDAAAYYCL GSYDCTNGDC FVFGGGTEVV VKR          113

SEQ ID NO: 75           moltype = AA  length = 109
FEATURE                 Location/Qualifiers
REGION                  1..109
                        note = Description of Artificial Sequence: Synthetic
                         polypeptide
source                  1..109
                        mol_type = protein
                        organism = synthetic construct
SEQUENCE: 75
QSLEESGGRL VTPGTPLTLT CSVSGIDLSG YYMNWVRQAP GKGLEWIGVI GINGATYYAS    60
WAKGRFTISK TSSTTVDLKM TSLTTEDTAT YFCARGDIWG PGTLVTVSS               109

SEQ ID NO: 76           moltype = AA  length = 113
FEATURE                 Location/Qualifiers
REGION                  1..113
                        note = Description of Artificial Sequence: Synthetic
                         polypeptide
source                  1..113
                        mol_type = protein
                        organism = synthetic construct
SEQUENCE: 76
QVLTQSPSSL SASVGDRVTI NCQASQSVYH NTYLAWYQQK PGKVPKQLIY DASTLASGVP    60
SRFSGSGSGT DFTLTISSLQ PEDVATYYCL GSYDCTNGDC FVFGGGTKVE IKR          113

SEQ ID NO: 77           moltype = AA  length = 111
FEATURE                 Location/Qualifiers
REGION                  1..111
                        note = Description of Artificial Sequence: Synthetic
                         polypeptide
source                  1..111
                        mol_type = protein
                        organism = synthetic construct
SEQUENCE: 77
EVQLVESGGG LVQPGGSLRL SCAVSGIDLS GYYMNWVRQA PGKGLEWVGV IGINGATYYA    60
SWAKGRFTIS RDNSKTTVYL QMNSLRAEDT AVYFCARGDI WGQGTLVTVS S            111

SEQ ID NO: 78           moltype = AA  length = 110
FEATURE                 Location/Qualifiers
REGION                  1..110
                        note = Description of Artificial Sequence: Synthetic
                         polypeptide
source                  1..110
                        mol_type = protein
                        organism = synthetic construct
SEQUENCE: 78
QSVLTQPPSV SAAPGQKVTI SCSGSSSNIG NNYVSWYQQL PGTAPKLLIY DNNKRPSGIP    60
DRFSGSKSGT STTLGITGLQ TGDEADYYCG TWDSRLSAVV FGGGTKLTVL              110

SEQ ID NO: 79           moltype = AA  length = 130
FEATURE                 Location/Qualifiers
REGION                  1..130
                        note = Description of Artificial Sequence: Synthetic
                         polypeptide
source                  1..130
                        mol_type = protein
                        organism = synthetic construct
SEQUENCE: 79
QVQLVESGGG VVQPGRSLRL SCAASGFTFS SFGMHWVRQA PGKGLEWVAV ISFDGSIKYS    60
VDSVKGRFTI SRDNSKNTLF LQMNSLRAED TAVYYCARDR LNYYDSSGYY HYKYYGMAVW   120
GQGTTVTVSS                                                         130
```

```
SEQ ID NO: 80              moltype = AA   length = 113
FEATURE                    Location/Qualifiers
REGION                     1..113
                           note = Description of Artificial Sequence: Synthetic
                            polypeptide
source                     1..113
                           mol_type = protein
                           organism = synthetic construct
SEQUENCE: 80
QVLTQSPSSL SASVGDRVTI NCQASQSVYH NTYLAWYQQK PGKVPKQLIY DASTLASGVP    60
SRFSGSGSGT DFTLTISSLQ PEDVATYYCL GSYDCTNGDC FVFGGGTKVE IKR          113

SEQ ID NO: 81              moltype = AA   length = 219
FEATURE                    Location/Qualifiers
REGION                     1..219
                           note = Description of Artificial Sequence: Synthetic
                            polypeptide
source                     1..219
                           mol_type = protein
                           organism = synthetic construct
SEQUENCE: 81
QVLTQSPSSL SASVGDRVTI NCQASQSVYH NTYLAWYQQK PGKVPKQLIY DASTLASGVP    60
SRFSGSGSGT DFTLTISSLQ PEDVATYYCL GSYDCTNGDC FVFGGGTKVE IKRTVAAPSV   120
FIFPPSDEQL KSGTASVVCL LNNFYPREAK VQWKVDNALQ SGNSQESVTE QDSKDSTYSL   180
SSTLTLSKAD YEKHKVYACE VTHQGLSSPV TKSFNRGEC                          219

SEQ ID NO: 82              moltype = AA   length = 111
FEATURE                    Location/Qualifiers
REGION                     1..111
                           note = Description of Artificial Sequence: Synthetic
                            polypeptide
source                     1..111
                           mol_type = protein
                           organism = synthetic construct
SEQUENCE: 82
EVQLVESGGG LVQPGGSLRL SCAVSGIDLS GYYMNWVRQA PGKGLEWVGV IGINGATYYA    60
SWAKGRFTIS RDNSKTTVYL QMNSLRAEDT AVYFCARGDI WGQGTLVTVS S            111

SEQ ID NO: 83              moltype = AA   length = 441
FEATURE                    Location/Qualifiers
REGION                     1..441
                           note = Description of Artificial Sequence: Synthetic
                            polypeptide
source                     1..441
                           mol_type = protein
                           organism = synthetic construct
SEQUENCE: 83
EVQLVESGGG LVQPGGSLRL SCAVSGIDLS GYYMNWVRQA PGKGLEWVGV IGINGATYYA    60
SWAKGRFTIS RDNSKTTVYL QMNSLRAEDT AVYFCARGDI WGQGTLVTVS SASTKGPSVF   120
PLAPSSKSTS GGTAALGCLV KDYFPEPVTV SWNSGALTSG VHTFPAVLQS SGLYSLSSVV   180
TVPSSSLGTQ TYICNVNHKP SNTKVDARVE PKSCDKTHTC PPCPAPELLG GPSVFLFPPK   240
PKDTLMISRT PEVTCVVVDV SHEDPEVKFN WYVDGVEVHN AKTKPREEQY ASTYRVVSVL   300
TVLHQDWLNG KEYKCKVSNK ALPAPIEKTI SKAKGQPREP QVYTLPPSRE EMTKNQVSLT   360
CLVKGFYPSD IAVEWESNGQ PENNYKTTPP VLDSDGSFFL YSKLTVDKSR WQQGNVFSCS   420
VMHEALHNHY TQKSLSLSPG K                                             441

SEQ ID NO: 84              moltype = AA   length = 13
FEATURE                    Location/Qualifiers
REGION                     1..13
                           note = Description of Artificial Sequence: Synthetic
                            polypeptide
source                     1..13
                           mol_type = protein
                           organism = synthetic construct
SEQUENCE: 84
QASQSVYHNT YLA                                                       13

SEQ ID NO: 85              moltype = AA   length = 7
FEATURE                    Location/Qualifiers
REGION                     1..7
                           note = Description of Artificial Sequence: Synthetic
                            polypeptide
source                     1..7
                           mol_type = protein
                           organism = synthetic construct
SEQUENCE: 85
DASTLAS                                                               7
```

```
SEQ ID NO: 86          moltype = AA  length = 13
FEATURE                Location/Qualifiers
REGION                 1..13
                       note = Description of Artificial Sequence: Synthetic
                       polypeptide
source                 1..13
                       mol_type = protein
                       organism = synthetic construct
SEQUENCE: 86
LGSYDCTNGD CFV                                                              13

SEQ ID NO: 87          moltype = AA  length = 5
FEATURE                Location/Qualifiers
REGION                 1..5
                       note = Description of Artificial Sequence: Synthetic
                       polypeptide
source                 1..5
                       mol_type = protein
                       organism = synthetic construct
SEQUENCE: 87
GYYMN                                                                        5

SEQ ID NO: 88          moltype = AA  length = 15
FEATURE                Location/Qualifiers
REGION                 1..15
                       note = Description of Artificial Sequence: Synthetic
                       polypeptide
source                 1..15
                       mol_type = protein
                       organism = synthetic construct
SEQUENCE: 88
IGINGATYYA SWAKG                                                            15

SEQ ID NO: 89          moltype =     length =
SEQUENCE: 89
000

SEQ ID NO: 90          moltype = AA  length = 9
FEATURE                Location/Qualifiers
REGION                 1..9
                       note = Description of Artificial Sequence: Synthetic
                       polypeptide
source                 1..9
                       mol_type = protein
                       organism = synthetic construct
SEQUENCE: 90
QQGDALPPT                                                                    9

SEQ ID NO: 91          moltype = AA  length = 10
FEATURE                Location/Qualifiers
REGION                 1..10
                       note = Description of Artificial Sequence: Synthetic
                       polypeptide
source                 1..10
                       mol_type = protein
                       organism = synthetic construct
SEQUENCE: 91
RASKDISKYL                                                                  10

SEQ ID NO: 92          moltype = AA  length = 7
FEATURE                Location/Qualifiers
REGION                 1..7
                       note = Description of Artificial Sequence: Synthetic
                       polypeptide
source                 1..7
                       mol_type = protein
                       organism = synthetic construct
SEQUENCE: 92
YTSGYSH                                                                      7

SEQ ID NO: 93          moltype = AA  length = 10
FEATURE                Location/Qualifiers
REGION                 1..10
                       note = Description of Artificial Sequence: Synthetic
                       polypeptide
source                 1..10
                       mol_type = protein
                       organism = synthetic construct
```

```
SEQUENCE: 93
GYTFGNYWMQ                                                               10

SEQ ID NO: 94          moltype = AA  length = 17
FEATURE                Location/Qualifiers
REGION                 1..17
                       note = Description of Artificial Sequence: Synthetic
                        polypeptide
source                 1..17
                       mol_type = protein
                       organism = synthetic construct
SEQUENCE: 94
AIYEGTGKTV YIQKFAD                                                       17

SEQ ID NO: 95          moltype = AA  length = 10
FEATURE                Location/Qualifiers
REGION                 1..10
                       note = Description of Artificial Sequence: Synthetic
                        polypeptide
source                 1..10
                       mol_type = protein
                       organism = synthetic construct
SEQUENCE: 95
LSDYVSGFGY                                                               10

SEQ ID NO: 96          moltype = AA  length = 107
FEATURE                Location/Qualifiers
REGION                 1..107
                       note = Description of Artificial Sequence: Synthetic
                        polypeptide
source                 1..107
                       mol_type = protein
                       organism = synthetic construct
SEQUENCE: 96
DIQMTQSPSS LSASVGDRVT ITCRASKDIS KYLNWYQQKP GKAPKLLIYY TSGYHSGVPS         60
RFSGSGSGTD FTLTISSLQP EDFATYYCQQ GDALPPTFGG GTKVEIK                      107

SEQ ID NO: 97          moltype = AA  length = 119
FEATURE                Location/Qualifiers
REGION                 1..119
                       note = Description of Artificial Sequence: Synthetic
                        polypeptide
source                 1..119
                       mol_type = protein
                       organism = synthetic construct
SEQUENCE: 97
QVQLVQSGAE VKKPGSSVKV SCKASGYTFG NYWMQWVRQA PGQGLEWMGA IYEGTGKTVY         60
IQKFADRVTI TADKSTSTAY MELSSLRSED TAVYYCARLS DYVSGFGYWG QGTTVTVSS         119

SEQ ID NO: 98          moltype = AA  length = 214
FEATURE                Location/Qualifiers
REGION                 1..214
                       note = Description of Artificial Sequence: Synthetic
                        polypeptide
source                 1..214
                       mol_type = protein
                       organism = synthetic construct
SEQUENCE: 98
DIQMTQSPSS LSASVGDRVT ITCRASKDIS KYLNWYQQKP GKAPKLLIYY TSGYHSGVPS         60
RFSGSGSGTD FTLTISSLQP EDFATYYCQQ GDALPPTFGG GTKVEIKRTV AAPSVFIFPP        120
SDEQLKSGTA SVVCLLNNFY PREAKVQWKV DNALQSGNSQ ESVTEQDSKD STYSLSSTLT        180
LSKADYEKHK VYACEVTHQG LSSPVTKSFN RGEC                                   214

SEQ ID NO: 99          moltype = AA  length = 445
FEATURE                Location/Qualifiers
REGION                 1..445
                       note = Description of Artificial Sequence: Synthetic
                        polypeptide
source                 1..445
                       mol_type = protein
                       organism = synthetic construct
SEQUENCE: 99
QVQLVQSGAE VKKPGSSVKV SCKASGYTFG NYWMQWVRQA PGQGLEWMGA IYEGTGKTVY         60
IQKFADRVTI TADKSTSTAY MELSSLRSED TAVYYCARLS DYVSGFGYWG QGTTVTVSSA        120
STKGPSVFPL APCSRSTSES TAALGCLVKD YFPEPVTVSW NSGALTSGVH TFPAVLQSSG        180
LYSLSSVVTV PSSSLGTKTY TCNVDHKPSN TKVDKRVESK YGPPCPPCPA PEAAGGPSVF        240
LFPPKPKDTL MISRTPEVTC VVVDVSQEDP EVQFNWYVDG VEVHNAKTKP REEQFNSTYR        300
```

```
VVSVLTVLHQ DWLNGKEYKC KVSNKGLPSS IEKTISKAKG QPREPQVYTL PPSQEEMTKN    360
QVSLTCLVKG FYPSDIAVEW ESNGQPENNY KTTPPVLDSD GSFFLYSRLT VDKSRWQEGN    420
VFSCSVMHEA LHNHYTQKSL SLSLG                                         445

SEQ ID NO: 100          moltype = AA   length = 13
FEATURE                 Location/Qualifiers
REGION                  1..13
                        note = Synthetic polypeptide
source                  1..13
                        mol_type = protein
                        organism = synthetic construct
SEQUENCE: 100
SGSSSNIGNN YVS                                                       13

SEQ ID NO: 101          moltype = AA   length = 7
FEATURE                 Location/Qualifiers
REGION                  1..7
                        note = Synthetic polypeptide
source                  1..7
                        mol_type = protein
                        organism = synthetic construct
SEQUENCE: 101
DNNKRPS                                                               7

SEQ ID NO: 102          moltype = AA   length = 11
FEATURE                 Location/Qualifiers
REGION                  1..11
                        note = Synthetic polypeptide
source                  1..11
                        mol_type = protein
                        organism = synthetic construct
SEQUENCE: 102
GTWDSRLSAV V                                                         11

SEQ ID NO: 103          moltype = AA   length = 5
FEATURE                 Location/Qualifiers
REGION                  1..5
                        note = Synthetic polypeptide
source                  1..5
                        mol_type = protein
                        organism = synthetic construct
SEQUENCE: 103
SFGMH                                                                 5

SEQ ID NO: 104          moltype = AA   length = 17
FEATURE                 Location/Qualifiers
REGION                  1..17
                        note = Synthetic polypeptide
source                  1..17
                        mol_type = protein
                        organism = synthetic construct
SEQUENCE: 104
VISFDGSIKY SVDSVKG                                                   17

SEQ ID NO: 105          moltype = AA   length = 21
FEATURE                 Location/Qualifiers
REGION                  1..21
                        note = Synthetic polypeptide
source                  1..21
                        mol_type = protein
                        organism = synthetic construct
SEQUENCE: 105
DRLNYYDSSG YYHYKYYGMA V                                              21

SEQ ID NO: 106          moltype = AA   length = 110
FEATURE                 Location/Qualifiers
REGION                  1..110
                        note = Synthetic polypeptide
source                  1..110
                        mol_type = protein
                        organism = synthetic construct
SEQUENCE: 106
QSVLTQPPSV SAAPGQKVTI SCSGSSSNIG NNYVSWYQQL PGTAPKLLIY DNNKRPSGIP    60
DRFSGSKSGT STTLGITGLQ TGDEADYYCG TWDSRLSAVV FGGGTKLTVL              110

SEQ ID NO: 107          moltype = AA   length = 130
FEATURE                 Location/Qualifiers
REGION                  1..130
                        note = Synthetic polypeptide
```

```
source                  1..130
                        mol_type = protein
                        organism = synthetic construct
SEQUENCE: 107
QVQLVESGGG VVQPGRSLRL SCAASGFTFS SFGMHWVRQA PGKGLEWVAV ISFDGSIKYS     60
VDSVKGRFTI SRDNSKNTLF LQMNSLRAED TAVYYCARDR LNYYDSSGYY HYKYYGMAVW    120
GQGTTVTVSS                                                           130

SEQ ID NO: 108          moltype = AA  length = 238
FEATURE                 Location/Qualifiers
REGION                  1..238
                        note = Synthetic_polypeptide
source                  1..238
                        mol_type = protein
                        organism = synthetic construct
SEQUENCE: 108
MDMRVPAQLL GLLLLWLRGA RCQSVLTQPP SVSAAPGQKV TISCSGSSSN IGNNYVSWYQ     60
QLPGTAPKLL IYDNNKRPSG IPDRFSGSKS GTSTTLGITG LQTGDEADYY CGTWDSRLSA    120
VVFGGGTKLT VLGQPKANPT VTLFPPSSEE LQANKATLVC LISDFYPGAV TVAWKADGSP    180
VKAGVETTKP SKQSNNKYAA SSYLSLTPEQ WKSHRSYSCQ VTHEGSTVEK TVAPTECS      238

SEQ ID NO: 109          moltype = AA  length = 478
FEATURE                 Location/Qualifiers
REGION                  1..478
                        note = Synthetic polypeptide
source                  1..478
                        mol_type = protein
                        organism = synthetic construct
SEQUENCE: 109
MDMRVPAQLL GLLLLWLRGA RCQVQLVESG GGVVQPGRSL RLSCAASGFT FSSFGMHWVR     60
QAPGKGLEWV AVISFDGSIK YSVDSVKGRF TISRDNSKNT LFLQMNSLRA EDTAVYYCAR    120
DRLNYYDSSG YYHKYYGMA VWGQGTTVTV SSASTKGPSV FPLAPCSRST SESTAALGCL    180
VKDYFPEPVT VSWNSGALTS GVHTFPAVLQ SSGLYSLSSV VTVPSSNFGT QTYTCNVDHK    240
PSNTKVDKTV ERKCCVECPP CPAPPVAGPS VFLFPPKPKD TLMISRTPEV TCVVVDVSHE    300
DPEVQFNWYV DGVEVHNAKT KPREEQFNST FRVVSVLTVV HQDWLNGKEY KCKVSNKGLP    360
APIEKTISKT KGQPREPQVY TLPPSREEMT KNQVSLTCLV KGFYPSDIAV EWESNGQPEN    420
NYKTTPPMLD SDGSFFLYSK LTVDKSRWQQ GNVFSCSVMH EALHNHYTQK SLSLSPGK      478
```